(12) United States Patent
Moriguchi et al.

(10) Patent No.: US 11,608,313 B2
(45) Date of Patent: *Mar. 21, 2023

(54) ADAMANTYLMETHYLAMINE DERIVATIVE AND USE THEREOF AS PHARMACEUTICAL

(71) Applicant: TOHOKU UNIVERSITY, Sendai (JP)

(72) Inventors: Shigeki Moriguchi, Miyagi (JP); Kohji Fukunaga, Miyagi (JP); Yoshiharu Iwabuchi, Miyagi (JP)

(73) Assignee: Tohoku University, Miyagi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/635,396

(22) PCT Filed: Aug. 2, 2018

(86) PCT No.: PCT/JP2018/029018
§ 371 (c)(1),
(2) Date: Jan. 30, 2020

(87) PCT Pub. No.: WO2019/026994
PCT Pub. Date: Feb. 7, 2019

(65) Prior Publication Data
US 2020/0181066 A1    Jun. 11, 2020

(30) Foreign Application Priority Data
Aug. 2, 2017  (JP) .............................. JP2017-150290

(51) Int. Cl.
| | | |
|---|---|---|
| C07C 233/66 | (2006.01) | |
| C07C 215/42 | (2006.01) | |
| C07C 235/06 | (2006.01) | |
| C07C 237/06 | (2006.01) | |
| C07C 275/28 | (2006.01) | |

(Continued)

(52) U.S. Cl.
CPC .......... *C07C 233/66* (2013.01); *C07C 215/42* (2013.01); *C07C 235/06* (2013.01);
(Continued)

(58) Field of Classification Search
None
See application file for complete search history.

(56) References Cited

U.S. PATENT DOCUMENTS 3,682,922 A    8/1972 Klimstra
3,852,352 A   12/1974 Polis et al.
(Continued)

FOREIGN PATENT DOCUMENTS

| CA | 3012312 A1 | 8/2017 |
|---|---|---|
| CN | 104001150 A | 8/2014 |

(Continued)

OTHER PUBLICATIONS

Database Registry (STN), Sep. 11, 2016, RN: 1990660-80-4 to 1499084-76-2, retrieved from STN International [online] on Oct. 10, 2018, 77 pages.
(Continued)

*Primary Examiner* — Sudhakar Katakam
*Assistant Examiner* — Jennifer C Sawyer
(74) *Attorney, Agent, or Firm* — Foley & Lardner LLP

(57) ABSTRACT

The present invention provides a pharmaceutical composition for treating or preventing a cognitive disease or disorder, comprising a compound represented by Formula (I), an enantiomer thereof a diastereomer thereof, or a pharmaceutically acceptable salt thereof.

19 Claims, 48 Drawing Sheets

Specification includes a Sequence Listing.

(51) Int. Cl.
  *C07C 311/16* (2006.01)
  *A61K 45/06* (2006.01)

(52) U.S. Cl.
  CPC .......... *C07C 237/06* (2013.01); *C07C 275/28* (2013.01); *C07C 311/16* (2013.01); *A61K 45/06* (2013.01); *C07C 2601/02* (2017.05); *C07C 2601/04* (2017.05); *C07C 2601/08* (2017.05); *C07C 2603/74* (2017.05)

(56) References Cited

U.S. PATENT DOCUMENTS

| | | | |
|---|---|---|---|
| 10,487,045 B2 * | 11/2019 | Moriguchi | ........... A61K 31/198 |
| 2006/0223855 A1 | 10/2006 | Kong et al. | |
| 2007/0072892 A1 | 3/2007 | Schrimpf et al. | |
| 2008/0255180 A1 | 10/2008 | Bunnelle | |
| 2010/0022546 A1 | 1/2010 | Jimenenz et al. | |
| 2010/0197675 A1 | 8/2010 | Claremon et al. | |
| 2011/0212943 A1 | 9/2011 | Balasubramanian et al. | |
| 2012/0270873 A1 | 10/2012 | Jiminez et al. | |
| 2013/0045177 A1 | 2/2013 | Takatoku et al. | |
| 2015/0265613 A1 | 9/2015 | Bitner et al. | |

FOREIGN PATENT DOCUMENTS

| | | |
|---|---|---|
| CN | 107556244 A | 1/2018 |
| JP | 2008-525425 A | 7/2008 |
| JP | 2009-508956 A | 3/2009 |
| JP | 2010-519304 A | 6/2010 |
| JP | 2010-522203 A | 7/2010 |
| JP | 2011-529057 A | 12/2011 |
| WO | WO 2009/020140 A1 | 2/2009 |
| WO | WO 2010/043953 A2 | 4/2010 |
| WO | WO 2011/142246 A1 | 11/2011 |
| WO | WO-2013/086131 A1 | 6/2013 |
| WO | WO 2015/087262 A1 | 6/2015 |
| WO | WO 2017/131097 A1 | 8/2017 |
| WO | WO-2018/179343 A1 | 10/2018 |
| WO | WO-2018/181986 A1 | 10/2018 |

OTHER PUBLICATIONS

Database Registry, 2015, RN 1782740-93-5, retrieved from STN international (online) on Jun. 4, 2018, 1 page.
Database Registry, 2016, RN 1981386-54-2 to RN-1500310-10-0, retrieved from STN international (online) on Jun. 4, 2018, 41 pages.
Folia Pharmacologica Japonica, 2004, 124:145-151, with English Abstract on last page.
Folia Pharmacologica Japonica, 2005, 126:311-316, with English abstract.
International Search Report dated Jun. 19, 2018, in PCT/JP2018/013853.
International Search Report dated Jun. 27, 2017, in PCT/JP2017/013616.
International Search Report dated Mar. 21, 2017, in PCT/JP2017/002760.
International Search Report dated Oct. 23, 2018, in PCT/JP2018/029018.
Lachenicht et al., "Synthesis of Modified 4H-1,2,4-Benzothiadizine-1,1-dioxides and Determination of their Affinity and Selectivity for Different Types of $K_{ATP}$ Channels," ChemMedChem, 2009, 4(11):1850-1858.
Moriguchi et al., "Blockade of the $K_{ATP}$ channel Kir6.2 by memantine represents a novel mechanism relevant to Alzheimer's disease therapy," Molecular Psychiatry, 2016, advance online publication, 1-11.
Teramoto, Noriyoshi, "Pharmacological Profile of U-37883A, a Channel Blocker of Smooth Muscle-Type ATP-Sensitive $K^+$Channels," Cardiovascular Drug Reviews, 2006, 24(1):25-32.
Office Action dated May 28, 2020 in Indian Patent Application No. 201817031803.
CAS Registry No. 1782740-93-5, STN entry date Jun. 17, 2015, 3 pages.
CAS Registry No. 1976622-08-8, STN entry date Aug. 21, 2016, 2 pages.
CAS Registry No. 1979901-23-9, STN entry date Aug. 25, 2016, 2 pages.
Office Action dated Feb. 28, 2022 in AU 2018310024.
Ge et al., "Progress of Derivatives of Adamantane," Chinese Journal of Pharmaceuticals, 2003, 34(11):583-586, with English abstract.
Henkel et al., "Structure-Anti-Parkinson Relationships in the Aminoadamantanes. Influence of Bridgehead Substitution," J. Med. Chem., 1982, 25:51-56.
Liang et al., "Synthesis of Memantine Derivatives," Chinese J. Synthetic Chemistry, 2010, 18(4):526-528, with English abstract.

* cited by examiner

Fig. 17-1

```
   1  GACGGATCGG GAGATCTCCC GATCCCCTAT GGTGCACTCT CAGTACAATC TGCTCTGATG
  61  CCGCATAGTT AAGCCAGTAT CTGCTCCCTG CTTGTGTGTT GGAGGTCGCT GAGTAGTGCG
 121  CGAGCAAAAT TTAAGCTACA ACAAGGCAAG GCTTGACCGA CAATTGCATG AAGAATCTGC
                                                        ───────CMV promoter───────
 181  TTAGGGTTAG GCGTTTTGCG CTGCTTCGCG ATGTACGGGC CAGATATACG CGTTGACATT
      ──────────────────────────────── CMV promoter ──────────────────────────────
 241  GATTATTGAC TAGTTATTAA TAGTAATCAA TTACGGGGTC ATTAGTTCAT AGCCCATATA
      ──────────────────────────────── CMV promoter ──────────────────────────────
 301  TGGAGTTCCG CGTTACATAA CTTACGGTAA ATGGCCCGCC TGGCTGACCG CCCAACGACC
      ──────────────────────────────── CMV promoter ──────────────────────────────
 361  CCCGCCCATT GACGTCAATA ATGACGTATG TTCCCATAGT AACGCCAATA GGGACTTTCC
      ──────────────────────────────── CMV promoter ──────────────────────────────
 421  ATTGACGTCA ATGGGTGGAC TATTTACGGT AAACTGCCCA CTTGGCAGTA CATCAAGTGT
      ──────────────────────────────── CMV promoter ──────────────────────────────
 481  ATCATATGCC AAGTACGCCC CCTATTGACG TCAATGACGG TAAATGGCCC GCCTGGCATT
      ──────────────────────────────── CMV promoter ──────────────────────────────
 541  ATGCCCAGTA CATGACCTTA TGGGACTTTC CTACTTGGCA GTACATCTAC GTATTAGTCA
      ──────────────────────────────── CMV promoter ──────────────────────────────
 601  TCGCTATTAC CATGGTGATG CGGTTTTGGC AGTACATCAA TGGGCGTGGA TAGCGGTTTG
      ──────────────────────────────── CMV promoter ──────────────────────────────
 661  ACTCACGGGG ATTTCCAAGT CTCCACCCCA TTGACGTCAA TGGGAGTTTG TTTTGGCACC
                                                             ── CMV forward primer ──
      ──────────────────────────────── CMV promoter ──────────────────────────────
 721  AAAATCAACG GGACTTTCCA AATGTCGTA  ACAACTCCGC CCCATTGACG CAAATGGGCG
      ── CMV forward prime ──
                          ──────────── CMV promoter ──────────────
 781  GTAGGCGTGT ACGGTGGGAG GTCTATATAA GCAGAGCTCT CTGGCTAACT AGAGAACCCA
                                                       ───── T7 primer ─────
                 ──── CMV promoter ────
                                          ───── T7 promoter ─────
 841  CTGCTTACTG GCTTATCGAA ATTAATACGA CTCACTATAG GGAGACCCAA GCTGGCTAGT
         HindIII              BamHI                         Kir6.2
  +2                                              M  L  S  R  K  G  I  I  P  E
 901  TAAGCTTGGT ACCGAGCTCG GATCCGCCAC CATGCTGTCC CGAAAGGGCA TTATCCCTGA
                                                    Kir6.2
  +2   E  E  Y  V  L  T  R  L  A  E  D  P  T  E  P  R  Y  R  T  R  E
 961  GGAATATGTG CTGACCCGGC TGGCAGAGGA CCCTACAGAG CCCAGGTACC GTACTCGGGA
                                                    Kir6.2
  +2   E  R  R  A  R  F  V  S  K  K  G  N  C  N  V  A  H  K  N  I  R
1021  GAGGAGGGCC CGCTTCGTGT CCAAGAAAGG CAACTGCAAC GTCGCCCACA AGAACATCCG
                                                    Kir6.2
  +2   R  E  Q  G  R  F  L  Q  D  V  F  T  T  L  V  D  L  K  W  P  H
1081  AGAGCAGGGC CGCTTCCTGC AAGATGTGTT CACCACGCTG GTGGACCTCA AGTGGCCCCA
                                                    Kir6.2
  +2   H  T  L  L  I  F  T  M  S  F  L  C  S  W  L  L  F  A  M  V  W
1141  CACGCTGCTC ATTTTCACCA TGTCCTTCCT GTGCAGCTGG CTGCTCTTCG CCATGGTCTG
                                                    Kir6.2
  +2   W  W  L  I  A  F  A  H  G  D  L  A  P  G  E  G  T  N  V  P  C
1201  GTGGCTCATC GCCTTTGCCC ACGGTGACTT GGCCCCCGGA GAGGGCACCA ATGTGCCCTG
```

Fig. 17-2

```
                                      Kir6.2
     +2   ·C  V  T  S     I  H  S  F  S  S     A  L  F     F  S  I  E  V  Q  V  T·
    1261  CGTCACAAGC  ATCCACTCCT  TTTCGTCTGC  CTTCCTTTTC  TCCATCGAGG  TCCAGGTGAC
                                      Kir6.2
     +2   ·T  I  G  F     G  G  R  M  V  T     E  E  C  P  L  A  I     L  I  L  I·
    1321  CATTGGTTTC  GGCGGGCGCA  TGGTGACAGA  GGAATGTCCC  CTGGCCATCC  TTATTCTGAT
                                      Kir6.2
     +2   ·I  V  Q  N     I  V  G  L  M  I     N  A  I  M  L  G  C     I  F  M  K·
    1381  CGTGCAGAAT  ATCGTAGGGC  TAATGATCAA  CGCCATCATG  CTGGGCTGCA  TCTTCATGAA
                                      Kir6.2
     +2   ·K  T  A     A  H  R  R     A  E  T     L  I  F     S  K  H     A  V  I  T·
    1441  AACGGCACAG  GCCCATCGGC  GGGCAGAAAC  CCTCATCTTC  AGCAAGCATG  CCGTGATCAC
                                      Kir6.2
     +2   ·T  L  R     H  G  R  L     C  F  M  L     R  V  G     D  L  R     K  S  M  I·
    1501  CCTGCGACAT  GGCCGCCTGT  GCTTCATGCT  TCGCGTAGGG  GACCTCCGAA  AAAGCATGAT
                                      Kir6.2
     +2   ·I  I  S  A     T  I  H  M  Q  V     V  R  K  T     T  S  P     E  G  E  V·
    1561  CATTAGCGCC  ACCATTCATA  TGCAGGTGGT  GCGCAAGACC  ACCAGCCCGG  AGGGCGAGGT
                                      Kir6.2
     +2   ·V  V  P     L  H  Q  V     D  I  P  M     E  N  G     V  G  G  N     S  I  F·
    1621  TGTGCCTCTC  CACCAGGTGG  ACATCCCCAT  GGAGAACGGT  GTGGGTGGTA  ACAGCATCTT
                                      Kir6.2
     +2   ·F  L  V  A     P  L  I     I  Y  H     V  I  D  S     N  S  P     L  Y  D  L·
    1681  TCTGGTGGCC  CCACTCATCA  TCTACCACGT  CATCGACTCC  AACAGCCCGC  TCTACGACCT
                                      Kir6.2
     +2   ·L  A  P  S     D  L  H     H  Q  D     L  E     I     I  V  I     L  E  G  V·
    1741  GGCTCCTAGT  GACCTGCACC  ACCACCAGGA  CCTGGAGATC  ATTGTCATCT  TGGAAGGTGT
                                      Kir6.2
     +2   ·V  V  E  T     T  G  I  T     T  Q  A  R     T  S     Y  L  A     D  E  I  L·
    1801  GGTAGAAACC  ACAGGCATTA  CCACCCAGGC  CCGCACCTCC  TATCTGGCTG  ACGAGATTCT
                                      Kir6.2
     +2   ·L  W  G  Q     R  F  V     P  I  V  A     E  E  D     G  R  Y     S  V  D  Y·
    1861  GTGGGGGCAG  CGTTTTGTCC  CCATCGTGGC  CGAGGAGGAT  GGCCGCTATT  CTGTGGACTA
                                      Kir6.2
     +2   ·Y  S  K  F     G  N  T     V  K  V  P     T  P  L     C  T  A  R     Q  L  D·
    1921  CTCCAAATTC  GGGAACACCG  TTAAAGTGCC  CACACCACTC  TGCACAGCCC  GCCAGCTTGA
                                      Kir6.2
     +2   ·D  E  D     R  S  L  L     D  A  L     T     L  A  S     S  R  G     P  L  R  K·
    1981  TGAGGACCGC  AGCCTGCTGG  ATGCCCTGAC  CCTCGCCTCG  TCGCGAGGGC  CCCTGCGCAA
                                      Kir6.2
     +2   ·K  R  S     V  A  V  A     K  A  K     P  K  F  S     I  S  P     D  S  L  S·
    2041  GCGCAGTGTG  GCTGTGGCAA  AGGCCAAGCC  CAAGTTTAGC  ATCTCTCCGG  ATTCCTTGTC
          Kir6.2          NotI              XbaI             SfuI
                                            XhoI
     +2   ·S  *
    2101  CTGATAGCGG  CCGCTCGAGT  CTAGAGGGCC  CTTCGAACAA  AAACTCATCT  CAGAAGAGGA
                          AgeI                              PmeI              BGH pA
    2161  TCTGAATATG  CATACCGGTC  ATCATCACCA  TCACCATTGA  GTTTAAACCC  GCTGATCAGC
                                                                        BGH reverse prime
                                      BGH pA
    2221  CTCGACTGTG  CCTTCTAGTT  GCCAGCCATC  TGTTGTTTGC  CCCTCCCCCG  TGCCTTCCTT
          BGH reverse primer
```

Fig. 17-3

```
                                              BGH pA
2281   GACCCTGGAA GGTGCCACTC CCACTGTCCT TTCCTAATAA AATGAGGAAA TTGCATCGCA
                                              BGH pA
2341   TTGTCTGAGT AGGTGTCATT CTATTCTGGG GGGTGGGGTG GGGCAGGACA GCAAGGGGGA
                       BGH pA
2401   GGATTGGGAA GACAATAGCA GGCATGCTGG GGATGCGGTG GGCTCTATGG CTTCTGAGGC
                                                              f1 origin
2461   GGAAAGAACC AGCTGGGGCT CTAGGGGGTA TCCCCACGCG CCCTGTAGCG GCGCATTAAG
                                         f1 origin
2521   CGCGGCGGGT GTGGTGGTTA CGCGCAGCGT GACCGCTACA CTTGCCAGCG CCCTAGCGCC
                                 f1 origin
2581   CGCTCCTTTC GCTTTCTTCC CTTCCTTTCT CGCCACGTTC GCCGGCTTTC CCCGTCAAGC
                                 f1 origin
2641   TCTAAATCGG GGGCTCCCTT TAGGGTTCCG ATTTAGTGCT TTACGGCACC TCGACCCCAA
                                 f1 origin
2701   AAAACTTGAT TAGGGTGATG GTTCACGTAG TGGGCCATCG CCCTGATAGA CGGTTTTTCG
                                 f1 origin
2761   CCCTTTGACG TTGGAGTCCA CGTTCTTTAA TAGTGGACTC TTGTTCCAAA CTGGAACAAC
                                 f1 origin
2821   ACTCAACCCT ATCTCGGTCT ATTCTTTTGA TTTATAAGGG ATTTTGCCGA TTTCGGCCTA
                       f1 origin
2881   TTGGTTAAAA AATGAGCTGA TTTAACAAAA ATTTAACGCG AATTAATTCT GTGGAATGTG
                                                       SV40 early promoter
2941   TGTCAGTTAG GGTGTGGAAA GTCCCCAGGC TCCCCAGCAG GCAGAAGTAT GCAAAGCATG
                                SV40 early promoter
3001   CATCTCAATT AGTCAGCAAC CAGGTGTGGA AAGTCCCCAG GCTCCCCAGC AGGCAGAAGT
                                SV40 early promoter
3061   ATCCAAAGCA TGCATCTCAA TTAGTCAGCA ACCATAGTCC CGCCCCTAAC TCCGCCCATC
                                SV40 early promoter
3121   CCGCCCCTAA CTCCGCCCAG TTCCGCCCAT TCTCCGCCCC ATGGCTGACT AATTTTTTTT
                                SV40 early promoter
3181   ATTTATGCAG AGGCCGAGGC CGCCTCTGCC TCTGAGCTAT TCCAGAAGTA GTGAGGAGGC
                                SV40 early promoter
3241   TTTTTTGGAG GCCTAGGCTT TTGCAAAAAG CTCCCGGGAG CTTGTATATC CATTTTCGGA
                                                              Neo(R)
3301   TCTGATCAAG AGACAGGATG AGGATCGTTT CGCATGATTG AACAAGATGG ATTGCACGCA
                                    Neo(R)
3361   GGTTCTCCGG CCGCTTGGGT GGAGAGGCTA TTCGGCTATG ACTGGGCACA ACAGACAATC
                                    Neo(R)
3421   GGCTGCTCTG ATGCCGCCGT GTTCCGGCTG TCAGCGCAGG GGCGCCCGGT TCTTTTTGTC
                                    Neo(R)
3481   AAGACCGACC TGTCCGGTGC CCTGAATGAA CTGCAGGACG AGGCAGCGCG GCTATCGTGG
                                    Neo(R)
3541   CTGGCCACGA CGGGCGTTCC TTGCGCAGCT GTGCTCGACG TTGTCACTGA AGCGGGAAGG
                                    Neo(R)
3601   GACTGGCTGC TATTGGGCGA AGTGCCGGGG CAGGATCTCC TGTCATCTCA CCTTGCTCCT
                                    Neo(R)
3661   GCCGAGAAAG TATCCATCAT GGCTGATGCA ATGCGGCGGC TGCATACGCT TGATCCGGCT
                                    Neo(R)
3721   ACCTGCCCAT TCGACCACCA AGCGAAACAT CGCATCGAGC GAGCACGTAC TCGGATGGAA
```

Fig. 17-4

```
                        Neo(R)
3781  GCCGGTCTTG TCGATCAGGA TGATCTGGAC GAAGAGCATC AGGGGCTCGC GCCAGCCGAA
                        Neo(R)
3841  CTGTTCGCCA GGCTCAAGGC GCGCATGCCC GACGGCGAGG ATCTCGTCGT GACCCATGGC
                        Neo(R)
3901  GATGCCTGCT TGCCGAATAT CATGGTGGAA AATGGCCGCT TTTCTGGATT CATCGACTGT
                        Neo(R)
3961  GGCCGGCTGG GTGTGGCGGA CCGCTATCAG GACATAGCGT TGGCTACCCG TGATATTGCT
                        Neo(R)
4021  GAAGAGCTTG GCGGCGAATG GGCTGACCGC TTCCTCGTGC TTTACGGTAT CGCCGCTCCC
                        Neo(R)
4081  GATTCGCAGC GCATCGCCTT CTATCGCCTT CTTGACGAGT TCTTCTGAGC GGGACTCTGG
4141  GGTTCGCGAA ATGACCGACC AAGCGACGCC CAACCTGCCA TCACGAGATT TCGATTCCAC
4201  CGCCGCCTTC TATGAAAGGT TGGGCTTCGG AATCGTTTTC CGGGACGCCG GCTGGATGAT
                                                          SV40 pA
4261  CCTCCAGCGC GGGGATCTCA TGCTGGAGTT CTTCGCCCAC CCCAACTTGT TTATTGCAGC
                        SV40 pA
4321  TTATAATGGT TACAAATAAA GCAATAGCAT CACAAATTTC ACAAATAAAG CATTTTTTTC
                        SV40 pA
4381  ACTGCATTCT AGTTGTGGTT TGTCCAAACT CATCAATGTA TCTTATCATG TCTGTATACC
4441  GTCGACCTCT AGCTAGAGCT TGGCGTAATC ATGGTCATAG CTGTTTCCTG TGTGAAATTG
4501  TTATCCGCTC ACAATTCCAC ACAACATACG AGCCGGAAGC ATAAAGTGTA AAGCCTGGGG
4561  TGCCTAATGA GTGAGCTAAC TCACATTAAT TGCGTTGCGC TCACTGCCCG CTTTCCAGTC
4621  GGGAAACCTG TCGTGCCAGC TGCATTAATG AATCGGCCAA CGCGCGGGGA GAGGCGGTTT
4681  GCGTATTGGG CGCTCTTCCG CTTCCTCGCT CACTGACTCG CTGCGCTCGG TCGTTCGGCT
4741  GCGGCGAGCG GTATCAGCTC ACTCAAAGGC GGTAATACGG TTATCCACAG AATCAGGGGA
4801  TAACGCAGGA AAGAACATGT GAGCAAAAGG CCAGCAAAAG GCCAGGAACC GTAAAAAGGC
                                                    pUC origin
4861  CGCGTTGCTG GCGTTTTTCC ATAGGCTCCG CCCCCCTGAC GAGCATCACA AAAATCGACG
                        pUC origin
4921  CTCAAGTCAG AGGTGGCGAA ACCCGACAGG ACTATAAAGA TACCAGGCGT TTCCCCCTGG
                        pUC origin
4981  AAGCTCCCTC GTGCGCTCTC CTGTTCCGAC CCTGCCGCTT ACCGGATACC TGTCCGCCTT
                        pUC origin
5041  TCTCCCTTCG GGAAGCGTGG CGCTTTCTCA TAGCTCACGC TGTAGGTATC TCAGTTCGGT
                        pUC origin
5101  GTAGGTCGTT CGCTCCAAGC TGGGCTGTGT GCACGAACCC CCCGTTCAGC CCGACCGCTG
                        pUC origin
5161  CGCCTTATCC GGTAACTATC GTCTTGAGTC CAACCCGGTA AGACACGACT TATCGCCACT
                        pUC origin
5221  GGCAGCAGCC ACTGGTAACA GGATTAGCAG AGCGAGGTAT GTAGGCGGTG CTACAGAGTT
                        pUC origin
5281  CTTGAAGTGG TGGCCTAACT ACGGCTACAC TAGAAGAACA GTATTTGGTA TCTGCGCTCT
                        pUC origin
5341  GCTGAAGCCA GTTACCTTCG GAAAAAGAGT TGGTAGCTCT TGATCCGGCA AACAAACCAC
                        pUC origin
5401  CGCTGGTAGC GGTGGTTTTT TTGTTTGCAA GCAGCAGATT ACGCGCAGAA AAAAAGGATC
                        pUC origin
```

Fig. 17-5

```
5461  TCAAGAAGAT CCTTTGATCT TTTCTACGGG GTCTGACGCT CAGTGGAACG AAAACTCACG
                 pUC origin
5521  TTAAGGGATT TTGGTCATGA GATTATCAAA AAGGATCTTC ACCTAGATCC TTTTAAATTA
5581  AAAATGAAGT TTTAAATCAA TCTAAAGTAT ATATGAGTAA ACTTGGTCTG ACAGTTACCA
                                                                 Amp(R)
5641  ATGCTTAATC AGTGAGGCAC CTATCTCAGC GATCTGTCTA TTTCGTTCAT CCATAGTTGC
                                        Amp(R)
5701  CTGACTCCCC GTCGTGTAGA TAACTACGAT ACGGGAGGGC TTACCATCTG GCCCCAGTGC
                                        Amp(R)
5761  TGCAATGATA CCGCGAGACC CACGCTCACC GGCTCCAGAT TTATCAGCAA TAAACCAGCC
                                        Amp(R)
5821  AGCCGGAAGG GCCGAGCGCA GAAGTGGTCC TGCAACTTTA TCCGCCTCCA TCCAGTCTAT
                                        Amp(R)
5881  TAATTGTTGC CGGGAAGCTA GAGTAAGTAG TTCGCCAGTT AATAGTTTGC GCAACGTTGT
                                        Amp(R)
5941  TGCCATTGCT ACAGGCATCG TGGTGTCACG CTCGTCGTTT GGTATGGCTT CATTCAGCTC
                                        Amp(R)
6001  CGGTTCCCAA CGATCAAGGC GAGTTACATG ATCCCCCATG TTGTGCAAAA AAGCGGTTAG
                                        Amp(R)
6061  CTCCTTCGGT CCTCCGATCG TTGTCAGAAG TAAGTTGGCC GCAGTGTTAT CACTCATGGT
                                        Amp(R)
6121  TATGGCAGCA CTGCATAATT CTCTTACTGT CATGCCATCC GTAAGATGCT TTTCTGTGAC
                                        Amp(R)
6181  TGGTGAGTAC TCAACCAAGT CATTCTGAGA ATAGTGTATG CGGCGACCGA GTTGCTCTTG
                                        Amp(R)
6241  CCCGGCGTCA ATACGGGATA ATACCGCGCC ACATAGCAGA ACTTTAAAAG TGCTCATCAT
                                        Amp(R)
6301  TGGAAAACGT TCTTCGGGGC GAAAACTCTC AAGGATCTTA CCGCTGTTGA GATCCAGTTC
                                        Amp(R)
6361  GATGTAACCC ACTCGTGCAC CCAACTGATC TTCAGCATCT TTTACTTTCA CCAGCGTTTC
                                        Amp(R)
6421  TGGGTGAGCA AAAACAGGAA GGCAAAATGC CGCAAAAAAG GGAATAAGGG CGACACGGAA
                                        Amp(R)
6481  ATGTTGAATA CTCATACTCT TCCTTTTTCA ATATTATTGA AGCATTTATC AGGGTTATTG
                                                              bla promoter
              Amp(R)
6541  TCTCATGAGC GGATACATAT TTGAATGTAT TTAGAAAAAT AAACAAATAG GGGTTCCGCG
                                        bla promoter
6601  CACATTTCCC CGAAAAGTGC CACCTGACGT C
```

Fig. 21-1

```
   1  GACGGATCGG GAGATCTCCC GATCCCCTAT GGTGCACTCT CAGTACAATC TGCTCTGATG
  61  CCGCATAGTT AAGCCAGTAT CTGCTCCCTG CTTGTGTGTT GGAGGTCGCT GAGTAGTGCG
 121  CGAGCAAAAT TTAAGCTACA ACAAGGCAAG GCTTGACCGA CAATTGCATG AAGAATCTGC
                                                         CMV promoter
 181  TTAGGGTTAG GCGTTTTGCG CTGCTTCGCG ATGTACGGGC CAGATATACG CGTTGACATT
                                        CMV promoter
 241  GATTATTGAC TAGTTATTAA TAGTAATCAA TTACGGGTC ATTAGTTCAT AGCCCATATA
                                        CMV promoter
 301  TGGAGTTCCG CGTTACATAA CTTACGGTAA ATGGCCCGCC TGGCTGACCG CCCAACGACC
                                        CMV promoter
 361  CCCGCCCATT GACGTCAATA ATGACGTATG TTCCCATAGT AACGCCAATA GGGACTTTCC
                                        CMV promoter
 421  ATTGACGTCA ATGGGTGGAC TATTTACGGT AAACTGCCCA CTTGGCAGTA CATCAAGTGT
                                        CMV promoter
 481  ATCATATGCC AAGTACGCCC CCTATTGACG TCAATGACGG TAAATGGCCC GCCTGGCATT
                                        CMV promoter
 541  ATGCCCAGTA CATGACCTTA TGGGACTTTC CTACTTGGCA GTACATCTAC GTATTAGTCA
                                        CMV promoter
 601  TCGCTATTAC CATGGTGATG CGGTTTTGGC AGTACATCAA TGGGCGTGGA TAGCGGTTTG
                                        CMV promoter
 661  ACTCACGGGG ATTTCCAAGT CTCCACCCCA TTGACGTCAA TGGGAGTTTG TTTTGGCACC
                                                                  CMV forward primer
                                        CMV promoter
 721  AAAATCAACG GGACTTTCCA AAATGTCGTA ACAACTCCGC CCCATTGACG CAAATGGGCG
      CMV forward prime
                                        CMV promoter
 781  GTAGGCGTGT ACGGTGGGAG GTCTATATAA GCAGAGCTCT CTGGCTAACT AGAGAACCCA
                                                      T7 primer
                     CMV promoter
                                                      T7 promoter
 841  CTGCTTACTG GCTTATCGAA ATTAATACGA CTCACTATAG GGAGACCCAA GCTGGCTAGT
              Kpnl           BamHI                          Kir6.1
      HindIII                          BstXI
  +2                                               M  L  A  R  K  S  I  I  P  E
 901  TAAGCTTGGT ACCGAGCTCG GATCCGCCAC CATGCTGGCC AGGAAGAGCA TCATCCCGGA
                                        Kir6.1
  +2  E  E  Y  V  L  A  R  I  A  A  E  N  L  R  K  P  R  I  R  D  R
 961  GGAGTATGTG CTGGCCCGCA TCGCGGCGGA GAACCTGCGC AAACCGCGCA TCCGCGACCG
                                        Kir6.1
  +2  R  L  P  K  A  R  F  I  A  K  S  G  A  C  N  L  A  H  K  N  I
1021  CCTCCCCAAA GCCCGCTTCA TCGCCAAGAG CGGAGCCTGC AACCTGGCTC ACAAGAACAT
                                        Kir6.1
  +2  I  R  E  Q  G  R  F  L  Q  D  I  F  T  T  L  V  D  L  K  W  R
1081  CCGAGAGCAA GGTCGCTTCC TGCAGGACAT CTTCACCACC TTGGTAGACC TGAAGTGGCG
                                        Kir6.1
  +2  R  H  T  L  V  I  F  T  M  S  F  L  C  S  W  L  L  F  A  I  M
1141  TCACACGCTG GTCATCTTCA CCATGTCCTT CCTCTGCAGC TGGCTGCTCT TCGCTATCAT
                                        Kir6.1
  +2  M  W  W  L  V  A  F  A  H  G  D  I  Y  A  Y  M  E  K  G  I  T
1201  GTGGTGGCTG GTGGCCTTCG CCCACGGGGA CATCTATGCT TACATGGAGA AAGGCATCAC
```

Fig. 21-2

```
                                      Kir6.1
     +2 ·T E  K   S    G  L  E   S   A  V   C   V  T   N   V  R   S   F  T   S  A·
   1261  GGAGAAGAGT  GGCCTGGAGT  CTGCCGTCTG  TGTGACCAAT  GTCAGGTCAT  TCACTTCTGC
                                      Kir6.1
     +2 ·A F  L   F   S  I  E   V   Q  V   T   I  G   F   G  G   R   M  M   I  E·
   1321  GTTTCTCTTC  TCCATCGAGG  TTCAAGTGAC  CATTGGGTTT  GGAGGGAGAA  TGATGACTGA
                                      Kir6.1
     +2 ·E E  C   P   L  A  I   T   V  L   I   L  Q   N   I  V   G   L  I   I  N·
   1381  GGAGTGCCCT  CTGGCCATCA  CGGTTTTGAT  TCTGCAGAAC  ATTGTGGGTC  TGATCATCAA
                                      Kir6.1
     +2 ·N A  V   M   L  G  C   I   F  M   K   T  A   Q   H  R   R   A  E   T·
   1441  CGCGGTCATG  TTGGGCTGCA  TCTTCATGAA  GACGGCCCAG  GCCCACAGAA  GGGCAGAGAC
                                      Kir6.1
     +2 ·T L  I   F   S  R  H   A   V  I   A   V  R   N   G  K   L   C  F   M  F·
   1501  GCTGATTTTC  AGCCGCCATG  CTGTAATTGC  GGTCCGTAAT  GGCAAGCTGT  GCTTCATGTT
                                      Kir6.1
     +2 ·F R  V   G   D  L  R   K   S  M   I   I  S   A   V  R   I   Q  V   V·
   1561  CCGGGTGGGT  GACCTGAGGA  AAAGCATGAT  CATTAGCGCC  TCGGTGCGCA  TCCAGGTGGT
                                      Kir6.1
     +2 ·V K  K   T   T  T  P   E   G  E   V   V  P   I   H  Q   Q   D  I   P  V·
   1621  CAAGAAAACC  ACGACGCCAG  AAGGAGAGGT  GGTGCCTATT  CACCAGCAGG  ACATCCCTGT
                                      Kir6.1
     +2 ·V D  N   P   I  E  S   N   N  I   F   L  V   A   P  L   I   I  C   H  V·
   1681  GGATAATCCC  ATCGAGAGCA  ATAACATCTT  CCTAGTGGCC  CCTTTGATCA  TCTGCCATGT
                                      Kir6.1
     +2 ·V I  D   K   R  S  P   L   Y  D   I   S  A   T   D  L   V   N  Q   D  L·
   1741  GATTGATAAG  CGTAGCCCCC  TGTACGATAT  CTCAGCCACT  GACCTTGTCA  ACCAAGACCT
                                      Kir6.1
     +2 ·L E  V   I   V  I  L   E   G  V   V   E  T   T   G  I   T   T  Q   A  R·
   1801  GGAGGTCATA  GTGATTCTCG  AGGGCGTGGT  GGAAACCACG  GGCATCACCA  CGCAAGCGCG
                                      Kir6.1
     +2 ·R T  S   Y   I  A  E   E   I  Q   W   G  H   R   F  V   S   I  V   T  E·
   1861  GACCTCCTAC  ATTGCAGAGG  AGATCCAGTG  GGGACACCGC  TTCGTGTCGA  TTGTGACTGA
                                      Kir6.1
     +2 ·E E  E   G   V  Y  S   V   D  Y   S   K  F   G   N  T   V   R  V   A  A·
   1921  GGAGGAGGGA  GTGTACTCTG  TGGACTATTC  TAAATTTGGT  AATACTGTGA  GAGTGGCGGC
                                      Kir6.1
     +2 ·A P  R   C   S  A  R   E   L  D   E   K  P   S   I  L   I   Q  T   L  Q·
   1981  GCCAAGATGC  AGTGCCCGGG  AGCTGGACGA  GAAACCTTCC  ATCTTGATTC  AGACCCTCCA
                                      Kir6.1
     +2 ·Q K  S   E   L  S  H   Q   N  S   L   R  K   R   N  S   M   R  N   N·
   2041  AAAGAGTGAA  CTGTCGCACC  AGAATTCTCT  GAGGAAGCGC  AACTCTATGA  GAAGAAACAA
                                      Kir6.1
     +2 ·N S  M   R   R  S  N   S   I  R   R   N  N   S   L  M   V   P  K   V·
   2101  CTCCATGAGG  AGGAGCAACT  CCATCCGGAG  GAATAACTCT  TCCCTCATGG  TGCCCAAGGT
                                 Kir6.1                               NotI
     +2 ·V Q  F   M   T  P  E   G   N  Q   C   P  S   E   S  *
   2161  GCAATTCATG  ACTCCAGAAG  GAAACCAGTG  CCCATCAGAA  TCATGATAGC  GGCCGCTCGA
                        ApaI
            XbaI            SfuI                                            AgeI
   2221  GTCTAGAGGG  CCCTTCGAAC  AAAAACTCAT  CTCAGAAGAG  GATCTGAATA  TGCATACCGG
```

Fig. 21-3

```
                Agel            Pmel              BGH pA
2281   TCATCATCAC CATCACCATT GAGTTTAAAC CCGCTGATCA GCCTCGACTG TGCCTTCTAG
                                                         BGH reverse primer
                                    BGH pA
2341   TTGCCAGCCA TCTGTTGTTT GCCCCTCCCC CGTGCCTTCC TTGACCCTGG AAGGTGCCAC
                                    BGH pA
2401   TCCCACTGTC CTTTCCTAAT AAAATGAGGA AATTGCATCG CATTGTCTGA GTAGGTGTCA
                                    BGH pA
2461   TTCTATTCTG GGGGGTGGGG TGGGGCAGGA CAGCAAGGGG GAGGATTGGG AAGACAATAG
              BGH pA
2521   CAGGCATGCT GGGGATGCGG TGGGCTCTAT GGCTTCTGAG GCGGAAAGAA CCAGCTGGGG
                                                    f1 origin
2581   CTCTAGGGGG TATCCCCACG CGCCCTGTAG CGGCGCATTA AGCGCGGCGG GTGTGGTGGT
                                    f1 origin
2641   TACGCGCAGC GTGACCGCTA CACTTGCCAG CGCCCTAGCG CCCGCTCCTT TCGCTTTCTT
                                    f1 origin
2701   CCCTTCCTTT CTCGCCACGT TCGCCGGCTT TCCCCGTCAA GCTCTAAATC GGGGGCTCCC
                                    f1 origin
2761   TTTAGGGTTC CGATTTAGTG CTTTACGGCA CCTCGACCCC AAAAAACTTG ATTAGGGTGA
                                    f1 origin
2821   TGGTTCACGT AGTGGGCCAT CGCCCTGATA GACGGTTTTT CGCCCTTTGA CGTTGGAGTC
                                    f1 origin
2881   CACGTTCTTT AATAGTGGAC TCTTGTTCCA AACTGGAACA ACACTCAACC CTATCTCGGG
                                    f1 origin
2941   CTATTCTTTT GATTTATAAG GGATTTTGCC GATTTCGGCC TATTGGTTAA AAAATGAGCT
                       f1 origin
3001   GATTTAACAA AAATTTAACG CGAATTAATT CTGTGGAATG TGTGTCAGTT AGGGTGTGGA
                                    SV40 early promoter
3061   AAGTCCCCAG GCTCCCCAGC AGGCAGAAGT ATGCAAAGCA TGCATCTCAA TTAGTCAGCA
                                    SV40 early promoter
3121   ACCAGGTGTG GAAAGTCCCC AGGCTCCCCA GCAGGCAGAA GTATGCAAAG CATGCATCTC
                                    SV40 early promoter
3181   AATTAGTCAG CAACCATAGT CCCGCCCCTA ACTCCGCCCA TCCCGCCCCT AACTCCGCCC
                                    SV40 early promoter
3241   AGTTCCGCCC ATTCTCCGCC CCATGGCTGA CTAATTTTTT TTATTTATGC AGAGGCCGAG
                                    SV40 early promoter
3301   GCCGCCTCTG CCTCTGAGCT ATTCCAGAAG TAGTGAGGAG GCTTTTTTGG AGGCCTAGGC
                       SV40 early promoter
3361   TTTTGCAAAA AGCTCCCGGG AGCTTGTATA TCCATTTTCG GATCTGATCA AGAGACAGGA
                                         Neo(R)
3421   TGAGGATCGT TTCGCATGAT TGAACAAGAT GGATTGCACG CAGGTTCTCC GGCCGCTTGG
                                         Neo(R)
3481   GTGGAGAGGC TATTCGGCTA TGACTGGGCA CAACAGACAA TCGGCTGCTC TGATGCCGCC
                                         Neo(R)
3541   GTGTTCCGGC TGTCAGCGCA GGGGCGCCCG GTTCTTTTTG TCAAGACCGA CCTGTCCGGT
                                         Neo(R)
3601   GCCCTGAATG AACTGCAGGA CGAGGCAGCG CGGCTATCGT GGCTGGCCAC GACGGGCGTT
                                         Neo(R)
3661   CCTTGCGCAG CTGTGCTCGA CGTTGTCACT GAAGCGGGAA GGGACTGGCT GCTATTGGGC
```

Fig. 21-4

```
                              Neo(R)
3721  GAAGTGCCGG GGCAGGATCT CCTGTCATCT CACCTTGCTC CTGCCGAGAA AGTATCCATC
                              Neo(R)
3781  ATGGCTGATG CAATGCGGCG GCTGCATACG CTTGATCCGG CTACCTGCCC ATTCGACCAC
                              Neo(R)
3841  CAAGCGAAAC ATCGCATCGA GCGAGCACGT ACTCGGATGG AAGCCGGTCT TGTCGATCAG
                              Neo(R)
3901  GATGATCTGG ACGAAGAGCA TCAGGGGCTC GCGCCAGCCG AACTGTTCGC CAGGCTCAAG
                              Neo(R)
3961  GCGCGCATGC CCGACGGCGA GGATCTCGTC GTGACCCATG GCGATGCCTG CTTGCCGAAT
                              Neo(R)
4021  ATCATGGTGG AAAATGGCCG CTTTTCTGGA TTCATCGACT GTGGCCGGCT GGGTGTGGCG
                              Neo(R)
4081  GACCGCTATC AGGACATAGC GTTGGCTACC CGTGATATTG CTGAAGAGCT TGGCGGCGAA
                              Neo(R)
4141  TGGGCTGACC GCTTCCTCGT GCTTTACGGT ATCGCCGCTC CCGATTCGCA GCGCATCGCC
                              Neo(R)
4201  TTCTATCGCC TTCTTGACGA GTTCTTCTGA GCGGGACTCT GGGGTTCGCG AAATGACCGA
4261  CCAAGCGACG CCCAACCTGC CATCACGAGA TTTCGATTCC ACCGCCGCCT TCTATGAAAG
4321  GTTGGGCTTC GGAATCGTTT TCCGGGACGC CGGCTGGATG ATCCTCCAGC GCGGGGATCT
                                                    SV40 pA
4381  CATGCTGGAG TTCTTCGCCC ACCCCAACTT GTTTATTGCA GCTTATAATG GTTACAAATA
                    SV40 pA
4441  AAGCAATAGC ATCACAAATT TCACAAATAA AGCATTTTTT TCACTGCATT CTAGTTGTGG
          SV40 pA
4501  TTTGTCCAAA CTCATCAATG TATCTTATCA TGTCTGTATA CCGTCGACCT CTAGCTAGAG
4561  CTTGGCGTAA TCATGGTCAT AGCTGTTTCC TGTGTGAAAT TGTTATCCGC TCACAATTCC
4621  ACACAACATA CGAGCCGGAA GCATAAAGTG TAAAGCCTGG GGTGCCTAAT GAGTGAGCTA
4681  ACTCACATTA ATTGCGTTGC GCTCACTGCC CGCTTTCCAG TCGGGAAACC TGTCGTGCCA
4741  GCTGCATTAA TGAATCGGCC AACGCGCGGG GAGAGGCGGT TTGCGTATTG GGCGCTCTTC
4801  CGCTTCCTCG CTCACTGACT CGCTGCGCTC GGTCGTTCGG CTGCGGCGAG CGGTATCAGC
4861  TCACTCAAAG GCGGTAATAC GGTTATCCAC AGAATCAGGG GATAACGCAG GAAAGAACAT
                                                              pUC origin
4921  GTGAGCAAAA GGCCAGCAAA AGGCCAGGAA CCGTAAAAAG GCCGCGTTGC TGGCGTTTTT
                              pUC origin
4981  CCATAGGCTC CGCCCCCCTG ACGAGCATCA CAAAAATCGA CGCTCAAGTC AGAGGTGGCG
                              pUC origin
5041  AAACCCGACA GGACTATAAA GATACCAGGC GTTTCCCCCT GGAAGCTCCC TCGTGCGCTC
                              pUC origin
5101  TCCTGTTCCG ACCCTGCCGC TTACCGGATA CCTGTCCGCC TTTCTCCCTT CGGGAAGCGT
                              pUC origin
5161  GGCGCTTTCT CATAGCTCAC GCTGTAGGTA TCTCAGTTCG GTGTAGGTCG TTCGCTCCAA
                              pUC origin
5221  GCTGGGCTGT GTGCACGAAC CCCCCGTTCA GCCCGACCGC TGCGCCTTAT CCGGTAACTA
                              pUC origin
5281  TCGTCTTGAG TCCAACCCGG TAAGACACGA CTTATCGCCA CTGGCAGCAG CCACTGGTAA
                              pUC origin
5341  CAGGATTAGC AGAGCGAGGT ATGTAGGCGG TGCTACAGAG TTCTTGAAGT GGTGGCCTAA
                              pUC origin
```

Fig. 21-5

```
5401  CTACGGCTAC ACTAGAAGAA CAGTATTTGG TATCTGCGCT CTGCTGAAGC CAGTTACCTT
                                       pUC origin
5461  CGGAAAAAGA GTTGGTAGCT CTTGATCCGG CAAACAAACC ACCGCTGGTA GCGGTGGTTT
                                       pUC origin
5521  TTTTGTTTGC AAGCAGCAGA TTACGCGCAG AAAAAAAGGA TCTCAAGAAG ATCCTTTGAT
                                       pUC origin
5581  CTTTTCTACG GGGTCTGACG CTCAGTGGAA CGAAAACTCA CGTTAAGGGA TTTTGGTCAT
      pUC origin
5641  GAGATTATCA AAAAGGATCT TCACCTAGAT CCTTTTAAAT TAAAAATGAA GTTTTAAATC
5701  AATCTAAAGT ATATATGAGT AAACTTGGTC TGACAGTTAC CAATGCTTAA TCAGTGAGGC
                                                         Amp(R)
5761  ACCTATCTCA GCGATCTGTC TATTTCGTTC ATCCATAGTT GCCTGACTCC CCGTCGTGTA
                                       Amp(R)
5821  GATAACTACG ATACGGGAGG GCTTACCATC TGGCCCCAGT GCTGCAATGA TACCGCGAGA
                                       Amp(R)
5881  CCCACGCTCA CCGGCTCCAG ATTTATCAGC AATAAACCAG CCAGCCGGAA GGGCCGAGCG
                                       Amp(R)
5941  CAGAAGTGGT CCTGCAACTT TATCCGCCTC CATCCAGTCT ATTAATTGTT GCCGGGAAGC
                                       Amp(R)
6001  TAGAGTAAGT AGTTCGCCAG TTAATAGTTT GCGCAACGTT GTTGCCATTG CTACAGGCAT
                                       Amp(R)
6061  CGTGGTGTCA CGCTCGTCGT TTGGTATGGC TTCATTCAGC TCCGGTTCCC AACGATCAAG
                                       Amp(R)
6121  GCGAGTTACA TGATCCCCCA TGTTGTGCAA AAAAGCGGTT AGCTCCTTCG GTCCTCCGAT
                                       Amp(R)
6181  CGTTGTCAGA AGTAAGTTGG CCGCAGTGTT ATCACTCATG GTTATGGCAG CACTGCATAA
                                       Amp(R)
6241  TTCTCTTACT GTCATGCCAT CCGTAAGATG CTTTTCTGTG ACTGGTGAGT ACTCAACCAA
                                       Amp(R)
6301  GTCATTCTGA GAATAGTGTA TGCGGCGACC GAGTTGCTCT TGCCCGGCGT CAATACGGGA
                                       Amp(R)
6361  TAATACCGCG CCACATAGCA GAACTTTAAA AGTGCTCATC ATTGGAAAAC GTTCTTCGGG
                                       Amp(R)
6421  GCGAAAACTC TCAAGGATCT TACCGCTGTT GAGATCCAGT TCGATGTAAC CCACTCGTGC
                                       Amp(R)
6481  ACCCAACTGA TCTTCAGCAT CTTTTACTTT CACCAGCGTT TCTGGGTGAG CAAAAACAGG
                                       Amp(R)
6541  AAGGCAAAAT GCCGCAAAAA AGGGAATAAG GGCGACACGG AAATGTTGAA TACTCATACT
                                                                    bla promoter
                                       Amp(R)
6601  CTTCCTTTTT CAATATTATT GAAGCATTTA TCAGGGTTAT TGTCTCATGA GCGGATACAT
                                       bla promoter
6661  ATTTGAATGT ATTTAGAAAA ATAAACAAAT AGGGGTTCCG CGCACATTTC CCCGAAAAGT
                                       bla promoter
6721  GCCACCTGAC GTC
```

ADAMANTYLMETHYLAMINE DERIVATIVE AND USE THEREOF AS PHARMACEUTICAL

CROSS-REFERENCE TO RELATED APPLICATIONS

This application is the U.S. National Stage of PCT/JP2018/029018, filed Aug. 2, 2018, which claims priority to JP 2017-150290, filed Aug. 2, 2017.

The instant application contains a Sequence Listing which has been submitted in ASCII format via EFS-WEB and is hereby incorporated by reference in its entirety. Said ASCII copy, created on Jan. 28, 2020, is named sequence.txt and is 17,939 bytes.

TECHNICAL FIELD

The present invention relates to an adamantylmethylamine derivative and a pharmaceutically acceptable salt thereof. The present invention further relates to a pharmaceutical composition comprising said compound and a method of treating or preventing a disease by using said compound.

BACKGROUND ART

ATP-sensitive $K^+$ channels ($K_{ATP}$ channels) are inwardly rectifying $K^+$ channels that couple intracellular metabolism with cell-membrane excitability, and are known to have a hetero-octamer structure constituted of sulfonyl urea receptors (SURs) belonging to the ABC protein family and two-membrane-spanning subunits Kir6.1 or Kir6.2. The activity of the KA channels is controlled by various types of $K^+$ channel openers, inhibitors or intracellular nucleotides. All of these drugs react with SUR subunits as their sites of action. It has been reported that the reactivity of these drugs differ depending on the subtype of SUR (NPL 1).

Some of adamantane derivatives having a cage type structure are used as medical drugs. Amantadine is used as an antiviral drug and a therapeutic agent for Parkinson's disease. Memantine hydrochloride has been approved as a therapeutic agent for moderate/severe Alzheimer's dementia in Japan. Memantine is reported to be a noncompetitive NMDA-receptor inhibitor having a mechanism of action which prevents neuronal cell death due to excessive glutamic acid release caused by ischemia (NPL 2).

There have been some reports on adamantane derivatives having pharmaceutical activity (PTLs 1 to 3).

CITATION LIST

Patent Literature

PTL 1: National Publication of International Patent Application No. 2011-529057
PTL 2: Japanese Patent Laid-Open No. 2010-522203
PTL 3: National Publication of International Patent Application No. 2009-508956

Non Patent Literature

NPL 1: *Folia Pharmacologica Japonica*, 126, 311-316 (2005)
NPL 2: *Folia Pharmacologica Japonica*, 124, 145-151 (2004)

SUMMARY OF INVENTION

Technical Problem

Therapeutic and prophylactic methods sufficiently effective against cognitive diseases or disorders such as Alzheimer's disease are yet to be established, and thus, development of a novel therapeutic and prophylactic agent different in mechanism of action from existing medicinal agents has been desired. Further, development of a novel therapeutic and prophylactic agent for diabetes has been strongly desired.

In one aspect, an object of the present invention is to provide a pharmaceutical composition for use in treating or preventing a cognitive disease or disorder. Another object of the present invention is to provide a method of treating or preventing a cognitive disease or disorder by using a particular adamantane derivative.

In one aspect, an object of the present invention is to provide a pharmaceutical composition for use in treating or preventing diabetes or a diabetic complication. Another object of the present invention is to provide a method of treating or preventing diabetes or a diabetic complication by using a particular adamantane derivative.

ATP-sensitive $K^+$ channels ($K_{ATP}$ channels) contain subunits Kir6.1 or Kir6.2, and are known to serve as a site of action of anti-diabetic and other drugs.

In one aspect, an object of the present invention is to provide an inhibitor of Kir6.1 or Kir6.2 channels, which are $K_{ATP}$ channels. Another object of the present invention is to provide a pharmaceutical composition for use in treating or preventing a disease in which Kir6.1 or Kir6.2 $K_{ATP}$ channels are involved. Another object of the present invention is to provide a method of treating or preventing a disease in which Kir6.1 or Kir6.2 $K_{ATP}$ channels are involved, by using a particular adamantylmethylamine derivative.

Solution to Problem

The present inventors conducted intensive studies with a view to attaining the aforementioned objects. As a result, the inventors found that adamantylmethylamine derivatives have a Kir6.2 channel inhibitory activity, a Kir6.1 channel inhibitory activity, a therapeutic effect for cognitive diseases or disorders, and a hypoglycemic effect; and thus, the inventors has completed the present invention. The present disclosure includes the invention as set forth in [1] to [17] below.

[1] A compound represented by Formula (I):

[Chemical Formula 1]

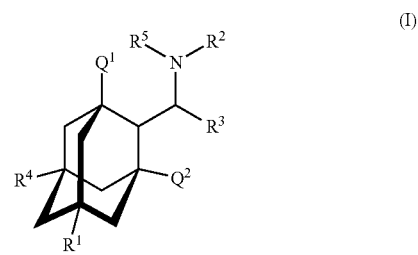

wherein $Q^1$, $Q^2$, $R^1$, and $R^4$ are each independently selected from a hydrogen atom, a halogen atom, $C_{1-6}$ alkyl optionally substituted with one or more halogen atoms, amino, $C_{6-10}$ aryl optionally substituted with one or more substituents selected from $X^1$, carboxy, $-OR^7$, and $-SR^8$;

$R^2$ represents a hydrogen atom, phenylsulfonyl optionally substituted with one or more substituents selected from $X^1$, ($C_{1-6}$ alkyl)sulfonyl optionally substituted with one or more halogen atoms, or $-COYR^6$;

Y represents a direct bond, O, or $NR^9$;

$R^3$ represents $C_{3-8}$ cycloalkyl optionally substituted with one or more substituents selected from $X^1$, $C_{6-10}$ aryl optionally substituted with one or more substituents selected from $X^1$, phenylaminocarboyl optionally substituted with one or more substituents selected from $X^1$, 5- to 10-membered monocyclic or bicyclic heteroaryl optionally substituted with one or more substituents selected from $X^1$, 5- to 10-membered monocyclic or bicyclic non-aromatic heterocyclyl optionally substituted with one or more substituents selected from $X^1$, or -$Q^3$-$R^{13}$;

$Q^3$ represents $C_{1-3}$ alkylene, or $C_{2-3}$ alkenylene;

$R^{13}$ represents $C_{6-10}$ aryl optionally substituted with one or more substituents selected from $X^1$;

$R^5$ represents a hydrogen atom, or $C_{1-6}$ alkyl optionally substituted with one or more halogen atoms;

$R^6$ represents $C_{1-6}$ alkyl, $C_{6-10}$ aryl optionally substituted with one or more substituents selected from $X^1$, or 5- or 6-membered heteroaryl optionally substituted with one or more substituents selected from $X^1$, wherein the alkyl is optionally substituted with one or more halogen atoms, and/or is optionally substituted with one substituent selected from $X^2$;

$R^7$ represents a hydrogen atom, $C_{1-6}$ alkyl optionally substituted with one or more halogen atoms, $C_{1-6}$ alkoxy$C_{1-6}$ alkyl, ($C_{1-6}$alkyl)carbonyl optionally substituted with one or more halogen atoms, or $C_{6-10}$ aryl optionally substituted with one or more substituents selected from $X^1$;

$R^8$ represents a hydrogen atom, $C_{1-6}$ alkyl optionally substituted with one or more halogen atoms, or $C_{6-10}$ aryl optionally substituted with one or more substituents selected from $X^1$;

$R^9$ represents a hydrogen atom, or $C_{1-6}$ alkyl optionally substituted with one or more halogen atoms;

each $X^1$ is independently selected from $C_{1-6}$ alkyl, a halogen atom, $C_{1-6}$ alkoxy, hydroxy, nitro, and cyano;

$X^2$ is selected from $C_{1-6}$ alkoxy, $C_{2-6}$ alkenyloxy, $C_{2-6}$ alkynyloxy, and —$NR^{11}R^{12}$;

$R^{11}$ represents a hydrogen atom, $C_{1-6}$ alkyl, ($C_{1-6}$ alkoxy)carbonyl, or [($C_{6-10}$ aryl)$C_{1-3}$ alkoxy]carbonyl whose aryl moiety is optionally substituted with one or more substituents selected from $X^1$, wherein the alkyl or alkoxy moiety is optionally substituted with one or more halogen atoms;

$R^{12}$ represents a hydrogen atom, or $C_{1-6}$ alkyl optionally substituted with one or more halogen atoms;

wherein the methylene present in the adamantyl group is optionally substituted with one or more groups independently selected from $C_{1-6}$ alkyl, $C_{1-6}$ alkoxy, and hydroxy, wherein the alkyl or alkoxy is optionally substituted with one or more halogen atoms, an enantiomer thereof, a diastereomer thereof, or a pharmaceutically acceptable salt thereof.

[2] The compound, enantiomer thereof, diastereomer thereof, or pharmaceutically acceptable salt thereof as set forth in [1], wherein the compound is represented by Formula (I):

[Chemical Formula 2]

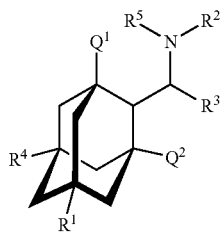

(I)

wherein $Q^1$ represents a hydrogen atom, a halogen atom, $C_{1-6}$ alkyl optionally substituted with one or more halogen atoms, amino, or —$OR^{10}$;

$R^{10}$ represents a hydrogen atom, $C_{1-6}$ alkyl optionally substituted with one or more halogen atoms, or ($C_{1-6}$ alkyl)carbonyl optionally substituted with one or more halogen atoms;

$Q^2$ represents a hydrogen atom, $C_{1-6}$ alkyl, or $C_{1-6}$ alkoxy, wherein the alkyl or alkoxy is optionally substituted with one or more halogen atoms;

$R^1$ represents a hydrogen atom, $C_{1-6}$ alkyl, or $C_{1-6}$ alkoxy, wherein the alkyl or alkoxy is optionally substituted with one or more halogen atoms;

$R^2$ represents a hydrogen atom, phenylsulfonyl optionally substituted with one or more substituents selected from $X^1$, ($C_{1-6}$ alkyl)sulfonyl optionally substituted with one or more halogen atoms, or —$COYR^6$;

Y represents a direct bond, 0, or $NR^9$;

$R^3$ represents $C_{3-8}$ cycloalkyl, $C_6$-10 aryl optionally substituted with one or more substituents selected from $X^1$, phenylaminocarboyl optionally substituted with one or more substituents selected from $X^1$, 5- to 10-membered monocyclic or bicyclic heteroaryl optionally substituted with one or more substituents selected from $X^1$, or -$Q^3$-$R^{13}$;

$Q^3$ represents $C_{1-3}$ alkylene, or $C_{2-3}$ alkenylene;

$R^{13}$ represents $C_{6-10}$ aryl optionally substituted with one or more substituents selected from $X^1$;

$R^4$ represents a hydrogen atom, a halogen atom, $C_{1-6}$ alkyl optionally substituted with one or more halogen atoms, phenyl optionally substituted with one or more substituents selected from $X^3$, carboxy, —$OR^7$, or —$SR^8$;

$R^5$ represents a hydrogen atom or $C_{1-6}$ alkyl;

$R^6$ represents $C_{1-6}$ alkyl, phenyl optionally substituted with one or more substituents selected from $X^1$, or 5- or 6-membered heteroaryl optionally substituted with one or more substituents selected from $X^1$, wherein the alkyl is optionally substituted with one or more halogen atoms, and/or is optionally substituted with one substituent selected from $X^2$;

$R^7$ represents a hydrogen atom, $C_{1-6}$ alkyl optionally substituted with one or more halogen atoms, $C_{1-6}$ alkoxy$C_{1-6}$ alkyl, or ($C_{1-6}$ alkyl)carbonyl optionally substituted with one or more halogen atoms;

$R^8$ represents $C_{1-6}$ alkyl, or phenyl optionally substituted with one or more substituents selected from $X^1$;

$R^9$ represents a hydrogen atom or $C_{1-6}$ alkyl;

each $X^1$ is independently selected from $C_{1-6}$ alkyl, a halogen atom, $C_{1-6}$ alkoxy, nitro, and cyano;

$X^2$ is selected from $C_{1-6}$ alkoxy, $C_{2-6}$ alkenyloxy, $C_{2-6}$ alkynyloxy, and —$NR^{11}R^{12}$;

each $X^3$ is independently selected from $C_{1-6}$ alkyl, a halogen atom, $C_{1-6}$ alkoxy, hydroxy, nitro, and cyano;

$R^{11}$ represents a hydrogen atom, $C_{1-6}$ alkyl, ($C_{1-6}$ alkoxy)carbonyl, or benzyloxycarbonyl whose phenyl moiety is optionally substituted with one or more substituents selected from $X^1$;

$R^{12}$ represents a hydrogen atom or $C_{1-6}$ alkyl;

wherein the methylene present in the adamantyl group is optionally substituted with one or more groups independently selected from $C_{1-6}$ alkyl and $C_{1-6}$ alkoxy, wherein the alkyl or alkoxy is optionally substituted with one or more halogen atoms.

[3] The compound, enantiomer thereof, diastereomer thereof, or pharmaceutically acceptable salt thereof as set forth in [1] or [2], wherein the compound is represented by Formula (Ia):

[Chemical Formula 3]

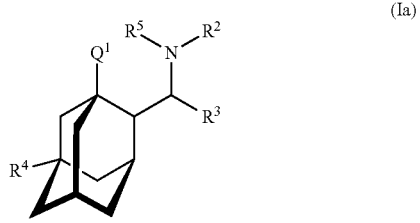

wherein $Q^1$ represents a hydrogen atom, a halogen atom, or —$OR^{10}$;

$R^{10}$ represents a hydrogen atom, or ($C_{1-6}$ alkyl)carbonyl optionally substituted with one or more halogen atoms;

$R^2$ represents a hydrogen atom, phenylsulfonyl optionally substituted with one or more substituents selected from $X^1$, ($C_{1-6}$ alkyl)sulfonyl optionally substituted with one or more halogen atoms, or —$COYR^6$;

Y represents a direct bond, O, or $NR^1$;

$R^3$ represents phenyl optionally substituted with one or more substituents selected from $X^1$, or 5- or 6-membered heteroaryl optionally substituted with one or more substituents selected from $X^1$;

$R^4$ represents a hydrogen atom, a halogen atom, —$OR^7$, or —$SR^8$;

$R^5$ represents a hydrogen atom or $C_{1-6}$ alkyl;

$R^6$ represents $C_{1-6}$ alkyl, phenyl optionally substituted with one or more substituents selected from $X^1$, or 5- or 6-membered heteroaryl optionally substituted with one or more substituents selected from $X^1$, wherein the $C_{1-6}$ alkyl is optionally substituted with one or more halogen atoms, and/or optionally substituted with one substituent selected from $X^2$;

$R^7$ represents a hydrogen atom, $C_{1-6}$ alkyl, $C_{1-6}$ alkoxy$C_{1-6}$ alkyl, or ($C_{1-6}$ alkyl)carbonyl optionally substituted with one or more halogen atoms;

$R^8$ represents $C_{1-6}$ alkyl, or phenyl optionally substituted with one or more substituents selected from $X^1$;

$R^9$ represents a hydrogen atom or $C_{1-6}$ alkyl;

each $X^1$ is independently selected from $C_{1-6}$ alkyl, a halogen atom, $C_{1-6}$ alkoxy, nitro, and cyano;

$X^2$ is selected from $C_{1-6}$ alkoxy, $C_{2-6}$ alkenyloxy, $C_{2-6}$ alkynyloxy, and —$NR^{11}R^{12}$;

$R^{11}$ represents a hydrogen atom, $C_{1-6}$ alkyl, ($C_{1-6}$ alkoxy) carbonyl, or benzyloxycarbonyl whose phenyl moiety is optionally substituted with one or more substituents selected from $X^1$;

$R^{12}$ represents a hydrogen atom or $C_{1-6}$ alkyl.

[4] The compound, enantiomer thereof, diastereomer thereof, or pharmaceutically acceptable salt thereof as set forth in any of [1] to [3], wherein $Q^1$ and $R^4$ represent hydrogen atoms.

[5] The compound, enantiomer thereof diastereomer thereof, or pharmaceutically acceptable salt thereof as set forth in any of [1] to [3], wherein $Q^1$ and $R^4$ are selected from halogen atoms.

[6] The compound, enantiomer thereof, diastereomer thereof, or pharmaceutically acceptable salt thereof as set forth in any of [1] to [3], and [5], wherein $Q^1$ and $R^4$ represent chlorine atoms.

[7] The compound, enantiomer thereof, diastereomer thereof, or pharmaceutically acceptable salt thereof as set forth in any of [1] to [6], wherein $R^2$ represents phenylsulfonyl optionally substituted with one or more substituents selected from $X^1$, ($C_{1-6}$ alkyl)sulfonyl optionally substituted with one or more halogen atoms, or —$COR^6$.

[8] The compound, enantiomer thereof, diastereomer thereof, or pharmaceutically acceptable salt thereof as set forth in any of [1] to [7], wherein $R^2$ represents trifluoroacetyl.

[9] The compound, enantiomer thereof, diastereomer thereof, or pharmaceutically acceptable salt thereof as set forth in any of [1] to [8], wherein $R^3$ represents phenyl optionally substituted with one or more substituents selected from $X^1$.

[10] The compound, enantiomer thereof, diastereomer thereof, or pharmaceutically acceptable salt thereof as set forth in any of [1] to [9], wherein $R^5$ represents a hydrogen atom.

[11] The compound, enantiomer thereof, diastereomer thereof, or pharmaceutically acceptable salt thereof as set forth in [1], wherein the compound is selected from:

(1S,2R,3S,5S,7S)-5-chloro-2-((R)-phenyl(2,2,2-trifluoroacetamido)methyl)adamantan-1-yl 2,2,2-trifluoroacetate;

N—((R)-((1S,2R,3S,5S,7S)-5-chloro-1-hydroxyadamantan-2-yl)(phenyl)methyl)-2,2,2-trifluoroacetamide;

(1S,2R,3S,5R,7S)-2-((R)-phenyl(2,2,2-trifluoroacetamido) methyl)adamantan-1-yl 2,2,2-trifluoroacetate;

(1S,2R,3S,5S,7R)-5-(2-methoxyethoxy)-2-((R)-phenyl(2,2, 2-trifluoroacetamido)methyl)adamantan-1-yl 2,2,2-trifluoroacetate;

N—((R)-((1S,2R,3S,5S,7S)-5-chloro-1-hydroxyadamantan-2-yl)(pyridin-3-yl)methyl)-2,2,2-trifluoroacetamide;

2,2,2-trifluoro-N—((R)-((1S,2R,3S,5R,7S)-1-hydroxyadamantan-2-yl)(phenyl)methyl)acetamide;

(1S,2R,3S,5S,7R)-5-methoxy-2-((R)-phenyl(2,2,2-trifluoroacetamido)methyl)adamantan-1-yl 2,2,2-trifluoroacetate;

N—((R)-((1S,2R,3S,5S,7R)-1,5-dichloroadamantan-2-yl) (phenyl)methyl)-2,2,2-trifluoroacetamide;

(R)-((1S,2R,3S,5S,7R)-1,5-dichloroadamantan-2-yl)(phenyl)methanamine;

N—((R)-((1S,2R,3S,5S,7R)-1,5-dichloroadamantan-2-yl) (phenyl)methyl)acetamide;

methyl ((R)-((1S,2R,3S,5S,7R)-1,5-dichloroadamantan-2-yl)(phenyl)methyl)carbamate;

1-((R)-((1S,2R,3S,5S,7R)-1,5-dichloroadamantan-2-yl) (phenyl)methyl)-3-phenylurea;

benzyl (2-(((R)-((1S,2R,3S,5S,7R)-1,5-dichloroadamantan-2-yl)(phenyl)methyl)amino)-2-oxoethyl)carbamate;

2-amino-N—((R)-((1S,2R,3S,5S,7R)-1,5-dichloroadamantan-2-yl)(phenyl)methyl)acetamide;

N—((R)-((1S,2R,3S,5S,7S)-1,5-dichloroadamantan-2-yl) (phenyl)methyl)methanesulfonamide;

2-bromo-N—((R)-((1S,2R,3S,5S,7R)-1,5-dichloroadamantan-2-yl)(phenyl)methyl)acetamide;

N—((R)-((1S,2R,3S,5S,7R)-1,5-dichloroadamantan-2-yl) (phenyl)methyl)-2-(prop-2-yn-1-yloxy)acetamide;

N—((R)-((1S,2R,3S,5S,7R)-1,5-dichloroadamantan-2-yl) (phenyl)methyl)-1,1,1-trifluoromethanesulfonamide;

N—((R)-((1S,2R,3S,5S,7R)-1,5-dichloroadamantan-2-yl) (phenyl)methyl)-2-nitrobenzenesulfonamide;

N—((R)-((1S,2R,3S,5S,7R)-1,5-dichloroadamantan-2-yl) (phenyl)methyl)-4-nitrobenzenesulfonamide;

N—((S)-((1S,3S,5S,7S)-adamantan-2-yl)(phenyl)methyl)-2,2,2-trifluoroacetamide;

N—((R)-((1R,3R,5R,7R)-adamantan-2-yl)(phenyl)methyl)-2,2,2-trifluoroacetamide;
(1S,2R,3S,5S,7S)-2-((R)-phenyl(2,2,2-trifluoroacetamido)methyl)-5-(phenylthio)adamantan-1-yl 2,2,2-trifluoroacetate;
N—((R)-((1S,2R,3S,5S,7R)-1,5-dichloroadamantan-2-yl)(phenyl)methyl)benzamide;
N—((R)-((1S,2R,3S,5S,7R)-1,5-dichloroadamantan-2-yl)(phenyl)methyl)picolinamide;
N—((R)-((1S,2R,3S,5S,7R)-1,5-dichloroadamantan-2-yl)(phenyl)methyl)benzenesulfonamide;
(1S,2R,3S,5S,7S)-5-chloro-2-((S)-phenyl(2,2,2-trifluoroacetamido)methyl)adamantan-1-yl 2,2,2-trifluoroacetate;
N-((1R)-((1R,2S,3R,5R,7R)-5-chloro-1-hydroxyadamantan-2-yl)(phenyl)methyl)-2,2,2-trifluoroacetamide;
(1R,2S,3R,5R,7R)-5-chloro-2-((R)-phenyl(2,2,2-trifluoroacetamido)methyl)adamantan-1-yl 2,2,2-trifluoroacetate;
(1S,2R,3S,5S,7S)-2-((R)-amino(phenyl)methyl)-5-chloroadamantan-1-ol;
N—((R)-((1S,2R,3S,5S,7S)-5-chloro-1-hydroxyadamantan-2-yl)(phenyl)methyl)acetamide;
N—((R)-((1S,2R,3S,5S,7S)-5-chloro-1-hydroxyadamantan-2-yl)(phenyl)methyl)propionamide;
N—((R)-((1S,2R,3S,5S,7S)-5-chloro-1-hydroxyadamantan-2-yl)(phenyl)methyl)butylamide;
N—((R)-((1S,2R,3S,5S,7S)-5-chloro-1-hydroxyadamantan-2-yl)(phenyl)methyl)hexanamide;
N—((R)-((1S,2R,3S,5S,7S)-5-chloro-1-hydroxyadamantan-2-yl)(phenyl)methyl)cyclopropanecarboxamide;
N—((R)-((1S,2R,3S,5S,7S)-5-chloro-1-hydroxyadamantan-2-yl)(phenyl)methyl)isobutylamide;
N—((R)-((1S,2R,3S,5S,7S)-5-chloro-1-hydroxyadamantan-2-yl)(phenyl)methyl)pivalamide;
N—((R)-((1S,2R,3S,5S,7S)-5-chloro-1-hydroxyadamantan-2-yl)phenyl)methyl)cyclobutanecarboxamide;
N—((R)-((1S,2R,3S,5S,7S)-5-chloro-1-hydroxyadamantan-2-yl)(phenyl)methyl)cyclopentanecarboxamide;
N—((R)-((1S,2R,3S,5S,7S)-5-chloro-1-hydroxyadamantan-2-yl)(phenyl)methyl)-2,2-difluoroacetamide;
N—((R)-((1S,2R,3S,5S,7S)-5-chloro-1-hydroxyadamantan-2-yl)(phenyl)methyl)-2,2-dimethylbutanamide; and
N—((R)-((1S,2R,3S,5S,7S)-5-chloro-1-hydroxyadamantan-2-yl)(phenyl)methyl)-3-methylbutanamide.

[12] A pharmaceutical composition comprising the compound, enantiomer thereof, diastereomer thereof, or pharmaceutically acceptable salt thereof as set forth in any of [1] to [11].

[13] The pharmaceutical composition as set forth in [12], for use in treating or preventing a cognitive disease or disorder.

[14] The pharmaceutical composition as set forth in [13], wherein the cognitive disease or disorder is selected from Alzheimer's dementia, cerebrovascular dementia, Lewy body dementia, frontotemporal dementia, Parkinson's disease, a mental disease and a neurodegenerative disease.

[15] The pharmaceutical composition as set forth in [12], for use in treating or preventing diabetes or a diabetic complication.

[16] A Kir6.2 channel inhibitor comprising the compound, enantiomer thereof, diastereomer thereof, or pharmaceutically acceptable salt thereof as set forth in any of [1] to [11].

[17] A Kir6.1 channel inhibitor comprising the compound, enantiomer thereof, diastereomer thereof, or pharmaceutically acceptable salt thereof as set forth in any of [1] to [11].

Further, the present disclosure includes the invention relating to an adamantane derivative as set forth in [1-1] to [1-14] below.

[1-1] A compound represented by Formula (Ib):

[Chemical Formula 4]

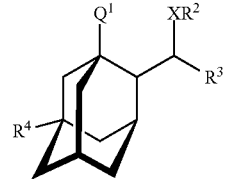

(Ib)

wherein one of $Q^1$ and $R^4$ represents a halogen atom, and the other represents a hydrogen atom or a halogen atom;
$R^2$ represents a hydrogen atom, phenylsulfonyl optionally substituted with one or more substituents selected from $X^1$, ($C_{1-6}$ alkyl)sulfonyl optionally substituted with one or more halogen atoms, or —$COYR^6$;
Y represents a direct bond, O, or $NR^7$;
$R^6$ represents $C_{1-6}$ alkyl, $C_{1-6}$ alkoxy optionally substituted with one or more halogen atoms, phenyl optionally substituted with one or more substituents selected from $X^1$, or 5- or 6-membered heteroaryl optionally substituted with one or more substituents selected from $X^1$, wherein the $C_{1-6}$ alkyl is optionally substituted with one or more halogen atoms, and/or optionally substituted with one substituent selected from $X^2$;
$R^7$ represents a hydrogen atom or $C_{1-6}$ alkyl;
X represents O or $NR^5$;
$R^3$ represents phenyl optionally substituted with one or more substituents selected from $X^1$, or 5- or 6-membered heteroaryl optionally substituted with one or more substituents selected from $X^1$;
$R^5$ represents a hydrogen atom or $C_{1-6}$ alkyl;
each $X^1$ is independently selected from $C_{1-6}$ alkyl, a halogen atom, $C_{1-6}$ alkoxy, nitro, and cyano;
$X^2$ is selected from $C_{1-6}$ alkoxy, $C_{2-6}$ alkenyloxy, $C_{2-4}$ alkynyloxy, and —$NR^{11}R^{12}$;
$R^{11}$ represents a hydrogen atom, $C_{1-6}$ alkyl, ($C_{1-6}$ alkoxy)carbonyl, or benzyloxycarbonyl whose phenyl moiety is optionally substituted with one or more substituents selected from $X^1$;
$R^{12}$ represents a hydrogen atom or $C_{1-6}$ alkyl,
an enantiomer thereof, a diastereomer thereof, or a pharmaceutically acceptable salt thereof.

[1-2] The compound, enantiomer thereof, diastereomer thereof, or pharmaceutically acceptable salt thereof as set forth in [1-1], wherein $Q^1$ and $R^4$ are selected from halogen atoms.

[1-3] The compound, enantiomer thereof, diastereomer thereof, or pharmaceutically acceptable salt thereof as set forth in [1-1] or [1-2], wherein $Q^1$ and $R^4$ represent chlorine atoms.

[1-4] The compound, enantiomer thereof, diastereomer thereof, or pharmaceutically acceptable salt thereof as set forth in any of [1-1] to [1-3], wherein $R^2$ represents phenylsulfonyl optionally substituted with one or more substituents selected from $X^1$, ($C_{1-6}$ alkyl)sulfonyl optionally substituted with one or more halogen atoms, or —$COYR^6$.

[1-5] The compound, enantiomer thereof, diastereomer thereof, or pharmaceutically acceptable salt thereof as set forth in any of [1-1] to [1-4], wherein $R^3$ represents phenyl optionally substituted with one or more substituents selected from $X^1$.

[1-6] The compound, enantiomer thereof, diastereomer thereof, or pharmaceutically acceptable salt thereof as set forth in any of [1-1] to [1-5], wherein X represents NH.

[1-7] The compound, enantiomer thereof, diastereomer thereof, or pharmaceutically acceptable salt thereof as set forth in [1-1], wherein the compound is selected from:
N—((R)-((1S,2R,3S,5S,7R)-1,5-dichloroadamantan-2-yl)(phenyl)methyl)-2,2,2-trifluoroacetamide;
(R)-((1S,2R,3S,5S,7R)-1,5-dichloroadamantan-2-yl)(phenyl)methanamine;
N—((R)-((1S,2R,3S,5S,7R)-1,5-dichloroadamantan-2-yl)(phenyl)methyl)acetamide;
methyl ((R)-((1S,2R,3S,5S,7R)-1,5-dichloroadamantan-2-yl)(phenyl)methyl)carbamate;
1-((R)-((S,2R,3S,5S,7R)-1,5-dichloroadamantan-2-yl)(phenyl)methyl)-3-phenylurea;
benzyl (2-(((R)-((1S,2R,3S,5S,7R)-1,5-dichloroadamantan-2-yl)(phenyl)methyl)amino)-2-oxoethyl)carbamate;
2-amino-N—((R)-((1S,2R,3S,5S,7R)-1,5-dichloroadamantan-2-yl)(phenyl)methyl)acetamide;
N—((R)-((1S,2R,3S,5S,7S)-1,5-dichloroadamantan-2-yl)(phenyl)methyl)methanesulfonamide;
2-bromo-N—((R)-((1S,2R,3S,5S,7R)-1,5-dichloroadamantan-2-yl)(phenyl)methyl)acetamide;
N—((R)-((1S,2R,3S,5S,7R)-1,5-dichloroadamantan-2-yl)(phenyl)methyl)-2-(prop-2-yn-1-yloxy)acetamide;
N—((R)-((1S,2R,3S,5S,7R)-1,5-dichloroadamantan-2-yl)(phenyl)methyl)-1,1,1-trifluoromethanesulfonamide;
N—((R)-((1S,2R,3S,5S,7R)-1,5-dichloroadamantan-2-yl)(phenyl)methyl)-2-nitrobenzenesulfonamide; and
N—((R)-((1S,2R,3S,5S,7R)-1,5-dichloroadamantan-2-yl)(phenyl)methyl)-4-nitrobenzenesulfonamide.

[1-8] A pharmaceutical composition comprising the compound, enantiomer thereof, diastereomer thereof, or pharmaceutically acceptable salt thereof as set forth in any of [1-1] to [1-7].

[1-9] The pharmaceutical composition as set forth in [1-8], for use in treating or preventing a cognitive disease or disorder.

[1-10] The pharmaceutical composition as set forth in [1-9], wherein the cognitive disease or disorder is selected from Alzheimer's dementia, cerebrovascular dementia, Lewy body dementia, frontotemporal dementia, Parkinson's disease, a mental disease and a neurodegenerative disease.

[1-11] The pharmaceutical composition as set forth in [1-8], for use in treating or preventing diabetes or a diabetic complication.

[1-12] A Kir6.2 channel inhibitor comprising the compound, enantiomer thereof, diastereomer thereof, or pharmaceutically acceptable salt thereof as set forth in any of [1-1] to [1-7].

[1-13] A Kir6.1 channel inhibitor comprising the compound, enantiomer thereof, diastereomer thereof, or pharmaceutically acceptable salt thereof as set forth in any of [1-1] to [1-7].

[1-14] A compound represented by Formula (III):

[Chemical Formula 5]

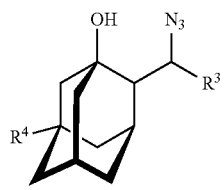

(III)

wherein $R^4$ represents a hydrogen atom or a halogen atom;
$R^3$ represents phenyl optionally substituted with one or more substituents selected from $X^1$, or 5- or 6-membered heteroaryl optionally substituted with one or more substituents selected from $X^1$;
each $X^1$ is independently selected from $C_{1-6}$ alkyl, a halogen atom, $C_{1-6}$ alkoxy, nitro, and cyano, an enantiomer thereof, a diastereomer thereof, or a salt thereof.

Furthermore, the present disclosure includes the invention relating to an adamantane derivative as set forth in [2-1] to [2-12] below.

[2-1] A compound represented by Formula (Ic):

[Chemical Formula 6]

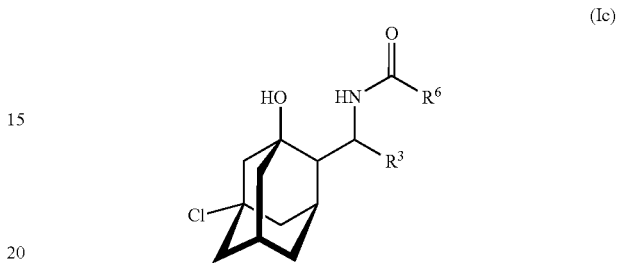

(Ic)

wherein $R^6$ is selected from $C_{1-6}$ alkyl and $C_{3-6}$ cycloalkyl;
$R^3$ represents phenyl optionally substituted with one or two halogen atoms, an enantiomer thereof, a diastereomer thereof, or a pharmaceutically acceptable salt thereof.

[2-2] The compound, enantiomer thereof diastereomer thereof, or pharmaceutically acceptable salt thereof as set forth in [2-1], wherein $R^6$ is selected from $C_2$-6 alkyl.

[2-3] The compound, enantiomer thereof, diastereomer thereof, or pharmaceutically acceptable salt thereof as set forth in [2-1] or [2-2], wherein $R^6$ is selected from n-propyl, i-propyl, n-butyl, s-butyl, i-butyl, and t-butyl.

[2-4] The compound, enantiomer thereof, diastereomer thereof, or pharmaceutically acceptable salt thereof as set forth in any of [2-1] to [2-3], wherein $R^3$ represents phenyl.

[2-5] The compound, or pharmaceutically acceptable salt thereof as set forth in any of [2-1] to [2-4], wherein the compound is represented by Formula (Id):

[Chemical Formula 7]

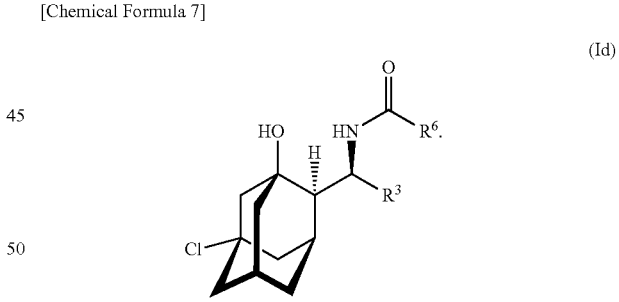

(Id)

[2-6] The compound, enantiomer thereof, diastereomer thereof, or pharmaceutically acceptable salt thereof as set forth in [2-1], wherein the compound is selected from:
N—((R)-((1S,2R,3S,5S,7S)-5-chloro-1-hydroxyadamantan-2-yl)(phenyl)methyl)butylamide; and
N—((R)-((1S,2R,3S,5S,7S)-5-chloro-1-hydroxyadamantan-2-yl)(phenyl)methyl)pivalamide.

[2-7] A pharmaceutical composition comprising the compound, enantiomer thereof, diastereomer thereof, or pharmaceutically acceptable salt thereof as set forth in any of [2-1] to [2-6].

[2-8] The pharmaceutical composition as set forth in [2-7], for use in treating or preventing a cognitive disease or disorder.

[2-9] The pharmaceutical composition as set forth in [2-8], wherein the cognitive disease or disorder is selected from Alzheimer's dementia, cerebrovascular dementia, Lewy body dementia, frontotemporal dementia, Parkinson's disease, a mental disease and a neurodegenerative disease.

[2-10] The pharmaceutical composition as set forth in [2-7], for use in treating or preventing diabetes or a diabetic complication.

[2-11] A Kir6.2 channel inhibitor comprising the compound, enantiomer thereof, diastereomer thereof, or pharmaceutically acceptable salt thereof as set forth in any of [2-1] to [2-6].

[2-12] A Kir6.1 channel inhibitor comprising the compound, enantiomer thereof, diastereomer thereof, or pharmaceutically acceptable salt thereof as set forth in any of [2-1] to [2-6].

Advantageous Effects of Invention

In one aspect, the present invention provides a pharmaceutical composition for use in treating or preventing a cognitive disease or disorder. In another aspect, the present invention provides an inhibitor of Kir6.1 channel or Kir6.2 channel, which are $K_{ATP}$ channels.

BRIEF DESCRIPTION OF DRAWINGS

FIG. 2-1 shows the results of immunoblotting of Kir6.2 channel-overexpressing cells using an anti-Kir6.2 channel antibody to determine the expression of Kir6.2 channels in the N2A cells. A significant difference relative to the non-drug-treated group (−) is indicated by **.

FIG. 2-2 shows the results of a whole-cell patch-clamp assay, which demonstrate that TP-014 suppresses outward potassium current in Kir6.2 channel-overexpressing cells. The results reveal that TP-014 inhibits Kir6.2 channels and attenuates potassium current.

FIG. 3-1 shows the results of a calcium imaging assay, which demonstrate that the treatment with TP-014 increases intracellular calcium concentration in Kir6.2 channel-overexpressing cells. Concentration-dependent change over time in calcium levels in the groups treated with the inventive compound or memantine was measured for four minutes. The results reveal that TP-014 inhibits Kir6.2 channels and increases intracellular calcium concentration.

FIG. 3-2 shows the results of a calcium imaging assay, which demonstrate that the treatment with TP-014 increases intracellular calcium concentration in Kir6.2 channel-overexpressing cells. The calcium levels were measured at 4 minutes after the treatment with memantine or the inventive compound. Significant differences relative to the non-drug-treated group (−) of Kir6.2 channel-overexpressing cells (Neuro2A cells) were observed. The results reveal that TP-014 inhibits Kir6.2 channels and increases intracellular calcium concentration.

FIG. 4-1 is a graph showing the results of an experiment in which Alzheimer's disease model mice (APP23 mice) (12 month-old) were treated with TP-014 for two months and were analyzed by Y-maze test to determine the cognitive function enhancing effect of TP-014 treatment.

FIG. 4-2 is a graph showing the results of an experiment in which Alzheimer's disease model mice (APP23 mice) (12 month-old) were treated with TP-014 for two months and were analyzed by Y-maze test to determine the cognitive function enhancing effect of TP-014 treatment. With respect to the correct answer rate (alteration) in memory and learning in APP23 mice, a significant difference relative to wild-type (WT) is indicated by **, and a significant difference relative to the control group (non-treated group) of APP23 mice is indicated by ++.

FIG. 4-3 is a graph showing the results of an experiment in which Alzheimer's disease model mice (APP23 mice) (12 month-old) were treated with TP-014 for two months and were analyzed by novel object recognition test to determine the cognitive function enhancing effect of TP-014 treatment. A significant difference observed by comparing Novel (novel object) with Familiar (same object) in each mouse group is indicated by **.

FIG. 4-4 is a graph showing the results of an experiment in which Alzheimer's disease model mice (APP23 mice) (12 month-old) were treated with TP-014 for two months and were analyzed by fear conditioning test to determine the cognitive function enhancing effect of TP-014 treatment. In retention trials, a significant difference relative to WT is indicated by **, and a significant difference relative to the control group of APP23 mice is indicated by +.

FIG. 4-5 shows the results of an experiment in which Alzheimer's disease model mice (APP23 mice) (12 month-old) were treated with TP-014 for two months and were analyzed by electrophysiological test regarding long-term potentiation phenomenon (LTP) serving as an index of memory formation.

FIG. 4-6 shows the results of an experiment in which Alzheimer's disease model mice (APP23 mice) (12 month-old) were treated with TP-014 for two months and were analyzed by electrophysiological test regarding long-term potentiation phenomenon (LTP) serving as an index for memory formation.

FIG. 4-7 shows the results of an experiment in which Alzheimer's disease model mice (APP23 mice) (12 month-old) were treated with TP-014 for two months and were analyzed by electrophysiological test regarding long-term potentiation phenomenon (LTP) serving as an index of memory formation. A significant difference relative to WT is indicated by **, and a significant difference relative to the control group of APP23 mice is indicated by ++ or +.

FIG. 5-1 is a set of bands (band images) obtained by electrophoresis of immunoblots, which show the results of protein phosphorylation analysis by immunoblotting using antibodies against CaMKII, CaMKIV and ERK.

FIG. 5-2 shows the results of quantitative analysis of the signal intensity of the bands obtained by electrophoresis of immunoblots as shown in FIG. 5-1. A significant differences relative to WT (−) (non-drug-treated group) is indicated by **, and a significant difference relative to the non-drug-treated group (−) of APP23 mice is indicated by +.

FIG. 5-3 is a set of bands (band images) obtained by electrophoresis of immunoblots, which show the results of protein phosphorylation analysis by immunoblotting using antibodies against CaMKII, CaMKIV and ERK.

FIG. 5-4 shows the results of quantitative analysis of the signal intensity of the bands obtained by electrophoresis of immunoblots as shown in FIG. 5-3. A significant differences relative to WT (−) (non-drug-treated group) is indicated by **, and a significant difference relative to the non-drug-treated group (−) of APP23 mice is indicated by +.

FIG. 6-1 is a graph showing the results of an experiment in which olfactory bulbectomized mice (OBX mice) used as a neurodegenerative disease model were treated with TP-014 for two weeks and were analyzed by Y-maze test to determine the cognitive function enhancing effect of TP-014 treatment.

FIG. 6-2 is a graph showing the results of an experiment in which olfactory bulbectomized mice (OBX mice) used as a neurodegenerative disease model were treated with TP-014 for two weeks and were analyzed by Y-maze test to determine the cognitive function enhancing effect of TP-014 treatment. A significant difference in correct answer rate (alteration) in memory and learning between OBX mice and Sham-operated (Sham) mice is indicated by **, and a significant difference relative to the control group (non-treated group) of OBX mice is indicated by ++.

FIG. 6-3 is a graph showing the results of an experiment in which olfactory bulbectomized mice (OBX mice) used as a neurodegenerative disease model were treated with TP-014 for two weeks and were analyzed by novel object recognition test to determine the cognitive function enhancing effect of TP-014 treatment. A significant difference observed by comparing Novel (novel object) with Familiar (same object) in each mouse group is indicated by **.

FIG. 6-4 is a graph showing the results of an experiment in which olfactory bulbectomized mice (OBX mice) used as a neurodegenerative disease model were treated with TP-014 for two weeks and were analyzed by fear conditioning test to determine the cognitive function enhancing effect of TP-014 treatment. In retention trials, a significant difference relative to Sham is indicated by **, and a significant difference relative to the control group of OBX mice is indicated by +.

FIG. 6-5 shows the results of an experiment in which olfactory bulbectomized mice (OBX mice) used as a neurodegenerative disease model were treated with TP-014 for two weeks and were analyzed by electrophysiological test regarding long-term potentiation phenomenon (LTP) serving as an index of memory formation.

FIG. 6-6 shows the results of an experiment in which olfactory bulbectomized mice (OBX mice) used as a neurodegenerative disease model were treated with TP-014 for two weeks and were analyzed by electrophysiological test regarding long-term potentiation phenomenon (LTP) serving as an index of memory formation.

FIG. 6-7 shows the results of an experiment in which olfactory bulbectomized mice (OBX mice) used as a neurodegenerative disease model were treated with TP-014 for two weeks and were analyzed by electrophysiological test regarding long-term potentiation phenomenon (LTP) serving as an index of memory formation. A significant difference relative to Sham is indicated by **, and a significant difference relative to the control group of OBX mice is indicated by ++ or +.

FIG. 7-1 is a set of bands (band images) obtained by electrophoresis of immunoblots, which show the results of protein phosphorylation analysis by immunoblotting using antibodies against CaMKII, CaMKIV and ERK.

FIG. 7-2 shows the results of quantitative analysis of the signal intensity of the bands obtained by electrophoresis of immunoblots as shown in FIG. 7-1.

FIG. 7-3 is a set of bands (band images) obtained by electrophoresis of immunoblots, which show the results of protein phosphorylation analysis by immunoblotting using antibodies against CaMKI, CaMKIV and ERK.

FIG. 7-4 shows the results of quantitative analysis of the signal intensity of the bands obtained by electrophoresis of immunoblots as shown in FIG. 7-3. A significant differences relative to Sham (non-drug-treated group) is indicated by **, and a significant difference relative to the non-drug-treated group (−) of OBX mice is indicated by ++.

FIG. 8-1 is a graph showing the results of an experiment in which Kir6.2 channel-deficient mice were treated with TP-014 for two months and were analyzed by Y-maze test to determine the cognitive function enhancing effect of TP-014 treatment.

FIG. 8-2 is a graph showing the results of an experiment in which Kir6.2 channel-deficient mice were treated with TP-014 for two months and were analyzed by Y-maze test to determine the cognitive function enhancing effect of TP-014 treatment. A significant difference in correct answer rate (alteration) in memory and learning observed by comparing Kir6.2-deficient mice with wild-type (WT) is indicated by * or **.

FIG. 8-3 is a graph showing the results of an experiment in which Kir6.2 channel-deficient mice were treated with TP-014 for two months and were analyzed by novel object recognition test to determine the cognitive function enhancing effect of TP-014 treatment. A significant difference observed by comparing Novel (novel object) with Familiar (same object) in each mouse group is indicated by **.

FIG. 8-4 is a graph showing the results of an experiment in which Kir6.2 channel-deficient mice were treated with TP-014 for two months and were analyzed by fear conditioning test to determine the cognitive function enhancing effect of TP-014 treatment. In retention trials, a significant difference relative to WT is indicated by *.

FIG. 8-5 shows the results of an experiment in which Kir6.2 channel-deficient mice were treated with TP-014 for two months and were analyzed by electrophysiological test regarding long-term potentiation phenomenon (LTP) serving as an index of memory formation.

FIG. 8-6 shows the results of an experiment in which Kir6.2 channel-deficient mice were treated with TP-014 for two months and were analyzed by electrophysiological test regarding long-term potentiation phenomenon (LTP) serving as an index of memory formation.

FIG. 8-7 shows the results of an experiment in which Kir6.2 channel-deficient mice were treated with TP-014 for two months and were analyzed by electrophysiological test regarding long-term potentiation phenomenon (LTP) serving as an index of memory formation. A significant difference relative to WT is indicated by ** or*.

FIG. 9-1 is a set of bands (band images) obtained by electrophoresis of immunoblots, which show the results of protein phosphorylation analysis by immunoblotting using antibodies against CaMKII, CaMKIV and ERK.

FIG. 9-2 shows the results of quantitative analysis of the signal intensity of the bands obtained by electrophoresis of immunoblots as shown in FIG. 9-1. A significant difference relative to WT (−) (non-drug-treated group) is indicated by ** or*.

FIG. 11-1 shows the results of a tail suspension test conducted to determine the effect of the compound of the present invention to ameliorate a depression-like symptom in OBX mice. A significant difference relative to Sham (control group) is indicated by **, and a significant difference relative to the control group of OBX mice is indicated by +.

FIG. 11-2 shows the results of a forced swim test conducted to determine the effect of the compound of the present invention to ameliorate a depression-like symptom in OBX mice. A significant difference relative to Sham (control group) is indicated by **, and a significant difference relative to the control group of OBX mice is indicated by +.

FIG. 12-1 shows the results of a test conducted to confirm that the compound of the present invention exerts a depression ameliorating effect through inhibition of Kir6.1 channels. A significant difference relative to WT (control group) is indicated by **.

FIG. 12-2 shows the results of a test conducted to confirm that the compound of the present invention exerts a depression ameliorating effect through inhibition of Kir6.1 channels. A significant difference relative to WT (control group) is indicated by **.

FIG. 13-1 shows the results of a test conducted to confirm that the compound of the present invention exerts a depression ameliorating effect through inhibition of Kir6.1 channels and activation of CaMKIV. A significant difference relative to WT (control group) is indicated by **.

FIG. 13-2 shows the results of a test conducted to confirm that the compound of the present invention exerts a depression ameliorating effect through inhibition of Kir6.1 channels and activation of CaMKIV. A significant difference relative to WT (control group) is indicated by **.

FIG. 17-1 is a diagram showing the sequence of the plasmid vector: pcDNA3.1-Kir6.2.

FIG. 17-2 is a diagram showing the sequence of the plasmid vector: pcDNA3.1-Kir6.2.

FIG. 17-3 is a diagram showing the sequence of the plasmid vector: pcDNA3.1-Kir6.2.

FIG. 17-4 is a diagram showing the sequence of the plasmid vector: pcDNA3.1-Kir6.2.

FIG. 17-5 is a diagram showing the sequence of the plasmid vector pcDNA3.1-Kir6.2.

FIG. 18-1 is a graph showing CaMKIV activity enhanced by the compound of the present invention in Kir6.1 channel-overexpressing cells (Neuro2A cells). All significant differences shown in the figure are relative to the control group (C: non-drug-treated group of Kir6.1 channel-overexpressing cells).

FIG. 18-2 shows the results of immunoblotting of Kir6.1 channel-overexpressing cells using an anti-Kir6.1 channel antibody to determine the expression of Kir6.1 channels in the N2A cells. A significant difference relative to the non-drug-treated group (−) is indicated by **.

FIG. 18-3 shows the results of a common patch-clamp assay performed on Kir6.1 channel-overexpressing cells to measure potassium current discharged out of the cells.

FIG. 19-1 shows the results of determining anxiety vulnerability of tested mice groups by elevated plus-maze test. With respect to the spending time of the mice in open arms, a significant difference relative to WT (−) is indicated by ** or *, and a significant difference relative to WT (CORT) is indicated by ++.

FIG. 19-2 is a photograph of an apparatus used in an elevated plus-maze test.

FIG. 19-3 shows the results of a light/dark test. A significant difference relative to WT (−) is indicated by **, and a significant difference relative to WT (CORT) is indicated by ++.

FIG. 19-4 is a photograph of an apparatus used in a light/dark test.

FIG. 19-5 shows the results of a marble burying test. A significant difference relative to WT (−) is indicated by **, and a significant difference relative to WT (CORT) is indicated by +.

FIG. 19-6 is a photograph of an apparatus used in a marble burying test.

FIG. 19-7 shows the results of an open field test. A significant difference relative to WT (−) is indicated by **, and a significant difference relative to WT (CORT) is indicated by ++.

FIG. 19-8 is a photograph of an apparatus used in an open field test.

FIG. 19-9 shows the results of a fear conditioning test. A significant difference relative to WT (−) is indicated by ** or *, and a significant difference relative to WT (CORT) is indicated by ++.

FIG. 21-1 is a diagram showing the sequence of the plasmid vector: pcDNA3.1-Kir6.1.

FIG. 21-2 is a diagram showing the sequence of the plasmid vector: pcDNA3.1-Kir6.1.

FIG. 21-3 is a diagram showing the sequence of the plasmid vector: pcDNA3.1-Kir6.1.

FIG. 21-4 is a diagram showing the sequence of the plasmid vector: pcDNA3.1-Kir6.1.

FIG. 21-5 is a diagram showing the sequence of the plasmid vector: pcDNA3.1-Kir6.1.

FIG. 22-1 shows the results of a tail suspension test conducted to determine the effect of the compound of the present invention to ameliorate a depression-like symptom in OBX mice. A significant difference relative to Sham (control group) is indicated by **, and a significant difference relative to the control group of OBX mice is indicated by + or ++.

FIG. 22-2 shows the results of a forced swim test conducted to determine the effect of the compound of the present invention to ameliorate a depression-like symptom in OBX mice. A significant difference relative to Sham (control group) is indicated by **, and a significant difference relative to the control group of OBX mice is indicated by + or ++.

FIG. 22-3 is a graph showing the results of an experiment in which olfactory bulbectomized mice (OBX mice) used as a neurodegenerative disease model were treated with a single dose of each of different test compounds like TP-014, and thereafter (after 1 h) analyzed by Y-maze test to determine the cognitive function enhancing effect of compound treatment. With respect to the total arm entries in OBX mice, a significant difference relative to Sham is indicated by **, and a significant difference relative to the control group (non-treated group) of OBX mice is indicated by + or ++.

FIG. 22-4 is a graph showing the results of an experiment in which olfactory bulbectomized mice (OBX mice) used as a neurodegenerative disease model were treated with a single dose of each of different test compounds like TP-014, and thereafter (after 1 h) analyzed by Y-maze test to determine the cognitive function enhancing effect of compound treatment. With respect to correct answer rate (alteration) in memory and learning in OBX mice, a significant difference relative to Sham is indicated by **, and a significant difference relative to the control group (non-treated group) of OBX mice is indicated by ++.

FIG. 22-5 is a graph showing the results of an experiment in which olfactory bulbectomized mice (OBX mice) used as a neurodegenerative disease model were treated with a single dose of each of different test compounds like TP-014, and thereafter (after 1 h) analyzed by novel object recognition test to determine the cognitive function enhancing effect of compound treatment. A significant difference observed by comparing Novel (novel object) with Familiar (same object) in each mouse group is indicated by * or **.

DESCRIPTION OF EMBODIMENTS

Figure 1:
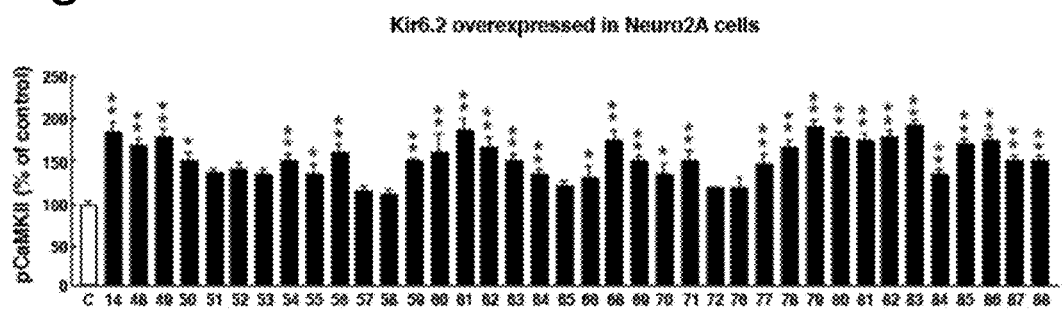
FIG. 1 is a graph showing CaMKII activity enhanced by the compound of the present invention in cells (Neuro2A cells) overexpressing Kir6.2 channels. All significant differences shown in the figure are relative to the control group (C: non-drug-treated group of Kir6.2 channel-overexpressing cells). With regard to significant differences shown in the figures presented herein, ** or ++ represents P<0.01, and + or * represents P<0.05.

On the pages that follow, the present invention will be more specifically described.

According to one aspect of the present invention, there is provided a pharmaceutical composition for treating or preventing a cognitive disease or disorder, comprising a compound represented by Formula (I), an enantiomer thereof, a diastereomer thereof, or a pharmaceutically acceptable salt thereof. More specifically, the compound of this invention includes compounds represented by Formula (I) or (II) as shown below.

[Chemical Formula 8]

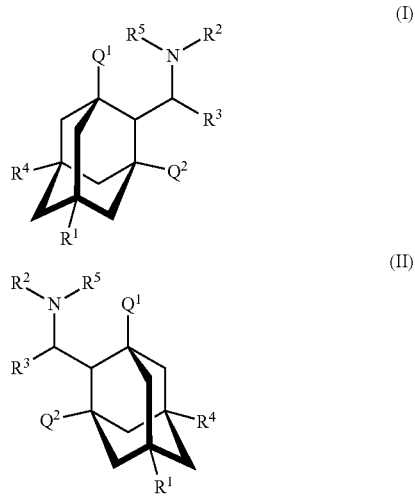

Also, the compound of this invention includes compounds represented by Formula (Ia) or (IIa) as shown below.

[Chemical Formula 9]

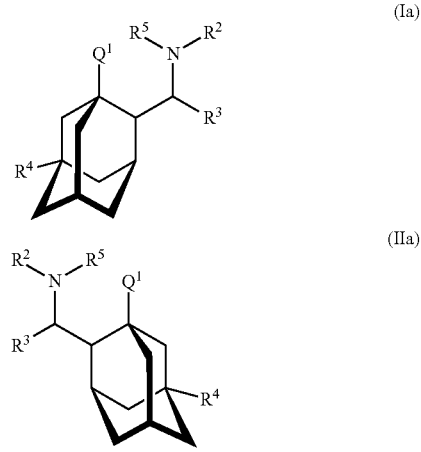

Further, the compound of this invention includes compounds represented by Formula (Ib) or (IIb) as shown below.

[Chemical Formula 10]

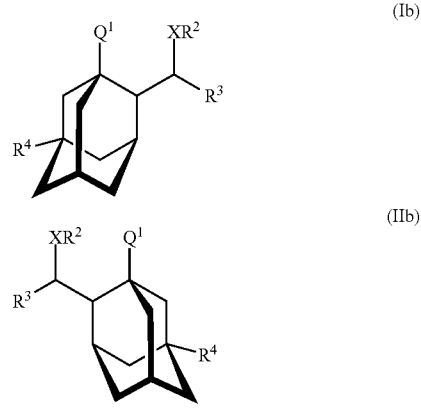

As used herein, the term "$C_{1-6}$ alkyl" refers to a linear, branched, cyclic or partially cyclic alkyl group having 1 to 6 carbon atoms. Examples thereof include methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, cyclopropyl, cyclobutyl, cyclopentyl, cyclohexyl and cyclopropylmethyl. For example, $C_{1-4}$ alkyl and $C_{1-3}$ alkyl are also included.

As used herein, the term "$C_{1-6}$ alkoxy" refers to an alkyloxy group [—O—($C_{1-6}$ alkyl)] having, as an alkyl moiety, an alkyl group having 1 to 6 carbon atoms as already defined. Examples thereof include methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cyclopentyloxy, cyclohexyloxy and cyclopropylmethyloxy. For example, $C_{1-4}$ alkoxy and $C_{1-3}$ alkoxy are also included. As used herein, the term "$C_{1-4}$ alkoxy" includes, for example, $C_{1-3}$ alkoxy.

As used herein, the term "$C_{2-6}$ alkenyloxy" refers to an alkenyloxy group [—O—($C_{2-6}$ alkenyl)] having a linear, branched, cyclic or partially cyclic alkenyl group having 2 to 6 carbon atoms. The alkenyl group has one or more, preferably 1 to 3, more preferably one double bond. Examples of $C_{2-6}$ alkenyloxy include vinyloxy, 2-propenyloxy, 1-propenyloxy, 1-methylvinyloxy, 3-butenyloxy, 2-butenyloxy, and 1-butenyloxy.

As used herein, the term "$C_{2-6}$ alkynyloxy" refers to an alkynyloxy group [—O—($C_{2-6}$ alkynyl)] having a linear, branched, cyclic or partially cyclic alkynyl group having 2 to 6 carbon atoms. The alkynyl group has one or more, preferably 1 to 3, more preferably one triple bond. Examples of $C_{2-6}$ alkynyloxy include ethynyloxy, 2-propynyloxy, 1-propynyloxy, 3-butynyloxy, 2-butynyloxy, and 1-butynyloxy.

As used herein, the term "($C_{1-6}$ alkyl)sulfonyl" refers to an alkylsulfonyl group having, as an alkyl moiety, a $C_{1-6}$ alkyl group as already defined. Examples thereof include methylsulfonyl, ethylsulfonyl, tert-buthylsulfonyl, and ($C_{1-3}$ alkyl)sulfonyl.

As used herein, the term "($C_{1-6}$ alkoxy)carbonyl" refers to an alkoxycarbonyl group having, as an alkoxy moiety, a $C_{1-6}$ alkoxy group as already defined. Examples thereof include methoxycarbonyl, ethoxycarbonyl, tert-butoxycarbonyl, and ($C_{1-3}$ alkoxy)carbonyl.

As used herein, the term "5- or 6-membered heteroaryl" is not particularly limited as long as it is a heteroaryl composed of a 5-membered ring or a 6-membered ring having one or more hetero atoms selected from an oxygen atom, a nitrogen atom and a sulfur atom. Examples thereof include pyridyl, pyrimidyl, pyridazinyl, pyrazyl, furanyl (furyl), thiophenyl(thienyl), oxazolyl, isoxazoyl, oxadiazolyl, thiazolyl, isothiazolyl, thiadiazolyl, pyrrolyl, imidazolyl, pyrazolyl, triazolyl, and tetrazolyl.

Examples of halogen atoms include a fluorine atom, a chlorine atom, a bromine atom and an iodine atom.

Examples of "($C_{1-6}$ alkyl)sulfonyl optionally substituted with one or more halogen atoms", as used herein, include trifluoromethylsulfonyl, difluoromethylsulfonyl, 2,2,2-trifluoroethylsulfonyl, and perfluoroethylsulfonyl.

As used herein, the term "($C_{1-6}$ alkyl)carbonyl optionally substituted with one or more halogen atoms" refers to that type of ($C_{1-6}$ alkyl)carbonyl group as defined above, wherein the alkyl moiety is optionally substituted with one or more, for example 1 to 5, specifically 1 to 3, halogen atoms. The alkyl moiety may be unsubstituted. Examples thereof include trifluoroacetyl, and pentafluoropropionyl.

As used herein, the term "$C_{1-6}$ alkyl optionally substituted with one or more halogen atoms" refers to that type of $C_{1-6}$ alkyl group as defined above, which is optionally substituted with one or more, for example 1 to 5, specifically 1 to 3, halogen atoms. The alkyl may be unsubstituted. Examples thereof include trifluoromethyl, pentafluoroethyl, and 2,2,2-trifluoroethyl.

As used herein, the term "$C_{1-6}$ alkoxy optionally substituted with one or more halogen atoms" refers to that type of $C_{1-6}$ alkoxygroup as defined above, which is optionally substituted with one or more, for example 1 to 5, specifically 1 to 3, halogen atoms. The alkoxy may be unsubstituted. Examples thereof include trifluoromethoxy, pentafluoroethoxy, and 2,2,2-trifluoroethoxy.

As used herein, the term "$C_{3-8}$ cycloalkyl" refers to a cyclic alkyl group having 3 to 8 carbon atoms. Examples thereof include cyclopropyl, cyclobutyl, cyclopentyl, cyclohexyl, cycloheptyl, and cyclooctyl.

As used herein, the term "phenylaminocarboyl optionally substituted with one or more substituents selected from $X^1$" refers to a —CONHPh group wherein the phenyl moiety may have one or more (for example 1 to 5, specifically 1 to 3) substituents selected from $X^1$. The phenyl moiety may be unsubstituted.

As used herein, the term "5- to 10-membered monocyclic or bicyclic heteroaryl optionally substituted with one or more substituents selected from $X^1$" refers to an aromatic heterocyclic group containing one or more hetero atoms selected from a nitrogen atom, an oxygen atom and a sulfur atom, and includes 5- or 6-membered monocyclic heteroaryl groups, and 8- to 10-membered bicyclic heteroaryl groups. The number of substituent(s) selected from $X^1$ may be one or more, for example 1 to 5, specifically 1 to 3, more specifically one. The heteroaryl may be unsubstituted. Examples of 5- or 6-membered monocyclic heteroaryl groups include pyridyl, pyrimidyl, pyridazinyl, pyrazyl, furanyl(furyl), thiophenyl(thienyl), oxazolyl, isoxazolyl, oxadiazolyl, thiazolyl, isothiazolyl, thiadiazolyl, pyrrolyl, imidazolyl, pyrazolyl, triazolyl, and tetrazolyl. Examples of 8- to 10-membered bicyclic heteroaryl groups include benzofuranyl, benzothienyl, benzothiadiazolyl, benzothiazolyl, benzooxazolyl, benzooxadiazolyl, benzoimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

As used herein, the term "5- to 10-membered monocyclic or bicyclic non-aromatic heterocyclyl optionally substituted with one or more substituents selected from $X^1$" refers to a non-aromatic heterocyclic group containing one or more hetero atoms selected from a nitrogen atom, an oxygen atom and a sulfur atom, and may be monocyclic or bicyclic heterocyclyl as long as it has 5 to 10 members. The number of substituent(s) selected from $X^1$ may be one or more, for example 1 to 5, specifically 1 to 3, more specifically one. The heterocyclyl may be unsubstituted. Examples thereof include tetrahydrofuranyl, pyrrolidinyl, piperidinyl, piperazinyl, and morpholinyl. In the bicyclic non-aromatic heterocyclyl, it is acceptable that as long as one ring is a non-aromatic cyclic group, the other ring may be an aromatic cyclic group. Examples of such a bicyclic non-aromatic heterocyclyl include 2,3-dihydroindolyl, 2,3-dihydrobenzofuranyl, and 1,2,3,4-tetrahydroquinolyl.

As used herein, the term "$C_{1-3}$ alkylene" refers to a divalent saturated hydrocarbon group having 1 to 3 carbon atoms, which may be linear or branched. Examples thereof include methylene, ethylene and propylene.

As used herein, the term "$C_{1-3}$ alkenylene" refers to a divalent hydrocarbon group having 2 or 3 carbon atoms, which has one double bond and may be linear or branched. Examples thereof include ethylene and propylene. Other examples thereof include ethenylene and propenylene.

As used herein, the term "$C_{6-10}$ aryl" refers to phenyl, 1-naphthyl, or 2-naphthyl. When it is optionally substituted by one or more substituents, the number of substituent(s) may be, for example 1 to 5, specifically 1 to 3, more specifically one. The aryl may be unsubstituted.

As used herein, the term "methylene present in the adamantyl group" refers to a $CH_2$ group which corresponds to a bridging portion that links bridgehead methines in an adamantane structure. When the methylene is substituted with one or more groups selected from $C_{1-6}$ alkyl, $C_{1-6}$ alkoxy, and hydroxy, the number of substituent(s) is, for example 1 to 5, specifically 1 to 3, more specifically one or two. One methylene group may have two substituents. All enantiomers, diastereomers and other isomers resulting from the substitution are included in the scope of the present invention. The alkyl or alkoxy may be substituted with one or more halogen atoms.

With regard to the formula —COYR$^6$, when Y is a direct bond, the formula represents —COR$^6$, and includes, for example, acetyl, trifluoroacetyl, and benzoyl.

If the compound represented by Formula (I) forms a solvate such as a hydrate, the present invention can be practiced by use of such a solvate. Furthermore, the compound of the present invention can be used as appropriate in the form of a mixture, solution, crystal polymorph or the like.

As used herein, the term "substituted with one or more substituents" refers to substitution with, for example, 1 to 3 substituents.

The present invention relating to a compound represented by Formula (I) as shown above includes various stereoisomers thereof such as tautomer, geometric isomer and optical isomer, diastereomers thereof, and mixtures of these. For example, the compound represented by Formula (I) includes compounds represented by Formulas (I-1) to (I-8) as shown below.

[Chemical Formula 11]

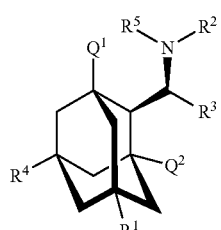
(I-1)

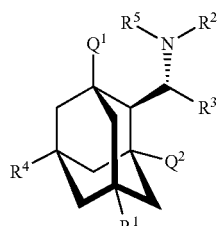
(I-2)

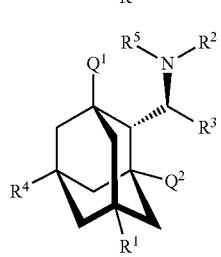
(I-3)

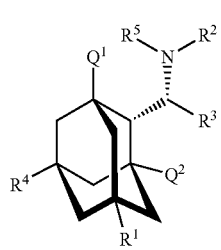
(I-4)

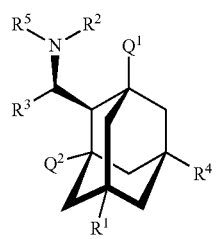
(I-5)

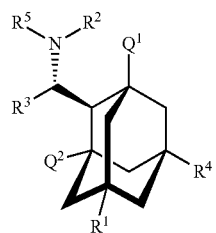
(I-6)

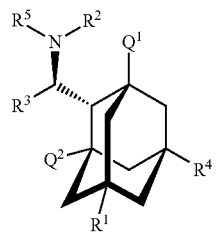
(I-7)

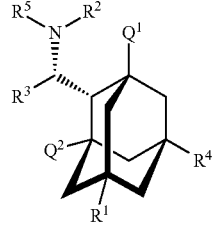
(I-8)

Also, the compound represented by Formula (I) includes compounds represented by Formulas (Ia-1) to (Ia-8) as shown below.

[Chemical Formula 12]

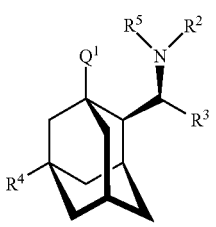
(Ia-1)

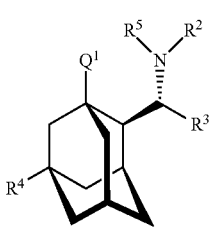
(Ia-2)

(Ia-3)
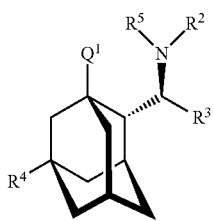
(Ia-4)
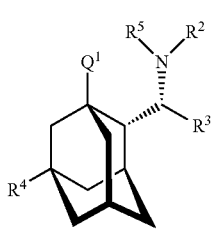
(Ia-5)
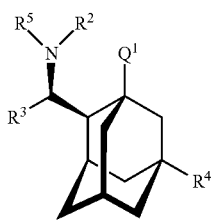
(Ia-6)
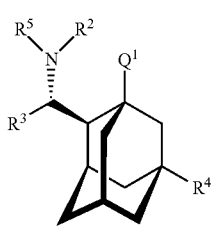
(Ia-7)
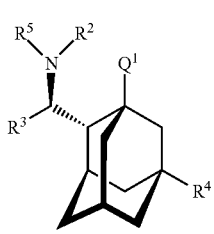
(Ia-8)
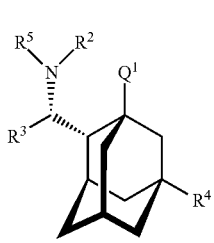
Further, the compound represented by Formula (I) includes compounds represented by Formulas (Ib-1) to (Ib-8) as shown below.
[Chemical Formula 13]
(Ib-1)
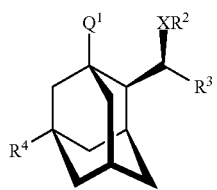
(Ib-2)
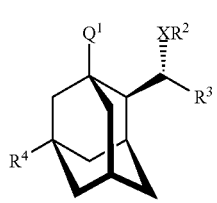
(Ib-3)
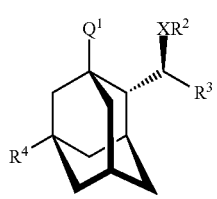
(Ib-4)
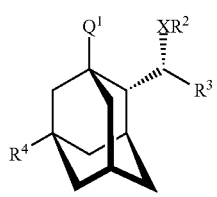
(Ib-5)
(Ib-6)
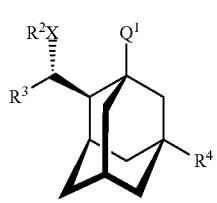
(Ib-7)
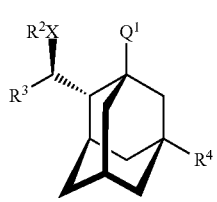
(Ib-8)

As examples of the compounds of the present invention, the compounds disclosed in Examples given herein can be used. More specifically, the following compounds can be used:

(1S,2R,3S,5S,7S)-5-chloro-2-((R)-phenyl(2,2,2-trifluoroacetamido)methyl)adamantan-1-yl 2,2,2-trifluoroacetate (TP-014);

N—((R)-((1S,2R,3S,5S,7S)-5-chloro-1-hydroxyadamantan-2-yl)(phenyl)methyl)-2,2,2-trifluoroacetamide (TP-048);

(1S,2R,3S,5R,7S)-2-(R)-phenyl(2,22-trifluoroacetamido)methyl)adamantan-1-yl 2,2,2-trifluoroacetate (TP-049);

(1S,2R,3S,5S,7R)-5-(2-methoxyethoxy)-2-((R)-phenyl(2,2,2-trifluoroacetamido)methyl)adamantan-1-yl 2,2,2-trifluoroacetate (TP-050);

N—((R)-((1S,2R,3S,5S,7S)-5-chloro-1-hydroxyadamantan-2-yl)(pyridin-3-yl)methyl)-2,2,2-trifluoroacetamide (TP-051);

2,2,2-trifluoro-N—((R)-((1S,2R,3S,5R,7S)-1-hydroxyadamantan-2-yl)(phenyl)methyl)acetamide (TP-052);

(1S,2R,3S,5S,7R)-5-methoxy-2-((R)-phenyl(2,2,2-trifluoroacetamido)methyl)adamantan-1-yl 2,2,2-trifluoroacetate (TP-053);

N—((R)-((1S,2R,3S,5S,7R)-1,5-dichloroadamantan-2-yl)(phenyl)methyl)-2,2,2-trifluoroacetamide (TP-054);

(R)-((1S,2R,3S,5S,7R)-1,5-dichloroadamantan-2-yl)(phenyl)methanamine hydrochloride (TP-055);

N—((R)-((1S,2R,3S,5S,7R)-1,5-dichloroadamantan-2-yl)(phenyl)methyl)acetamide (TP-056);

methyl ((R)-((1S,2R,3S,5S,7R)-1,5-dichloroadamantan-2-yl)(phenyl)methyl)carbamate (TP-057);

1-((R)-((1S,2R,3S,5S,7R)-1,5-dichloroadamantan-2-yl)(phenyl)methyl)-3-phenylurea (TP-058);

benzyl (2-(((R)-((1S,2R,3S,5S,7R)-1,5-dichloroadamantan-2-yl)(phenyl)methyl)amino)-2-oxoethyl)carbamate (TP-059);

2-amino-N—((R)-((1S,2R,3S,5S,7R)-1,5-dichloroadamantan-2-yl)(phenyl)methyl)acetamide (TP-060);

N—((R)-((1S,2R,3S,5S,7S)-1,5-dichloroadamantan-2-yl)(phenyl)methyl)methanesulfonamide (TP-061);

2-bromo-N—((R)-((1S,2R,3S,5S,7R)-1,5-dichloroadamantan-2-yl)(phenyl)methyl)acetamide (TP-062);

N—((R)-((1S,2R,3S,5S,7R)-1,5-dichloroadamantan-2-yl)(phenyl)methyl)-2-(prop-2-yn-1-yloxy)acetamide (TP-063);

N—((R)-((1S,2R,3S,5S,7R)-1,5-dichloroadamantan-2-yl)(phenyl)methyl)-1,1,1-trifluoromethanesulfonamide (TP-064);

N—((R)-((1S,2R,3S,5S,7R)-1,5-dichloroadamantan-2-yl)(phenyl)methyl)-2-nitrobenzenesulfonamide (TP-065);

N—((R)-((1S,2R,3S,5S,7R)-1,5-dichloroadamantan-2-yl)(phenyl)methy)-4-nitrobenzenesulfonamide (TP-066);

N—((S)-((1S,3S,5S,7S)-adamantan-2-yl)(phenyl)methyl)-2,2,2-trifluoroacetamide (TP-067);

N—((R)-((1R,3R,5R,7R)-adamantan-2-yl)(phenyl)methyl)-2,2,2-trifluoroacetamide (TP-068);

(1S,2R,3S,5S,7S)-2-((R)-phenyl(2,2,2-trifluoroacetamido)methyl)-5-(phenylthio)adamantan-1-yl 2,2,2-trifluoroacetate (TP-069);

N—((R)-((1S,2R,3S,5S,7R)-1,5-dichloroadamantan-2-yl)(phenyl)methyl)benzamide (TP-070);

N—((R)-((1S,2R,3S,5S,7R)-1,5-dichloroadamantan-2-yl)(phenyl)methyl)picolinamide (TP-071);

N—((R)-((1S,2R,3S,5S,7R)-1,5-dichloroadamantan-2-yl)(phenyl)methyl)benzenesulfonamide (TP-072);

(1S,2R,3S,5S,7S)-5-chloro-2-((S)-phenyl(2,2,2-trifluoroacetamido)methyl)adamantan-1-yl 2,2,2-trifluoroacetate (TP-073);

N-((1R)-((1R,2S,3R,5R,7R)-5-chloro-1-hydroxyadamantan-2-yl)(phenyl)methyl)-2,2,2-trifluoroacetamide (TP-074);

(1R,2S,3R,5R,7R)-5-chloro-2-((R)-phenyl(2,2,2-trifluoroacetamido)methyl)adamantan-1-yl 2,2,2-trifluoroacetate (TP-075);

(1S,2R,3S,5S,7S)-2-((R)-amino(phenyl)methyl)-5-chloroadamantan-1-ol (TP-076);

N—((R)-((1S,2R,3S,5S,7S)-5-chloro-1-hydroxyadamantan-2-yl)(phenyl)methyl)acetamide (TP-077);

N—((R)-((1S,2R,3S,5S,7 S)-5-chloro-1-hydroxyadamantan-2-yl)(phenyl)methyl)propionamide (TP-078);

N—((R)-((1S,2R,3S,5S,7S)-5-chloro-1-hydroxyadamantan-2-yl)(phenyl)methyl)butylamide (TP-079);

N—((R)-((1S,2R,3S,5S,7S)-5-chloro-lI-hydroxyadamantan-2-yl)(phenyl)methyl)hexanamide (TP-080);

N—((R)-((1S,2R,3S,5S,7S)-5-chloro-1-hydroxyadamantan-2-yl)(phenyl)methyl)cyclopropanecarboxamide (TP-081);

N—((R)-((1S,2R,3S,5S,7S)-5-chloro-1-hydroxyadamantan-2-yl)(phenyl)methyl)isobutylamide (TP-082);

N—((R)-((1S,2R,3S,5S,7S)-5-chloro-1-hydroxyadamantan-2-yl)(phenyl)methyl)pivalamide (TP-083);

N—((R)-((1S,2R,3S,5S,7S)-5-chloro-1-hydroxyadamantan-2-yl)(phenyl)methyl)cyclobutanecarboxamide (TP-084);

N—((R)-((1S,2R,3S,5S,7S)-5-chloro-1-hydroxyadamantan-2-yl)(phenyl)methyl)cyclopentanecarboxamide (TP-085);

N—((R)-((1S,2R,3S,5S,7S)-5-chloro-1-hydroxyadamantan-2-yl)(phenyl)methyl)-2,2-difluoroacetamide (TP-086);

N—((R)-((1S,2R,3S,5S,7S)-5-chloro-1-hydroxyadamantan-2-yl)(phenyl)methyl)-2,2-dimethylbutanamide (TP-087); and N—((R)-((1S,2R,3S,5S,7S)-5-chloro-1-hydroxyadamantan-2-yl)(phenyl)methyl)-3-methylbutanamide (TP-088).

The "pharmaceutically acceptable salt" of the compound represented by Formula (I) is not particularly limited as long as it is a salt that can be used as a pharmaceutical product. Examples of a salt formed by the compound of the present invention with a base include salts with inorganic bases such as sodium, potassium, magnesium, calcium and aluminum; and salts with organic bases such as methylamine, ethylamine and ethanolamine. The salt may be an acid addition salt. Examples of the acid addition salt include acid addition salts with mineral acids such as hydrochloric acid, hydrobromic acid, hydriodic acid, sulfuric acid, nitric acid and phosphoric acid; and acid addition salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid.

The atoms (for example, hydrogen atom, carbon atom, oxygen atom, nitrogen atom and sulfur atom) contained in the compound represented by Formula (I) may be isotope atoms other than most frequent naturally occurring isotopes. Such isotope atoms may be radioactive isotope atoms. More specifically, according to one aspect of the present invention, there is provided a compound represented by Formula (I) as already defined herein which is labeled with an isotope atom, or a salt thereof. As referred to above, the labelling with an isotope atom may be, for example, labelling with a radioactive isotope (e.g., $^{3}$H, $^{14}$C, $^{32}$P). From the viewpoint of the ease of preparing the compound, labeling with $^{3}$H is preferred.

In one embodiment of the present invention, the compound represented by Formula (I), an enantiomer thereof, a diastereomer thereof, or a pharmaceutically acceptable salt thereof is administered as a prodrug and converted into an active compound in vivo.

Examples of the treatment of a cognitive disease or disorder, as referred to herein, include treatments of Alzheimer's dementia, cerebrovascular dementia, Lewy body dementia, frontotemporal dementia, Parkinson's disease, a mental disease and a neurodegenerative disease. In the present invention, the pharmaceutical composition can be used for amelioration of various brain function impairments, such as those impairments caused by cerebral vascular disorder, brain injury, brain tumor, viral encephalitis, hypoxic encephalopathy and alcoholic intoxication. The present invention can be applied particularly to cognitive function impairments such as memory disturbance, attentional deficit, executive function disorder and social behavior disorder. Examples of cognitive function impairments include neurodegenerative diseases (e.g., Alzheimer's disease, Parkinson's disease, Pick's disease and Huntington's disease), mental diseases (e.g., schizophrenia, bipolar disorder, depression, phobia, sleep disorder, drug addiction) and pervasive developmental disorders (autism, Asperger's syndrome, mental retardation, hyperactivity disorder, tic disorder).

In the present invention, examples of the diabetic complications include hyperglycemia, diabetic coma, ketonic coma, nonketonic hyperosmolar coma, lactic acidosis, hypoglycemic coma, acute infection, microangiopathy, diabetic retinopathy, diabetic nephropathy, diabetic neuropathy, macroangiopathy, cerebral vascular disorder, ischemic heart disease, diabetic gangrene, hyperlipidemia, chronic infection, cholelithiasis and cataract.

In one embodiment of the present invention, the compound represented by Formula (I), an enantiomer thereof, a diastereomer thereof, or a pharmaceutically acceptable salt thereof is used as a Kir6.2 channel inhibitor or a Kir6.1 channel inhibitor. More specifically, the compound represented by Formula (I), an enantiomer thereof, a diastereomer thereof, or a pharmaceutically acceptable salt thereof can be used for treating or preventing Kir6.2 channel-associated diseases, such as cognitive disease or disorder, hyperglycemia, diabetes and diabetic complications, as well as Kir6.1 channel-associated diseases, such as cognitive disease or disorder, hyperglycemia, diabetes, diabetic complications and mental diseases.

The pharmaceutical composition of the present invention can be in various dosage forms—for example, oral dosage forms such as tablet, capsule, powder medicine, granule, pill, liquid medicine, emulsion, suspension, solution, sprit, syrup, extract, and elixir. The pharmaceutical composition of the present invention can also be in various parenteral dosage forms, including but not limited to: injections such as subcutaneous injection, intravenous injection, intramuscular injection, and intraperitoneal injection; patch, ointment or lotion for transdermal administration; sublingual formulation and oral patch for intraoral administration; and aerosol for transnasal administration. Such dosage forms can be prepared by a known method commonly used in drug preparation.

The pharmaceutical composition may contain various commonly used components, such as one or more pharmaceutically acceptable excipients, disintegrants, diluents, lubricants, flavoring agents, colorants, sweeteners, corrigents, suspending agents, wetting agents, emulsifiers, dispersants, adjuvants, preservatives, buffers, binders, stabilizers and coating agents. The pharmaceutical composition of the present invention may be in a long-acting or sustained-release dosage form.

The dose of the therapeutic agent, prophylactic agent or the pharmaceutical composition of the present invention can be selected as appropriate depending on, for example, the route of administration, the body shape, age or physical condition of the patient, the severity of the disease, and/or the time lapsed after disease onset. The pharmaceutical composition of this invention can comprise a therapeutically effective amount and/or prophylactically effective amount of the compound represented by Formula (I). In this invention, the compound represented by Formula (I) can be generally used in a dose of 1 to 1000 mg/day/adult or 0.01 to 20 mg/day/kg body weight. The pharmaceutical composition can be administered in a single dose or in multiple doses.

In the composition for oral administration comprising the compound of the present invention, the content of said compound per unit dosage form is in the range of, for example, 0.001 to 1000 mg, specifically 0.01 to 500 mg, particularly specifically 0.005 to 100 mg. As referred to above, the compound of the present invention is, for example, a compound represented by Formula (I) or a pharmaceutically acceptable salt thereof; specifically TP-014 or TP-048, or a pharmaceutically acceptable salt thereof more specifically TP-048 or a pharmaceutically acceptable salt thereof.

The pharmaceutical composition of the present invention may contain, if necessary, known components such as colorant, preservative, flavor, flavoring agent, coating agent, antioxidant, vitamin, amino acid, peptide, protein, and mineral (e.g., iron, zinc, magnesium, iodine). The therapeutic agent or prophylactic agent of the present invention may be prepared in different forms suitable for e.g., pharmaceutical composition, functional food, healthy food, beverage and supplement—for example, in the form of solid preparations such as granule (including dry syrup), capsule (soft capsule, hard capsule), tablet (including chewable medicine), powder medicine (powder) and pill; or liquid preparations such as internal medicine solution (including liquid medicine, suspension, syrup). The therapeutic agent or prophylactic agent of this invention can also be used, as it is, as a pharmaceutical composition, functional food, healthy food, supplement or the like.

Examples of additives used for drug preparation include excipient, lubricant, binder, disintegrant, fluidizing agent, dispersant, wetting agent, preservative, thickening agent, pH adjustor, colorant, flavoring agent, surfactant and solubilizing agent. When the compound is formulated into the form of a liquid medicine, a thickener such as pectin, xanthan gum or guar gum can be added. Also, the compound may be formulated into a coated tablet using a coating agent, or into a pasty glue. Further, when the compound is formulated in other forms, drug preparation can be done by following a conventional method.

In one aspect of the present invention, there is provided a compound represented by Formula (III), which is a synthetic intermediate useful for the synthesis of a compound of Formula (I) or the like, an enantiomer thereof, a diastereomer thereof, or a salt thereof. More specifically, the compound of this invention includes compounds represented by Formulas (III) and (IV) as shown below.

[Chemical Formula 14]

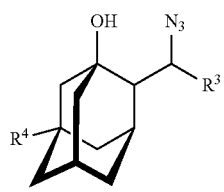
(III)

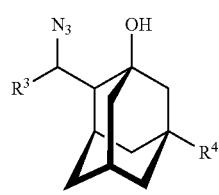
(IV)

The present invention relating to the compound represented by Formula (I) as shown above includes various stereoisomers thereof such as tautomer, geometric isomer and optical isomer, diastereomers thereof, and mixtures of these. For example, the compound represented by Formula (I) includes compounds represented by Formulas (IIIa) to (IIIh) as shown below.

[Chemical Formula 15]

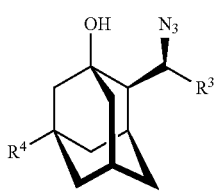
(IIIa)

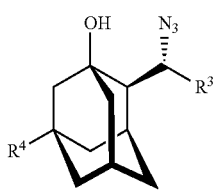
(IIIb)

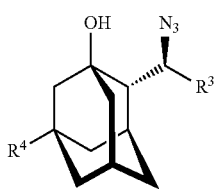
(IIIc)

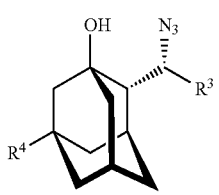
(IIId)

-continued

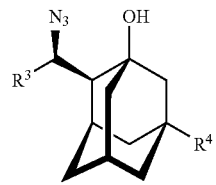
(IIIe)

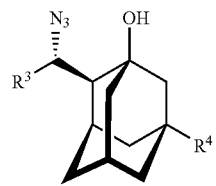
(IIIf)

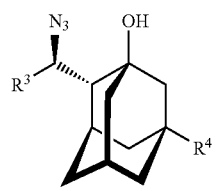
(IIIg)

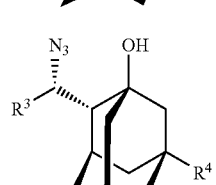
(IIIh)

In one embodiment of the present invention, there is provided a compound represented by Formula (III), wherein $R^4$ represents a halogen atom, and $R^3$ represents optionally substituted phenyl. In a preferred embodiment, said compound is a compound represented by Formula (IIIa).

EXAMPLES

Hereunder, the present invention will be more specifically described by way of working examples, but this invention is not limited to these examples.

Example 1

[Chemical Formula 16]

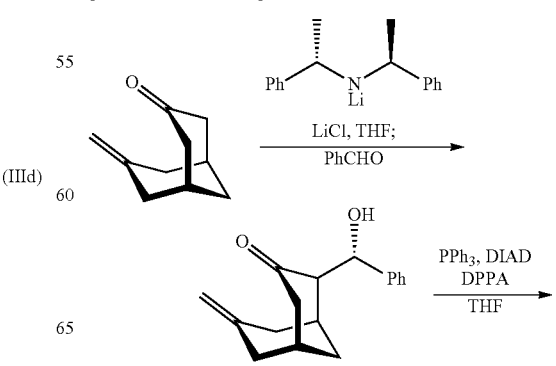

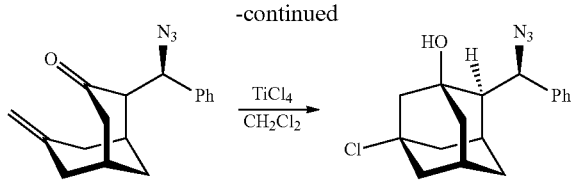

[Step 1] Preparation of (1S,2R,5R)-2-((S)-hydroxy (phenyl)methyl)-7-methylenebicyclo[3.3.1]nonan-3-one To a solution of bis((S)-1-phenylethyl)amine (10.0 mL, 44 mmol) and lithium chloride (3.4 g, 80 mmol) in THF (100 mL), a solution of n-butyllithium in hexane (1.56 M, 28.2 mL, 44 mmol) was added dropwise under cooling with ice. After stirring at the same temperature for 30 minutes, the reaction solution was cooled down to a temperature of −78° C. To the reaction mixture, a solution of 7-methylenebicyclo [3.3.1]nonan-3-one (6.00 g, 40 mmol) in THF (60 mL) was added by cannulation. After stirring for one hour, a solution of benzaldehyde (6.1 mL, 60 mmol) in THF (40 mL) was added by cannulation. After stirring for two hours, acetic acid and a saturated aqueous solution of ammonium chloride were added in sequence to the reaction solution, and then the mixture was extracted with diethyl ether. The resultant organic layer was washed with saturated saline and dried over $MgSO_4$. The solvent was distilled off under reduced pressure, and the residues were subjected to silica gel chromatography (hexane:ethyl acetate=4:1) to obtain (1S, 2R,5R)-2-((S)-hydroxy(phenyl)methyl)-7-methylenebicy-clo[3.3.1]nonan-3-one (8.3 g, 81%) as a white solid. The solid was recrystallized from diethyl ether to afford a colorless needle-like crystal.

mp 122° C.; $[\alpha]_D^{21}$=−17.9 (c=0.32, $CHCl_3$); $^1$H-NMR (400 MHz, $CDCl_3$): δ7.38-7.25 (m, 5H), 4.79 (d, J=1.8 Hz, 1H), 4.76 (d, J=1.8 Hz, 1H), 4.71 (d, J=6.8 Hz, 1H), 2.90 (s, 1H), 2.64 (dd, J=15.7, 6.8 Hz, 1H), 2.48-2.18 (m, 6H), 2.01 (br d, J=14.3 Hz, 1H); $^{13}$C-NMR (100 MHz, $CDCl_3$): δ211.0, 141.6, 128.8, 127.6, 114.8, 74.6, 62.7, 45.7, 42.2, 41.3, 32.4, 31.9, 28.4; IR (neat, $cm^{-1}$): 3390, 1711; MS (EI): m/z 256 ($M^+$), 95 (100%); HRMS (EI): calcd for $C_{17}H_{20}O_2$ ($M^+$) 256.1463, found 256.1450.

[Step 2] Preparation of (1S,2R,3S,5S,7S)-2-((R)-azido(phenyl)methyl)-5-chloroadamantan-1-ol To a solution of (1S,2R,5R)-2-((S)-hydroxy(phenyl) methyl)-7-methylenebicyclo[3.3.1]nonan-3-one (1.00 g, 3.9 mmol), DPPA (0.93 mL, 4.3 mmol) and triphenylphosphine (1.1 g, 4.3 mmol) in THF (20 mL), DIAD (0.85 mL, 4.3 mmol) was added under cooling with ice. After stirring for one hour at the same temperature, the solvent was distilled off under reduced pressure. The residues were subjected to silica gel column chromatography (hexane:ethyl acetate=30:1 to 8:1) to obtain a crude azide.

To the resultant crude azide, dichloromethane (18 mL) was added, and $TiCl_4$ (0.12 mL, 1.1 mmol) was added under cooling with ice. After stirring at room temperature for one hour, a saturated aqueous solution of $NaHCO_3$ was added under cooling with ice. The reaction solution was filtrated through Celite®, and the filtrate was extracted with diethyl ether. The resultant organic layer was washed with saline and dried over $MgSO_4$. The residues were subjected to silica gel column chromatography (hexane:ethyl acetate=8:1 to 4:1) to obtain (1S,2R,3S,5S,7S)-2-((R)-azido(phenyl) methyl)-5-chloroadamantan-1-ol (969.9 mg, 83%) as a colorless solid.

$[\alpha]_D^{27}$=+154.2 (c=0.99, $CHCl_3$); $^1$H-NMR (400 MHz, $CDCl_3$): δ7.42-7.24 (m, 5H), 4.76 (d, J=9.5 Hz, 1H), 2.57 (s, 1H), 2.34 (s, 1H), 2.13-1.98 (m, 8H), 1.89 (d, J=13.1 Hz, 1H), 1.45 (t, J=14.3 Hz, 2H), 0.93 (s, 1H); $^{13}$C-NMR (100 MHz, $CDCl_3$): δ139.7, 129.1, 128.6, 127.5, 71.8, 66.6, 65.5, 56.8, 53.2, 47.8, 46.5, 38.6, 33.5, 32.0, 28.8; IR (neat, $cm^{-1}$): 3418; MS (EI): m/z 275 ($M^+$-N3), 104 (100%); HRMS (EI): calcd for $C_{17}H_{20}OCl$ ($M^+$-N3) 275.1295, found 275.1186.

[Chemical Formula 17]

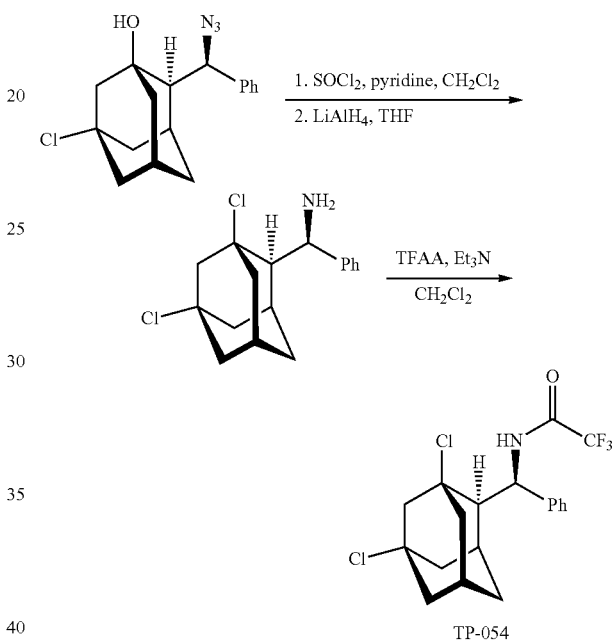

TP-054

[Step 3] Preparation of N—((R)-((1S,2R,3S,5S,7R)-1,5-dichloroadamantan-2-yl)(phenyl)methyl)-2,2,2-trifluoroacetamide To a solution of (1S,2R,3S,5S,7S)-2-((R)-azido(phenyl) methyl)-5-chloroadamantan-1-ol (229 mg, 0.721 mmol) in dichloromethane (7 mL), pyridine (0.15 mL, 1.8 mmol) and thionyl chloride (0.11 mL, 1.4 mmol) were added under cooling with ice. After stirring at room temperature for two hours, thionyl chloride (0.22 mL, 2.9 mmol) was added. After the reaction solution was refluxed under heating overnight, a saturated aqueous solution of $NaHCO_3$ was added under cooling with ice, and the mixture was extracted with dichloromethane. The resultant organic layer was dried over $MgSO_4$. The solvent was distilled off under reduced pressure, and the residues were subjected to silica gel column chromatography (hexane:ethyl acetate=15:1) to obtain (1S,2R,3S,5S,7S)-2-((R)-azido(phenyl)methyl)-1,5-dichloroadamantan (156 mg, 64%) as a colorless oily product.

To a solution of the resultant azide compound (156 mg, 0.463 mmol) in THF (5 mL), $LiAlH_4$ (26 mg, 0.69 mmol) was added under cooling with ice. After stirring at the same temperature for one hour, ammonia water was added to the reaction solution, and the mixture was filtrated through Celite®. The residues were subjected to silica gel column chromatography (hexane:ethyl acetate=1:1) to obtain (R)-((1S,2R,3S,5S,7R)-1,5-dichloroadamantan-2-yl)(phenyl)methanamine as a colorless oily product.

To a solution of the resultant amine (23.5 mg, 0.0757 mmol) in dichloromethane (1 mL), triethylamine (42 µL, 3.03 mmol) and trifluoroacetic anhydride (TFAA, 21 µL, 0.15 mmol) were added under cooling with ice. After stirring at room temperature overnight, a saturated aqueous solution of NaHCO$_3$ was added under cooling with ice, and the mixture was extracted with dichloromethane. The resultant organic layer was dried over Na$_2$SO$_4$. The solvent was distilled off under reduced pressure, and the residues were subjected to silica gel column chromatography (hexane:ethyl acetate=10:1) to obtain N—((R)-((1S,2R,3S,5S,7R)-1,5-dichloroadamantan-2-yl)(phenyl)methyl)-2,2,2-trifluoroacetamide (TP-054, 30.3 mg, 98%) as a white solid.

$[\alpha]_D^{23}$=+146.6 (c=0.469, CHCl$_3$); $^1$H-NMR (400 MHz, CDCl$_3$): δ7.39-7.26 (m, 5H), 6.49 (br d, J=9.7 Hz, 1H), 5.52 (dd, J=9.7, 8.9 Hz, 1H), 2.69 (br d, J=8.9 Hz, 1H), 2.53-2.43 (m, 4H), 2.33 (br s, 1H), 2.24-2.15 (m, 2H), 2.09 (br s, 2H), 1.92 (br d, J=13.0 Hz, 1H), 1.77 (br d, J=13.5 Hz, 1H), 1.46 (br d, J=12.1 Hz, 1H); $^{13}$C-NMR (100 MHz, CDCl$_3$): δ156.0 (q, J=37.1 Hz), 141.6, 129.0, 128.2, 127.2, 115.8 (q, J=288.4 Hz), 68.2, 65.3, 59.1, 54.1, 52.9, 47.5, 45.8, 40.8, 35.4, 32.7, 28.7; IR (neat, cm$^{-1}$): 3308, 2944, 1696, 1552, 1206, 1183; MS (EI): m/z 405 (M+), 202 (100%); HRMS (EI): calcd for C$_{19}$H$_{20}$Cl$_2$F$_3$NO (M$^+$) 405.0874, found 405.0864.

Example 2

[Chemical Formula 18]

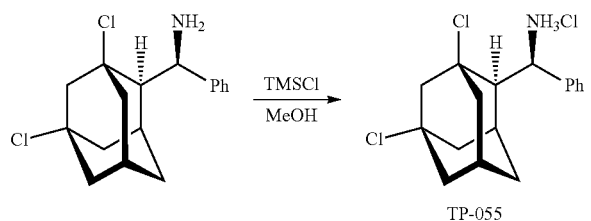

TP-055

To a solution of (R)-((1S,2R,3S,5S,7R)-1,5-dichloroadamantan-2-yl)(phenyl)methanamine (19.6 mg, 0.0632 mmol) in methanol (1 mL), chlorotrimethylsilane (TMSCl, 30 µL, 0.24 mL) was added under cooling with ice. After stirring at the same temperature for 30 minutes, the solvent was distilled off under reduced pressure to obtain (R)-((1S,2R,3S,5S,7R)-1,5-dichloroadamantan-2-yl)(phenyl)methanamine hydrochloride (TP-055, 20.1 mg, 92%) as a white solid.

$[\alpha]_D^{24}$=+32.5 (c=0.2775, MeOH); $^1$H-NMR (400 MHz, DMSO-d$_6$): δ8.33 (br, 3H), 7.55 (d, J=6.8 Hz, 1H), 7.38-7.32 (m, 3H), 4.73 (br d, J=10.6 Hz, 1H), 3.16 (br s, 1H), 2.80 (br d, J=10.6 Hz, 1H), 2.54-2.44 (m, 2H), 2.34-2.14 (m, 4H), 2.06 (br s, 2H), 1.93 (br d, J=14.0 Hz, 1H), 1.79 (br d, J=13.0 Hz, 1H), 1.42 (br d, J=13.0 Hz, 1H); $^{13}$C-NMR (100 MHz, DMSO-d$_6$): 139.8, 128.7, 128.4, 128.2, 68.8, 67.1, 58.4, 54.2, 51.1, 45.8, 44.9, 33.9, 32.7, 27.5; IR (neat, cm$^{-1}$): 3299, 2937; HRMS (ESI): calcd for C$_{17}$H$_{22}$Cl$_2$N (M$^+$-Cl) 310.1129, found 310.1120.

Example 3

[Chemical Formula 19]

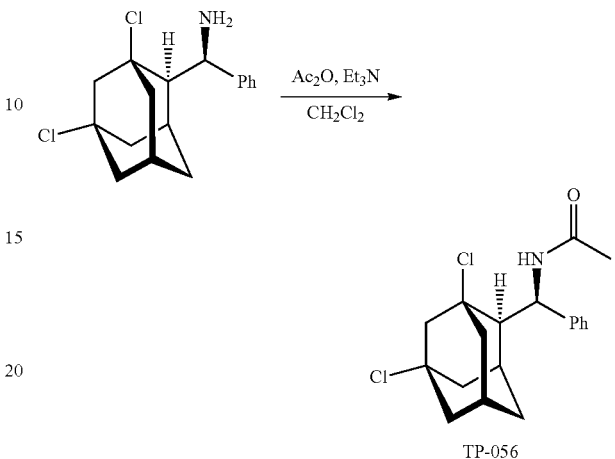

TP-056

To a solution of (R)-((1S,2R,3S,5S,7R)-1,5-dichloroadamantan-2-yl)(phenyl)methanamine (23.6 mg, 0.0762 mmol) in dichloromethane (2 mL), triethylamine (21 µL, 0.15 mmol) and acetic anhydride (11 µL, 0.11 mmol) were added under cooling with ice. After stirring at room temperature for 30 minutes, a saturated aqueous solution of NaHCO$_3$ was added under cooling with ice, and the mixture was extracted with dichloromethane. The resultant organic layer was dried over MgSO$_4$. The solvent was distilled off under reduced pressure, and the residues were subjected to silica gel column chromatography (hexane:ethyl acetate=1:1) to obtain N—((R)-((1S,2R,3S,5S,7R)-1,5-dichloroadamantan-2-yl)(phenyl)methyl)acetamide (TP-056, 16.4 mg, 61%) as a white solid.

$[\alpha]_D^{23}$=+67.9 (c=0.276, CHCl$_3$); $^1$H-NMR (400 MHz, CDCl$_3$): δ7.31 (m, 5H), 5.61-5.50 (m, 2H), 2.60-2.57 (m, 2H), 2.48-2.44 (m, 3H), 2.31 (br s, 1H), 2.23-2.14 (m, 2H), 2.08 (br s, 2H), 1.93-1.86 (m, 5H), 1.39 (br d, J=13.5 Hz, 1H); $^{13}$C-NMR (100 MHz, CDCl$_3$): δ168.6, 144.1, 128.7, 127.4, 127.3, 68.8, 66.0, 59.1, 53.1, 52.9, 47.7, 46.0, 40.8, 35.6, 32.9, 28.7, 23.7; IR (neat, cm$^{-1}$): 3277, 2942, 1645, 1547; MS (EI): m/z 351 (M$^+$), 148 (100%); HRMS (EI): calcd for C$_{19}$H$_{23}$Cl$_2$NO (M$^+$) 351.1157, found 351.1167.

Example 4

[Chemical Formula 20]

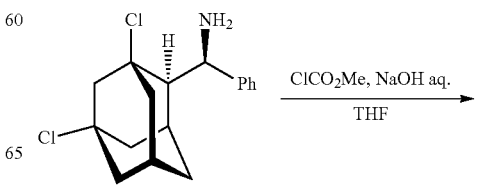

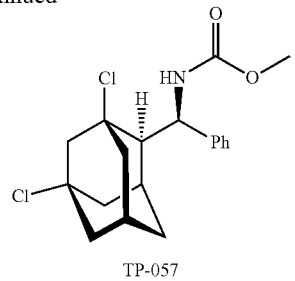

TP-057

To a solution of (R)-((1S,2R,3S,5S,7R)-1,5-dichloroadamantan-2-yl)(phenyl)methanamine (49.8 mg, 0.161 mmol) in THF (2 mL), an aqueous solution of 2 M NaOH (1 mL) and methyl chloroformate (25 μL, 0.32 mmol) were added under cooling with ice. After stirring at the same temperature for 15 minutes, distilled water was added to the reaction solution, and the mixture was extracted with ethyl acetate. The resultant organic layer was washed with saturated saline and dried over MgSO$_4$. The solvent was distilled off under reduced pressure, and the residues were subjected to silica gel column chromatography (hexane:ethyl acetate=8:1 to 4:1) to obtain methyl ((R)-((1S,2R,3S,5S,7R)-1,5-dichloroadamantan-2-yl)(phenyl)methyl)carbamate (TP-057, 54.4 mg, 92%) as a white solid.

$[\alpha]_D^{23}$=+115.9 (c=0.272, CHCl$_3$); $^1$H-NMR (400 MHz, CDCl$_3$): δ7.34-7.23 (m, 5H), 5.22 (dd, J=9.7, 8.7 Hz, 1H), 4.91 (br d, J=9.7 Hz, 1H), 3.63 (s, 3H), 2.58-2.45 (m, 5H), 2.34 (br s, 1H), 2.20-2.05 (m, 4H), 1.90 (br d, J=11.6 Hz, 1H), 1.43 (br d, J=13.5 Hz, 1H); $^{13}$C-NMR (100 MHz, CDCl$_3$): δ156.2, 144.1, 128.7, 127.3, 126.9, 68.9, 66.0, 59.2, 55.3, 53.4, 52.3, 47.8, 46.0, 40.8, 35.1, 32.9, 29.0; IR (neat, cm$^{-1}$): 3327, 2943, 1692, 1537; MS (EI): m/z 367 (M$^+$), 164 (100%); HRMS (EI): calcd for C$_{19}$H$_{23}$Cl$_2$NO$_2$ (M$^+$) 367.1106, found 367.1123.

Example 5

[Chemical Formula 21]

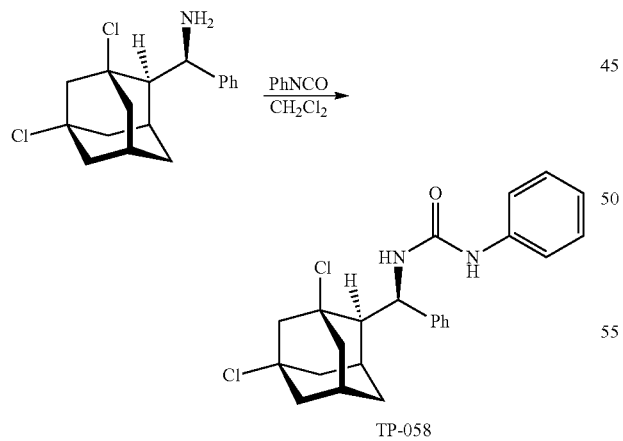

TP-058

To a solution of (R)-((1S,2R,3S,5S,7R)-1,5-dichloroadamantan-2-yl)(phenyl)methanamine (56.2 mg, 0.181 mmol) in dichloromethane (2 mL), phenyl isocyanate (24 μL, 0.22 mmol) was added under cooling with ice. After stirring at the same temperature for 15 minutes, distilled water was added to the reaction solution, and the mixture was extracted with dichloromethane. The resultant organic layer was dried over MgSO$_4$, and the solvent was distilled off under reduced pressure. The resultant white solid was recrystallized from methanol-chloroform to afford 1-((R)-((1S,2R,3S,5S,7R)-1,5-dichloroadamantan-2-yl)(phenyl)methyl)-3-phenylurea (TP-058, 63.8 mg, 82%) as a colorless crystal.

$[\alpha]_D^{23}$=+91.8 (c=0.351, MeOH); $^1$H-NMR (400 MHz, CD$_3$OD): δ7.88 (s, 1H), 7.35-7.28 (m, 6H), 7.22-7.18 (m, 3H), 6.94 (t, J=7.2 Hz, 1H), 5.40 (d, J=7.2 Hz, 1H), 2.65-2.60 (m, 2H), 2.52-2.40 (m, 3H), 2.30 (br s, 1H), 2.10 (br s, 2H), 2.08 (br s, 2H), 2.00 (br d, J=13.5 Hz, 1H), 1.89 (br d, J=13.0 Hz, 1H), 1.45 (br d, J=13.5 Hz, 1H); $^{13}$C-NMR (100 MHz, CD$_3$OD): δ156.9, 146.4, 140.8, 129.8, 129.5, 128.3, 127.9, 123.5, 120.1, 70.5, 67.3, 60.6, 54.9, 54.5, 49.6, 48.9, 47.2, 42.0, 36.5, 34.5, 29.8; IR (neat, cm$^{-1}$): 3310, 2941, 1642, 1154, 748; MS (EI): m/z 428 (M$^+$), 132 (100%); HRMS (EI): calcd for C$_{24}$H$_{26}$C$_{12}$N$_2$O (M$^+$) 428.1422, found 428.1416.

Example 6

[Chemical Formula 22]

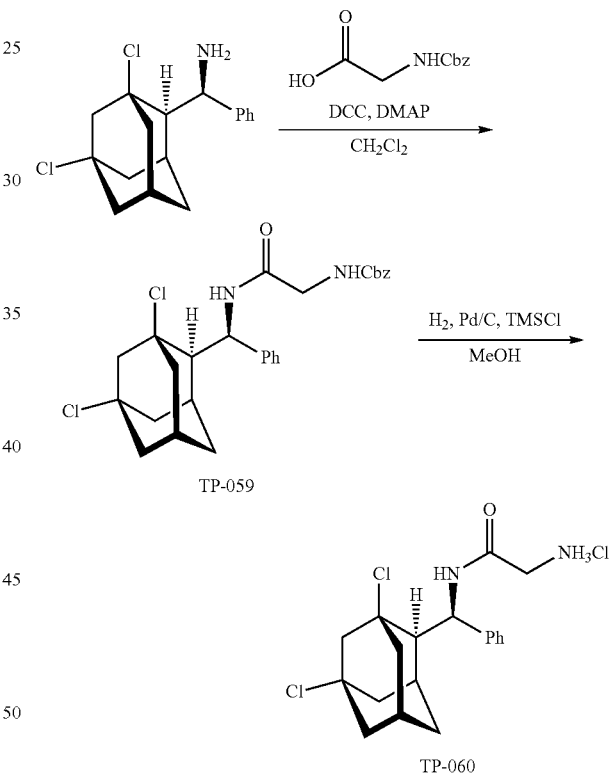

TP-059

TP-060

To a solution of (R)-((1S,2R,3S,5S,7R)-1,5-dichloroadamantan-2-yl)(phenyl)methanamine (49.1 mg, 0.158 mmol) in dichloromethane (2 mL), benzyloxycarbonylglycine (prepared according to the method described in F.-T. Tsai, et al., J. Am. Chem. Soc. 2016, 138, 4626.) (50 mg, 0.24 mmol), N,N'-dicyclohexylcarbodiimide (DCC, 49 mg, 0.24 mmol), and N,N-dimethyl-4-aminopyridine (DMAP, 2 mg, 0.02 mmol) were added under cooling with ice. After stirring at room temperature for 15 minutes, distilled water was added to the reaction solution, and the mixture was extracted with diethyl ether. The resultant organic layer was washed with saturated saline and dried over MgSO$_4$. The solvent was distilled off under reduced pressure, and the residues were subjected to silica gel column chromatography (hexane:

ethyl acetate=2:1) to obtain benzyl (2-(((R)-((1S,2R,3S,5S,7R)-1,5-dichloroadamantan-2-yl)(phenyl)methyl)amino)-2-oxoethyl)carbamate (TP-059, 55.11 mg, 69%) as a white solid.

$[\alpha]_D^{25}$=+73.1 (c=0.621, CHCl$_3$); 1H-NMR (400 MHz, CDCl$_3$): δ7.36-7.23 (m, 10H), 6.52 (br, 1H), 5.52 (dd, J=9.8, 8.8 Hz, 1H), 5.36 (br, 1H), 5.10 (s, 2H), 3.78 (dd, J=16.3, 5.9 Hz, 1H), 3.70 (dd, J=16.3, 5.9 Hz, 1H), 2.54-2.46 (m, 4H), 2.37 (br s, 1H), 2.15-2.05 (m, 4H), 1.88-1.78 (m, 2H), 1.31 (m, 1H); $^{13}$C-NMR (100 MHz, CDCl$_3$): δ167.7, 156.8, 143.5, 136.0, 128.64, 128.61, 128.4, 128.0, 127.4, 127.2, 68.8, 67.3, 65.9, 59.1, 53.3, 52.9, 47.7, 45.9, 45.1, 40.8, 35.1, 32.8, 28.8; IR (neat, cm$^{-1}$): 3306, 2938, 1712, 1655, 1528, 1262; MS (EI): m/z 392 (M$^+$-C$_7$H$_8$O), 189 (100%); HRMS (EI): calcd for C$_{20}$H$_{22}$Cl$_2$N$_2$O$_2$ (M$^+$-C$_7$H$_8$O) 392.1058, found 392.1043.

To a solution of 2-amino-N—((R)-((1S,2R,3S,5S,7R)-1,5-dichloroadamantan-2-yl)(phenyl)methyl)acetamide (TP-059, 82.8 mg, 0.165 mmol) in methanol (1.5 mL), chlorotrimethylsilane (104 μL, 0.83 mmol) and palladium 10% on carbon (10 mg) were added. After stirring under hydrogen atmosphere at room temperature overnight, the reaction solution was filtrated through Celite®), and the solvent was distilled off under reduced pressure to obtain TP-060 (70.6 mg, quant.) as a yellow solid.

$[\alpha]_D^{25}$=+79.5 (c=0.824, CHCl$_3$); $^1$H-NMR (400 MHz, DMSO-d$_6$): δ9.13 (br 1H), 8.12 (br, 2H), 7.38 (d, J=7.2 Hz, 2H), 7.26 (dd, J=7.2, 7.0 Hz, 2H), 7.18 (t, J=7.0 Hz, 1H), 5.35 (m, 1H), 3.56 (br d, J=15.0 Hz, 1H), 3.46 (br d, J=15.0 Hz, 1H), 2.70-2.59 (m, 2H), 2.43-2.37 (m, 2H), 2.24 (br s, 1H), 2.14 (br s, 2H), 2.05 (br s, 2H), 1.86 (br d, J=12.1 Hz, 1H), 1.73-1.70 (m, 2H), 1.35 (br d, J=13.0 Hz, 1H); $^{13}$C-NMR (100 MHz, DMSO-d$_6$): δ164.4, 144.1, 128.0, 127.8, 126.7, 70.4, 67.7, 58.4, 52.3, 52.2, 46.6, 45.2, 40.2, 34.6, 32.6, 28.0; IR (neat, cm$^{-1}$): 3210, 2937, 1684, 1558; HRMS (ESI): calcd for C$_{19}$H$_{25}$Cl$_2$N$_2$O(M$^+$-Cl) 367.1338, found 367.1331.

Example 7

[Chemical Formula 23]

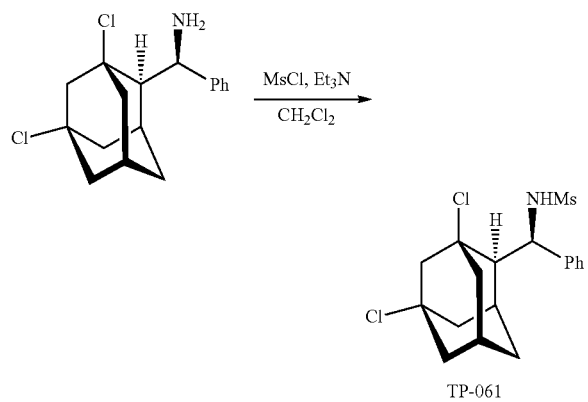

TP-061

To a solution of (R)-((1S,2R,3S,5S,7R)-1,5-dichloroadamantan-2-yl)(phenyl)methanamine (35.2 mg, 0.114 mmol) in dichloromethane (1 mL), methanesulfonyl chloride (10.5 μL, 0.14 mmol) and triethylamine (24 μL, 0.17 mmol) were added under cooling with ice. After stirring at the same temperature for 30 minutes, a saturated solution of NaHCO$_3$ was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=2:1) to obtain N—((R)-((1S,2R,3S,5S,7S)-1,5-dichloroadamantan-2-yl)(phenyl)methyl)methanesulfonamide (TP-061, 35.8 mg, 81%) as a white solid.

$[\alpha]_D^{25}$=+47.7 (c=0.380, CHCl$_3$); $^1$H-NMR (400 MHz, CDCl$_3$): δ7.39-7.28 (m, 5H), 4.88 (m, 2H), 2.67 (br s, 1H), 2.58 (br d, J=12.6 Hz, 1H), 2.47-2.37 (m, 7H), 2.21-2.06 (m, 5H), 1.90 (br d, J=13.0 Hz, 1H), 1.46 (br d, J=14.0 Hz, 1H); $^{13}$C-NMR (100 MHz, CDCl$_3$): δ143.0, 129.0, 128.0, 127.2, 69.0, 65.8, 59.3, 58.4, 54.5, 47.7, 45.9, 41.7, 40.7, 34.7, 32.9, 28.5; IR (neat, cm$^{-1}$): 3263, 2941, 1456, 1319, 1157; HRMS (ESI): calcd for C$_{18}$H$_{23}$Cl$_2$NNaO$_2$S (M$^+$+Na) 410.0724, found 410.0719.

Example 8

[Chemical Formula 24]

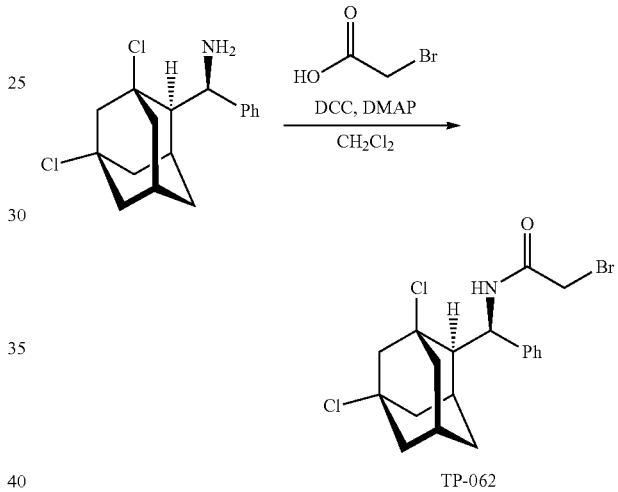

TP-062

To a solution of (R)-((1S,2R,3S,5S,7R)-1,5-dichloroadamantan-2-yl)(phenyl)methanamine (51.4 mg, 0.166 mmol) in dichloromethane (2 mL), bromoacetic acid (27 mg, 0.20 mmol), N,N'-dicyclohexylcarbodiimide (DCC, 41 mg, 0.20 mmol), and N,N-dimethyl-4-aminopyridine (DMAP, 2 mg, 0.02 mmol) were added under cooling with ice. After stirring at room temperature overnight, distilled water was added to the reaction solution, and the mixture was extracted with diethyl ether. The resultant organic layer was washed with saturated saline and dried over MgSO$_4$. The solvent was distilled off under reduced pressure, and the residues were subjected to silica gel column chromatography (hexane:ethyl acetate=4:1 to 2:1) to obtain 2-bromo-N—((R)-((1S,2R,3S,5S,7R)-1,5-dichloroadamantan-2-yl)(phenyl)methyl)acetamide (TP-062, 64.3 mg, 90%) as a white solid.

$[\alpha]_D^{28}$=+84.9 (c=0.256, CHCl$_3$); $^1$H-NMR (400 MHz, CDCl$_3$): δ7.36-7.27 (m, 5H), 6.82 (br d, J=9.3 Hz, 1H), 5.53 (dd, J=9.3, 9.3 Hz, 1H), 3.87 (d, J=13.7 Hz, 1H), 3.81 (d, J=13.7 Hz, 1H), 2.62-2.33 (m, 5H), 2.21 (br s, 1H), 2.18-2.08 (m, 4H), 1.90 (br d, J=12.7 Hz, 1H), 1.84 (br d, J=13.7 Hz, 1H), 1.45 (br d, J=13.7 Hz, 1H); $^{13}$C-NMR (100 MHz, CDCl$_3$): δ163.8, 142.9, 128.8, 127.6, 127.1, 68.7, 65.7, 59.1, 53.7, 53.3, 47.8, 45.9, 40.8, 35.1, 32.7, 29.6, 29.0; IR (neat, cm$^{-1}$): 3276, 2942, 1647; MS (EI): m/z 350 (M$^+$-Br), 226 (100%); HRMS (EI): calcd for C$_{19}$H$_{22}$C$_2$NO (M$^+$-Br) 350.1078, found 350.1075.

Example 9

[Chemical Formula 25]

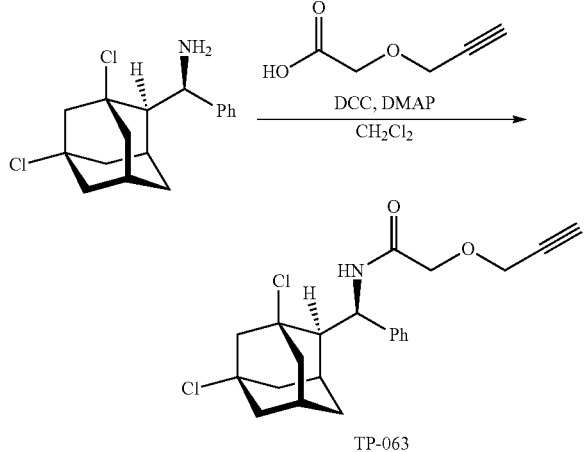

To a solution of (R)-((1S,2R,3S,5S,7R)-1,5-dichloroadamantan-2-yl)(phenyl)methanamine (21.0 mg, 0.0678 mmol) in dichloromethane (1 mL), 2-(2-propynyloxy)acetic acid (prepared according to the method described in X. Zhang, et al., Green Chem. 2011, 13, 397.) (15 mg, 0.13 mmol), N,N'-dicyclohexylcarbodiimide (DCC, 20 mg, 0.097 mmol), and N,N-dimethyl-4-aminopyridine (DMAP, 1 mg, 0.008 mmol) were added under cooling with ice. After stirring at room temperature for 6 hours, distilled water was added to the reaction solution, and the mixture was extracted with diethyl ether. The resultant organic layer was washed with saturated saline and dried over MgSO$_4$. The solvent was distilled off under reduced pressure, and the residues were subjected to silica gel column chromatography (hexane:ethyl acetate=4:1 to 2:1) to obtain N—((R)-((1S,2R,3S,5S,7R)-1,5-dichloroadamantan-2-yl)(phenyl)methyl)-2-(prop-2-yn-1-yloxy)acetamide (TP-063, 19.25 mg, 70%) as a white solid.

$[\alpha]_D^{20}$=+96.2 (c=0.283, CHCl$_3$); $^1$H-NMR (400 MHz, CDCl$_3$): δ7.33-7.25 (m, 5H), 6.75 (br d, J=10.1 Hz, 1H), 5.60 (dd, J=10.1, 8.7 Hz, 1H), 4.16 (s, 2H), 4.08 (d, J=14.8 Hz, 1H), 3.93 (d, J=14.8 Hz, 1H), 2.62-2.57 (m, 2H), 2.53-20.45 (m, 3H), 2.38 (m, 1H), 2.33 (br s, 1H), 2.17-2.08 (m, 4H), 1.91-1.88 (m, 2H), 1.41 (br d, J=13.5 Hz, 1H); $^{13}$C-NMR (100 MHz, CDCl$_3$): δ167.5, 143.5, 128.7, 127.4, 127.3, 78.0, 75.9, 69.1, 68.7, 65.9, 59.2, 58.7, 53.3, 52.2, 47.8, 46.0, 40.8, 35.2, 32.9, 28.9; IR (neat, cm$^{-1}$): 3295, 2938, 1658, 1528, 1107; MS (EI): m/z 404 (M$^+$-H), 202 (100%); HRMS (EI): calcd for C$_{22}$H$_{24}$C$_{12}$NO$_2$ (M$^+$-H) 404.1184, found 404.1201.

Example 10

[Chemical Formula 26]

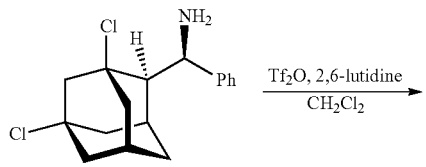

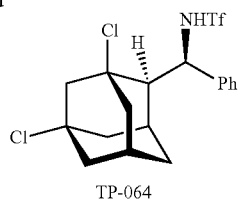

TP-064

To a solution of (R)-((1S,2R,3S,5S,7R)-1,5-dichloroadamantan-2-yl)(phenyl)methanamine (24.2 mg, 0.0781 mmol) in dichloromethane (1 mL), 2,6-lutidine (27 μL, 0.23 mmol) and trifluoromethanesulfonic anhydride (15.7 μL, 0.094 mmol) were added at −78° C. After stirring at the same temperature for 10 minutes, a saturated aqueous solution of NaHCO$_3$ was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=15:1 to 8:1) to obtain N—((R)-((1S,2R,3S,5S,7R)-1,5-dichloroadamantan-2-yl)(phenyl)methyl)-1,1,1-trifluoromethanesulfonamide (TP-064, 27.8 mg, 81%) as a white solid.

$[\alpha]_D^{29}$=+54.1 (c=0.494, CHCl$_3$); $^1$H-NMR (400 MHz, CDCl$_3$): δ7.37-7.25 (m, 5H), 5.42 (br s, 1H), 5.01 (br s, 1H), 2.61 (br s, 1H), 2.48-2.44 (m, 4H), 2.36 (br s, 1H), 2.23-2.03 (m, 5H), 1.90 (br d, J=12.7 Hz, 1H), 1.50 (br d, J=13.7 Hz, 1H); $^{13}$C-NMR (100 MHz, CDCl$_3$): δ141.2, 128.8, 128.4, 127.0, 120.0 (q, J=321.7 Hz), 68.6, 65.3, 60.4, 59.3, 55.0, 47.7, 45.8, 40.5, 34.9, 32.7, 28.5; IR (neat, cm$^{-1}$): 3263, 2950, 1457, 1364, 1196; MS (EI): m/z 441 (M$^+$), 238 (100%); HRMS (EI): calcd for C$_{18}$H$_{20}$Cl$_2$F$_3$NO$_2$S (M) 441.0544, found 441.0521.

Example 11

[Chemical Formula 27]

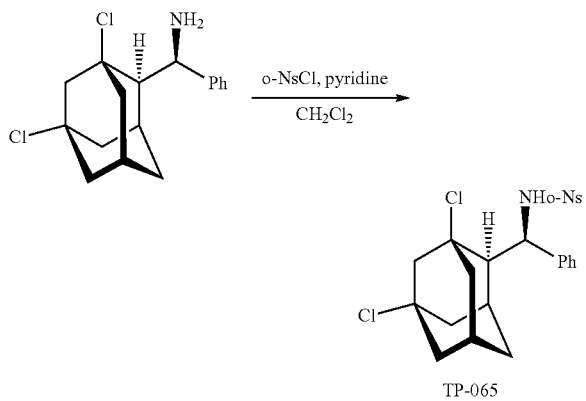

To a solution of (R)-((1S,2R,3S,5S,7R)-1,5-dichloroadamantan-2-yl)(phenyl)methanamine (26.1 mg, 0.0841 mmol) in dichloromethane (1 mL), pyridine (14 μL, 0.19 mmol) and 2-nitrobenzenesulfonyl chloride (22 mg, 0.10 mmol) were added under cooling with ice. After stirring at the same temperature for 3 hours, distilled water was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=8:1 to 4:1) to obtain N—((R)-((1S,2R,3S,5S,7R)-1,5-dichloroadamantan-2-yl)(phenyl)methyl)-2-nitrobenzenesulfonamide (TP-065, 17.1 mg, 41%) as a white solid.

$[\alpha]_D^{29}$=+202.4 (c=0.290, CHCl$_3$); $^1$H-NMR (400 MHz, CDCl$_3$): δ7.80 (d, J=7.8 Hz, 1H)), 7.61 (d, J=7.3 Hz, 1H), 7.51-7.44 (m, 2H), 7.00-6.93 (m, 5H), 5.99 (br d, J=10.4 Hz, 1H), 4.97 (dd, J=10.4, 7.8 Hz, 1H), 2.78 (br s, 1H), 2.49 (br d, J=12.2 Hz, 1H), 2.46-2.41 (m, 4H), 2.22-2.10 (m, 5H), 1.91 (br d, J=12.1 Hz, 1H), 1.55 (br d, J=13.2 Hz, 1H); $^{13}$C-NMR (100 MHz, CDCl$_3$): δ146.7, 140.8, 134.5, 132.9, 132.7, 131.0, 128.1, 127.4, 127.2, 125.2, 69.0, 656.8, 59.5, 54.5, 47.6, 46.0, 40.8, 34.7, 32.9, 38.7; IR (neat, cm$^{-1}$): 3223, 2940, 1537, 1168; HRMS (ESI): calcd for C$_{23}$H$_{24}$Cl$_2$N$_2$NaO$_4$S (M$^+$+Na) 517.0732, found 517.0721.

Example 12

[Chemical Formula 28]

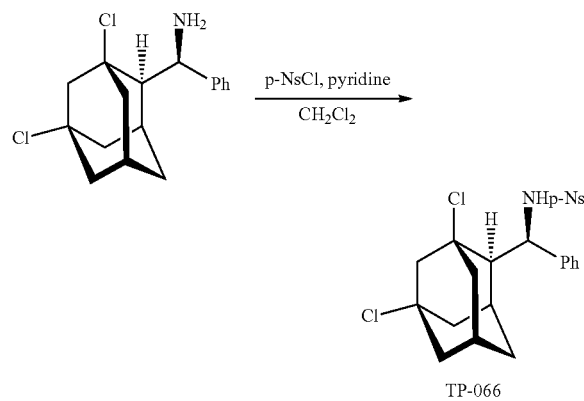

To a solution of (R)-((1S,2R,3S,5S,7R)-1,5-dichloroadamantan-2-yl)(phenyl)methanamine (11.7 mg, 0.0363 mmol) in dichloromethane (1 mL), pyridine (6.0 μL, 0.073 mmol) and 4-nitrobenzenesulfonyl chloride (10 mg, 0.044 mmol) were added under cooling with ice. After stirring at the same temperature for 2 hours, distilled water was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=8:1 to 4:1) to obtain N—((R)-((1S,2R,3S,5S,7R)-1,5-dichloroadamantan-2-yl)(phenyl)methyl)-4-nitrobenzenesulfonamide (TP-066, 11.3 mg, 63%) as a white solid.

$[\alpha]_D^{29}$=+21.4 (c=0.253, CHCl$_3$); $^1$H-NMR (400 MHz, CDCl$_3$): δ7.98 (d, J=8.5 Hz, 2H), 7.61 (d, J=8.5 Hz, 2H), 7.03-6.97 (m, 3H), 6.86 (d, J=7.3 Hz, 1H), 5.17 (m, 1H), 4.79 (dd, J=9.8, 85.3 Hz, 1H), 2.70 (br s, 1H), 2.52 (br d, J=12.7 Hz, 1H), 2.45-2.39 (m, 4H), 2.20-2.09 (m, 5H), 1.90 (br d, J=12.2 Hz, 1H), 1.52 (br d, J=13.2 Hz, 1H); $^{13}$C-NMR (100 MHz, CDCl$_3$): δ149.5, 145.8, 141.5, 128.4, 128.2, 127.6, 126.9, 123.7, 68.9, 65.5, 59.2, 58.8, 54.7, 47.7, 45.9, 40.7, 34.8, 32.8, 28.6; IR (neat, cm$^{-1}$1): 3279, 2939, 1159; HRMS (ESI): calcd for C$_{23}$H$_{24}$Cl$_2$N$_2$NaO$_4$S (M$^+$+Na) 517.0732, found 517.0728.

Example 13

[Chemical Formula 29]

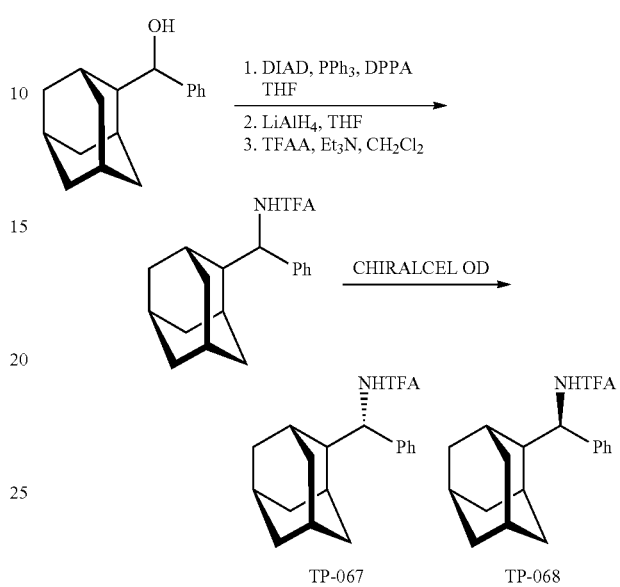

To a solution of 2-adamantyl(phenyl)methanol (prepared according to the method described in N. Arunkumar, et al., J. Org. Chem. 2002, 67, 8339; 944 mg, 3.90 mmol), diphenylphosphoryl azide (DPPA, 921 μL, 4.29 mmol) and triphenylphosphine (1.12 g, 4.29 mmol) in THF (20 mL), diisopropyl azodicarboxylate (DIAD, 841 μL, 4.29 mmol) was added under cooling with ice. After stirring at room temperature for 2 hours, the solvent was distilled off under reduced pressure. The residues were subjected to silica gel column chromatography (hexane:ethyl acetate=15:1) to obtain a crude azide. To a solution of the resultant crude azide in THF (20 mL), LiAlH$_4$ (222 mg, 5.84 mmol) was added under cooling with ice. After the temperature was slowly elevated to room temperature, followed by stirring overnight, ammonia water was added to the reaction solution under cooling with ice. The reaction solution was filtrated through Celite®, and the solvent was distilled off under reduced pressure. The residues were subjected to silica gel column chromatography (chloroform:chloroform/methanol=10:1) to obtain a crude amine. To a solution of the resultant crude amine in dichloromethane (15 mL), triethylamine (1.0 mL, 7.8 mmol) and trifluoroacetic anhydride (TFAA, 0.83 mL, 5.8 mmol) were added under cooling with ice. After stirring at the same temperature for 10 minutes, a saturated aqueous solution of NaHCO$_3$ was added, and the mixture was extracted with dichloromethane. The resultant organic layer was dried over MgSO$_4$. The solvent was distilled off under reduced pressure, and the residues were subjected to silica gel column chromatography (hexane:ethyl acetate=15:1) to obtain N-(2-adamantyl(phenyl)methyl)2,2,2-trifluoroacetamide (379 mg, 29%). Parts of the product were subjected to preparative HPLC (CHIRALCEL OD) to obtain N—((S)-((1S,3S,5S,7S)-adamantan-2-yl)(phenyl)methyl)-2,2,2-trifluoroacetamide (TP-067) and N—((R)-((1R,3R,5R,7R)-adamantan-2-yl)(phenyl)methyl)-2,2,2-trifluoroacetamide (TP-068).

$^1$H-NMR (400 MHz, CDCl$_3$): δ7.38-7.29 (m, 5H), 6.36 (br d, J=8.9 Hz, 1H), 5.30 (dd, J=11.4 Hz, 8.9 Hz, 1H), 2.12-1.90 (m, 7H), 1.77-1.72 (m, 4H), 1.69-1.58 (m, 2H), 1.44 (br d, J=11.1 Hz, 1H), 1.34 (br s, 1H); $^{13}$C-NMR (100 MHz, CDCl$_3$): δ156.4 (q, J=36.6 Hz), 139.7, 129.0, 128.1, 127.0, 115.9 (q, J=288.4 Hz), 55.0, 49.0, 38.8, 38.7, 37.9, 31.6, 31.4, 28.9, 28.7, 27.7, 27.4; IR (neat, cm$^{-1}$): 3295, 2911, 1695, 1557, 1186; MS (EI): m/z 337 (M$^+$), 135 (100%); HRMS (EI): calcd for C$_{19}$H$_{22}$F$_3$NO (M$^+$) 337.1653, found 337.1662.

Example 14

[Chemical Formula 30]

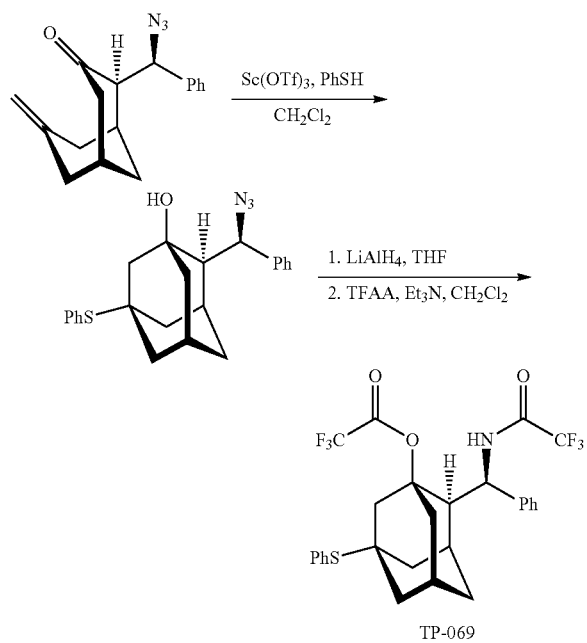

TP-069

To a solution of (1S,2R,5R)-2-((R)-azido(phenyl)methyl)-7-methylenebicyclo[3.3.1.]nonan-3-one (88.1 mg, 0.315 mmol) in dichloromethane (3 mL), thiophenol (97 μL, 0.95 mmol) and scandium trifluoromethanesulfonate (8 mg, 0.016 mmol) were added under cooling with ice. After stirring at room temperature for 24 hours, a saturated aqueous solution of NaHCO$_3$ was added under cooling with ice, and the mixture was extracted with dichloromethane. The resultant organic layer was dried over MgSO$_4$, and the solvent was distilled off under reduced pressure. The residues were subjected to silica gel column chromatography (hexane:ethyl acetate=1:10 to 1:4) to obtain (1S,2R,3S,5S,7S)-2-((R)-azido(phenyl)methyl)-5-(phenylthio)adamantan-1-ol (50.7 mg, 41%) as a colorless oily product.

To a solution of the resultant azide compound (31.5 mg, 0.085 mmol) in THF (1 mL), LiAlH$_4$ (5 mg, 0.13 mmol) was added under cooling with ice. After stirring at room temperature for 5 hours, ammonia water was added to the reaction solution under cooling with ice. The reaction solution was filtrated through Celite®, and the solvent was distilled off under reduced pressure. To the residues, dichloromethane (1 mL) was added, and then triethylamine (56 μL, 0.4 mmol) and trifluoroacetic anhydride (TFAA, 34 μL, 0.24 mmol) were added under cooling with ice. After stirring at the same temperature 40 minutes, a saturated aqueous solution of NaHCO$_3$ was added under cooling with ice, and the mixture was extracted with dichloromethane. The resultant organic layer was dried over MgSO$_4$. The solvent was distilled off under reduced pressure, and the residues were subjected to silica gel column chromatography (hexane:ethyl acetate=1:10) to obtain TP-069 (23.6 mg, 52%) as a white solid.

[α]$_D^{23}$=+50.1 (c=0.357, CHCl$_3$); $^1$H-NMR (400 MHz, CDCl$_3$): δ7.48-7.46 (m, 2H), 7.45-7.28 (m, 6H), 7.23-7.22 (m, 2H), 6.34 (br d, J=9.5 Hz, 1H), 5.42 (dd, J=11.0, 9.5 Hz, 1H), 3.08 (br d, J=11.0 Hz, 1H), 2.68 (br d, J=11.7 Hz, 1H), 2.37-2.36 (m, 3H), 1.96-1.79 (m, 7H), 1.36 (br d, J=12.2 Hz, 1H); $^{13}$C-NMR (100 MHz, CDCl$_3$): δ156.0 (q, J=37.1 HZ), 154.9 (q, J=42.1 Hz), 139.3, 137.7, 129.3, 129.2, 129.1, 128.7, 128.6, 127.0, 116.3 (q, J=288.9 Hz), 115.7 (q, J=288.1 Hz), 87.2, 53.4, 48.4, 48.1, 46.8, 43.1, 42.1, 36.0, 33.8, 31.0, 29.0; IR (neat, cm$^{-1}$): 3302, 2933, 1776, 1697, 1552, 1222, 1172, 1148; MS (EI): m/z 557 (M$^+$), 202 (100%); HRMS (EI): calcd for C$_{27}$H$_{25}$F$_6$NO$_3$S (M$^+$) 557.1459, found 557.1461.

Example 15

[Chemical Formula 31]

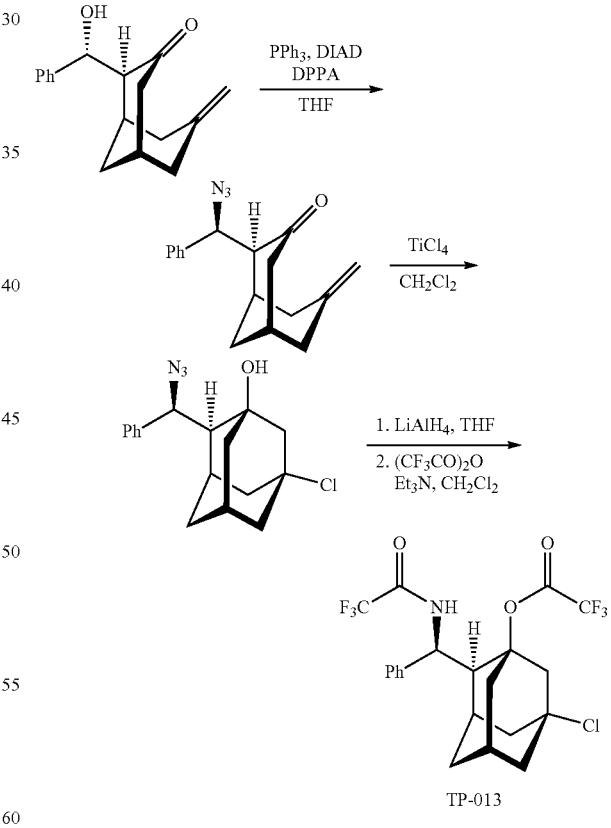

TP-013

To a solution of (1R,2S,5S)-2-((R)-hydroxy(phenyl)methyl)-7-methylenebicyclo[3.3.1]nonan-3-one (prepared according to the method described in *J. Am. Chem. Soc.* 2014, 136, 17591-17600; 750 mg, 2.9 mmol), diphenylphosphoryl azide (DPPA, 820 μL, 3.81 mmol) and triphenylphosphine (1.20 g, 4.4 mmol) in THF (15 mL), diisopropyl azodicarboxylate (DIAD, 2.2 mL, 4.4 mmol) was added under cooling with ice. After stirring at the same temperature for 1 hour, the solvent was distilled off under reduced pressure. To the residues, dichloromethane (15 mL) was added, and then TiCl$_4$ (820 µL, 2.3 mmol) was added under cooling with ice. After stirring at room temperature for 4 hours, a saturated aqueous solution of NaHCO$_3$ was added under cooling with ice. The reaction solution was filtrated through Celite®, and the filtrate was extracted with diethyl ether. The resultant organic layer was washed with saturated saline and dried over MgSO$_4$. The solvent was distilled off under reduced pressure, and the residues were subjected to silica gel column chromatography (hexane:ethyl acetate=10:1) to obtain (1R,2S,3R,5R,7R)-2-((S)-azido(phenyl)methyl)-5-chloroadamantan-1-ol (756 mg, 92%) as a white solid.

To a solution of the resultant azide compound (750 mg, 2.67 mmol) in THF (14 mL), LiAlH$_4$ (300 mg, 8.00 mmol) was added under cooling with ice. After stirring at the same temperature for 1 hour, ammonia water was added to the reaction solution. The reaction solution was filtrated through Celite®, and the solvent was distilled off under reduced pressure. To the residues, dichloromethane (15 mL) was added, and then triethylamine (2.2 mL, 16.0 mmol) and trifluoroacetic anhydride (TFAA, 1.2 mL, 8.0 mmol) were added under cooling with ice. After stirring at room temperature overnight, a saturated aqueous solution of NaHCO$_3$ was added, and the mixture was extracted with dichloromethane. The resultant organic layer was dried over MgSO$_4$. The solvent was distilled off under reduced pressure, and the residues were subjected to silica gel column chromatography (hexane:ethyl acetate=15:1) to obtain TP-013 (871 mg, 56%) as a white solid.

mp 83-85° C. (colorless needle-like crystal, n-hexane-Et$_2$O); [α]$_D^{31}$=-84.1 (c=1.08, CHCl$_3$); $^1$H-NMR (400 MHz, CDCl$_3$): δ7.35-7.27 (m, 5H), 6.63 (d, J=11.1 Hz, 1H), 5.44 (t, J=10.4 Hz, 1H), 3.26 (d, J=11.1 Hz, 1H), 2.99 (d, J=11.1 Hz, 1H), 2.45-2.41 (m, 3H), 2.26-2.13 (m, 5H), 1.96 (br d, J=12.4 Hz, 2H), 1.47 (br d, J=14.0 Hz, 1H); $^{13}$C-NMR (100 MHz, CDCl$_3$): δ156.2 (q, J=37.4 Hz), 154.9 (q, J=42.3 Hz), 139.1, 129.2, 128.7, 127.1, 115.8 (q, J=288.1 Hz), 113.3 (q, J=287.3 Hz), 86.6, 65.1, 53.4, 50.2, 48.0, 46.9, 46.1, 35.6, 34.6, 31.7, 28.5; IR (neat, cm$^{-1}$): 3296, 2945, 1775, 1698; MS (EI): m/z 483 (M$^+$), 202 (100%); HRMS (EI): calcd for C$_{21}$H$_{20}$ClF$_6$NO$_3$ (M$^+$) 483.1036, found 483.1046.

Example 16

[Chemical Formula 32]

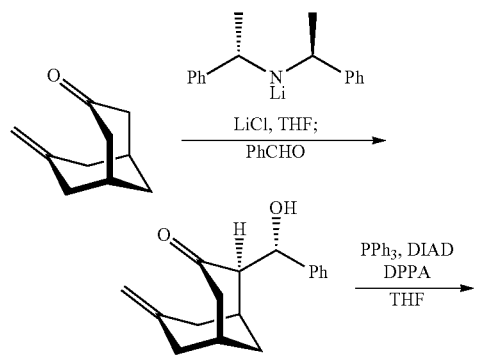

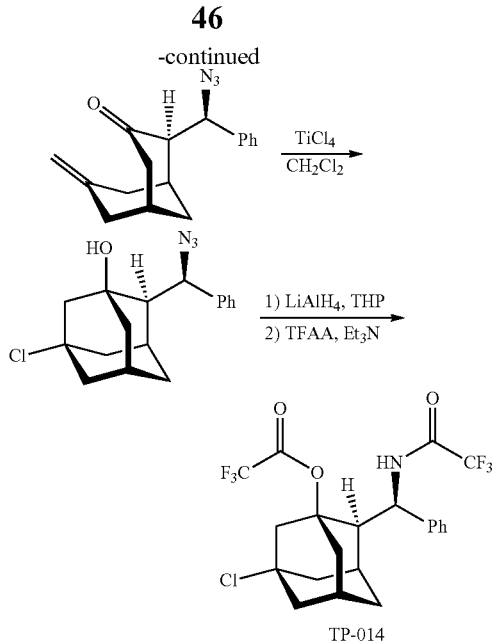

TP-014

To a solution of bis((S)-1-phenylethyl)amine (10.0 mL, 44 mmol) and lithium chloride (3.4 g, 80 mmol) in THF (100 mL), a solution of n-butyllithium in hexane (1.56 M, 28.2 mL, 44 mmol) was added dropwise under cooling with ice. After stirring at the same temperature for 30 minutes, the reaction solution was cooled down to −78° C. To the reaction mixture, a solution of 7-methylenebicyclo[3.3.1]nonan-3-one (6.00 g, 40 mmol) in THF (60 mL) was added by cannulation. After stirring for 1 hour, a solution of benzaldehyde (6.1 mL, 60 mmol) in THF (40 mL) was added by cannulation. After stirring for 2 hours, acetic acid and a saturated aqueous solution of ammonium chloride were added in sequence to the reaction solution, and then the mixture was extracted with diethyl ether. The resultant organic layer was washed with saturated saline and dried over MgSO$_4$. The solvent was distilled off under reduced pressure, and the residues were subjected to silica gel column chromatography (hexane:ethyl acetate=4:1) to obtain (1S,2R,5R)-2-((S)-hydroxy(phenyl)methyl)-7-methylenebicyclo[3.3.1]nonan-3-one (8.3 g, 81%) as a white solid. The solid was recrystallized from diethyl ether to afford a colorless needle-like crystal.

mp 122° C.; [α]$_D^{21}$=-17.9 (c=0.32, CHCl$_3$); $^1$H-NMR (400 MHz, CDCl$_3$): δ7.38-7.25 (m, 5H), 4.79 (d, J=1.8 Hz, 1H), 4.76 (d, J=1.8 Hz, 1H), 4.71 (d, J=6.8 Hz, 1H), 2.90 (s, 1H), 2.64 (dd, J=15.7, 6.8 Hz, 1H), 2.48-2.18 (m, 6H), 2.01 (br d, J=14.3 Hz, 1H); $^{13}$C-NMR (100 MHz, CDCl$_3$): δ211.0, 141.6, 128.8, 127.6, 114.8, 74.6, 62.7, 45.7, 42.2, 41.3, 32.4, 31.9, 28.4; IR (neat, cm$^{-1}$): 3390, 1711; MS (EI): m/z 256 (M$^+$), 95 (100%); HRMS (EI): calcd for C$_{17}$H$_{20}$O$_2$ (M$^+$) 256.1463, found 256.1450.

To a solution of (1S,2R,5R)-2-((S)-hydroxy(phenyl)methyl)-7-methylenebicyclo[3.3.1]nonan-3-one (2.00 g, 7.5 mmol), DPPA (2.3 mL, 11 mmol) and triphenylphosphine (3.0 g, 11 mmol) in THF (38 mL), DIAD (2.2 mL, 11 mmol) was added under cooling with ice. After stirring at the same temperature for 1 hour, the solvent was distilled off under reduced pressure. To the residues, dichloromethane (38 mL) was added, and then TiCl$_4$ (0.8 mL, 7.5 mmol) was added under cooling with ice. After stirring at room temperature for 4 hours, a saturated aqueous solution of NaHCO$_3$ was added under cooling with ice. The reaction solution was filtrated through Celite®, and the filtrate was extracted with diethyl ether. The resultant organic layer was washed with saturated saline and dried over MgSO$_4$. The solvent was distilled off under reduced pressure, and tetrahydropyran (THP, 40 mL) was added to the residues. To the mixture, LiAlH$_4$ (430 mg, 11 mmol) was added under cooling with ice. After stirring at the same temperature for 30 minutes, ammonia water was added to the reaction solution. The reaction solution was filtrated through Celite®, and the solvent was distilled off under reduced pressure. To the residues, dichloromethane (40 mL) was added, and then triethylamine (6.3 mL, 45 mmol) and TFAA (3.2 mL, 23 mmol) were added under cooling with ice. After stirring at room temperature overnight, a saturated aqueous solution of NaHCO$_3$ was added, and the mixture was extracted with dichloromethane. The resultant organic layer was dried over MgSO$_4$. The solvent was distilled off under reduced pressure, and the residues were subjected to silica gel column chromatography (hexane:ethyl acetate=15:1) to obtain a crude product as a white solid. The solid was recrystallized from diethyl ether/hexane to afford TP-014 (1.27 g, 35%) as a white solid.

mp 89° C.; $[\alpha]_D^{21}$=+89.1 (c=0.31, CHCl$_3$); $^1$H-NMR (400 MHz, CDCl$_3$): δ7.35-7.27 (m, 5H), 6.63 (d, J=11.1 Hz, 1H), 5.44 (t, J=10.4 Hz, 1H), 3.26 (d, J=11.1 Hz, 1H), 2.99 (d, J=11.1 Hz, 1H), 2.45-2.41 (m, 3H), 2.26-2.13 (m, 5H), 1.96 (br d, J=12.4 Hz, 2H), 1.47 (br d, J=14.0 Hz, 1H); $^{13}$C-NMR (100 MHz, CDCl$_3$): 5156.2 (q, J=37.4 Hz), 154.9 (q, J=42.3 Hz), 139.1, 129.2, 128.7, 127.1, 115.8 (q, J=288.1 Hz), 113.3 (q, J=287.3 Hz), 86.6, 65.1, 53.4, 50.2, 48.0, 46.9, 46.1, 35.6, 34.6, 31.7, 28.5; IR (neat, cm$^{-1}$): 3296, 2945, 1775, 1698; MS (EI): m/z 483 (M$^+$), 202 (100%); HRMS (EI): calcd for C$_{21}$H$_{20}$ClF$_6$NO$_3$ (M$^+$) 483.1036, found 483.1046; elemental analysis: calcd for C$_{21}$H$_{20}$ClF$_6$NO$_3$: C, 52.13; H, 4.17; N, 2.89. found C, 52.27; H, 4.18; N, 2.88.

Example 17

[Chemical Formula 33]

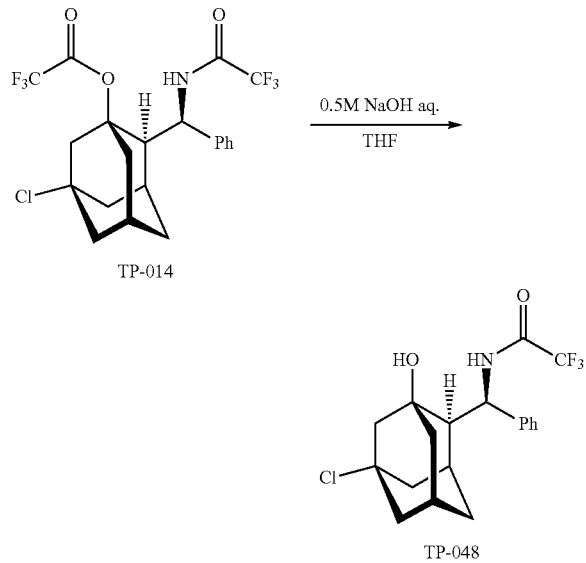

To a solution of TP-014 (84.7 mg, 0.175 mmol) in THF (2 mL), an aqueous solution of 0.5 M NaOH (1 mL) was added under cooling with ice. After stirring at the same temperature for 15 minutes, a saturated aqueous solution of NH$_4$Cl was added, and the mixture was extracted with ethyl acetate. The resultant organic layer was washed with saturated saline and dried over MgSO$_4$. The solvent was distilled off under reduced pressure, and the residues were subjected to silica gel column chromatography (hexane:ethyl acetate=8:1 to 4:1) to obtain TP-048 (65.5 mg, 96%) as a white solid.

$[\alpha]_D^{26}$=+109.2 (c=0.772, CHCl$_3$); $^1$H-NMR (400 MHz, CDCl$_3$): δ7.41-7.32 (m, 5H), 6.98 (br, 1H), 5.34 (t, J=9.7 Hz, 1H), 2.36-2.29 (m, 3H), 2.19-2.00 (m, 7H), 1.77 (br d, J=11.6 Hz, 1H), 1.41-1.33 (m, 2H); $^{13}$C-NMR (100 MHz, CDCl$_3$): δ156.2 (q, J=37.1), 140.5, 129.4, 128.6, 127.4, 115.8 (q, J=288.1 Hz), 72.3, 66.1, 56.7, 54.2, 52.4, 47.7, 46.3, 38.6, 34.4, 31.8, 28.8; IR (neat, cm$^{-1}$): 3553, 3297, 2940, 1698, 1552, 1208, 1183, 1165; MS (EI): m/z 387 (M$^+$), 202 (100%); HRMS (EI): calcd for C$_{19}$H$_{21}$ClF$_3$NO$_2$ (M$^+$) 387.1213, found 387.1196.

Example 18

[Chemical Formula 34]

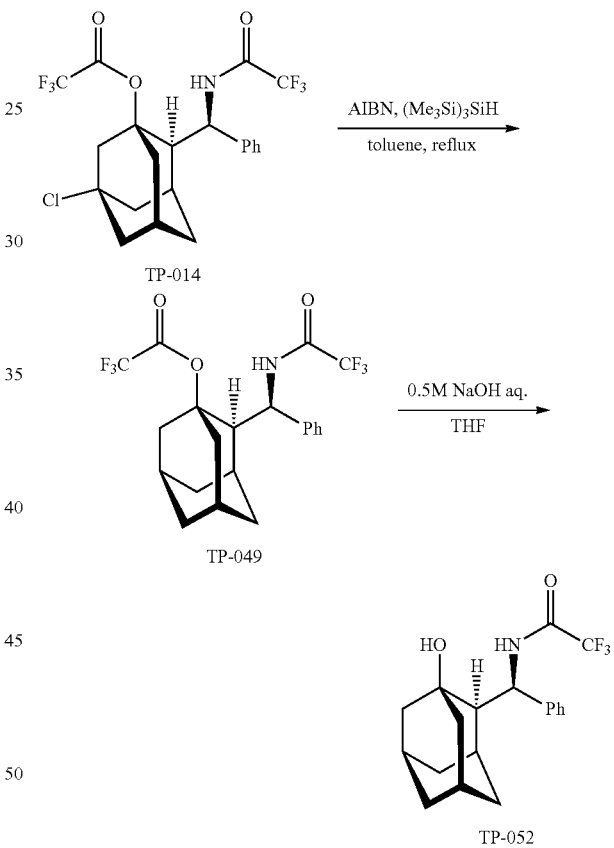

To a solution of TP-014 (30.0 mg, 0.062 mmol) in toluene (2 mL), tris(trimethylsilyl)silane (29 μL, 0.095 mmol) and azobisisobutyronitrile (AIBN, 2.0 mg, 0.012 mmol) were added at room temperature. After the mixture was refluxed under heating overnight, the solvent was distilled off under reduced pressure. The residues were subjected to silica gel column chromatography (hexane:ethyl acetate=15:1) to obtain TP-049 (23.0 mg, 83%) as a white solid.

$[\alpha]_D^{29}$=+106.4 (c=0.385, CHCl$_3$); $^1$H-NMR (400 MHz, CDCl$_3$): δ7.33-7.27 (m, 5H), 6.31 (br d, J=10.1 Hz, 1H), 5.50 (dd, J=10.9, 10.1 Hz, 1H), 3.20 (br d, J=10.9 Hz, 1H), 2.60 (br d, J=11.6 Hz, 1H), 2.45 (br d, J=12.1 Hz, 1H), 2.28-2.27 (m, 3H), 2.04-1.80 (m, 6H), 1.72 (br s, 2H); $^{13}$C-NMR (100 MHz, CDCl$_3$): δ156.0 (q, J=37.1 Hz), 155.1

(q, J=41.8 Hz), 139.8, 129.0, 128.4, 127.2, 115.8 (q, J=288.1 Hz), 113.5 (q, J=287.3 Hz), 87.5, 53.6, 49.4, 41.3, 37.2, 36.1, 33.0, 30.6, 30.4, 30.2; IR (neat, cm$^{-1}$): 3335, 2927, 1775, 1700, 1556, 1218, 1169; MS (EI): m/z 449 (M$^+$), 202 (100%); HRMS (EI): calcd for $C_{21}H_{21}F_3NO_3$ (M$^+$) 449.1426, found 449.1447.

To a solution of TP-049 (61.5 mg, 0.137 mmol) in THF (1.4 mL), an aqueous solution of NaOH (0.5 M, 0.5 mL) was added under cooling with ice. After stirring at the same temperature for 5 minutes, 2 M hydrochloric acid was added to the reaction solution, and the mixture was extracted with ethyl acetate. The resultant organic layer was washed with saturated saline and dried over MgSO$_4$. The solvent was distilled off under reduced pressure, and the residues were subjected to silica gel column chromatography (hexane:ethyl acetate=4:1 to 2:1) to obtain TP-052 (49.4 mg, quant.) as a white solid.

TP-052: $[\alpha]_D^{14}$=+130.7 (c=0.243, CHCl$_3$); $^1$H-NMR (400 MHz, CDCl$_3$): δ7.39-7.31 (m, 5H), 6.77 (br d, J=8.9 Hz, 1H), 5.40 (dd, J=9.7, 8.9 Hz, 1H), 2.32 (br d, J=9.7 Hz, 1H), 2.31-2.07 (m, 4H), 1.85-1.79 (m, 2H), 1.72-1.57 (m, 5H), 1.52-1.44 (m, 2H), 1.29 (br, 1H); $^{13}$C-NMR (100 MHz, CDCl$_3$): δ156.1 (q, 37.1 Hz), 140.7, 129.4, 128.5, 127.5, 115.9 (q, 288 Hz), 77.2, 54.3, 53.0, 50.5, 48.5, 41.4, 39.6, 39.4, 33.2, 30.6, 29.6; IR (neat, cm$^{-1}$): 3566, 3291, 2919, 1698, 1183; MS (EI): m/z 353 (M$^+$), 151 (100%); HRMS (EI): calcd for $C_{19}H_{22}F_3NO_2$ (M$^+$) 353.1603, found 353.1604.

Example 19

[Chemical Formula 35]

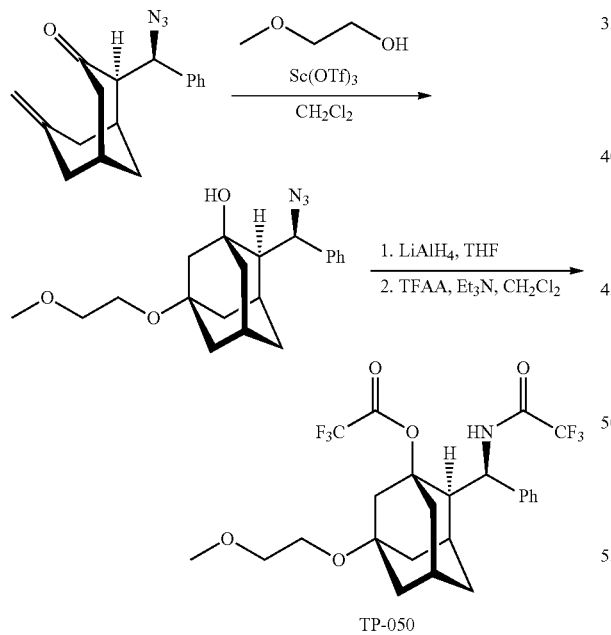

TP-050

To a solution of (S,2R,5R)-2-(R-azido(phenyl)methyl)-7-methylenebicyclo[3.3.1.]nonan-3-one (57.4 mg, 0.204 mmol) in dichloromethane (2 mL), 2-methoxyethanol (78 μL, 1.0 mmol) and scandium trifluoromethanesulfonate (5.0 mg, 0.01 mmol) were added in sequence under cooling with ice. After stirring at room temperature for 2 days, a saturated aqueous solution of NaHCO$_3$ was added under cooling with ice, and the mixture was extracted with dichloromethane. The resultant organic layer was dried over MgSO$_4$, and the solvent was distilled off under reduced pressure. The residues were subjected to silica gel column chromatography (hexane:ethyl acetate=1:2 to 1:1) to obtain (1S,2R,3S,5S,7S)-2-((R)-azido(phenyl)methyl)-5-(2-methoxyethoxy)adamantan-1-ol (41.2 mg, 56%) as a colorless oily product.

To a solution of the resultant azide compound (39.6 mg, 0.111 mmol) in THF (1 mL), LiAlH$_4$ (8.0 mg, 0.21 mmol) was added under cooling with ice. After the temperature was slowly elevated to room temperature, followed by stirring for 1 hour, the reaction solution was cooled with ice, and LiAlH$_4$ (8.0 mg, 0.21 mmol) was added. After stirring at room temperature for 1 hour, ammonia water was added to the reaction solution under cooling with ice. The reaction solution was filtrated through Celite®, the filtrate was dried over Na$_2$SO$_4$, and the solvent was distilled off under reduced pressure. To the residues, dichloromethane (1 mL) was added, and then triethylamine (77 μL, 0.56 mmol) and trifluoroacetic anhydride (TFAA, 47 μL, 0.33 mmol) were added under cooling with ice. After stirring at room temperature for 5 hours, a saturated aqueous solution of NaHCO$_3$ was added under cooling with ice, and the mixture was extracted with dichloromethane. The resultant organic layer was dried over MgSO$_4$. The solvent was distilled off under reduced pressure, and the residues were subjected to silica gel column chromatography (hexane:ethyl acetate=1:4 to 1:2) to obtain TP-050 (31.6 mg, 54%) as a colorless oily product.

$[\alpha]_D^{25}$=+72.1 (c=0.965, CHCl$_3$); $^1$H-NMR (400 MHz, CDCl$_3$): δ7.34-7.23 (m, 5H), 6.33 (br d, J=9.9 Hz, 1H), 5.44 (dd, J=10.9, 9.9 Hz, 1H), 3.59-3.56 (m, 2H), 3.51-3.48 (m, 2H), 3.37 (s, 3H), 3.17 (br d, J=10.9 Hz, 1H), 2.65 (br d, J=10.6 Hz, 1H), 2.43-2.37 (m, 3H), 1.95-1.81 (m, 7H), 1.38 (br d, J=11.6 Hz, 1H); $^{13}$C-NMR (100 MHz, CDCl$_3$): δ156.1 (q, J=37.4 Hz), 154.9 (q, J=42.1 Hz), 139.4, 129.1, 128.5, 127.2, 115.8 (q, J=288.1 Hz), 113.4 (q, J=287.3 Hz), 87.6, 73.7, 72.3, 60.2, 59.1, 53.5, 48.5, 45.0, 41.1, 39.9, 36.3, 30.5, 29.2; IR (neat, cm$^{-1}$): 3303, 2936, 1775, 1698, 1554, 1221, 1172; MS (EI): m/z 523 (M$^+$), 202 (100%); HRMS (EI): calcd for $C_{24}H_{27}F_6NO_5$ (M$^+$) 523.1793, found 523.1797.

Example 20

[Chemical Formula 36]

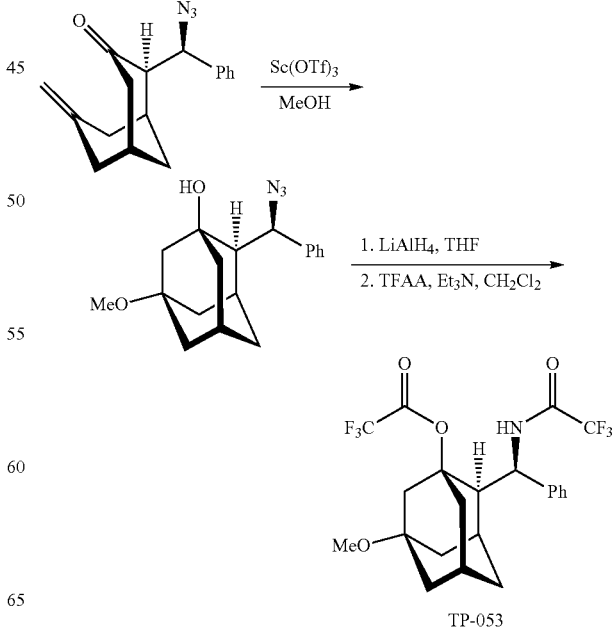

TP-053

To a solution of (1S,2R,5R)-2-(R-azido(phenyl)methyl)-7-methylenebicyclo[3.3.1.]nonan-3-one (238 mg, 0.848 mmol) in methanol (8.5 mL), scandium trifluoromethanesulfonate (20 mg, 0.04 mmol) was added under cooling with ice. After stirring at room temperature for 18 hours, a saturated aqueous solution of NaHCO$_3$ was added under cooling with ice, and the mixture was extracted with ethyl acetate. The resultant organic layer was washed with saturated saline and dried over MgSO$_4$, and then the solvent was distilled off under reduced pressure. The residues were subjected to silica gel column chromatography (hexane:ethyl acetate=1:4 to 1:2) to obtain (1S,3S,5S,7S)-2-((R)-azido(phenyl)methyl)-5-methoxyadamantan-1-ol (225 mg, 85%) as a colorless oily product.

To a solution of the resultant azide compound (225 mg, 0.716 mmol) in THF (4 mL), LiAlH$_4$ (41 mg, 1.1 mmol) was added under cooling with ice. After stirring at the same temperature for 1 hour, ammonia water was added to the reaction solution. The reaction solution was filtrated through Celite®, and the solvent was distilled off under reduced pressure. To the residues, dichloromethane (4 mL) was added, and then triethylamine (497 µL, 3.86 mmol) and trifluoroacetic anhydride (TFAA, 299 µL, 2.15 mmol) were added under cooling with ice. After stirring at room temperature for 40 hours, a saturated aqueous solution of NaHCO$_3$ was added under cooling with ice, and the mixture was extracted with dichloromethane. The resultant organic layer was dried over MgSO$_4$. The solvent was distilled off under reduced pressure, and the residues were subjected to silica gel column chromatography (hexane:ethyl acetate=1:8 to 1:2) to obtain TP-053 (262 mg, 75%) as a white solid.

[α]$_D^{14}$=+97.2 (c=0.179, CHCl$_3$); $^1$H-NMR (400 MHz, CDCl$_3$): δ7.33 (m, 5H), 6.35 (br d, J=9.9 Hz, 1H), 5.45 (dd, J=10.6, 9.9 Hz, 1H), 3.25 (s, 3H), 3.17 (br d, J=10.6 Hz, 1H), 2.61 (br d J=10.6 Hz, 1H), 2.45-2.37 (m, 3H), 1.97-1.73 (m, 7H), 1.39 (br d, J=13.5 Hz, 1H); 13C-NMR (100 MHz, CDCl$_3$): δ156.0 (q, J=37.4 Hz), 155.0 (q, J=41.8 Hz), 139.4, 129.1, 128.6, 127.1, 115.8 (q, 288.1 Hz), 113.4 (q, 287.0 Hz), 87.7, 75.5, 53.5, 48.7, 48.6, 44.5, 40.8, 39.5, 36.3, 33.3, 30.4, 29.3; IR (neat, cm$^{-1}$): 3299, 2941, 1776, 1697, 1221, 1172; MS (EI): m/z 479 (M$^+$), 202 (100%); HRMS (EI): calcd for C$_{22}$H$_{23}$F$_6$NO$_4$ (M$^+$) 479.1531, found 479.1486.

Example 21

[Chemical Formula 37]

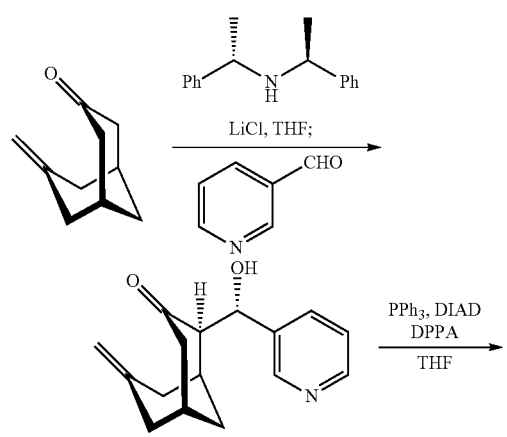

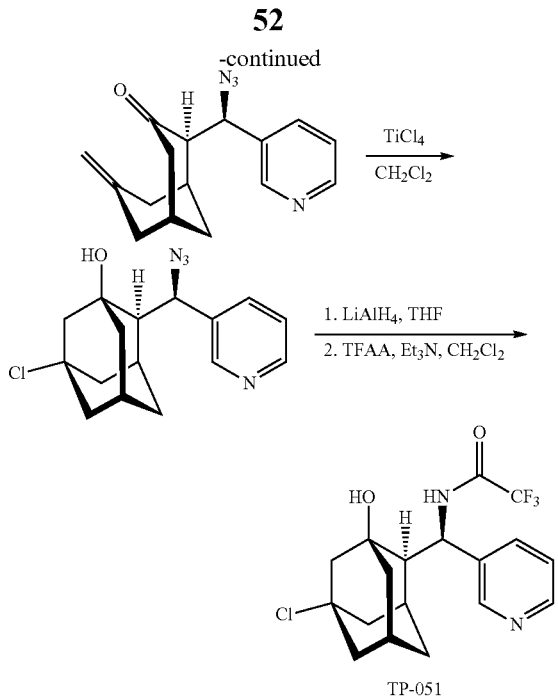

TP-051

To a solution of bis((S)-1-phenylethyl)amine (2.5 mL, 11 mmol) and lithium chloride (850 mg, 20 mmol) in THF (25 mL), a solution of n-butyllithium in hexane (1.56 M, 7.1 mL, 11 mmol) was added dropwise under cooling with ice. After stirring at the same temperature for 30 minutes, the reaction solution was cooled down to −78° C. A solution of 7-methylenebicyclo[3.3.1]nonan-3-one (1.52 g, 10 mmol) in THF (15 mL) was added to the reaction mixture by cannulation. After stirring for 30 minutes, a solution of nicotinaldehyde (1.1 mL, 12 mmol) in THF (10 mL) was added by cannulation. After stirring for 40 minutes, acetic acid and a saturated aqueous solution of ammonium chloride were added in sequence to the reaction solution, and the mixture was extracted with ethyl acetate. The resultant organic layer was washed with saturated saline and dried over K$_2$CO$_3$. The solvent was distilled off under reduced pressure, and the residues were subjected to silica gel column chromatography (hexane:acetone=3:2 to 1:2) to obtain (1S,2R,5R)-2-((S)-hydroxy(pyridin-3-yl)methyl)-7-methylenebicyclo[3.3.1]nonan-3-one (2.7 g, 81%) as a white solid. The solid was recrystallized from ethyl acetate to afford a colorless crystal (99% ee).

To a solution of the resultant alcohol (258 mg, 1.0 mmol), diphenylphosphoryl azide (DPPA, 237 µL, 1.1 mmol) and triphenylphosphine (239 mg, 1.1 mmol) in THF (5 mL), diisopropyl azodicarboxylate (DIAD, 214 µL, 1.1 mmol) was added under cooling with ice. After the temperature was slowly elevated to room temperature, followed by stirring for 5 hours, the solvent was distilled off under reduced pressure. The residues were subjected to silica gel column chromatography (hexane:ethyl acetate=4:1 to 2:1) to obtain (1S,2R,5R)-2-((R)-azido(pyridin-3-yl)methyl)-7-methylenebicyclo[3.3.1]nonan-3-one (187 mg, 66%) as a colorless oily product.

To a solution of the resultant azide compound (187 mg, 0.66 mmol) in dichloromethane (7 mL), TiCl$_4$ (300 µL, 0.27 mmol) was added under cooling with ice. After stirring at room temperature for 3 hours, a saturated aqueous solution of NaHCO$_3$ was added under cooling with ice, and the filtrate was extracted with diethyl ether. The resultant organic layer was washed with saturated saline and dried over MgSO$_4$. The solvent was distilled off under reduced pressure, and the resultant solid was washed with cool diethylether to obtain (1S,2R,3S,5S,7S)-2-((R)-azido(pyridin-3-yl)methyl)-5-chloroadamantan-1-ol (98.5 mg, 92%).

To a solution of the resultant compound (75.4 mg, 0.257 mmol) in THF (2 mL), LiAlH$_4$ (23 mg, 0.61 mmol) was added under cooling with ice. After stirring at the same temperature for 1 hour, ammonia water was added to the reaction solution under cooling with ice. The reaction solution was filtrated through Celite®, and the solvent was distilled off under reduced pressure. The residues were subjected to silica gel column chromatography (CHCl$_3$:methanol=1:0 to 4:1) to obtain a crude amine.

To the resultant crude amine, dichloromethane (2 mL) was added, and then triethylamine (178 µL, 1.28 mmol) and trifluoroacetic anhydride (TFAA, 107 µL, 0.76 mmol) were added under cooling with ice. After the temperature was elevated to room temperature, followed by stirring for 4 hours, a saturated aqueous solution of NaHCO$_3$ was added under cooling with ice, and the mixture was extracted with dichloromethane. The resultant organic layer was dried over Na$_2$SO$_4$. The solvent was distilled off under reduced pressure, and the residues were subjected to silica gel column chromatography (hexane:ethyl acetate=2:1 to 1:4) to obtain TP-051 (48.8 mg, 49%) as a white solid.

$[\alpha]_D^{20}$=+53.9 (c=0.379, CHCl$_3$); $^1$H-NMR (400 MHz, CDCl$_3$): δ8.57 (d, J=1.0 Hz, 1H), 8.50 (dd, J=4.9, 1.5 Hz, 1H), 7.72 (br d, J=7.8 Hz, 1H), 7.41 (br d, J=9.8 Hz, 1H), 7.32 (dd, J=7.8, 4.9 Hz, 1H), 5.35 (dd, J=9.8, 9.3 Hz, 1H), 2.40-2.38 (m, 2H), 2.29 (br s, 1H), 2.22-1.99 (m, 7H), 1.75 (br, 1H), 1.68 (br d, J=13.7 Hz, 1H), 1.48 (br d, J=13.2 Hz, 1H), 1.42 (br d, J=13.2 Hz, 1H); $^{13}$C-NMR (100 MHz, CDCl$_3$): δ156.4 (q, J=37.1 Hz), 148.2, 147.7, 138.3, 136.5, 124.0, 115.8 (q, J=287.8 Hz), 71.9, 66.1, 57.3, 52.6, 51.7, 47.6, 46.3, 38.3, 34.3, 31.6, 28.6; IR (neat, cm$^{-1}$): 3292, 2938, 1700, 1558, 1212, 1184, 1161, 759; MS (EI): m/z 388 (M$^+$), 203 (100%); HRMS (EI): calcd for C$_{18}$H$_{20}$ClF$_3$N$_2$O$_2$ (M) 388.1165, found 388.1177.

Example 22

[Chemical Formula 38]

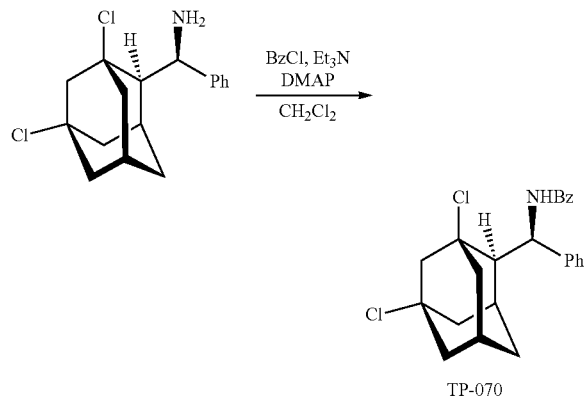

TP-070

To a solution of (R)-((1S,2R,3S,5S,7R)-1,5-dichloroadamantan-2-yl)(phenyl)methanamine (25.0 mg, 0.0806 mmol) in dichloromethane (1 mL), triethylamine (17 µL, 0.13 mmol), DMAP (1 mg) and benzoyl chloride (11 µL, 0.097 mmol) were added under cooling with ice. After stirring for 20 minutes, a saturated aqueous solution of NaHCO$_3$ was added to the reaction solution under cooling with ice, and the mixture was extracted with dichloromethane. The resultant organic layer was dried over MgSO$_4$. The solvent was distilled off under reduced pressure, and the residues were subjected to silica gel column chromatography (hexane:ethyl acetate=4:1) to obtain TP-070 (28.0 mg, 84%) as a yellow solid.

$^1$H-NMR (400 MHz, CDCl$_3$): δ7.69 (d, J=7.7 Hz, 2H), 7.49-7.25 (m, 8H), 6.34 (d, J=9.5 Hz, 1H), 5.77 (dd, J=9.5, 9.0 Hz, 1H), 2.73 (d, J=9.0 Hz, 1H), 2.65 (d, J=13.0 Hz, 1H), 2.59 (s, 1H), 2.51 (m, 2H), 2.32 (s, 1H), 2.20 (s, 2H), 2.08 (s, 2H), 1.99 (d, J=13.5 Hz, 1H), 1.91 (d, J=14.0 Hz, 1H), 1.39 (br d, J=13.5 Hz, 1H); $^{13}$C-NMR (100 MHz, CDCl$_3$): δ166.1, 143.9, 134.4, 131.7, 128.8, 128.6, 127.5, 127.3, 126.8, 69.0, 66.0, 59.2, 53.44, 53.39, 47.8, 46.0, 40.9, 35.8, 32.9, 28.8; IR (neat, cm$^{-1}$): 3583, 3290, 2940, 2092, 1631, 1536; MS (EI): m/z 413 (M$^+$), 210 (100%), HRMS (EI): calcd for C$_{24}$H$_{25}$C$_2$NO (M$^+$) 413.1313, found 413.1314.

Example 23

[Chemical Formula 39]

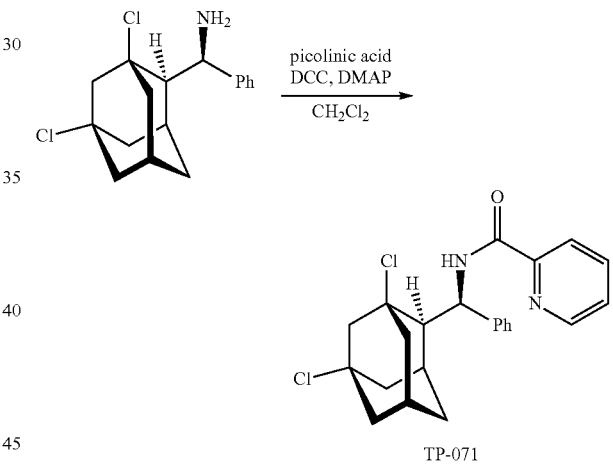

TP-071

To a solution of (R)-((1S,2R,3S,5S,7R)-1,5-dichloroadamantan-2-yl)(phenyl)methanamine (29.6 mg, 0.0955 mmol) in dichloromethane (1 mL), picolinic acid (18 mg, 0.14 mmol), DCC (30 mg, 0.14 mmol) and DMAP (1 mg, 10 mol %) were added under cooling with ice. After stirring under cooling with ice for 1 hour, water was added to the reaction solution, and the mixture was extracted with dichloromethane. After the resultant organic layer was dried over MgSO$_4$, the solvent was distilled off under reduced pressure, and the residues were subjected to silica gel column chromatography (hexane:ethyl acetate=2:1) to obtain TP-071 (29.8 mg, 75%) as a yellow oily product.

$^1$H-NMR (400 MHz, CDCl$_3$): δ8.52 (d, J=4.3 Hz, 1H), 8.46 (d, J=10.6 Hz, 1H), 8.17 (d, J=8.0 Hz, 1H), 7.82 (ddd, J=8.0, 7.7, 1.4 Hz, 1H), 7.44-7.39 (m, 3H), 7.33 (dd, J=7.7, 7.5 Hz, 2H), 7.23 (t, J=7.5 Hz, 1H), 5.79 (dd, J=10.6, 7.7 Hz, 1H), 2.71 (d, J=7.7 Hz, 1H), 2.66 (br d, J=13.0 Hz, 1H), 2.57-2.48 (m, 3H), 2.34 (s, 1H), 2.17 (m, 2H), 2.08 (m, 2H), 2.01 (br d, J=13.5 Hz, 1H), 1.91 (br d, J=13.0 Hz, 1H), 1.81 (br d, J=13.5 Hz, 1H); $^{13}$C-NMR (100 MHz, CDCl$_3$):

δ162.8, 149.6, 148.1, 143.7, 137.4, 128.7, 127.24, 127.20, 126.3, 122.5, 69.0, 66.1, 59.3, 53.7, 52.8, 47.9, 46.1, 40.9, 35.1, 32.9, 29.1; IR (neat, cm$^{-1}$): 3583, 3369, 2939, 2092, 1673, 1513; MS (EI): m/z 414 (M$^+$), 211 (100%); HRMS (EI): calcd for $C_{23}H_{24}Cl_2N_2O$ (M$^+$) 414.1266, found 414.1279.

Example 24

[Chemical Formula 40]

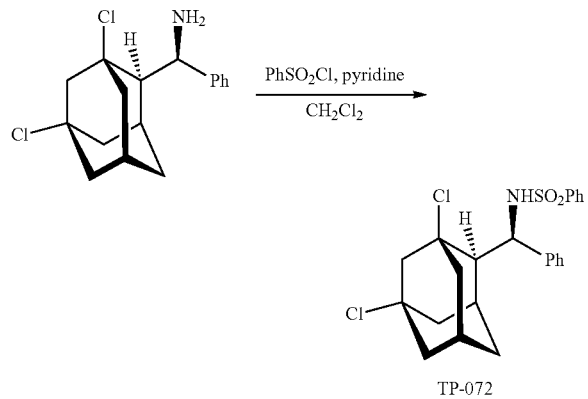

To a solution of (R)-((1S,2R,3S,5S,7R)-1,5-dichloroadamantan-2-yl)(phenyl)methanamine (18.8 mg, 0.0604 mmol) in dichloromethane (1 mL), pyridine (10 μL, 0.12 mmol) and benzenesulfonyl chloride (12 μL, 0.091 mmol) were added under cooling with ice. After stirring for 2.5 hours, water was added to the reaction solution, and the mixture was extracted with dichloromethane. After the resultant organic layer was dried over MgSO$_4$, the solvent was distilled off under reduced pressure, and the residues were subjected to silica gel column chromatography (hexane:ethyl acetate=8:1) to obtain TP-072 (11.1 mg, 41%) as a yellow oily product.

$^1$H-NMR (400 MHz, CDCl$_3$): δ7.49 (d, J=7.2 Hz, 2H), 7.36 (t, J=7.5 Hz, 1H), 7.20 (t, J=7.7 Hz, 2H), 7.02-6.98 (m, 3H), 6.84-6.82 (dd, J=1.4, 1.9 Hz, 2H), 4.76-4.71 (m, 1H), 2.70 (s, 1H), 2.55 (d, J=13.5 Hz, 1H), 2.43 (s, 2H), 2.37 (s, 2H), 2.28 (d, J=13.5 Hz, 1H), 2.19 (d, J=12.6 Hz, 1H), 2.10 (s, 3H), 1.86 (d, J=12.6 Hz, 1H), 1.48 (d, J=14.0 Hz, 1H), 1.25 (s, 1H); $^{13}$C-NMR (100 MHz, CDCl$_3$): δ142.3, 140.1, 132.2, 128.7, 128.3, 127.1, 127.0, 126.4, 69.4, 65.9, 59.3, 58.4, 55.0, 47.9, 46.0, 40.6, 34.8, 33.0, 28.6; IR (neat, cm$^{-1}$): 3583, 3276, 2938, 1589, 1454; MS (EI): m/z 246 (M$^+$-$C_{10}H_{12}Cl_2$), 246 (100%); HRMS (EI): calcd for $C_{13}H_{12}NO_2S$ (M$^+$-$C_{10}H_{12}Cl_2$) 246.0589, found 246.0591.

Example 25

[Chemical Formula 41]

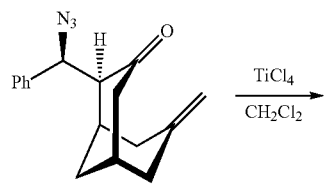

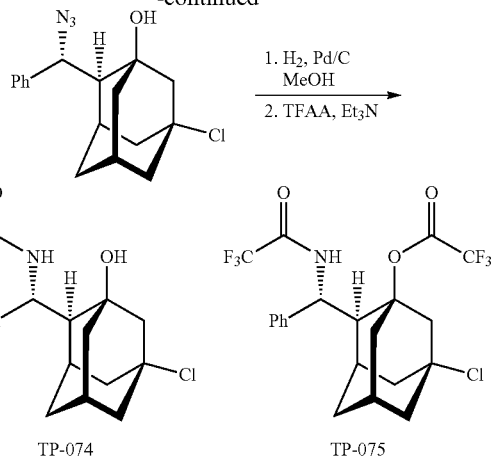

To a solution of (1R,2S,5S)-2-((S)-azido(phenyl)methyl)-7-methylenebicyclo[3.3.1]nonan-3-one (418 mg, 1.48 mmol) in dichloromethane (8 mL), titanium tetrachloride (0.10 mL, 0.89 mmol) was added at −30° C. After stirring at the same temperature for 1 hour, the reaction solution was diluted with diethylether. The reaction was quenched by adding water and extracted with diethylether. The resultant organic layer was washed with saturated saline and dried over MgSO$_4$. The solvent was distilled off under reduced pressure, and the residues were subjected to silica gel column chromatography (hexane:ethyl acetate=10:1) to obtain (1R,2S,3R,5R,7R)-2-((R)-azido(phenyl)methyl)-5-chloroadamantan-1-ol (446 mg, 95%) as a colorless oily product.

To a solution of the resultant alcohol (72.1 mg, 0.227 mmol) in methanol (1 mL), palladium 10% on carbon (7 mg) was added. After stirring under hydrogen atmosphere at room temperature overnight, the reaction solution was filtrated through Celite®, and the solvent was distilled off under reduced pressure. To the residues, dichloromethane (1 mL) was added, and then triethylamine (157 μL, 1.14 mmol) and TFAA (96 μL, 0.68 mmol) were added in sequence under cooling with ice. After stirring under cooling with ice for 10 minutes, a saturated aqueous solution of NaHCO$_3$ was added, and the mixture was extracted with dichloromethane and dried over MgSO$_4$. The solvent was distilled off under reduced pressure, and the residues were subjected to silica gel column chromatography (hexane:ethyl acetate=10:1) to obtain TP-074 (20.1 mg, 18%) and TP-075 (12.7 mg, 12%), respectively, as colorless solids.

Also, TP-073 was synthesized from (1S,2R,5R)-2-((R)-azido(phenyl)methyl)-7-methylenebicyclo[3.3.1]nonan-3-one by using the same procedure.

-TP-074

$^1$H-NMR (400 MHz, CDCl$_3$): δ8.94 (s, 1H), 7.37-7.27 (m, 5H), 4.90-4.86 (m, 1H), 2.36 (s, 1H), 2.26-2.20 (m, 2H), 2.11-2.05 (m, 3H), 2.02 (s, 3H), 1.98-1.94 (m, 1H), 1.87-1.83 (m, 2H), 1.72 (s, 1H), 1.54 (d, J=12.1 Hz, 1H), 1.32 (d, J=13.5 Hz, 1H); $^{13}$C-NMR (100 MHz, CDCl$_3$): δ156.6 (q, J=36.1 Hz), 140.5, 128.8, 127.9, 127.0, 115.8 (q, 287.5 Hz), 74.1, 65.7, 57.4, 56.3, 51.3, 47.1, 46.3, 38.7, 33.3, 32.0, 28.7; IR (neat, cm$^{-1}$): 3584, 3256, 2938, 1711, 1543; MS (EI): m/z 387 (M$^+$), 202 (100%).

-TP-075

$^1$H-NMR (400 MHz, CDCl$_3$): δ7.35-7.27 (m, 5H), 6.63 (d, J=10.1 Hz, 1H), 5.44 (dd, J=10.6 Hz, 10.1 Hz, 1H), 3.26 (d, J=11.1 Hz, 1H), 2.99 (d, J=11.1 Hz, 1H), 2.45-2.41 (m,

3H), 2.26-2.13 (m, 5H), 1.96 (br d, J=12.4 Hz, 2H), 1.47 (br d, J=14.0 Hz, 1H); $^{13}$C-NMR (100 MHz, CDCl$_3$): δ156.2 (q, 37.4 Hz), 154.9 (q, 42.3 Hz), 139.1, 129.2, 128.7, 127.1, 115.8 (q, 288.1 Hz), 113.3 (q, 287.3 Hz), 86.6, 65.1, 53.4, 50.2, 48.0, 46.9, 46.1, 35.6, 34.6, 31.7, 28.5; IR (neat, cm$^{-1}$): 3296, 2945, 1775, 1698, 1172; MS (EI): m/z 483 (M$^+$), 202 (100%); HRMS (EI): calcd for C$_{21}$H$_{20}$ClF$_6$NO$_3$ (M$^+$), 483.1036, found 483.1046.

Example 26

[Chemical Formula 42]

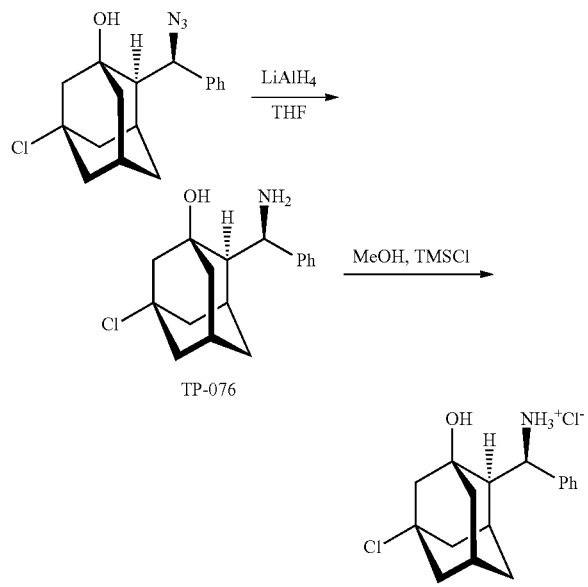

TP-076

To a solution of (1S,2R,3S,5S,7S)-2-((R)-azido(phenyl) methyl)-5-chloroadamantane (156 mg, 0.49 mmol) in THF (5 mL), lithium aluminum hydride (26 mg, 0.74 mmol) was added under cooling with ice. After stirring at the same temperature for 1 hour, the reaction was quenched by adding 28% ammonia water, thereafter, the reaction solution was filtrated through Celite®, the solvent was distilled off under reduced pressure, and the residues were subjected to silica gel column chromatography (chloroform:methanol=10:1) to obtain TP-076 (75 mg, 52%) as a colorless oily product.

$^1$H-NMR (400 MHz, CDCl$_3$): δ7.38-7.35 (m, 5H), 4.13 (d, J=10.1 Hz, 1H), 2.66 (brs, 1H), 2.30 (brs, 1H), 2.21-1.98 (m, 8H), 1.80 (brd, J=13.0 Hz, 1H), 1.60-1.46 (m, 3H), 1.44 (brd, J=13.5 Hz, 2H); IR (neat, cm$^{-1}$): 3581, 3300, 3359, 2935, 2861, 1600, 1492, 1453; MS (EI): m/z 291 (M$^+$), 106 (100%); HRMS (ESI): calcd for C$_{17}$H$_{23}$NOCl (M$^+$+H), 292.1459, found 292.1463.

To a solution TP-076 (62 mg, 0.21 mmol) in methanol (2.6 mL), chlorotrimethylsilane (32.6 μL, 0.74 mmol) was added at room temperature. After stirring at the same temperature for 1 hour, the solvent was distilled off under reduced pressure to obtain (R)-((1S,2R,3S,5S,7S)-5-chloro-1-hydroxyadamantan-2-yl)(phenyl)methaneammonium chloride salt (27 mg 39%) as a white solid.

[α]$_D^{24}$=+18.4 (c=0.50, MeOH); $^1$H-NMR (400 MHz, CD$_3$COCD$_3$): δ8.80 (brs, 2H), 7.65 (d, J=6.8 Hz, 2H), 7.34-7.27 (m, 3H), 4.67 (d, J=9.7 Hz, 1H), 3.14 (brs, 1H), 3.00-2.70 (m, 3H), 2.23-1.88 (m, 8H), 1.48-1.35 (m, 2H); $^{13}$C-NMR (100 MHz, CD$_3$COCD$_3$): 140.4, 129.7, 129.1, 128.9, 72.2, 68.2, 66.1, 58.2, 52.2, 48.4, 47.3, 38.7, 34.5, 32.8, 29.8; IR (neat, cm$^{-1}$): 3583, 3294, 2933, 2864; HRMS (EI): calcd for C$_{17}$H$_{23}$Cl$_2$NO (M$^+$-NH$_4$Cl), 274.1124, found 274.1153.

Example 27

[Chemical Formula 43]

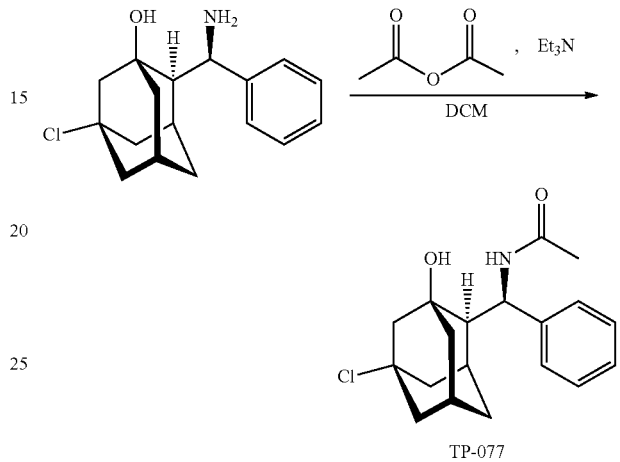

TP-077

To a solution of (R)-((1S,2R,3S,5S,7R)-5-chloro-1-hydroxyadamantan-2-yl)(phenyl)methanamine (70.0 mg, 0.240 mmol) in dichloromethane (1 mL), acetic anhydride (34.0 μL, 0.360 mmol) and triethylamine (100 μL, 0.720 mmol) were added. After stirring at room temperature for 1 hour, a saturated aqueous solution of NaHCO$_3$ was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=1:1) to obtain TP-077 (69.7 mg, 87%) as a colorless solid.

1H-NMR (400 MHz, CDCl$_3$): δ7.39-7.28 (m, 5H), 5.86 (d, J=2.4 Hz, 1H), 5.41 (t, J=9.7 Hz, 1H), 2.34 (d, J=20.3 Hz, 2H), 2.15 (t, J=9.4 Hz, 2H), 2.06-2.03 (m, 6H), 1.95 (s, 3H), 1.68 (s, 2H), 1.50 (d, J=12.6 Hz, 1H), 1.38 (d, J=13.5 Hz, 1H); $^{13}$C-NMR (100 MHz, CDCl$_3$): δ169.3, 142.2, 129.2, 127.9, 127.2, 71.9, 66.8, 56.3, 53.0, 52.6, 47.9, 46.5, 38.7, 33.8, 32.0, 29.2, 23.4; IR (neat, cm$^{-1}$): 3567, 3278, 2935, 2863, 1645, 1541; MS (EI): m/z 333 (M$^+$), 148 (1000/), HRMS (EI): calcd for C$_{19}$H$_{24}$ClNO$_2$ (M$^+$) 333.1496, found 333.1496.

Example 28

[Chemical Formula 44]

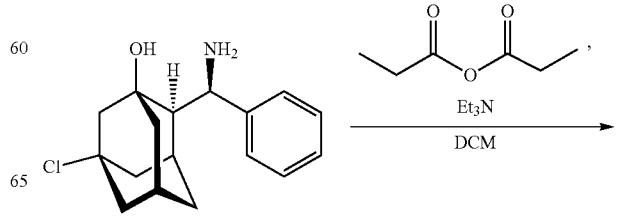

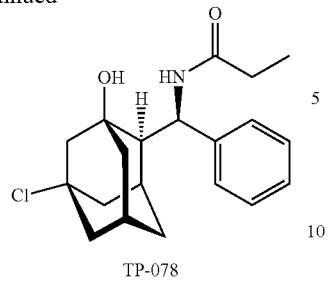

TP-078

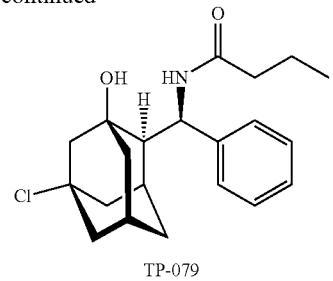

TP-079

To a solution of (R)-((1S,2R,3S,5S,7R)-5-chloro-1-hydroxyadamantan-2-yl)(phenyl)methanamine (70.0 mg, 0.240 mmol) in dichloromethane (1 mL), propionic anhydride (46.4 μL, 0.360 mmol) and triethylamine (100 μL, 0.720 mmol) were added. After stirring at room temperature for 1 hour, a saturated aqueous solution of NaHCO$_3$ was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=1:1) to obtain TP-078 (76.9 mg, 92%) as a colorless solid.

$^1$H-NMR (400 MHz, CDCl$_3$): δ7.35-7.28 (m, 5H), 6.21 (d, J=9.2 Hz, 1H), 5.43 (t, J=9.4 Hz, 1H), 2.33 (d, J=21.7 Hz, 2H), 2.20-2.09 (m, 4H), 2.06-2.04 (m, 7H), 1.91 (d, J=13.5 Hz, 1H), 1.50 (d, J=13.0 Hz, 1H), 1.37 (d, J=14.0 Hz, 1H), 1.09 (t, J=7.5 Hz, 3H); $^{13}$C-NMR (100 MHz, CDCl$_3$): δ173.0, 142.2, 129.2, 127.8, 127.1, 71.9, 66.8, 56.4, 53.1, 52.4, 48.0, 46.5, 38.7, 33.8, 32.0, 29.8, 29.3, 9.6; IR (neat, cm$^{-1}$): 3550, 3285, 2937, 2864, 1639, 1543; MS (EI): m/z 347 (M$^+$), 162 (100%), HRMS (EI): calcd for C$_{20}$H$_{26}$ClNO$_2$ (M) 347.1652, found 347.1644.

Example 29

[Chemical Formula 45]

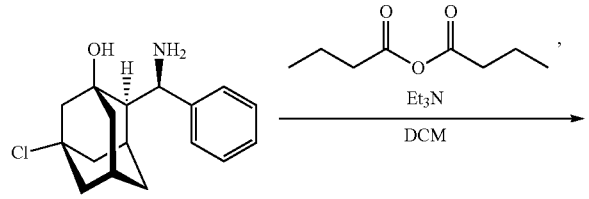

To a solution of (R)-((1S,2R,3S,5S,7R)-5-chloro-1-hydroxyadamantan-2-yl)(phenyl)methanamine (100 mg, 0.342 mmol) in dichloromethane (1 mL), butyric anhydride (85.4 μL, 0.516 mmol) and triethylamine (144 μL, 1.03 mmol) were added. After stirring at room temperature for 1 hour, a saturated aqueous solution of NaHCO$_3$ was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=2:1) to obtain TP-079 (118 mg, 95%) as a colorless solid.

$^1$H-NMR (400 MHz, CDCl$_3$): δ7.39-7.27 (m, 5H), 5.91 (s, 1H), 5.43 (t, J 9.7 Hz, 1H), 2.34 (d, J=19.8 Hz, 2H), 2.18 (d, J=30.0 Hz, 1H), 2.12 (t, J=6.3 Hz, 3H), 2.09-2.03 (m, 8H), 1.93 (d, J=13.5 Hz, 2H), 1.60 (q, J=16.6 Hz, 2H), 1.50 (d, J=12.6 Hz, 1H), 1.38 (d, J=13.5 Hz, 1H), 1.26 (t, J=7.2 Hz, 1H); $^{13}$C-NMR (100 MHz, CDCl$_3$): δ172.3, 142.4, 129.0, 127.7, 127.1, 71.9, 66.8, 56.4, 52.9, 52.4, 47.9, 46.5, 38.68, 38.66, 33.8, 31.9, 29.1, 19.0, 13.6; IR (neat, cm$^{-1}$): 3554, 3289, 3063, 3031, 2936, 2866, 2246, 1637, 1541; MS (EI): m/z 361 (M$^+$), 106 (100%), HRMS (EI): calcd for C$_{21}$H$_{28}$ClNO$_2$ (M$^+$) 361.1809, found 361.1811.

Example 30

[Chemical Formula 46]

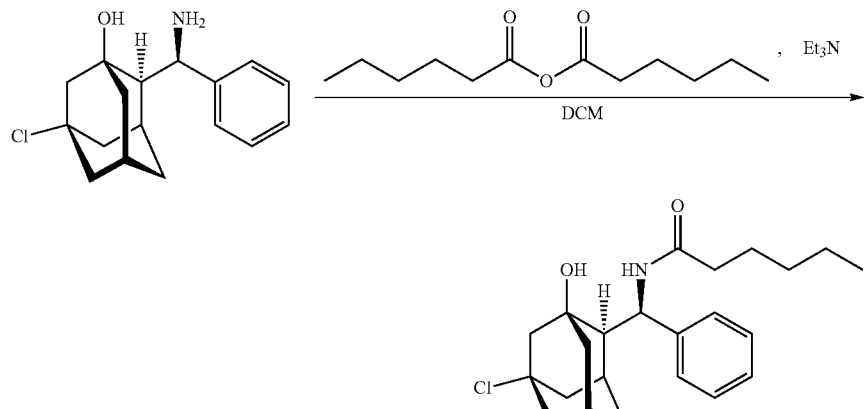

TP-080

To a solution of (R)-((1S,2R,3S,5S,7R)-1-chloro-1-hydroxyadamantan-2-yl)(phenyl)methanamine (60.0 mg, 0.206 mmol) in dichloromethane (1 mL), hexanoic anhydride (71.2 µL, 0.308 mmol) and triethylamine (86.0 µL, 0.617 mmol) were added. After stirring at room temperature for 1 hour, a saturated aqueous solution of NaHCO$_3$ was added to the reaction solution, and the mixture was extracted with dichloromethane. The resultant organic layer was dried over MgSO$_4$. The solvent was distilled off under reduced pressure, and the residues were subjected to silica gel column chromatography (hexane:ethyl acetate=2:1) to obtain TP-080 (73.5 mg, 92%) as a colorless solid.

$^1$H-NMR (400 MHz, CDCl$_3$): δ7.40-7.29 (m, 5H), 5.67 (d, J=9.7 Hz, 1H), 5.43 (t, J=9.7 Hz, 1H), 2.33 (d, J=15.5 Hz, 2H), 2.18 (s, 1H), 2.14 (t, J=7.5 Hz, 3H), 2.05-2.03 (m, 6H), 1.93 (d, J=13.5 Hz, 1H), 1.78 (s, 1H), 1.60 (d, J=8.5 Hz, 1H), 1.50 (d, J=12.6 Hz, 1H), 1.38 (d, J=11.6 Hz, 1H), 1.28-1.20 (m, 5H), 0.84 (t, J=7.0 Hz, 3H); $^{13}$C-NMR (100 MHz, CDCl$_3$): δ172.4, 143.2, 129.2, 127.8, 127.1, 71.9, 66.8, 56.4, 53.0, 52.4, 48.0, 46.5, 38.7, 36.8, 33.8, 32.0, 31.2, 29.2, 25.2, 22.2, 13.8; IR (neat, cm$^{-1}$): 3578, 3286, 2932, 2862, 1637, 1542; MS (EI): m/z 389 (M$^+$), 106 (100%), HRMS (EI): calcd for C$_{23}$H$_{32}$ClNO$_2$ (M$^+$) 389.2122, found 389.2107.

Example 31

[Chemical Formula 47]

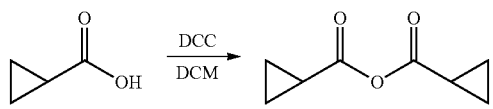

To a solution of cyclopropanecarboxylic acid (80 mg, 0.929 mmol) in dichloromethane (1 mL), DCC (105 µL, 0.465 mmol) was added at room temperature. After stirring at room temperature for 24 hours, the reaction solution was diluted with cool hexane and filtrated through cotton plug. The resultant filtrate was distilled under reduced pressure for solvent removal to obtain a crude product of cyclopropanecarboxylic anhydride (141 mg). The obtained product was used without purification for the reaction shown below.

[Chemical Formula 48]

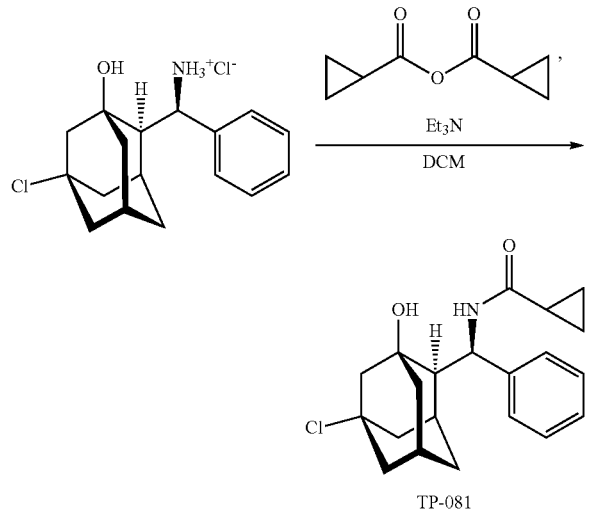

To a solution of (R)-((1S,2R,3S,5S,7S)-5-chloro-1-hydroxyadamantan-2-yl)(phenyl)methaneammonium chloride salt (60.3 mg, 0.184 mmol) in dichloromethane (1 mL), the crude product of cyclopropanecarboxylic anhydride (141 mg) and triethylamine (86.8 µL, 0.918 mmol) were added at room temperature. After stirring at room temperature for 1 hour, a saturated aqueous solution of sodium bicarbonate was added to the reaction solution, and the mixture was extracted with dichloromethane. After the resultant organic layer was dried over MgSO$_4$, the solvent was distilled off under reduced pressure, and the residues were subjected to silica gel column chromatography (hexane:ethyl acetate=2:1) to obtain TP-081 (55.7 mg, 84%) as a colorless solid.

$[α]_D^{24}$=+51.1 (c=0.109, CHCl$_3$); $^1$H-NMR (400 MHz, CDCl$_3$): δ7.41-7.29 (m, 5H), 5.89 (d, J=9.2 Hz, 1H), 5.46 (t, J=9.2 Hz, 1H), 2.34 (d, J=24.6 Hz, 2H), 2.15 (d, J=8.7 Hz, 1H), 2.10 (s, 2H), 2.07-2.03 (m, 6H), 1.93 (d, J=13.5 Hz, 1H), 1.50 (d, J=12.6 Hz, 1H), 1.39 (d, J=13.5 Hz, 1H), 1.34-1.24 (m, 1H), 0.98-0.90 (m, 2H), 0.76-0.69 (m, 2H); $^{13}$C-NMR (100 MHz, CDCl$_3$): δ182.1, 142.1, 129.3, 127.9, 127.0, 88.4, 71.8, 56.4, 53.5, 52.6, 48.2, 46.6, 38.8, 33.6, 32.1, 29.5, 15.1, 7.6, 7.2; IR (neat, cm$^{-1}$): 3554, 3299, 2937, 2864, 2361, 1637, 1542; MS (EI): m/z 359 (M$^+$), 174 (100%), HRMS (EI): calcd for C$_{21}$H$_{26}$ClNO$_2$ (M$^+$) 359.1652, found 359.1655.

Example 32

[Chemical Formula 49]

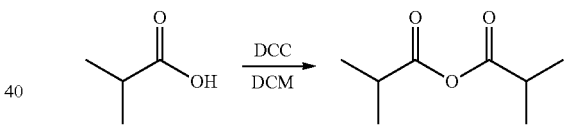

To a solution of isobutyric acid (80 mg, 0.908 mmol) in dichloromethane (1 mL), DCC (102 µL, 0.454 mmol) was added at room temperature. After stirring at room temperature for 24 hours, the reaction solution was diluted with cool hexane and filtrated through cotton plug. The resultant filtrate was distilled under reduced pressure for solvent removal to obtain a crude product of isobutyric anhydride (121 mg). The obtained product was used without purification for the reaction shown below.

[Chemical Formula 50]

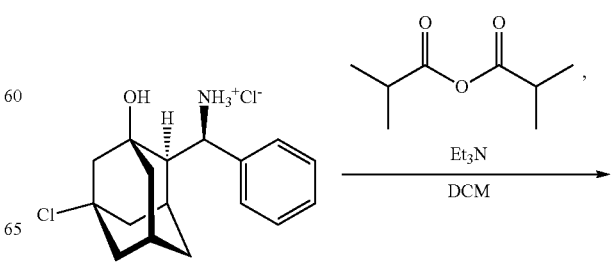

-continued

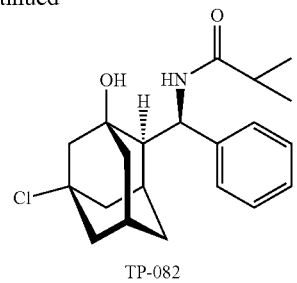

TP-082

To a solution of (R)-((1S,2R,3S,5S,7S)-5-chloro-1-hydroxyadamantan-2-yl)(phenyl)methaneammonium chloride salt (55.1 mg, 0.168 mmol) in dichloromethane (1 mL), the crude product of isobutyric anhydride (121 mg) and triethylamine (88.1 µL, 0.839 mmol) were added at room temperature. After stirring at room temperature for 1 hour, a saturated aqueous solution of sodium bicarbonate was added to the reaction solution, and the mixture was extracted with dichloromethane. After the resultant organic layer was dried over $MgSO_4$, the solvent was distilled off under reduced pressure, and the residues were subjected to silica gel column chromatography (hexane:ethyl acetate=2:1) to obtain TP-082 (57.0 mg, 94%) as a colorless solid.

$[\alpha]_D^{25}$=+83.1 (c=0.234, $CHCl_3$); $^1$H-NMR (400 MHz, $CDCl_3$): δ7.28-7.27 (m, 3H), 7.25-7.20 (m, 2H), 6.07 (d, J=9.2 Hz, 1H), 5.35 (t, J=9.2 Hz, 1H), 2.28-2.23 (m, 3H), 2.11 (d, J=8.7 Hz, 1H), 2.07 (d, J=5.8 Hz, 1H), 2.03 (s, 1H), 1.99 (d, J=4.8 Hz, 3H), 1.95 (s, 3H), 1.81 (d, J=13.0 Hz, 1H), 1.42 (d, J=12.6 Hz, 1H), 1.30 (d, J=13.0 Hz, 1H), 1.06 (d, J=6.8 Hz, 3H), 0.98 (d, J=7.2 Hz, 3H); $^{13}$C-NMR (100 MHz, $CDCl_3$): δ176.2, 142.2, 129.1, 127.7, 127.0, 71.8, 66.9, 56.4, 53.1, 52.2, 48.1, 46.5, 38.6, 35.6, 33.7, 31.9, 29.2, 19.5, 19.2; IR (neat, $cm^{-1}$): 3566, 3300, 2934, 2864, 1643, 1540; MS (EI): m/z 361 (M), 106 (100%), HRMS (EI): calcd for $C_{21}H_{28}ClNO_2$ ($M^+$) 361.1809, found 361.1818.

Example 33

[Chemical Formula 51]

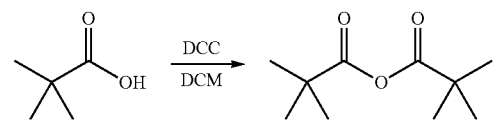

To a solution of pivalic acid (100 mg, 0.980 mmol) in dichloromethane (1 mL), DCC (101 mg, 0.490 mmol) was added at room temperature. After stirring at room temperature for 24 hours, the reaction solution was diluted with cool hexane and filtrated through cotton plug. The resultant filtrate was distilled under reduced pressure for solvent removal to obtain a crude product of pivalic anhydride (156 mg). The obtained product was used without purification for the reaction shown below.

[Chemical Formula 52]

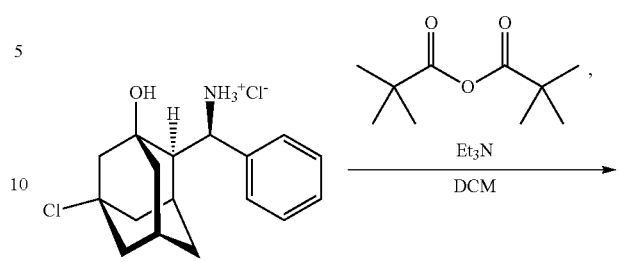

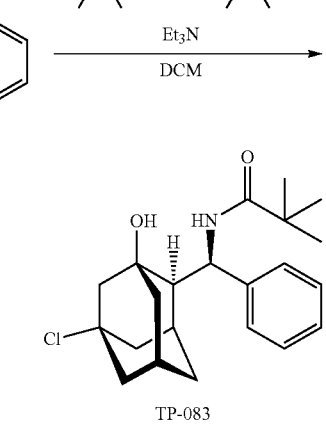

TP-083

To a solution of (R)-((1S,2R,3S,5S,7S)-5-chloro-1-hydroxyadamantan-2-yl)(phenyl)methaneammonium chloride salt (45.0 mg, 0.137 mmol) in dichloromethane (1 mL), the crude product of pivalic anhydride (156 mg) and triethylamine (38.9 µL, 0.279 mmol) were added at room temperature. After stirring at room temperature for 1 hour, a saturated aqueous solution of sodium bicarbonate was added to the reaction solution, and the mixture was extracted with dichloromethane. After the resultant organic layer was dried over $MgSO_4$, the solvent was distilled off under reduced pressure, and the residues were subjected to silica gel column chromatography (hexane:ethyl acetate=2:1) to obtain TP-083 (46.7 mg, 91%) as a white solid.

$[\alpha]_D^{28}$=+89.2 (c=0.149, $CHCl_3$); $^1$H-NMR (400 MHz, $CDCl_3$): δ7.34-7.29 (m, 5H), 6.01 (d, J=9.2 Hz, 1H), 5.44 (t, J=8.9 Hz, 1H), 2.39 (s, 1H), 2.30 (s, 2H), 2.15 (d, J=8.2 Hz, 1H), 2.11-2.00 (m, 7H), 1.85 (d, J=13.5 Hz, 1H), 1.51 (d, J=12.6 Hz, 1H), 1.39 (d, J=13.0 Hz, 1H), 1.16 (s, 9H); $^{13}$C-NMR (100 MHz, $CDCl_3$): δ177.7, 142.1, 129.2, 127.8, 126.8, 71.7, 66.9, 56.4, 53.4, 52.2, 48.3, 46.6, 38.7, 38.6, 33.5, 32.0, 29.5, 27.4; IR (neat, $cm^{-1}$): 3346, 2934, 2864, 2362, 1638, 1516; MS (EI): m/z 375 ($M^+$), 190 (100%); HRMS (EI): calcd for $C_{22}H_{30}ClNO_2$ ($M^+$) 375.1965, found 375.1969.

Example 34

[Chemical Formula 53]

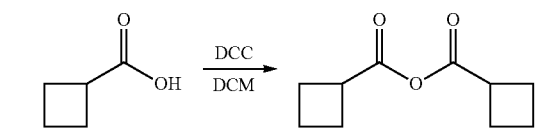

To a solution of cyclobutanecarboxylic acid (100 mg, 0.999 mmol) in dichloromethane (1 mL), DCC (112 µL, 0.499 mmol) was added at room temperature. After stirring at room temperature for 24 hours, the reaction solution was diluted with cool hexane and filtrated through cotton plug. The resultant filtrate was distilled under reduced pressure for solvent removal to obtain a crude product of cyclobutanecarboxylic anhydride (120 mg). The obtained product was used without purification for the reaction shown below.

[Chemical Formula 54]

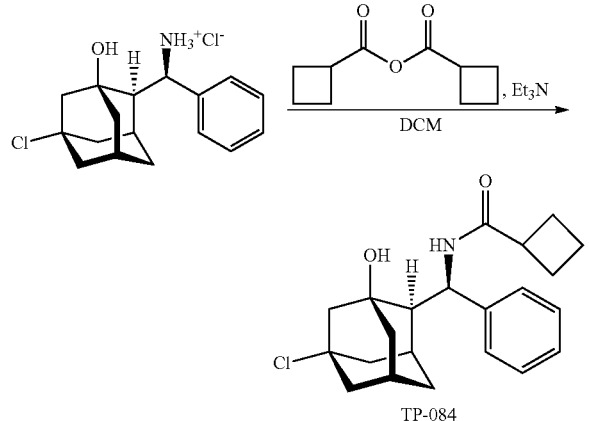

TP-084

To a solution of (R)-((1S,2R,3S,5S,7S)-5-chloro-1-hydroxyadamantan-2-yl)(phenyl)methaneammonium chloride salt (43.2 mg, 0.132 mmol) in dichloromethane (1 mL), the crude product of cyclobutanecarboxylic anhydride (120 mg) and triethylamine (61.9 µL, 0.658 mmol) were added at room temperature. After stirring at room temperature for 1 hour, a saturated aqueous solution of sodium bicarbonate was added to the reaction solution, and the mixture was extracted with dichloromethane. After the resultant organic layer was dried over MgSO$_4$, the solvent was distilled off under reduced pressure, and the residues were subjected to silica gel column chromatography (hexane:ethyl acetate=2:1) to obtain TP-084 (43.8 mg, 89%) as a colorless solid.

$[\alpha]_D^{26}$=+87.3 (c=0.171, CHCl$_3$); $^1$H-NMR (400 MHz, CDCl$_3$): δ7.42-7.21 (m 5H), 5.76 (d, J=9.2 Hz, 1H), 5.43 (t, J=9.2 Hz, 1H), 2.96 (quint, 1H), 2.31 (brs, 2H), 2.26-1.78 (m, 15H), 1.50 (d, J=12.6 Hz, 1H), 1.38 (d, J=14.0 Hz, 1H); $^{13}$C-NMR (100 MHz, CDCl$_3$): δ174.2, 142.2, 129.2, 127.8, 127.0, 71.8, 66.9, 56.4, 53.3, 52.2, 48.1, 46.5, 39.9, 38.7, 33.7, 32.0, 29.4, 25.3, 24.9, 18.1; IR (neat, cm$^{-1}$): 3567, 3296, 2938, 2863, 1637, 1540; MS (EI): m/z 373 (M$^+$), 106 (100%); HRMS (EI): calcd for C$_{22}$H$_{28}$ClNO$_2$ (M$^+$) 373.1809, found 373.1800.

Example 35

[Chemical Formula 55]

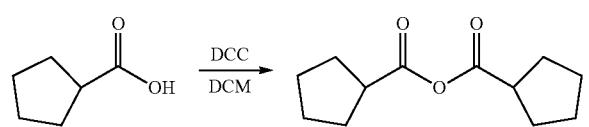

To a solution of cyclopentanecarboxylic acid (100 mg, 0.876 mmol) in dichloromethane (1 mL), DCC (98 µL, 0.438 mmol) was added at room temperature. After stirring at room temperature for 24 hours, the reaction solution was diluted with cool hexane and filtrated through cotton plug. The resultant filtrate was distilled under reduced pressure for solvent removal to obtain a crude product of cyclopentanecarboxylic anhydride (157 mg). The obtained product was used without purification for the reaction shown below.

[Chemical Formula 56]

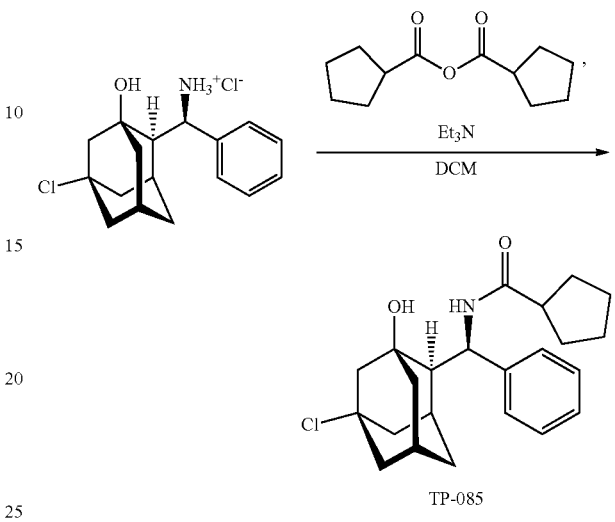

TP-085

To a solution of (R)-((1S,2R,3S,5S,7S)-5-chloro-1-hydroxyadamantan-2-yl)(phenyl)methaneammonium chloride salt (50.0 mg, 0.152 mmol) in dichloromethane (1 mL), the crude product of cyclopentanecarboxylic anhydride (157 mg) and triethylamine (61.9 µL, 0.658 mmol) were added at room temperature. After stirring at room temperature for 1 hour, a saturated aqueous solution of sodium bicarbonate was added to the reaction solution, and the mixture was extracted with dichloromethane. After the resultant organic layer was dried over MgSO$_4$, the solvent was distilled off under reduced pressure, and the residues were subjected to silica gel column chromatography (hexane:ethyl acetate=2:1) to obtain TP-085 (54.5 mg, 92%) as a colorless solid.

$[\alpha]_D^{26}$=+82.5 (c=0.171, CHCl$_3$); $^1$H-NMR (400 MHz, CDCl$_3$): δ7.42-7.19 (m, 5H), 5.91 (d, J=9.2 Hz, 1H), 5.43 (t, J=9.2 Hz, 1H), 2.49 (m, 1H), 2.34 (s, 1H), 2.30 (s, 1H), 2.19-1.97 (m, 9H), 1.95-1.81 (m, 2H), 1.78-1.62 (m, 5H), 1.62-1.46 (m, 3H), 1.38 (d, 13.5 Hz, 1H); $^{13}$C-NMR (100 MHz, CDCl$_3$): δ175.5, 142.2, 129.2, 127.8, 127.0, 71.8, 66.9, 56.4, 53.3, 52.3, 48.1, 46.6, 46.0, 38.7, 33.7, 32.0, 30.5, 29.9, 29.4, 25.9, 25.7; IR (neat, cm$^{-1}$): 3555, 3303, 2940, 2866, 1638, 1536; MS (EI): m/z 387 (M$^+$), 106 (100%); HRMS (EI): calcd for C$_{23}$H$_{30}$ClNO$_2$ (M$^+$) 387.1965, found 387.1959.

Example 36

[Chemical Formula 57]

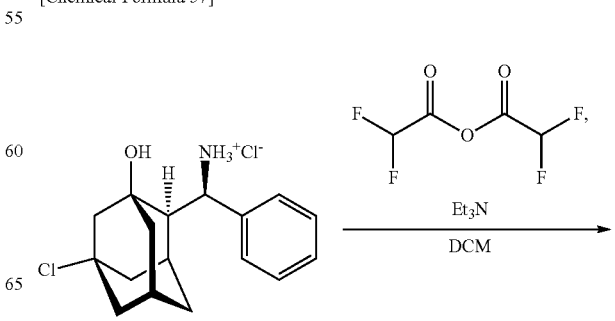

-continued

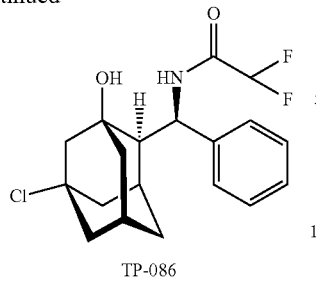

TP-086

To a solution of (R)-((1S,2R,3S,5S,7S)-5-chloro-1-hydroxyadamantan-2-yl)(phenyl)methaneammonium chloride salt (30.0 mg, 0.0914 mmol) in dichloromethane (1 mL), difluoroacetic anhydride (34.1 μL, 0.274 mmol) and triethylamine (63.7 μL, 0.457 mmol) were added at room temperature. After stirring at room temperature for 1 hour, a saturated aqueous solution of sodium bicarbonate was added to the reaction solution, and the mixture was extracted with dichloromethane. After the resultant organic layer was dried over $MgSO_4$, the solvent was distilled off under reduced pressure, and the residues were subjected to silica gel column chromatography (hexane:ethyl acetate=4:1) to obtain TP-086 (11.5 mg, 34%) as a colorless solid.

$[\alpha]_D^{29}$=+100.2 (c=0.171, $CHCl_3$); $^1$H-NMR (400 MHz, $CDCl_3$): δ7.39-7.32 (m, 5H), 6.64 (d, J=9.2 Hz, 1H), 5.84 (t, J=54.1 Hz, 1H), 5.38 (t, J=9.9 Hz, 1H), 2.32 (t, J=8.9 Hz, 3H), 2.18 (d, J=12.1 Hz, 1H), 2.09 (d, J=12.1 Hz, 3H), 2.04 (s, 3H), 1.85 (d, J=13.5 Hz, 1H), 1.51 (d, J=12.6 Hz, 1H), 1.40 (d, J=13.5 Hz, 1H), 1.10 (s, 1H); $^{13}$C-NMR (100 MHz, $CDCl_3$): δ161.5 (t, J=25.0 Hz), 141.2, 129.5, 128.5, 127.3, 108.5 (t, J=252.7 Hz), 72.1, 66.3, 56.6, 53.0, 52.8, 47.8, 46.4, 38.8, 34.2, 31.9, 29.0; IR (neat, $cm^{-1}$): 3288, 2931, 2864, 2361, 1678, 1548; MS (EI): m/z 369 ($M^+$), 184 (100%); HRMS (EI): calcd for $C_{19}H_{22}ClF_2NO_2$ (M) 369.1307, found 369.1285.

Example 37

[Chemical Formula 58]

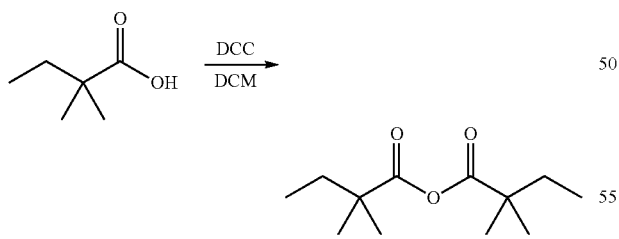

To a solution of 2,2-dimethylbutyric acid (200 mg, 1.72 mmol) in dichloromethane (2 mL), DCC (193 μL, 0.861 mmol) was added at room temperature. After stirring at room temperature for 24 hours, the reaction solution was diluted with cool hexane and filtrated through cotton plug. The resultant filtrate was distilled under reduced pressure for solvent removal to obtain a crude product of 2,2-dimethylbutyric anhydride (271 mg). The obtained product was used without purification for the reaction shown below.

[Chemical Formula 59]

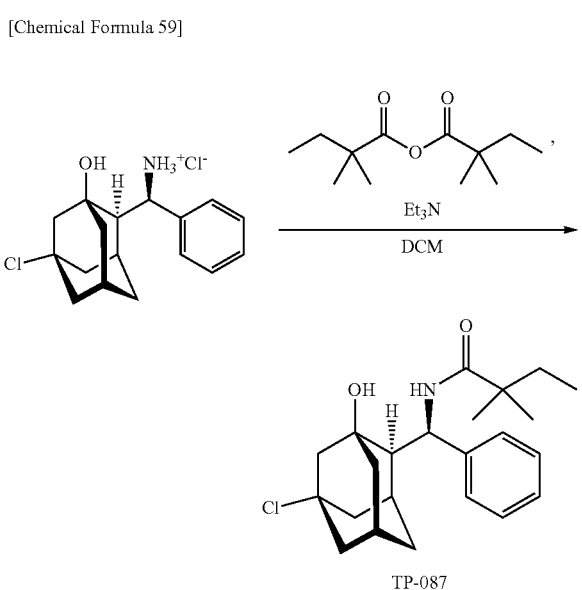

TP-087

To a solution of (R)-((1S,2R,3S,5S,7S)-5-chloro-1-hydroxyadamantan-2-yl)(phenyl)methaneammonium chloride salt (83.0 mg, 0.253 mmol) in dichloromethane (2 mL), the crude product of 2,2-dimethylbutyric anhydride (271 mg) and triethylamine (176 μL, 1.26 mmol) were added at room temperature. After stirring at room temperature for 1 hour, a saturated aqueous solution of sodium bicarbonate was added to the reaction solution, and the mixture was extracted with dichloromethane. After the resultant organic layer was dried over $MgSO_4$, the solvent was distilled off under reduced pressure, and the residues were subjected to silica gel column chromatography (hexane:ethyl acetate=4:1) to obtain TP-087 (83.7 mg, 85%) as a colorless solid.

$[\alpha]_D^{28}$=+100.3 (c=0.227, $CHCl_3$); $^1$H-NMR (400 MHz, $CDCl_3$): δ7.36-7.30 (m, 5H), 5.92 (d, J=9.2 Hz, 1H), 5.43 (t, J=9.2 Hz, 1H), 2.31 (s, 2H), 2.18 (d, J=9.2 Hz, 1H), 2.08-2.03 (m, 8H), 1.87 (d, J=13.5 Hz, 1H), 1.51-1.48 (m, 3H), 1.37 (d, J=13.5 Hz, 1H), 1.10 (s, 6H), 0.70 (t, J=7.6 Hz, 3H); $^{13}$C-NMR (100 MHz, $CDCl_3$): δ177.0, 142.5, 129.2, 127.8, 126.9, 71.9, 66.8, 56.4, 53.1, 52.3, 48.2, 46.6, 42.4, 38.7, 33.8, 33.7, 32.0, 29.3, 24.8, 24.7; IR (neat, $cm^{-1}$): 3574, 3358, 2937, 2865, 1637, 1515; MS (EI): m/z 389 ($M^+$), 204 (100%); HRMS (EI): calcd for $C_{23}H_{32}ClNO_2$ ($M^+$) 389.2111, found 389.2135.

Example 38

[Chemical Formula 60]

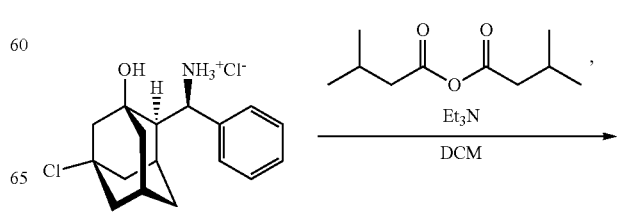

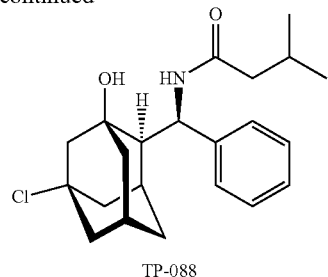

TP-088

To a solution of (R)-((1S,2R,3S,5S,7S)-5-chloro-1-hydroxyadamantan-2-yl)(phenyl)methaneammonium chloride salt (30.0 mg, 0.0914 mmol) in dichloromethane (1 mL), isovaleric anhydride (54.8 µL, 0.274 mmol) and triethylamine (63.7 µL, 0.457 mmol) were added at room temperature. After stirring at room temperature for 1 hour, a saturated aqueous solution of sodium bicarbonate was added to the reaction solution, and the mixture was extracted with dichloromethane. After the resultant organic layer was dried over $MgSO_4$, the solvent was distilled off under reduced pressure, and the residues were subjected to silica gel column chromatography (hexane:ethyl acetate=2:1) to obtain TP-088 (34.5 mg, 97%) as a colorless solid.

$[\alpha]_D^{29}$=+89.3 (c=0.191, $CHCl_3$); $^1$H-NMR (400 MHz, $CDCl_3$): δ7.38-7.27 (m, 5H), 5.83 (d, J=9.2 Hz, 1H), 5.42 (t, J=9.7 Hz, 1H), 2.35 (d, J=25.6 Hz, 2H), 2.19 (d, J=9.7 Hz, 1H), 2.16-1.99 (m, 10H), 1.93 (d, J=14.0 Hz, 1H), 1.66 (s, 1H), 1.50 (d, J=12.1 Hz, 1H), 1.37 (d, J=13.5 Hz, 1H), 0.88 (d, J=6.3 Hz, 3H), 0.83 (d, J=6.3 Hz, 3H); $^{13}$C-NMR (100 MHz, $CDCl_3$): δ171.7, 142.5, 129.2, 127.9, 127.1, 72.0, 66.8, 56.4, 52.9, 52.4, 48.0, 46.5, 46.3, 38.8, 34.0, 32.1, 29.2, 26.1, 22.4, 22.3; IR (neat, $cm^{-1}$): 3556, 3285, 2935, 2867, 1636, 1540; MS (EI): m/z 375 ($M^+$), 106 (100%); HRMS (EI): calcd for $C_{22}H_{30}ClNO_2$ (M) 375.1965, found 375.2003.

Test Example 1

The plasmid vector having inserted therein Kir6.2 channel cDNA: pcDNA3.1-Kir6.2, was obtained from Dr. Toru Ishizuka at the Graduate School of Life Sciences, Tohoku University. The plasmid vector, pcDNA3.1 1-Kir6.2, was prepared using GenElute HP Plasmid Maxiprep Kit (produced by Sigma-Aldrich) in accordance with the attached manual. A DMEM culture medium (Gibco) (composed of 450 mL of DMEM culture medium supplemented with 50 mL of bovine serum and 100 units of penicillin/streptomycin), in which Neuro2A cells (N2A cells, National Instituted of Biomedical Innovation) were cultured, was replaced with Opti-Mem (Gibco) supplemented with the vector pcDNA3.1-Kir6.2 (1 µg/µL) prepared above (containing Lipofectamine R2000 at 1 µg/1 mL), and cell culture was continued for 5 hours to obtain N2A cells engineered to overexpress Kir6.2 channels. The culture medium was replaced back with a DMEM culture medium, and cell culture was continued for two days. Then, any of memantine (produced by Sigma-Aldrich) and the compounds of the present invention (n=4 per group) was added to each aliquot of the culture medium (DMEM, Gibco) to give a concentration of 10 nM, and the aliquots were allowed to stand for one hour. Thereafter, Kir6.2 channel-overexpressing N2A cells were collected, suspended in an SDS sample buffer, and analyzed for CaMKII activation by immunoblotting using an anti-phosphorylated CaMKII antibody (Fukunaga K., et al., *J. Biol. Chem.* 1992, 267, 22527-22533) as a primary antibody and an anti-rabbit IgG antibody (produced by SouthernBiotech) as a secondary antibody (by following conventional immunoblotting conditions except for using the aforementioned antibodies). The results are shown in FIG. 1.

In FIG. 1, the levels of CaMKII activation in the groups treated with the test compounds are shown relative to that in the group not treated with a test compound (control: c), which is taken as 100%.

Test Example 2

Figures 1, 2:
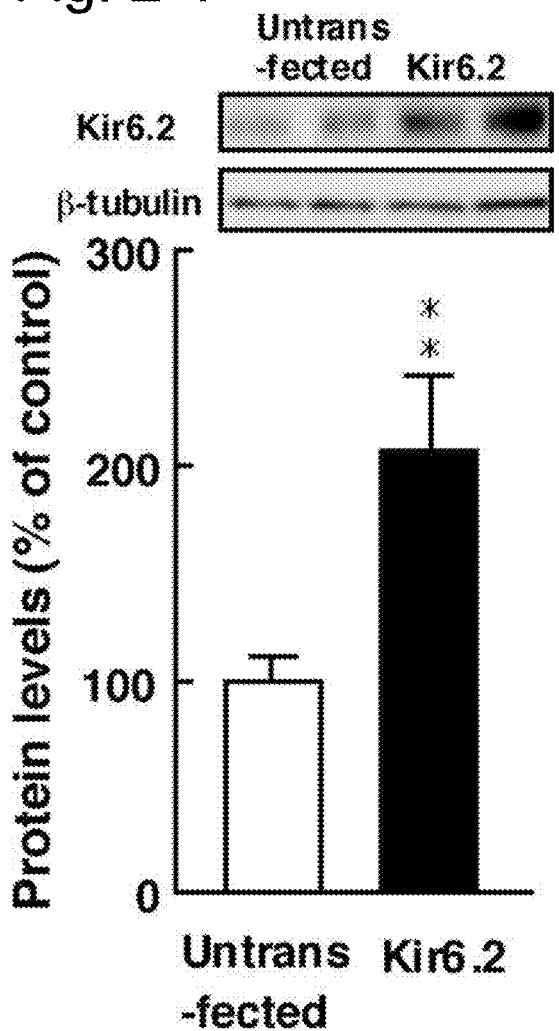
Figure 2:
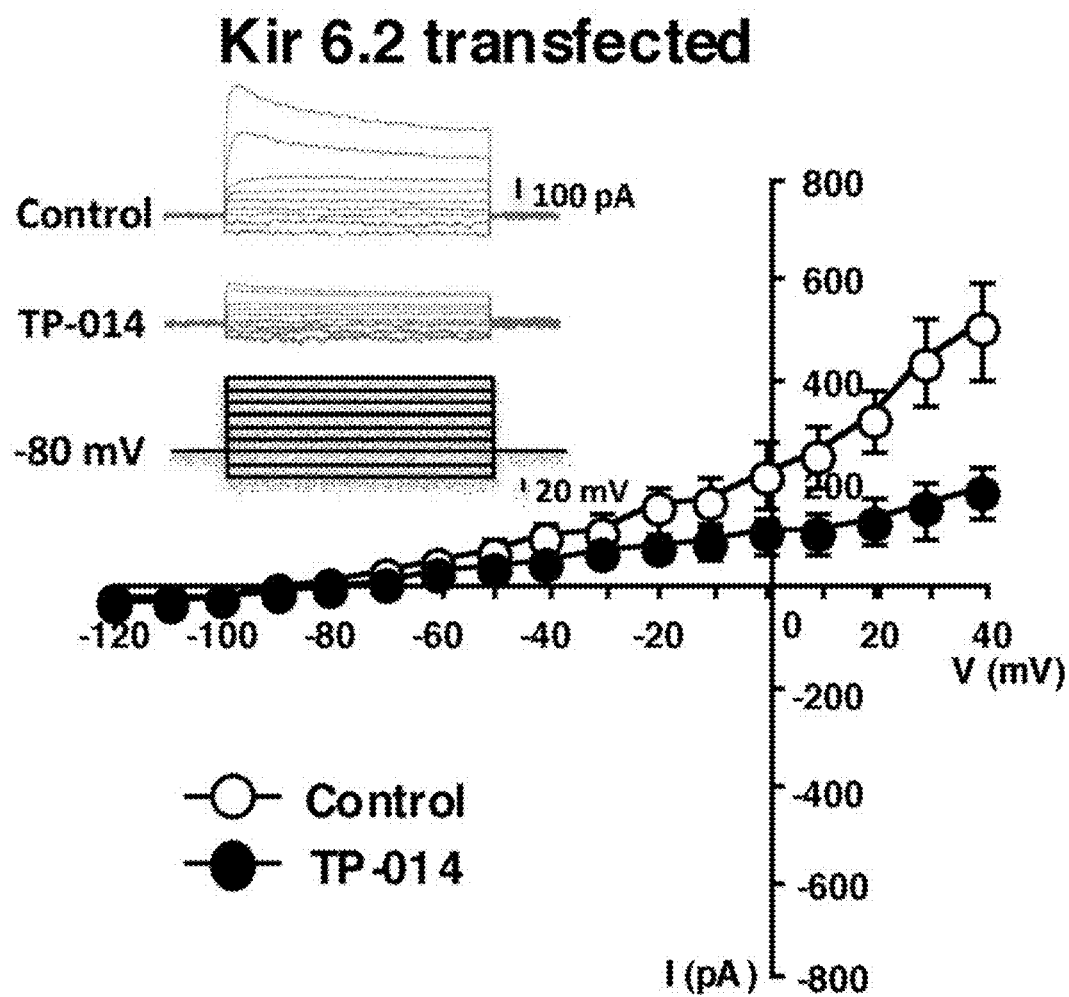

The Kir6.2 channel-overexpressing cells obtained in Test Example 1 were used to measure potassium current discharged out of the cells by a conventional patch-clamp assay. The results are shown in FIGS. 2-1 and 2-2. ATP-sensitive potassium channels (Kir6.2 channels) are localized in the cell membranes of nerve cells. When the channels are inhibited and closed, the threshold of the nerve cell membranes increases to create a condition analogous to temporal generation of action potential, with the result that intracellular potassium current is discharged out of the cells and instead extracellular calcium current enters the cells. Immunoblotting of Kir6.2 channel-overexpressing cells (prepared by the aforementioned method) using an anti-Kir6.2 channel antibody (prepared by a conventional method) (n=5, under the same conditions as in Test Example 1, except for using the anti-Kir6.2 channel antibody) confirmed that Kir6.2 channels were overexpressed in N2A cells (FIG. 2-1; upper: immunoblot staining images; lower: quantitative representations of the signal intensity of staining bands). No change was observed in the levels of the housekeeping gene product β tubulin (the conditions were the same as those for Kir6.2 detection, except for using an anti-n tubulin antibody obtained from Sigma-Aldrich). FIG. 2-2 shows the results of a test (n=5 per group) confirming that when Kir6.2 channel-overexpressing cells were allowed to stand in an electrophysiological analysis buffer supplemented with TP-014 to a concentration of 10 nM, outwardly flowing potassium current for shifting the membrane potential of nerve cells to positive was suppressed. The results revealed that TP-014 inhibited Kir6.2 channels and prevented intracellular potassium current from being discharged out of the cells.

Test Example 3

Figures 1, 3:
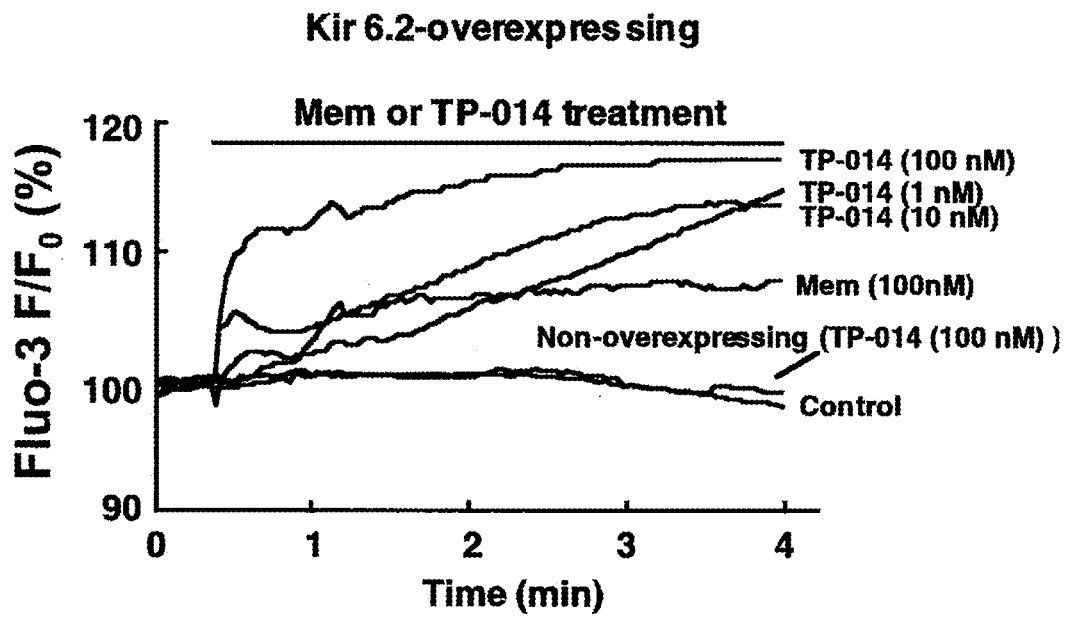
Figures 2, 3:
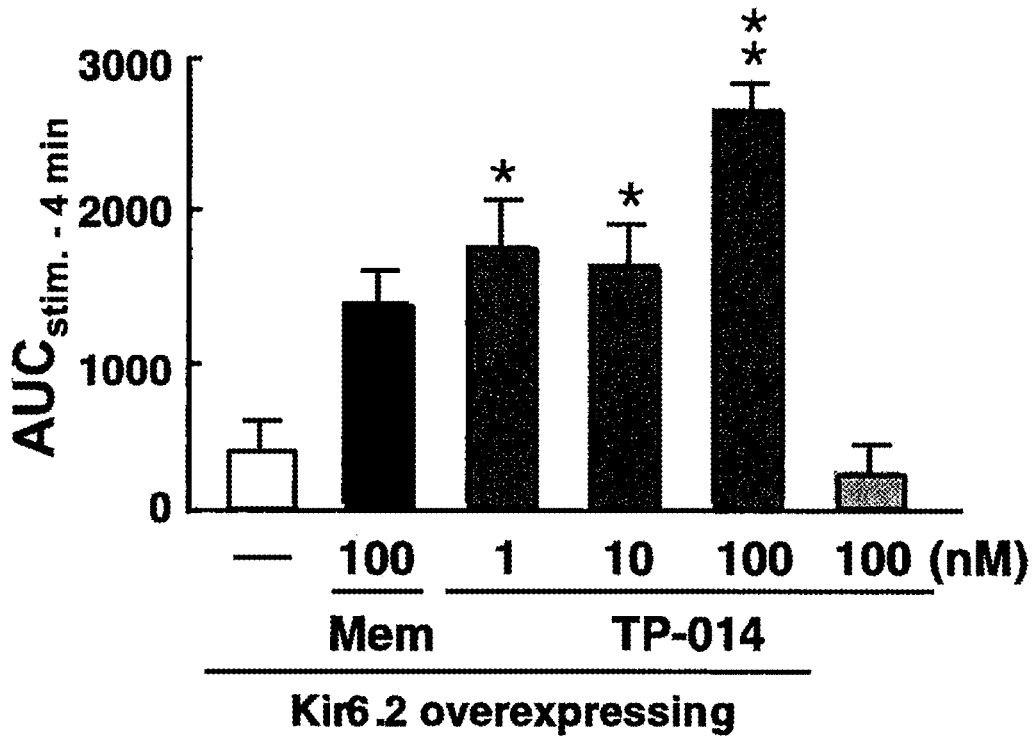

The same Kir6.2 channel-overexpressing cells as used in Test Example 1 were used to measure, by calcium imaging, the levels of calcium entering the cells after TP-014 treatment. The results are shown in FIGS. 3-1 and 3-2. The calcium imaging is a method in which cultured nerve cells are treated with a culture medium supplemented with a calcium fluorescent dye (Fura2, produced by Dojindo Laboratories) to a concentration of 4 µM, and measured for the levels of calcium based on fluorescence intensity. The imaging was carried out using an imaging apparatus (LAMBDA 10-2, produced by Sutter Instrument) in accordance with the attached manual. FIG. 3-1 shows the results of measurement for 4 minutes of TP-014 concentration-dependent change over time in calcium levels in the groups treated with TP-014 (1 to 100 nM) or memantine (100 nM). FIG. 3-2 shows the results of measurement of calcium levels at 4 minutes after the treatment with memantine (100 nM) or TP-014 (1-100 nM) (n=5 per group). TP-014 is more potent to enhance calcium levels than memantine. It was confirmed that the treatment with TP-014 significantly increased intracellular calcium levels through inhibition of potassium discharge out of the cells as observed in Test Example 2.

Test Example 4

Alzheimer's disease model mice (APP23 mice; Sturchler-Pierrat, et al., *Proc. Natl. Acad. Sci. U.S.A.* 1997, 94, 13287-13292) (12 month-old) were chronically treated (orally) with TP-014 (1 mg/kg) once a day for two months, and as a result, a significant cognitive function enhancing effect was observed. The results are shown in FIGS. 4-1 to 4-7. The test compound was orally administered in a dissolved state in a 0.5% aqueous solution of carboxymethyl cellulose (vehicle) (the same applies hereunder).

Figures 1, 4:
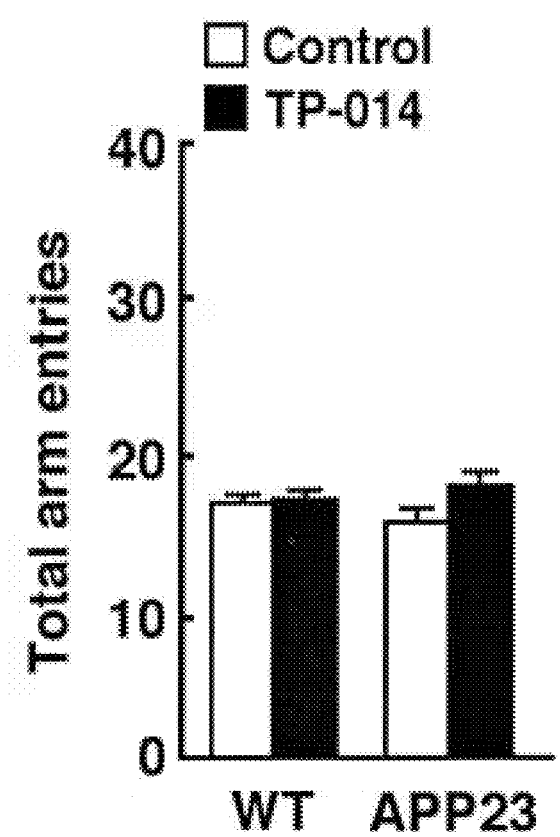
Figures 2, 4:
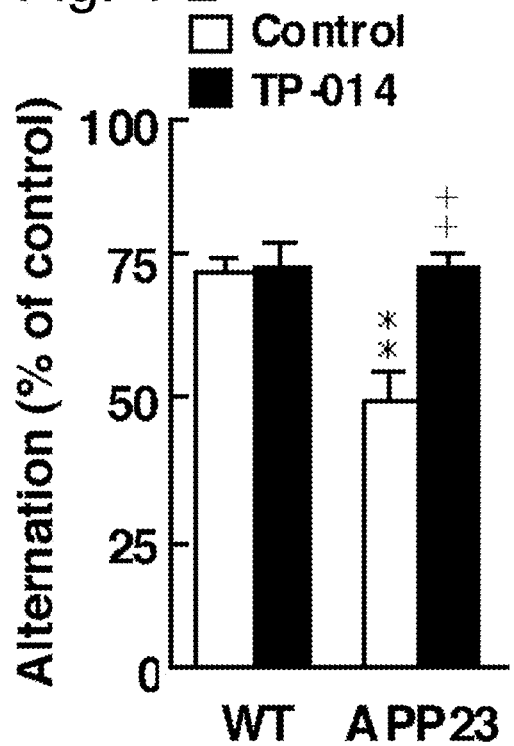
Figures 3, 4:
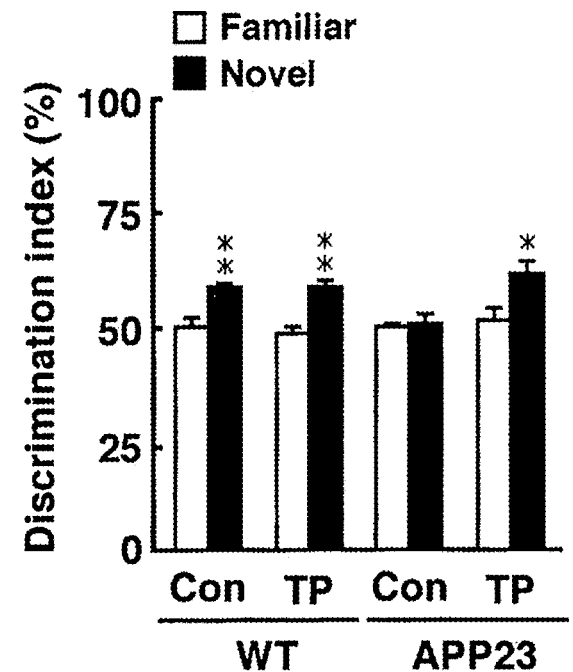
Figure 4:
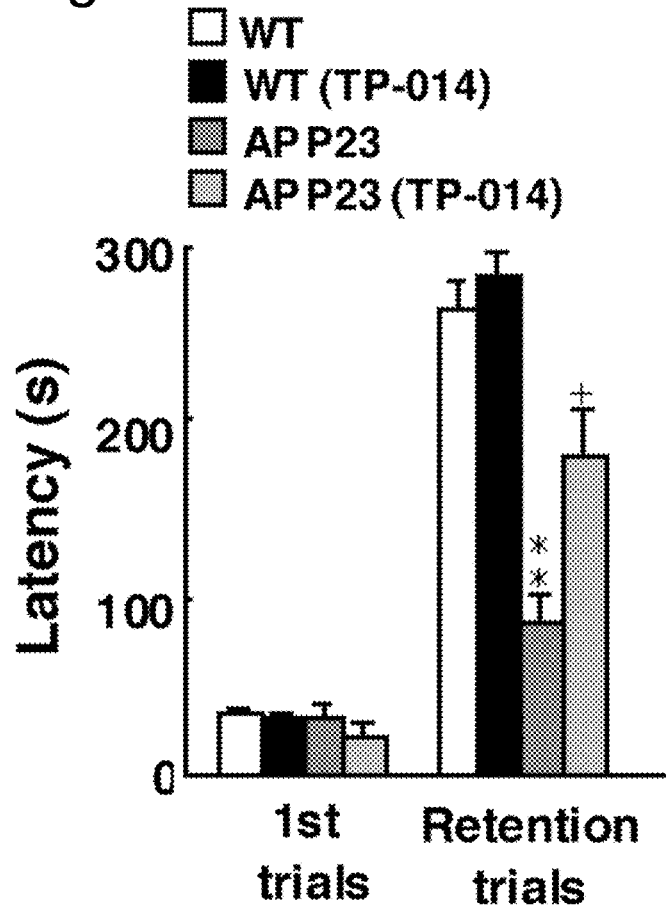

FIGS. 4-1 to 4-4 show the results of behavioral analyses. FIGS. 4-1 and 4-2 show the results of analysis of attentional function in wild-type mice (C57BL/6J, Japan SLC) v.s. APP23 mice (n=5 per group) by conventional Y-maze test. It was observed that the treatment with TP-014 significantly enhanced the attentional function in mice. In the Y-maze test, mice are allowed to freely walk between three arms for 8 minutes. Here, the different arms are designated as A, B and C. A mouse positioned in arm A can move to arm B or C. If the mouse moves to arm B, then the mouse may move to arm C. Such a mouse moving sequentially between arms A, B and C is regarded as a mouse giving correct answer. In contrast, a mouse moving from arm A to B then back to A and not entering a new arm is regarded as a mouse making wrong answer. The arms to which a mouse move are recorded in the order they are chosen by the mouse, and the number of times that a mouse moves between three arms within a specified time is counted and regarded as "total arm entries". Further, the number of correct-answers (the number of times that a mouse moving sequentially between three different arms) is counted and regarded as the number of alternation behaviors ("No. of alternations"). The percentage of "No. of alternations" relative to the number obtained by subtracting 2 from "total arm entries" is expressed as percent alternation (%) which serves as an index for normal alternation behavior (correct answer rate in spatial working memory).

Mice have a tendency to prefer a novel object. Normal mice show a correct answer rate of 70%, whereas APP23 mice show a decrease in correct answer rate down to about 50%. The analysis of attentional function (cognitive function) was done using this percent alternation as an index.

FIG. 4-3 shows the results of analysis of the memory for novel object recognition in WT mice v.s. APP23 mice (both, n=5) by conventional novel object recognition test. In the novel object recognition test, two building blocks of the same shape are placed in a mouse cage, and a mouse is allowed to play with these blocks (for 10 minutes; this play is called a practice trial). One hour later, one of the building blocks is replaced with a different shape of block. A normal mouse shows interest in a novel object, and plays a longer time with the different shape of building block. In contrast, a mouse with Alzheimer's disease does not recognize a novel object and has impaired memory. After the replacement with a different shape of block, the mouse is allowed to freely play for another 5 minutes (this play is called a retention trial). During the practice and retention trials, the number of times that a mouse contacts with each of the two objects is counted. The percentage (%) of the number of contacts with the different shape of building block relative to the total number of contacts during the retention trial is calculated as a discrimination index.

FIG. 4-4 shows the results of fear memory analysis by conventional fear conditioning test (n=5 per group). The fear conditioning test is an analysis method that takes advantage of the characteristic preference of mice for a dark place over a bright place. On day 1, a mouse is placed in a bright place. The mouse, which prefers darkness, enters a dark place (dark box), but then electrical simulation is delivered to the mouse. The mouse is surprised, returns to the bright place, and never enters the dark place. On day 2, the mouse is placed again in the bright place (the same place as on day 1) and observed for 5 minutes to see whether the mouse enters a dark place. If the mouse immediately enters the dark place, it is determined that the mouse experiences a decline in fear memory. "Latency" refers to the number of seconds until the mouse placed in the bright place on day 2 enters a dark place. APP23 mice immediately entered a dark place and were observed to experience a decline in fear memory. However, those mice treated with TP-014 for two months were observed to show an improvement in fear memory.

Figures 4, 5:
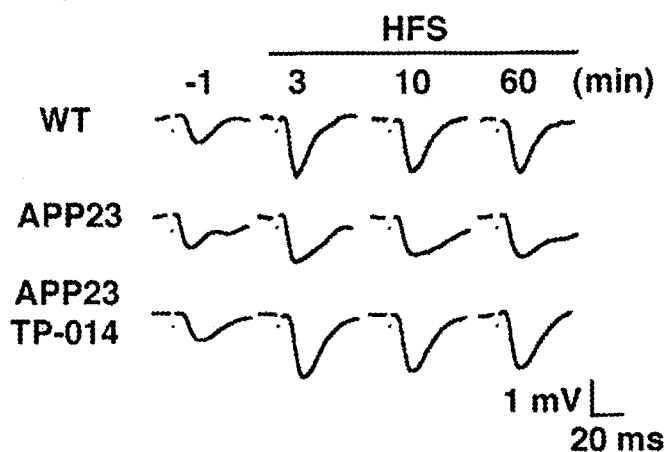

FIGS. 4-5 to 4-7 show the results of analysis by electrophysiological test regarding long-term potentiation phenomenon (LTP) which serves as an index for memory formation. The hippocampus in the brain plays an important role in memorization. A hippocampus sample was cut into slices (400 m thick), and the slices were recovered at 34° C. for two hours in an artificial cerebrospinal fluid (composed of 126 mM NaCl, 5 mM KCL, 26 mM $NaHCO_3$, 1.3 mM $MgSO_4$-$7H_2O$, 1.26 mM $KH_2PO_4$, 2.4 mM $CaCl_2$-$2H_2O$, and 10 mM glucose) saturated with a 95% $O_2$/5% $CO_2$ gas. The hippocampal slices were transferred to a measuring chamber and perfused with an artificial cerebrospinal fluid supplemented with TP-014. Recording of the activity of nerve cells after electrical stimulation and measurement of postsynaptic mass potential (fEPSP) were taken to evaluate the degree of improvement in LTP. The waveforms recorded are shown in FIG. 4-5. Thereafter, electrical stimulation (100 Hz) was applied to produce a plastic change in the hippocampus (it is believed that memory is formed by a plastic change in the hippocampus). It was observed that the percent increase in the excitability of nerve cells decreased in APP23 mice but was improved in those mice chronically treated with TP-014, which demonstrates that memory and learning are enhanced by improvement in LTP.

Test Example 5

Hippocampus samples were excised from APP23 mice, and hippocampal slices were suspended in an SDS sample buffer and analyzed for protein phosphorylation by immunoblotting using antibodies against CaMKII, CaMKIV and ERK (CaMKII: Fukunaga, et al., *J. Biol. Chem.* 1992, 267, 22527-22533; CaMKIV: Kasahara, et al., *J. Biol. Chem.* 2001, 276, 24044-24050; ERK: produced by Sigma-Aldrich). The results are shown in FIGS. 5-1 and 5-2. CaMKII, CaMKIV and ERK are all considered as molecules playing an important role in memory formation. As a result of the analysis, decreased CaMKII phosphorylation was observed in untreated APP23 mice, whereas increased CaMKII phosphorylation was observed in APP23 mice chronically treated orally with TP-014 (the treatment conditions were the same as in Test Example 4). The results demonstrate that activation of CaMKII is important in the effect of TP-014 treatment to improve memory in APP23 mice.

Hippocampal slices were suspended in an SDS sample buffer and analyzed by immunoblotting for GluAl (Ser-831), Synapsin I (Ser-603) and CREB (Ser-133), which are known as molecules that are activated by activation of CaMKII. The antibodies against these molecules were all obtained from Millipore. The results are shown in FIGS. 5-3 and 5-4. The results show that activation of GluAl (Ser-831) and CREB (Ser-133) was induced by activation of CaMKII. FIGS. 5-1 and 5-3 show bands (band images) actually obtained by electrophoresis of immunoblots. FIGS. 5-2 and 5-4 show the results of quantitative analysis of the signal intensity of the bands shown in FIGS. 5-1 and 5-3.

Test Example 6

Figures 4, 5, 6:
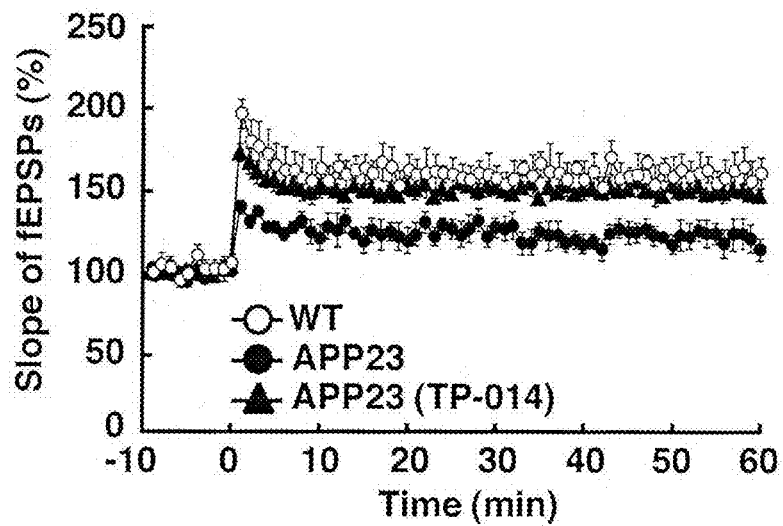
Figures 4, 5, 6, 7:
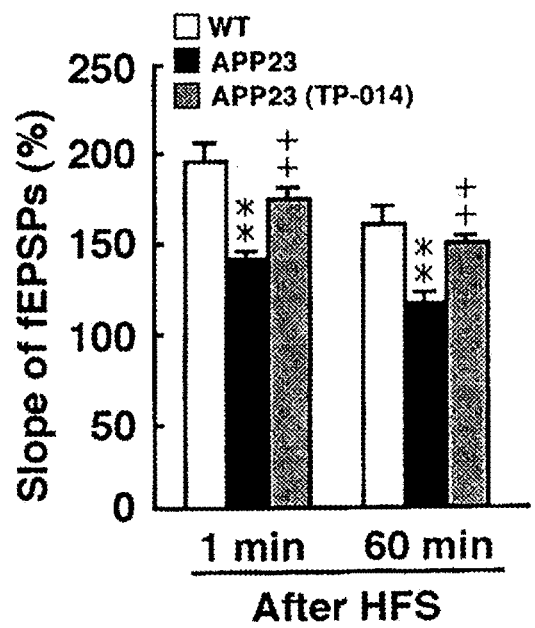
Figures 1, 5:
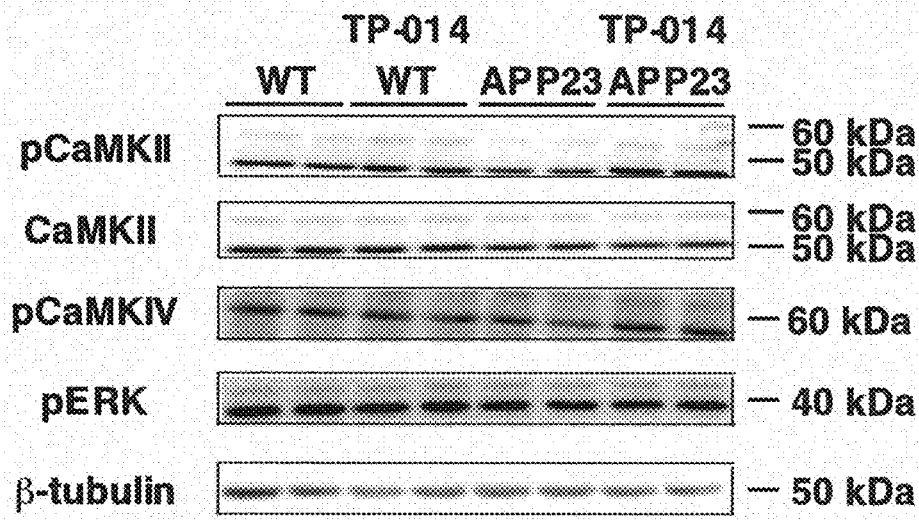
Figures 2, 5:
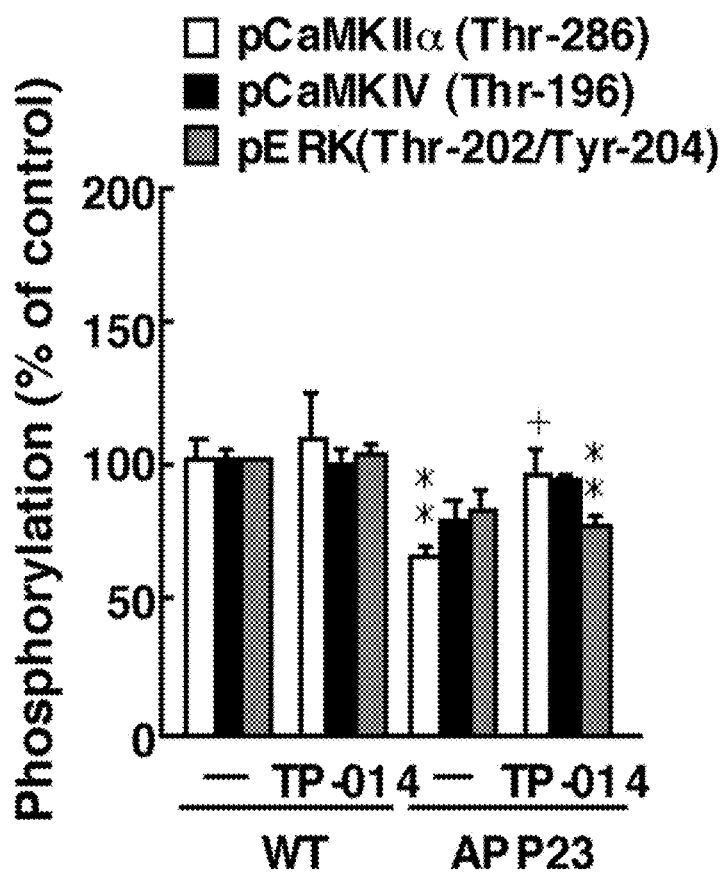
Figures 3, 5:
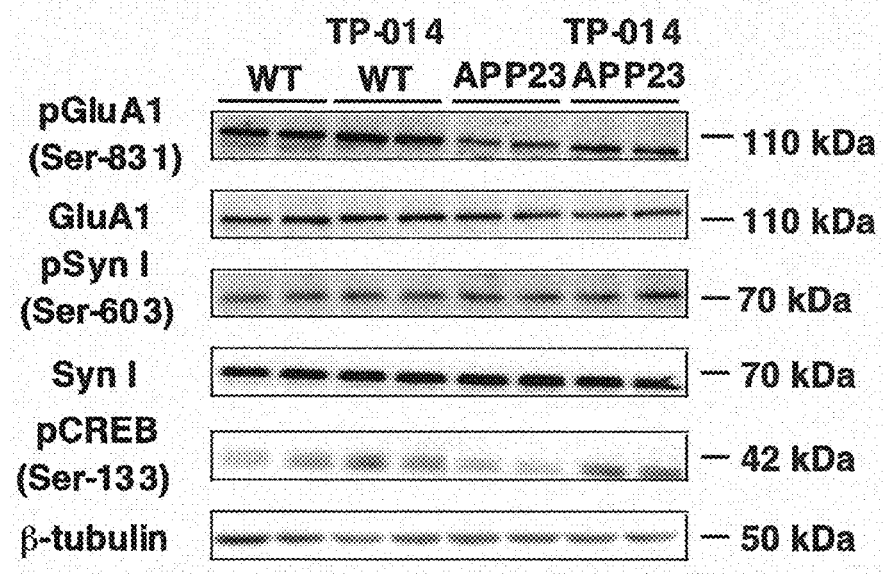
Figures 4, 5:
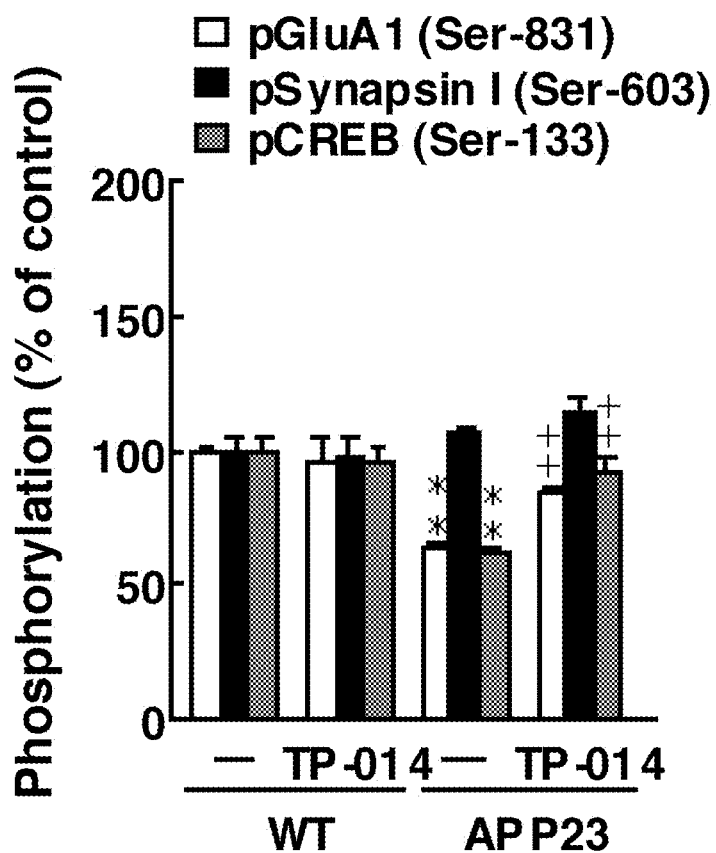
Figures 1, 6:
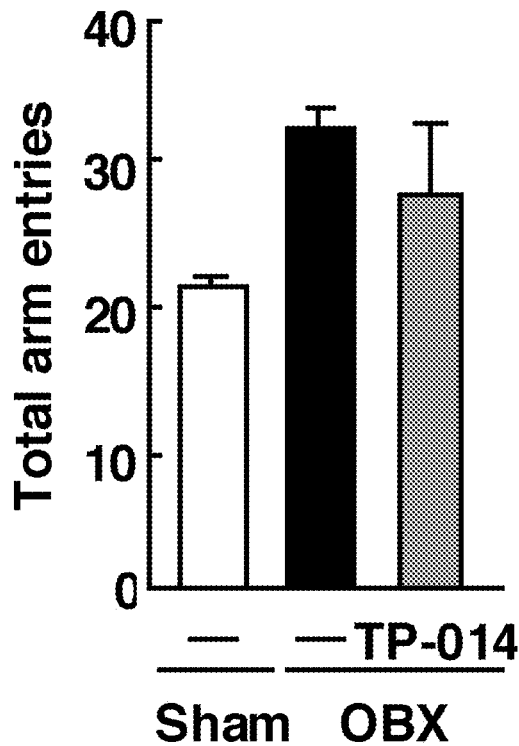
Figures 2, 6:
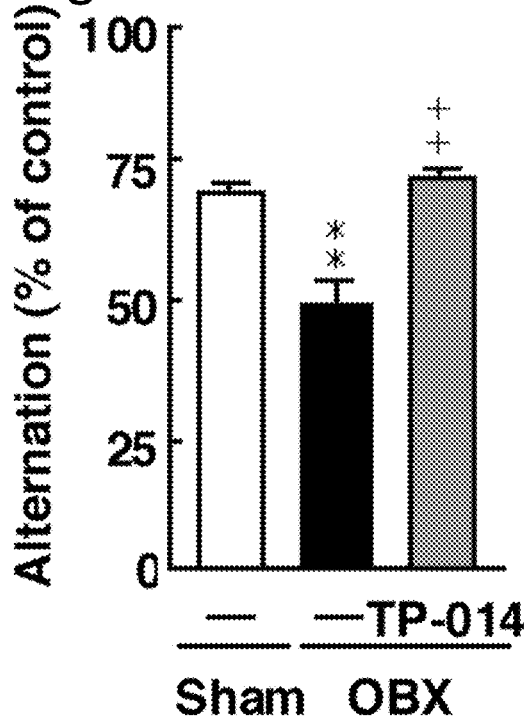
Figures 3, 6:
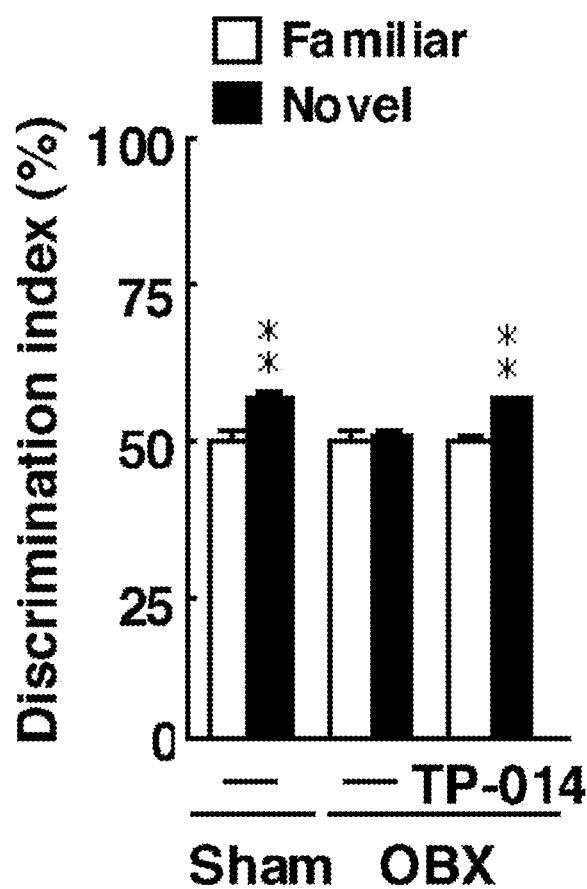
Figures 4, 6:
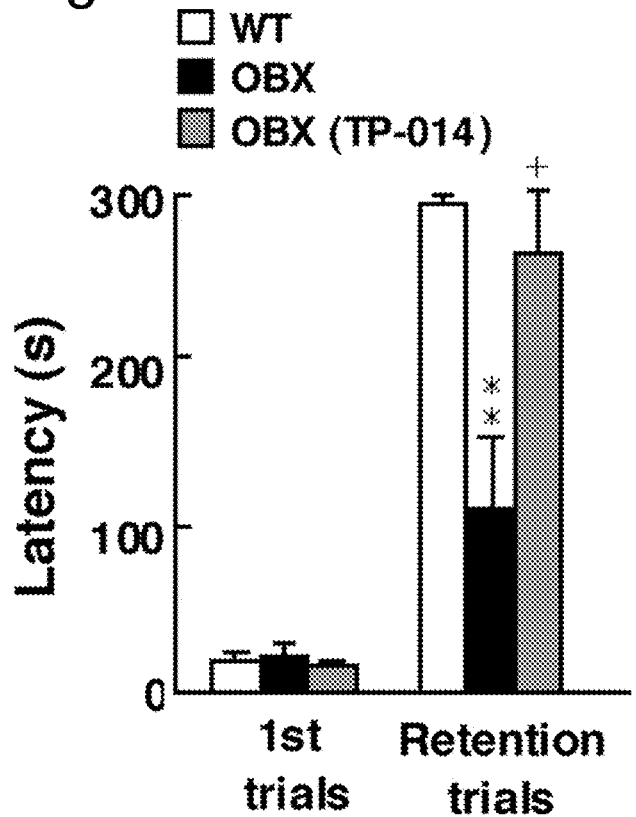
Figures 5, 6:
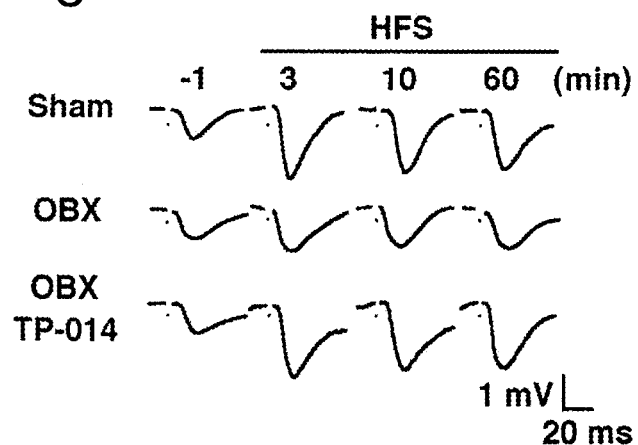
Figure 6:
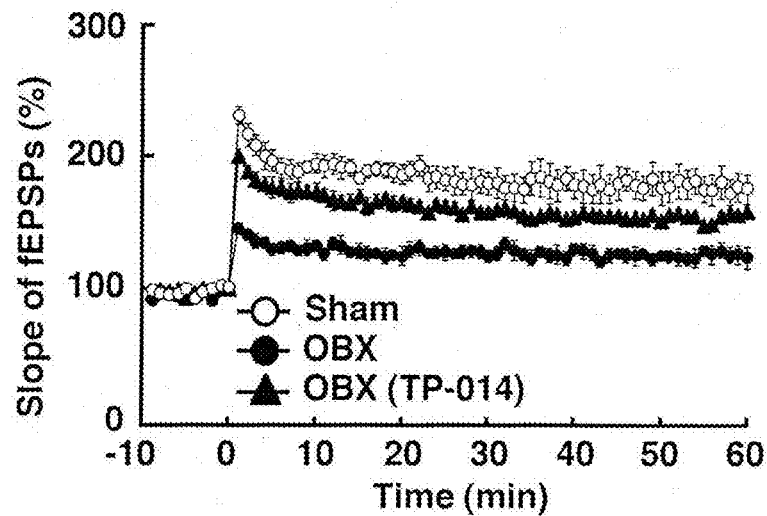
Figures 6, 7:
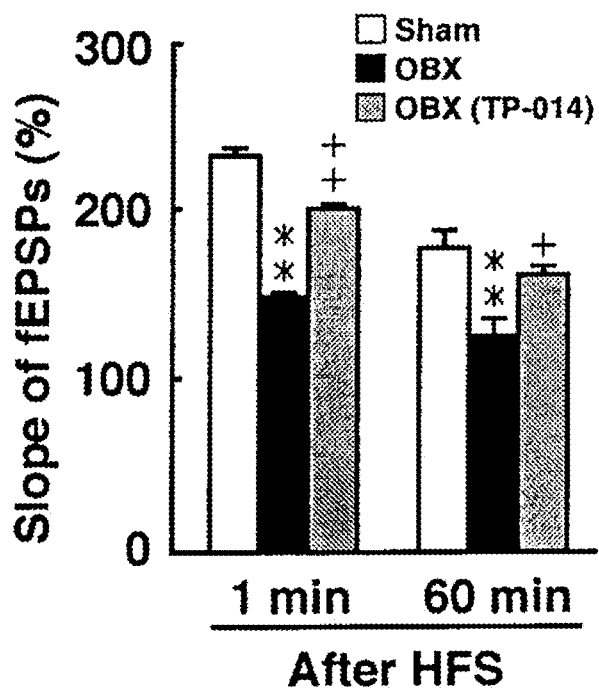
Figures 1, 7:
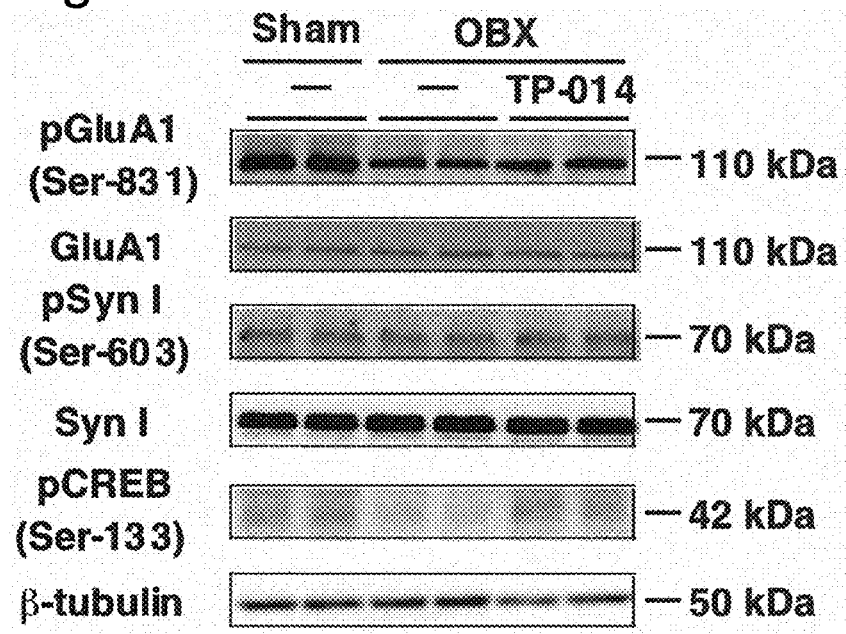
Figures 2, 7:
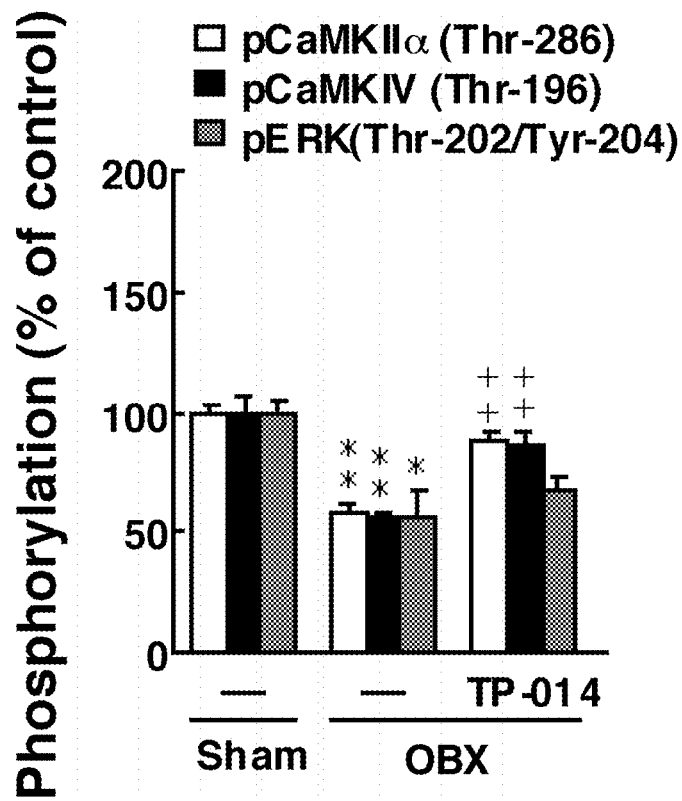
Figures 3, 7:
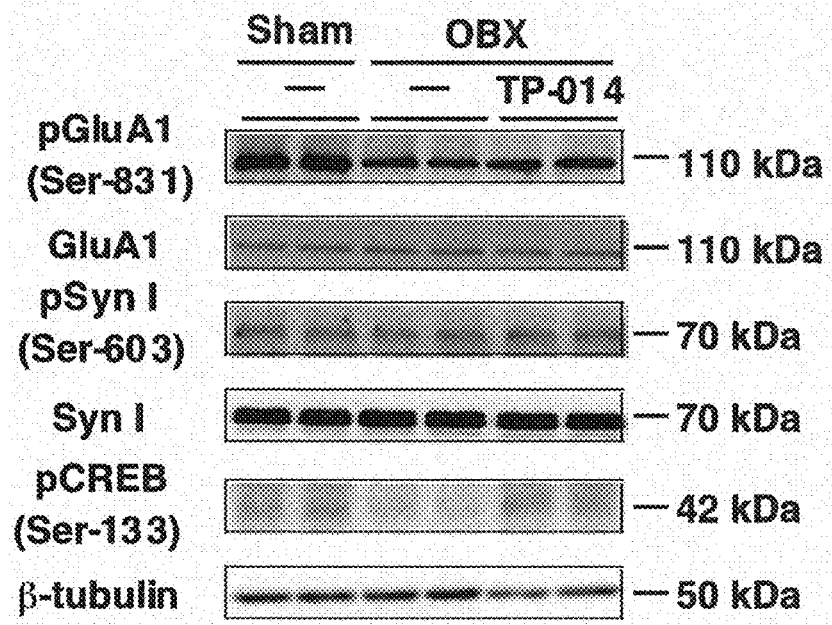
Figures 4, 7:
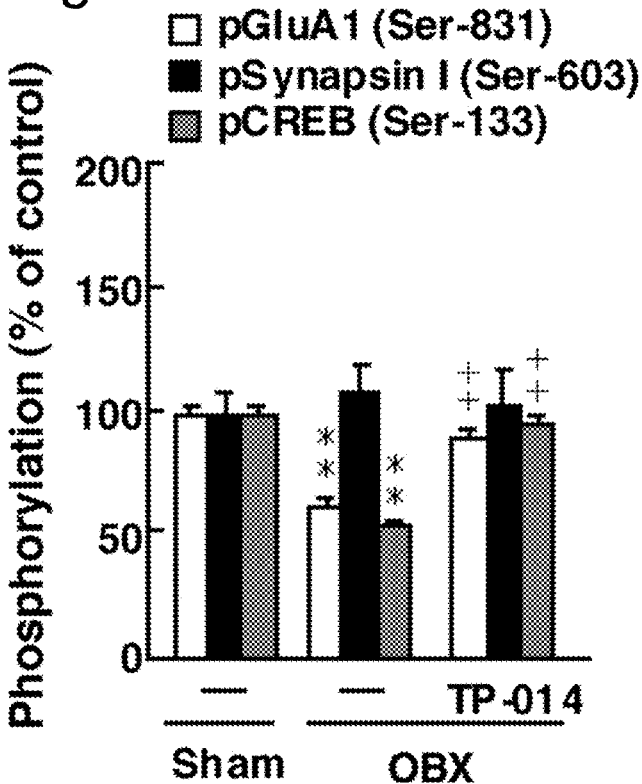

The same experiment as in Test Example 4 was carried out using olfactory bulbectomized mice (OBX mice) as a neurodegenerative disease model. The results are shown in FIGS. 6-1 to 6-7. Cognitive function impairment in the OBX mice was significantly improved by chronic oral treatment with TP-014 (for 2 weeks). The OBX mice were prepared from 10-week-old DDY male mice (Nippon SLC, Hamamatsu, Japan). Olfactory bulbectomy surgery was carried out under anesthesia with pentobarbital sodium (50 mg/kg i.p.; Dainippon, Osaka, Japan). The mice were fixed on a stereotaxic apparatus to drill a 1 mm diameter hole in the skull above the olfactory bulb. The olfactory bulb was aspirated without causing damage to the prefrontal cortex. A sham group was prepared by the same procedure as that for the OBX group, without aspiration of olfactory bulb. One week was allowed for recovery from surgery, and behavioral analyses were performed on the day following the treatment with the test compound for 14 days (2 weeks).

Figures 1, 22:
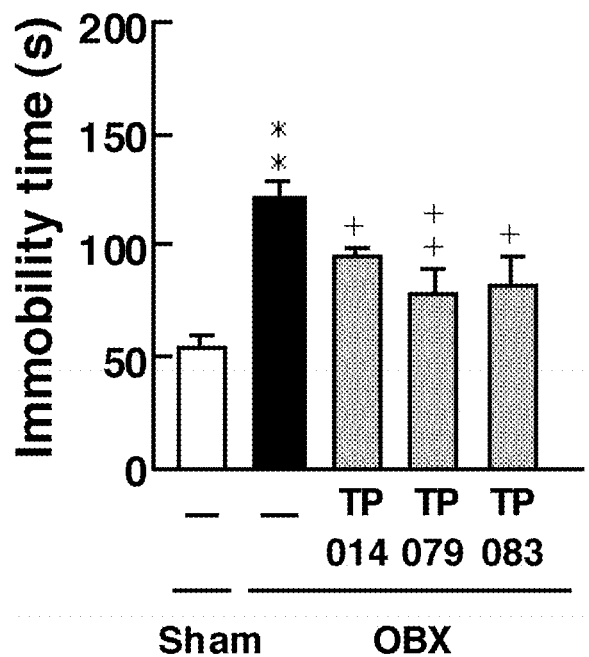
Figures 2, 22:
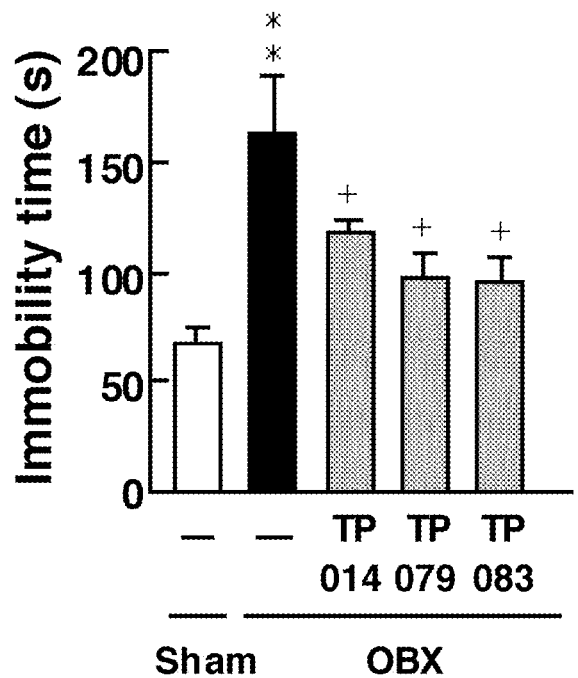
Figures 3, 22:
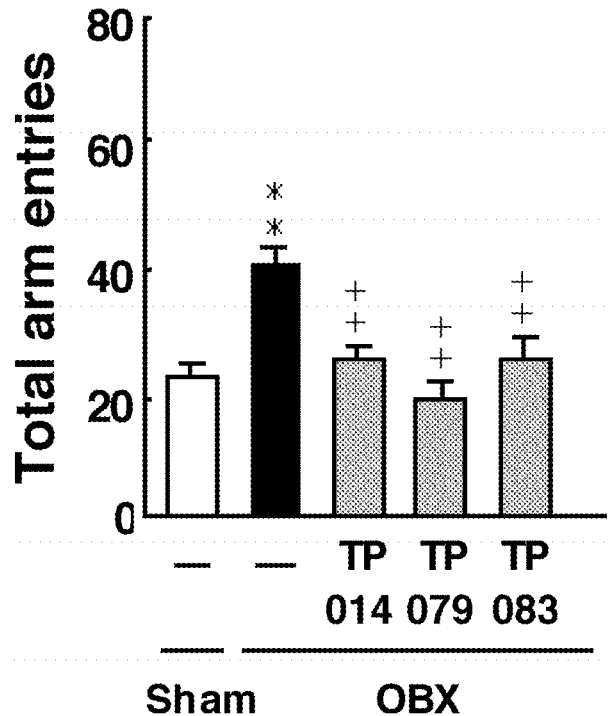
Figures 4, 22:
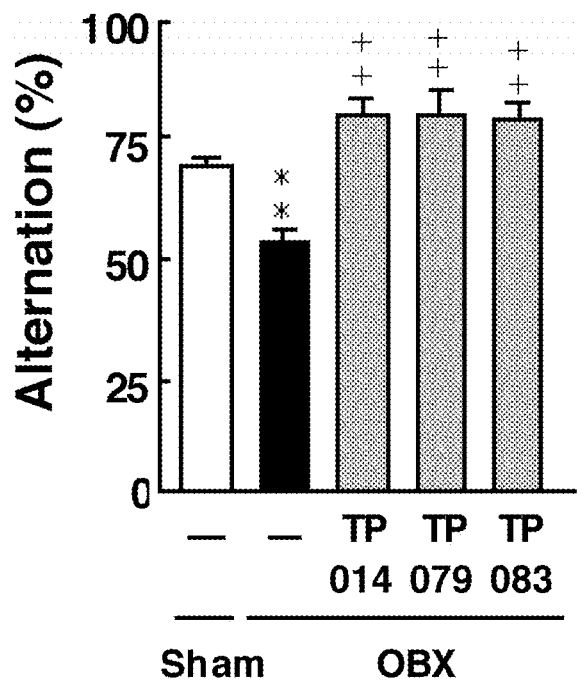
Figures 5, 22:
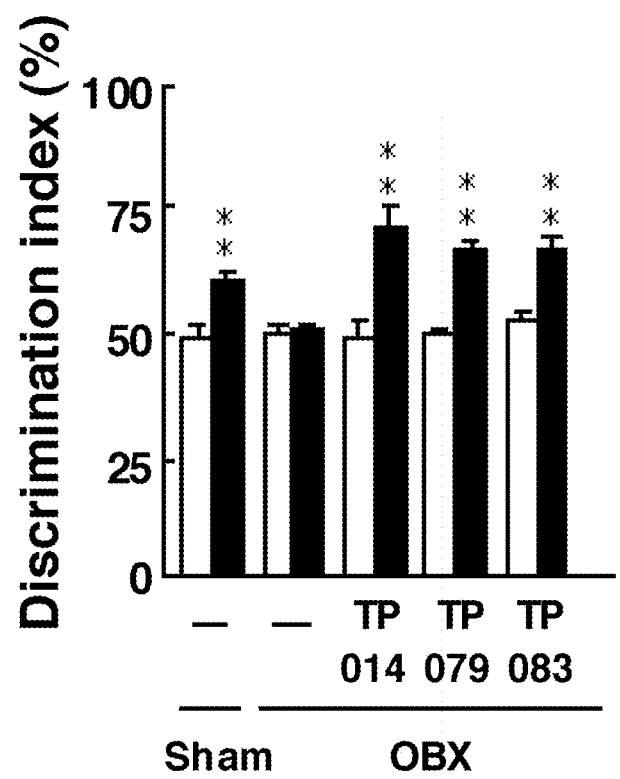

The same model mice as described above were orally treated with a single dose of each of the test compounds (1 mg/kg), and analyzed after 1 hour by Y-maze test and novel object recognition test. The results are shown in FIGS. 22-3 and 22-4 (Y-maze test), and FIG. 22-5 (novel object recognition test). The results shown in FIGS. 22-4 (Y-maze test) and 22-5 (novel object recognition test) confirmed that all the test compounds exhibited a significant cognitive function enhancing effect in the OBX groups as compared with the sham group.

Test Example 7

The intracellular mechanism of cognitive function impairment in OBX mice was investigated by the same procedure as in Test Example 5. The results are shown in FIGS. 7-1 to 7-4. It was found that activation of CaMKII and CaMKIV is important in the hippocampus which plays an important role in memory formation. Also, it was confirmed that activation of GluAl (Ser-831) and CREB (Ser-133), which are molecules downstream of CaMKII and CaMKIV activation, is likewise important in the hippocampus. The antibodies against GluAl (Ser-831) and CREB (Ser-133) were both obtained from Millipore. The results obtained in Test Examples 4 to 7 revealed that increased CaMKII and CaMKIV activities are important for the cognitive function enhancing effect of TP-014. In view of the fact that no cognitive function impairment is observed in CaMKIV gene-deficient mice, CaMKII is considered important for enhancement of cognitive function.

Test Example 8

Figures 1, 8:
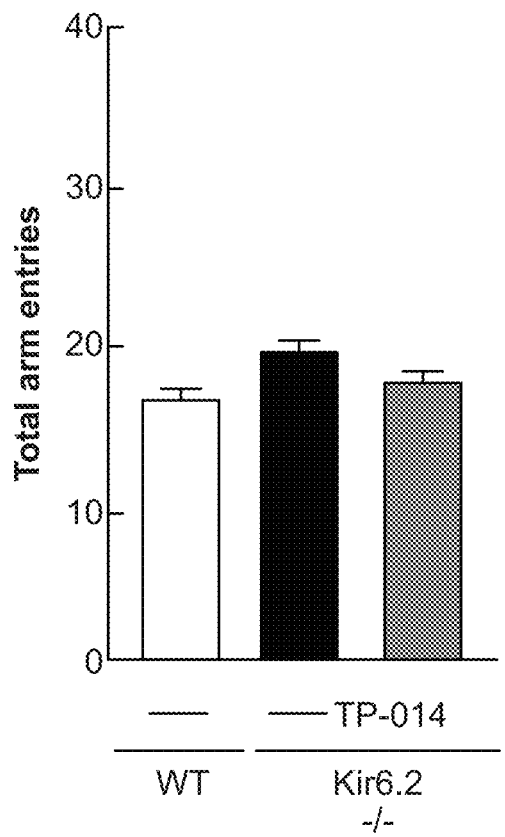
Figures 2, 8:
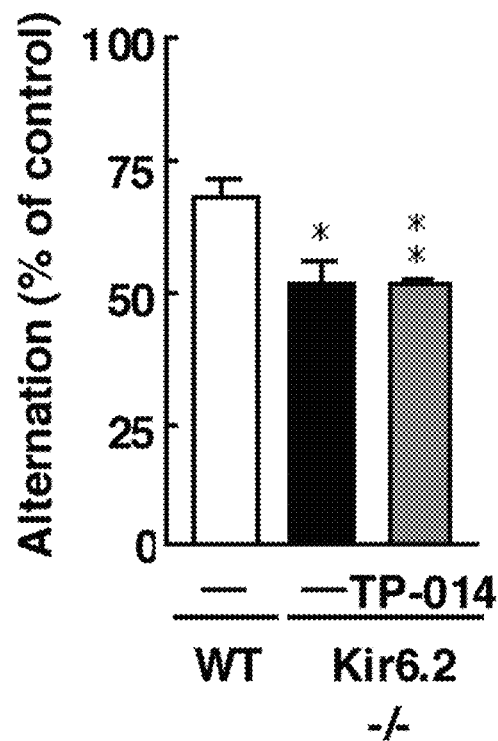
Figures 3, 8:
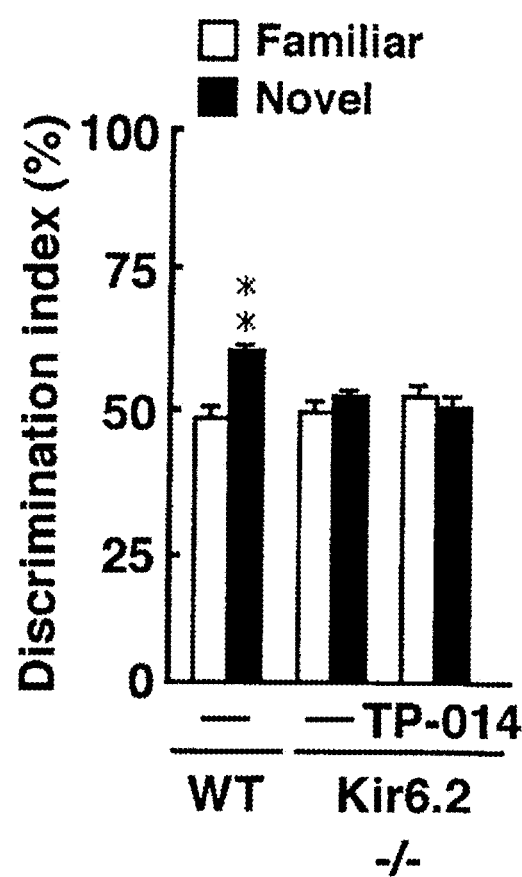
Figures 4, 8:
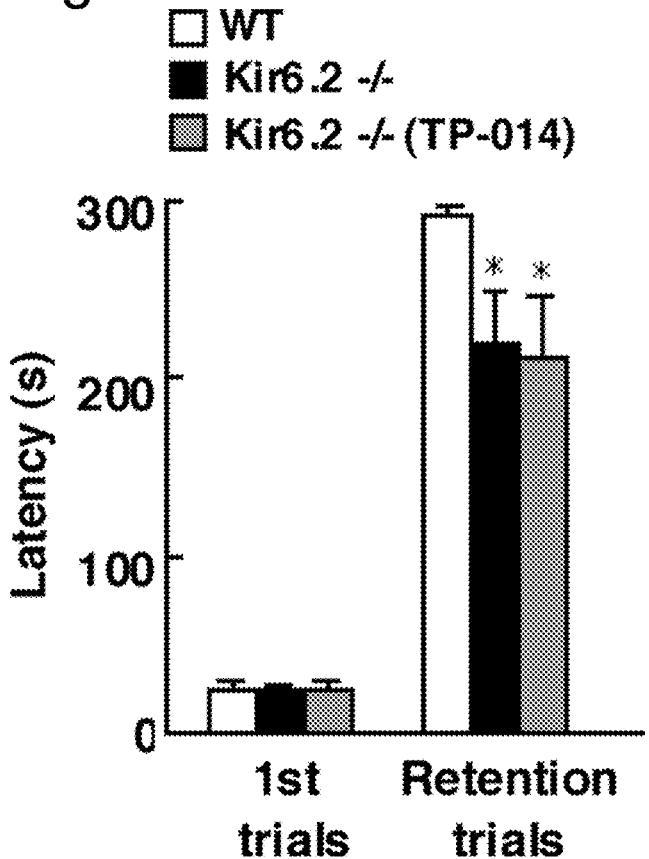
Figures 5, 8:
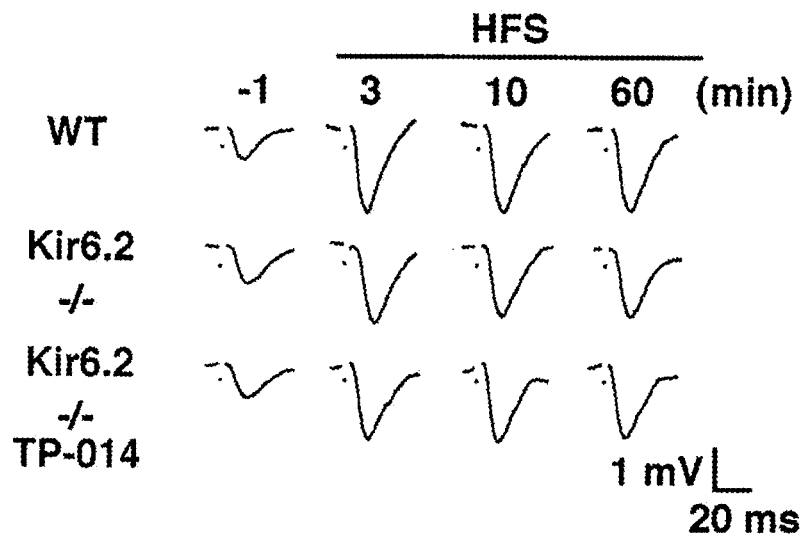
Figures 6, 8:
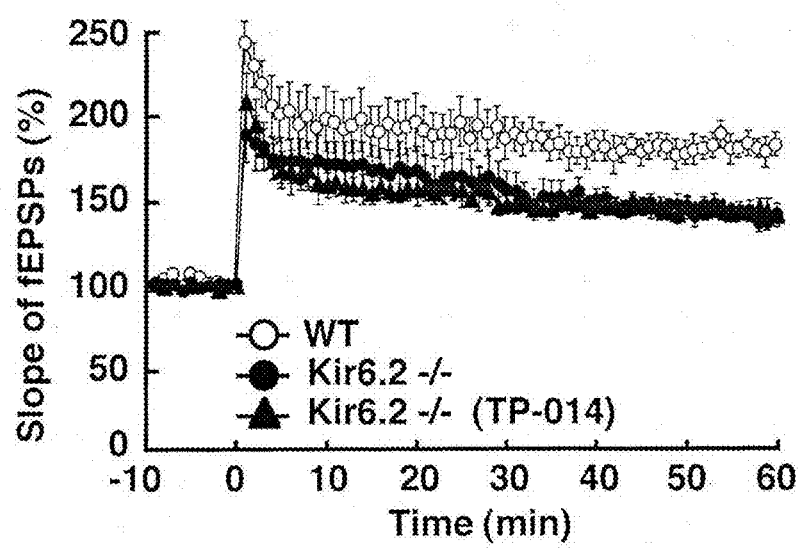
Figures 7, 8:
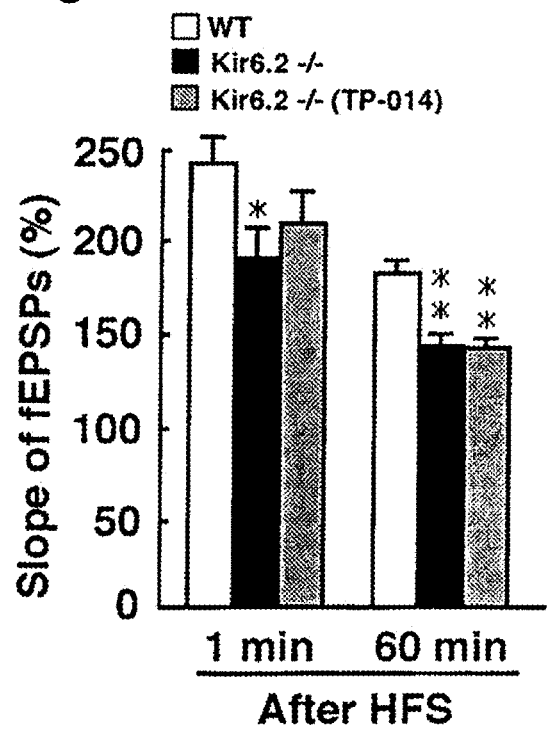

In order to confirm that TP-014 acts to inhibit Kir6.2 channels, Kir6.2 channel-deficient mice were analyzed by the same behavioral tests as in Test Example 4 (FIGS. 8-1 and 8-2: Y-maze test; FIG. 8-3: new object recognition test; FIG. 8-4: fear conditioning test; FIGS. 8-5 to FIG. 8-7: LTP improvement evaluation; n=5 per group) to identify the action site of TP-014. The results shown in FIGS. 8-1 to 8-7 confirmed that cognitive function impairment was induced in the Kir6.2-deficient mice. This fact suggests that Kir6.2 channels are important for memory formation. It was also found that memory impairment and LTP attenuation in the Kir6.2-deficient mice are not improved by chronic treatment with TP-014 (two months). This fact suggests that Kir6.2 channels are the action site of TP-014. The analysis methods were the same as in Test Examples 4 to 7. Kir6.2-deficient mice were obtained from Professor Susumu Seino, School of Medicine of Kobe University (Miki T., et al., *Proc. Natl. Acad. Sci. U.S.A.* 1998, 95, 10402-10406).

Test Example 9

Figures 1, 9:
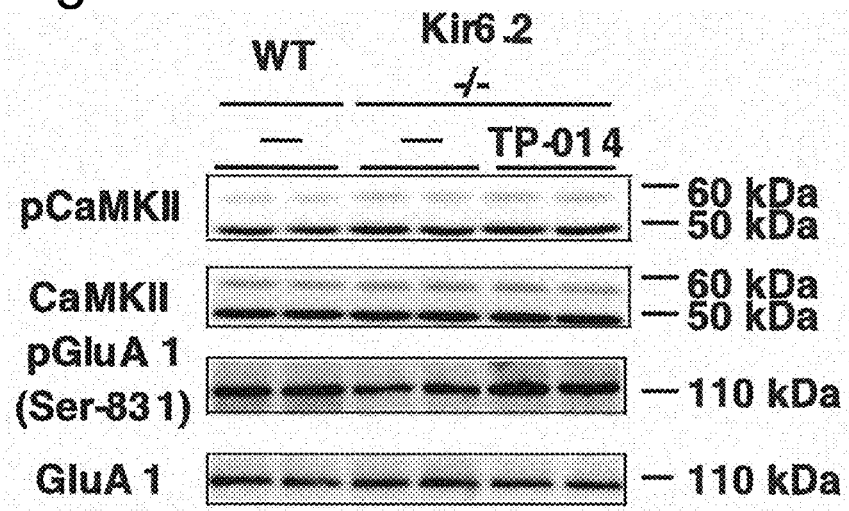
Figures 2, 9:
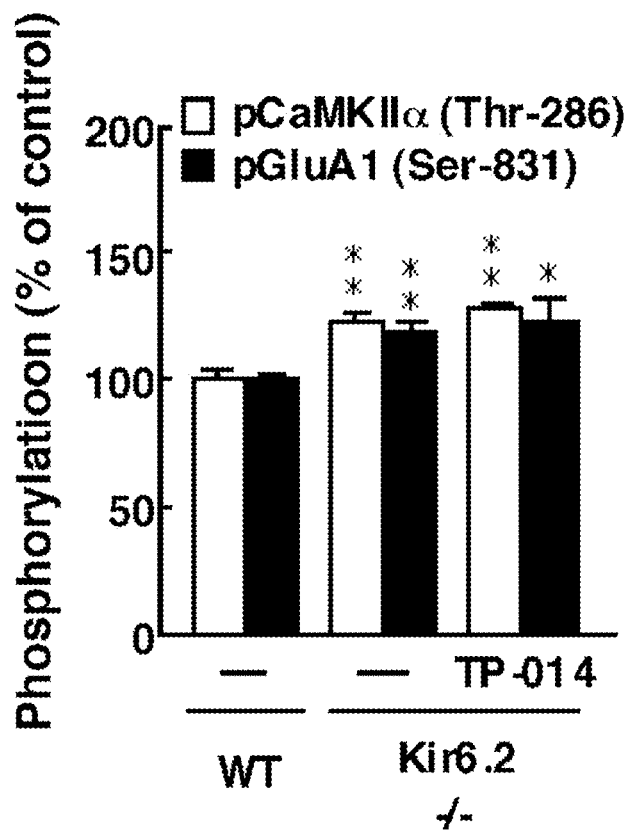

By following the same procedure as in Test Examples 4 to 7, hippocampal slices were suspended in an SDS sample buffer and analyzed by immunoblotting for GluAl (Ser-831), which is known as a molecule that is activated by activation of CaMKII and CaMKIV, to thereby investigate the intracellular mechanism of cognitive function impairment in Kir6.2-deficient mice. The results are shown in FIGS. 9-1 and 9-2 (FIG. 9-1: band images obtained by immunoblotting; FIG. 9-2: results of quantification of the signal intensity of bands). In the hippocampus of the Kir6.2-deficient mice, increased CaMKII activation was seen and no effect was found of chronic treatment with TP-014. Deficiency in Kir6.2 channels resulted in abnormality in intracellular/extracellular calcium homeostasis (balance), leading to increased CaMKII phosphorylation. It was demonstrated that TP-014 has no effect on activation of CaMKII, and that Kir6.2 channels are the action site of TP-014.

Test Example 10

Figure 10:
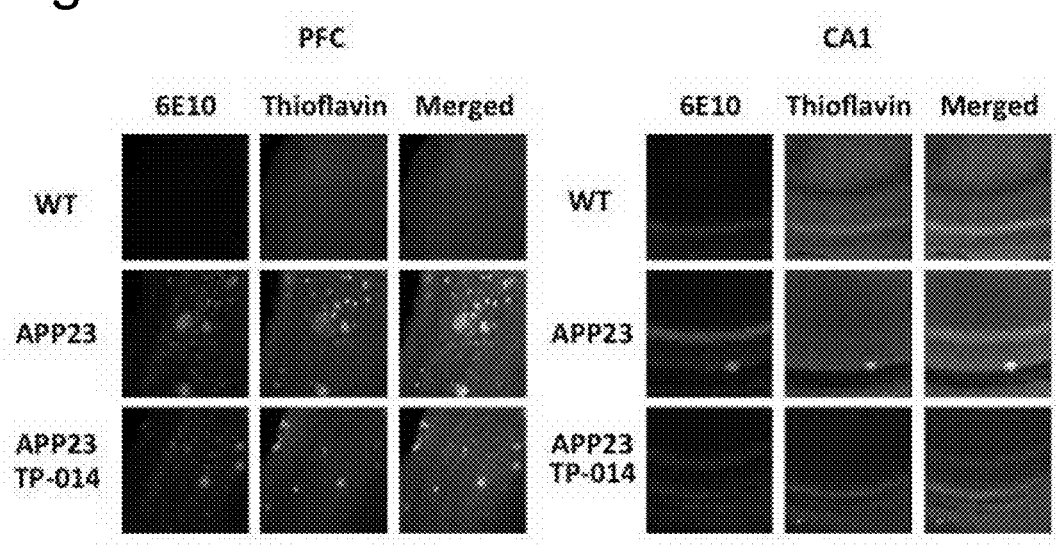
FIG. 10 shows the results of staining of sliced brain sections from APP23 mice, which demonstrate the effect of the compound of the present invention on Aβ aggregation.

The amyloid-$\beta$ (A$\beta$) hypothesis regarding the pathogenesis of Alzheimer's disease has still been of great importance. It has been confirmed by immunostaining that A$\beta$ aggregation occurs in APP23 mice (14 month-old). 50 μm brain slices were prepared from each of WT (control) and APP23 mice, and stained with 6E10 (anti-A$\beta$ antibody, produced by Abcam) and thioflavin. The results (index to reflect aggregates) are shown in FIG. 10. The other conditions were in line with conventional immunostaining methods. It was found that A$\beta$ aggregation was enhanced in the APP23 mice—in particular, many A$\beta$ aggregates were observed in the cerebral cortex (PFC). In contrast, little aggregation was observed in the hippocampus (CAI). A$\beta$ aggregation was suppressed by chronic treatment with TP-014 (chronic oral treatment for 2 months (1 mg/kg)). This fact suggests that TP-014 has a suppressing effect on A$\beta$ aggregation.

Test Example 11

Figures 1, 11:
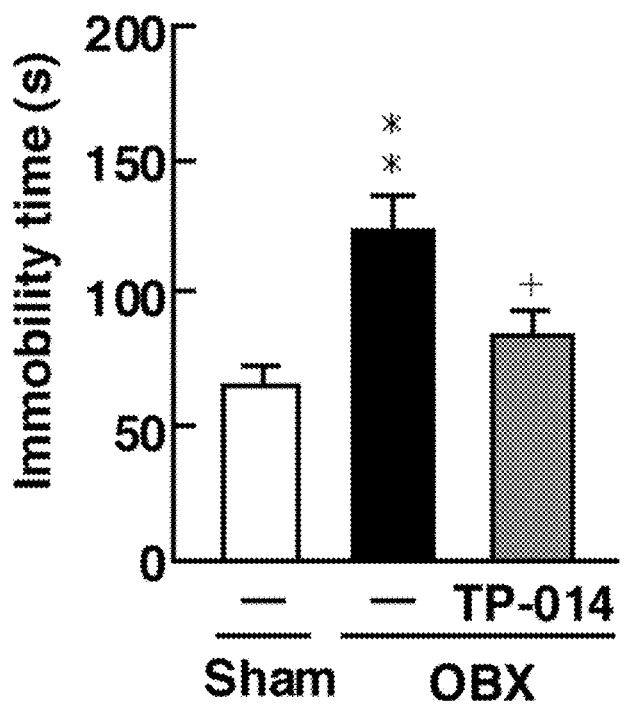
Figures 2, 11:
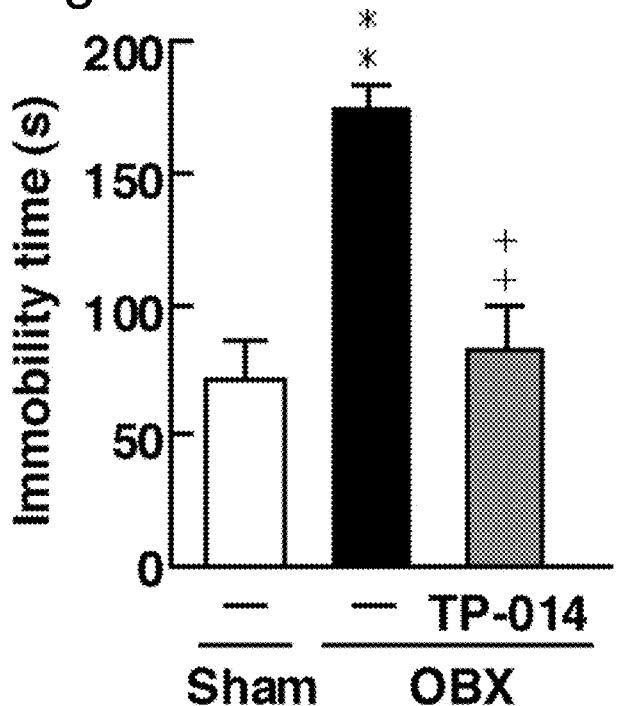

OBX mice were used as a depression model to determine the effect of TP-014 (chronic oral treatment for 2 weeks (1 mg/kg)) to ameliorate a depression-like symptom. The results are shown in FIGS. 11-1 and 11-2. OBX mice are reported to show a decline in cognitive function, but have originally been established as a depression model. Depression analysis was done by tail-suspension test and forced swim test. In the tail-suspension test, mice are hung upside-down by their tail. If the hung mice are affected by depression, they show a longer immobility time. The immobility time of normal mice is shorter since they move actively when hung. In the forced swim test, mice are forced to swim in a beaker filled with water. Depression mice neither swim nor move (just float). The time (immobility time(s)) for which mice stay still in such a way is measured. The OBX mice showed an increase in immobility time in the tail-suspension test (FIG. 11-1) and the forced swim test (FIG. 11-2), but the immobility time was improved in those mice chronically treated with TP-014 (for 2 weeks by the same procedure as in the preceding examples). These results revealed that TP-014 has an ameliorating effect on a depression-like symptom in OBX mice (n=5 per group).

The same model mice were orally treated with a single dose of each of the test compounds (1 mg/kg), and analyzed after 1 hour by tail-suspension test and forced swim test. The results are shown in FIGS. 22-1 (tail-suspension test) and 22-2 (forced swim test). The results shown in FIGS. 22-1 and 22-2 revealed that TP-079 and TP-083 showed a higher ameliorating effect on a depression-like symptom than TP-014.

Test Example 12

Figures 1, 12:
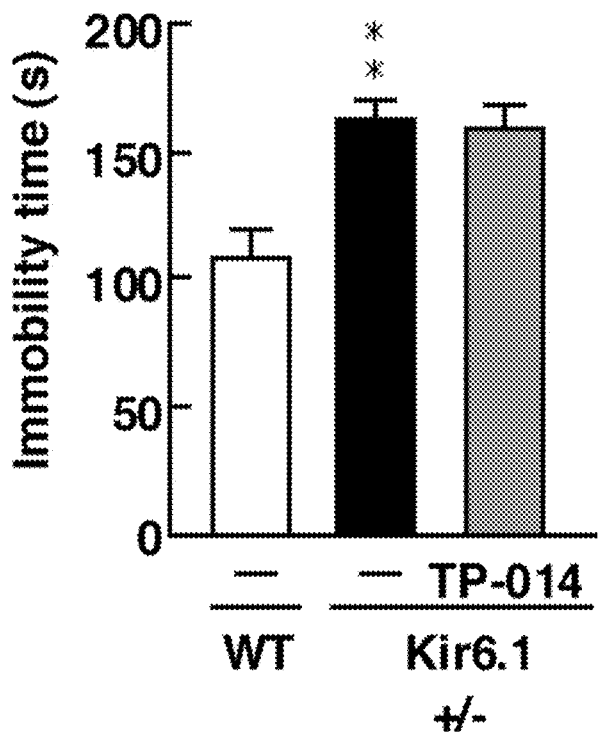
Figures 2, 12:
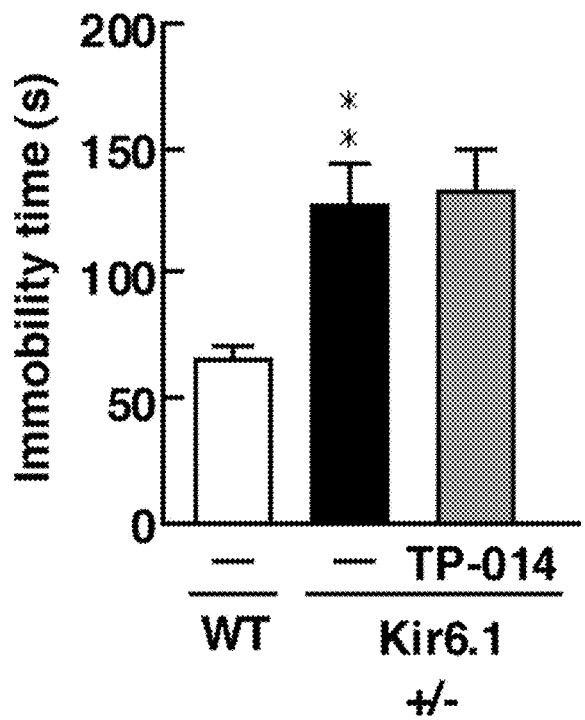

Kir6.1-deficient mice (heterozygous, n=5 per group) were used to measure immobility time by tail-suspension test (FIG. 12-1) and forced swim test (FIG. 12-2) according to the same procedure as in Test Example 11. The heterozygous mice are those with half expression of Kir6.1 channels, unlike homozygous mice (complete Kir6.1-deficient mice) (homozygous mice die of arrhythmia after birth). The results are shown in FIGS. 12-1 and 12-2. The Kir6.1-deficient mice showed an exacerbated depression-like symptom—this fact indicates that Kir6.1 plays an important role in depression. Also, the chronic treatment with TP-014 took no effect in the Kir6.1-deficient mice—this demonstrated that TP-014 (chronic oral treatment for 2 weeks (1 mg/kg)) exhibits a depression ameliorating effect through inhibition of Kir6.1 channels. The Kir6.1-deficient mice were obtained from Professor Susumu Seino, School of Medicine of Kobe University (Mild T., et al., *Nature Medicine,* 2002, 8, 466-472).

Test Example 13

Figures 1, 13:
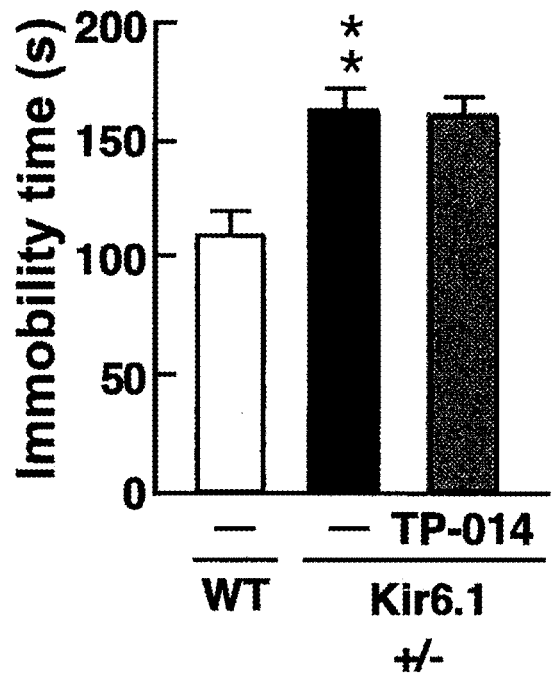
Figures 2, 13:
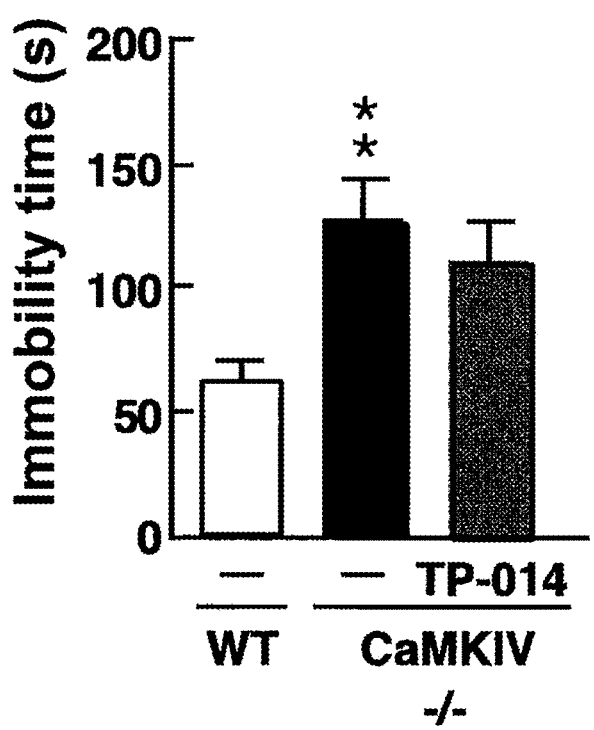

By following the same procedure as in Test Example 12, CaMKIV-deficient mice (n=5*per group) were analyzed for CaMKIV induced by Kir6.1 channels. The results are shown in FIGS. 13-1 and 13-2. The CaMKIV-deficient mice were also observed to show an exacerbated depression-like symptom—this fact indicates that CaMKIV also plays an important role in the mechanism of depression development.

TP-014 (chronic oral treatment for 2 weeks (1 mg/kg)) took no effect on a depression-like symptom associated with CaMKIV (increased immobility time)—this demonstrated that TP-014 exhibits a depression ameliorating effect through inhibition of Kir6.1 channels and activation of CaMKIV. The CaMKIV-deficient mice were obtained from professor Hiroyuki Sakagami, Kitasato University School of Medicine (Takao K., et al., *PLoS One* 2010, 5, e9460).

Test Example 14

Figure 14:
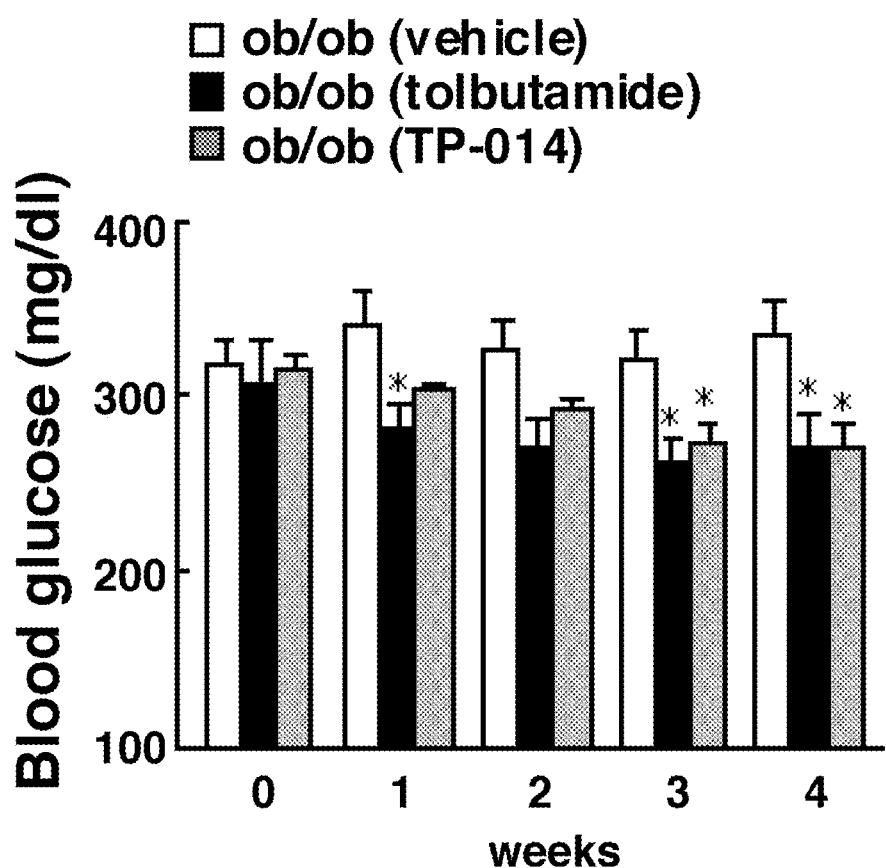
FIG. 14 shows the results of a test conducted to confirm that the compound of the present invention has a hypoglycemic effect. The "weeks" refers to a time period of chronic treatment. A significant difference relative to ob/ob (vehicle) in each week is indicated by *.
Figure 15:
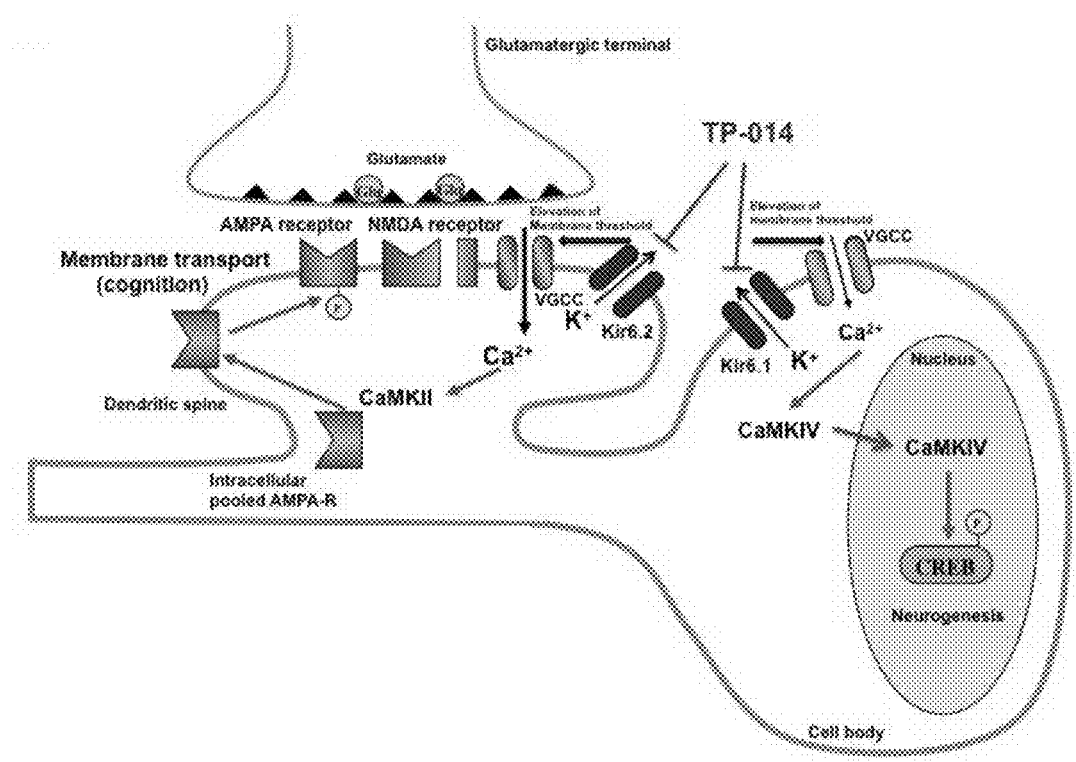
FIG. 15 is an illustration depicting the mechanism of action of TP-014. When the Kir6.2 channel localized in the spine is inhibited, intracellular potassium cannot flow out, resulting in depolarization of cell membrane potential. Then, the voltage-dependent calcium channel opens, thereby promoting calcium entry from outside cells, triggering activation of CaMKII, and activating GluA1 (Ser-831)(AMPA acceptor) downstream of CaMKII, whereby enhancement of cognitive function is achieved. Also, TP-014 inhibits the Kir6.1 channel localized in the nerve cell body, and calcium enters cells by the same mechanism. The entered calcium activates CaMKIV, activates CREB (Ser-133) and induces neurogenesis, whereby amelioration of depression is achieved. TP-014 is a novel cognitive function enhancing drug having both an enhancing effect on cognitive function (core symptom of Alzheimer's disease) through inhibition of Kir6.2 channels and an ameliorating effect on depression (peripheral symptom of Alzheimer's disease) through inhibition of Kir6.1 channels.
Figure 16:
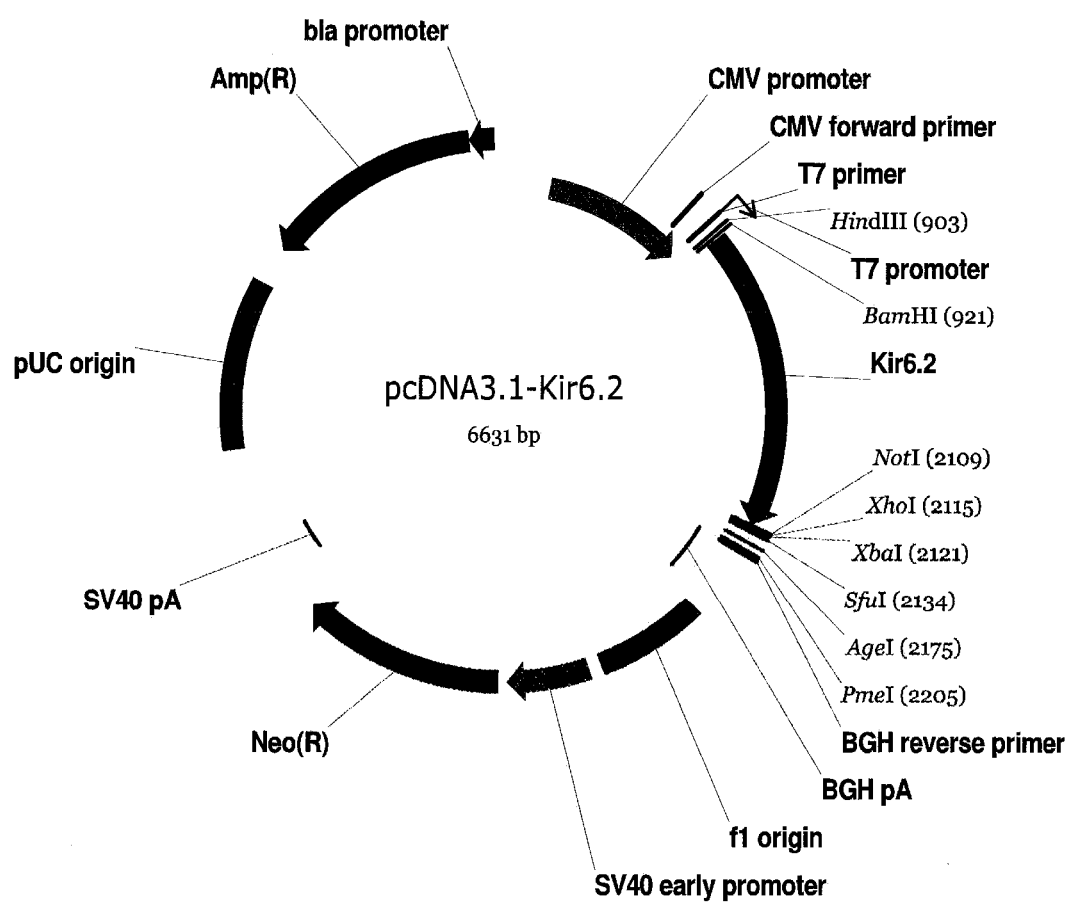
FIG. 16 is a diagram depicting the structure of the plasmid vector pcDNA3.1-Kir6.2.

In order to determine the hypoglycemic effect of TP-014, ob/ob mice were measured for blood glucose levels using an assay kit (produced by Technicon International Inc.). The results are shown in FIG. 14. The measurement was taken for 4 weeks, and chronic treatment with TP-014 (1 mg/kg) was continued for 4 weeks. As a result, it was observed that blood glucose levels significantly decreased on and after week 3. Tolbutamide was used as a control drug. Kir6.2 channels bind to SUR1 (urea receptors) on the cell membrane to form channels. The mechanism of action is considered to be inhibition of Kir6.2 channels. Tolbutamide inhibits Kir6.2 channels by binding to SUR1.

Test Example 15

The plasmid vector having inserted therein Kir6.1 channel cDNA: pcDNA3.1-Kir6.1, was obtained from professor Toru Ishizuka at the Graduate School of Life Sciences, Tohoku University. Except that the aforementioned plasmid was used, N2A cells engineered to overexpress Kir6.1 channels were obtained by the same procedure as that for preparing Kir6.2 channel-overexpressing N2A cells as adopted in Test Example 1.

The obtained Kir6.1 channel-overexpressing cells were analyzed for CaMKIV activation. The analysis was made by immunoblotting in the same manner as in Test Example 1 using an anti-phosphorylated CaMKIV antibody (Kasahara J., et al., *J. Biol. Chem.* 2001, 276, 24044-50) as a primary antibody and an anti-rabbit IgG antibody (produced by SouthernBiotech) as a secondary antibody.

Figures 1, 18:
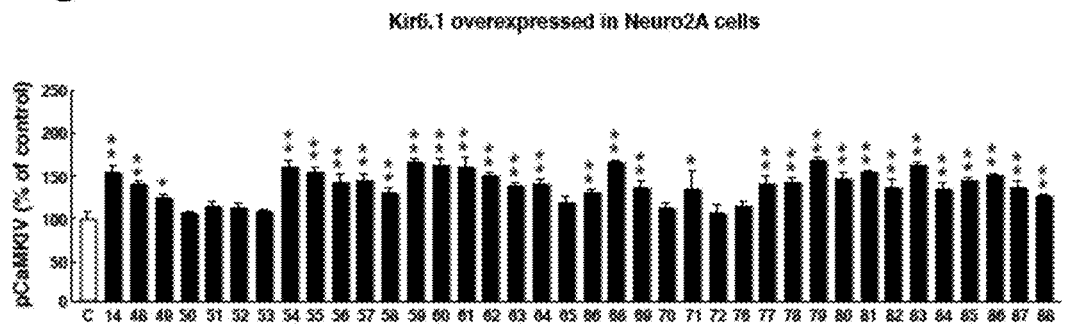
Figures 2, 18:
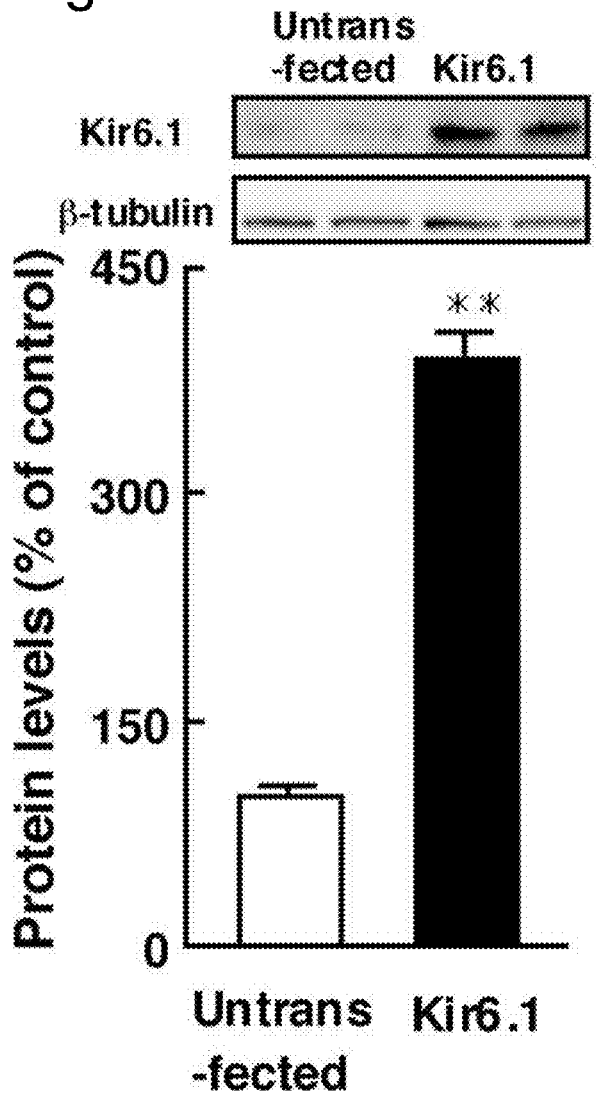
Figures 3, 18:
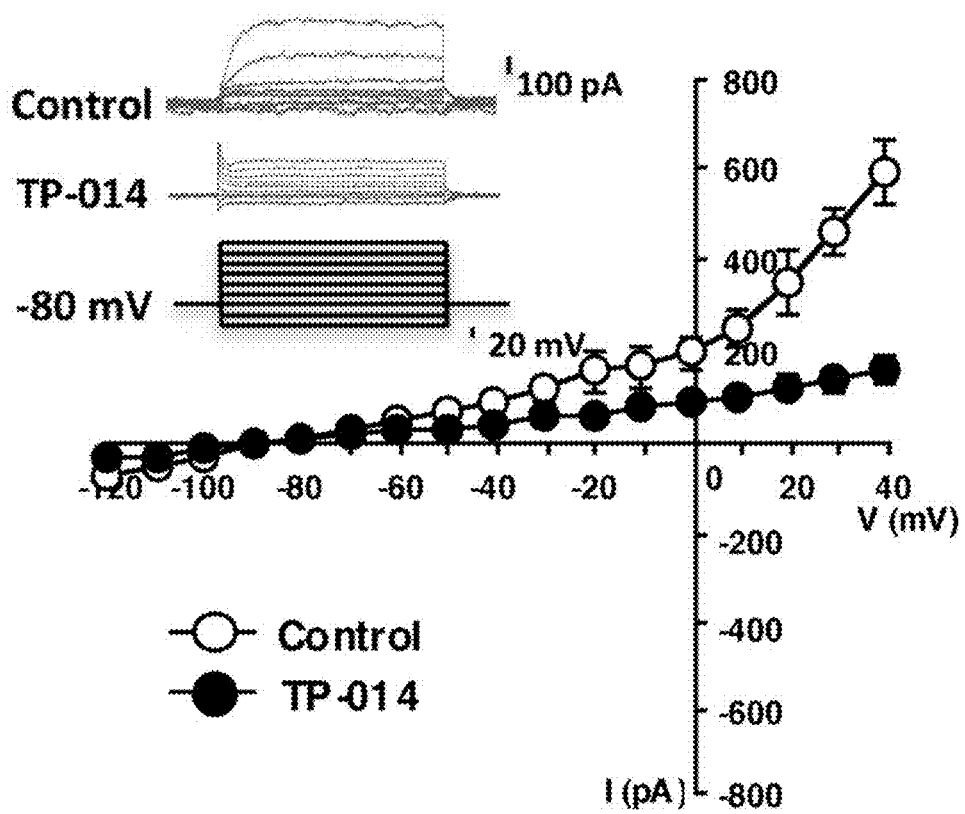

Further, the obtained Kir6.1 channel-overexpressing cells were used to measure potassium current discharged out of the cells by a conventional patch-clamp assay. The results are shown in FIGS. 18-1 to 18-3. ATP-sensitive potassium channels (Kir6.1 channels) are localized in the cell membranes of nerve cells. If the channels are inhibited and closed, the threshold of the nerve cell membranes rises to create a condition analogous to temporal generation of action potential, with the result that intracellular potassium current is discharged out of the cells and instead extracellular calcium current enters the cells. Immunoblotting of Kir6.1 channel-overexpressing cells (prepared by the aforementioned method) using an anti-Kir6.1 channel antibody (prepared by a conventional method) (n=5, under the same conditions as in Test Example 1, except for using the anti-Kir6.1 channel antibody) confirmed that Kir6.1 channels were overexpressed in N2A cells (FIG. 18-2; upper: immunoblot staining images; lower: quantitative representations of the signal intensity of staining bands). No change was observed in the levels of the housekeeping gene product 0 tubulin (the conditions were the same as those for Kir6.1 detection, except for using an anti-n tubulin antibody obtained from Sigma-Aldrich). FIG. 18-3 shows the results of a test (n=5 per group) confirming that when Kir6.1 channel-overexpressing cells were allowed to stand in an electrophysiological analysis buffer supplemented with TP-014 to a concentration of 10 nM, outwardly flowing potassium current for shifting the membrane potential of nerve cells to positive was suppressed. The results revealed that TP-014 inhibited Kir6.1 channels and prevented intracellular potassium current from being discharged out of the cells.

Test Example 16

Wild-type mice (C57BL/6J, Japan SLC, two month-old) treated with corticosterone (at a dose of 5 mg/kg once a day for 2 weeks) and Kir6.1-deficient mice treated with corticosterone were used as disease models showing anxiety-like symptoms, to perform five behavioral tests regarding anxiety-related behaviors. The Kir6.1-deficient mice were obtained from Professor Susumu Seino, School of Medicine of Kobe University (Miki T., et al., *Nature Medicine* 2002, 8, 466-472).

When the corticosterone-treated WT mice and Kir6.1-deficient mice were chronically treated (orally) with TP-014 (1 mg/kg) once a day for 2 weeks, significant amelioration of exacerbated anxiety symptoms was obtained. The results are shown in FIGS. 19-1 to 19-9.

Figures 1, 19:
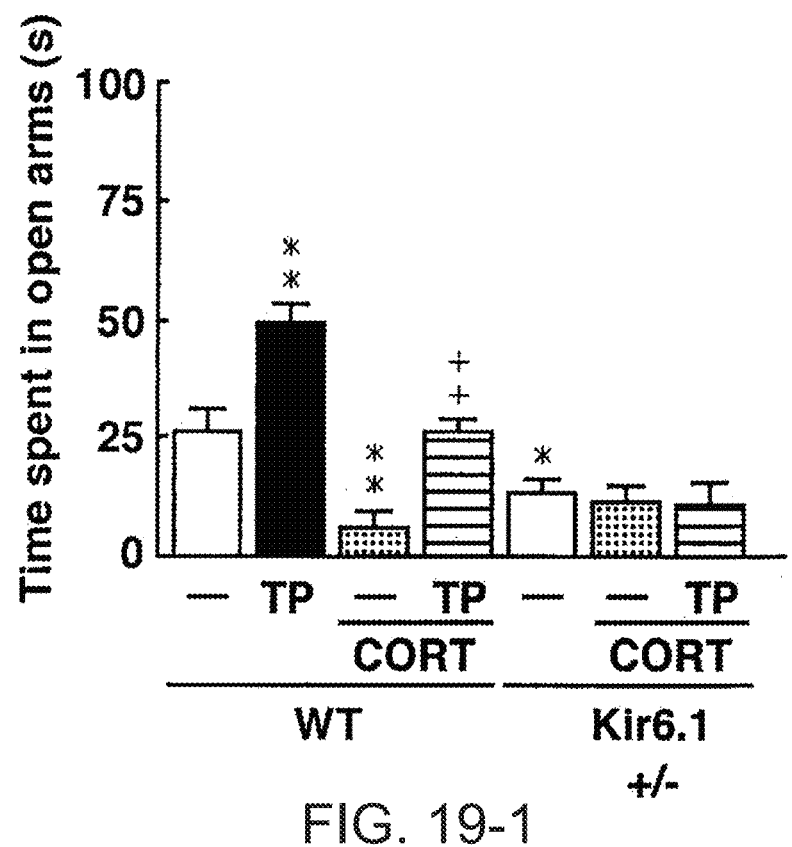
Figures 2, 19:
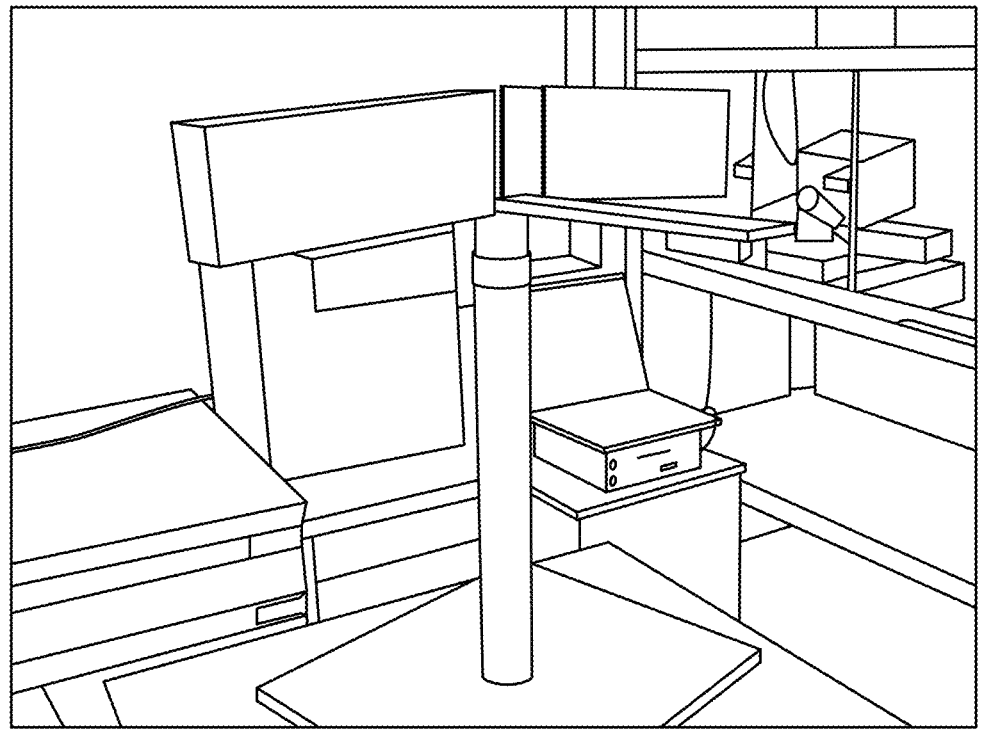
Figures 3, 19:
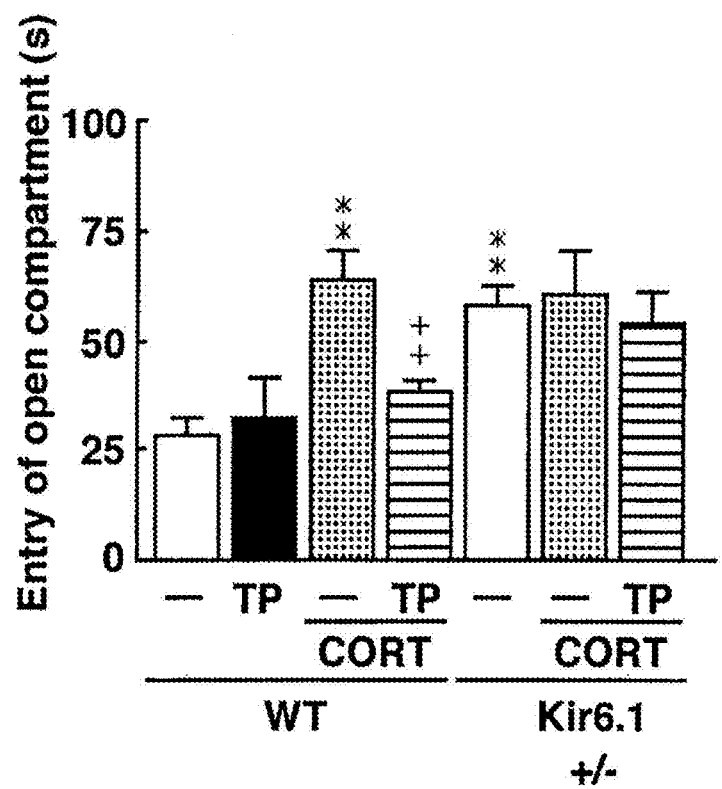
Figures 4, 19:
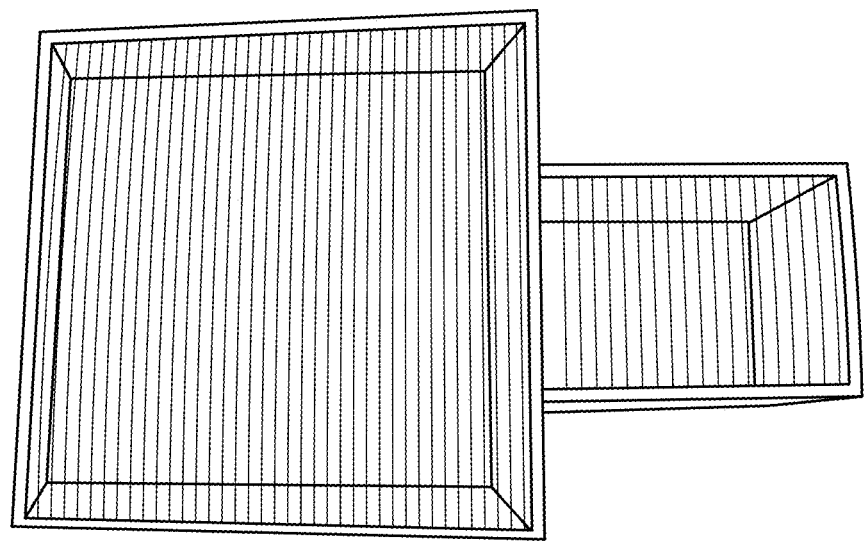
Figures 5, 19:
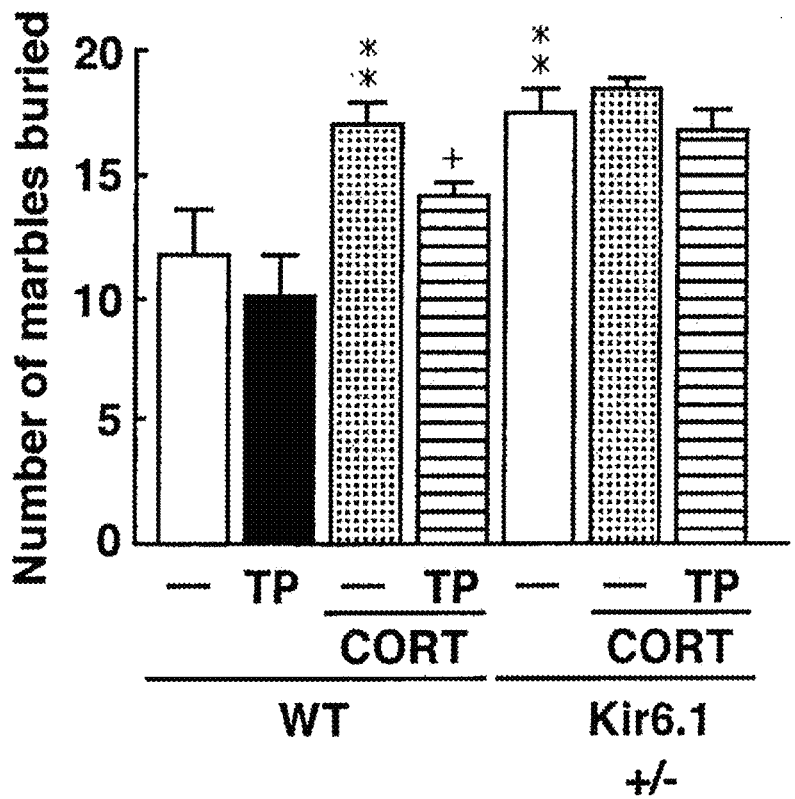
Figures 6, 19:
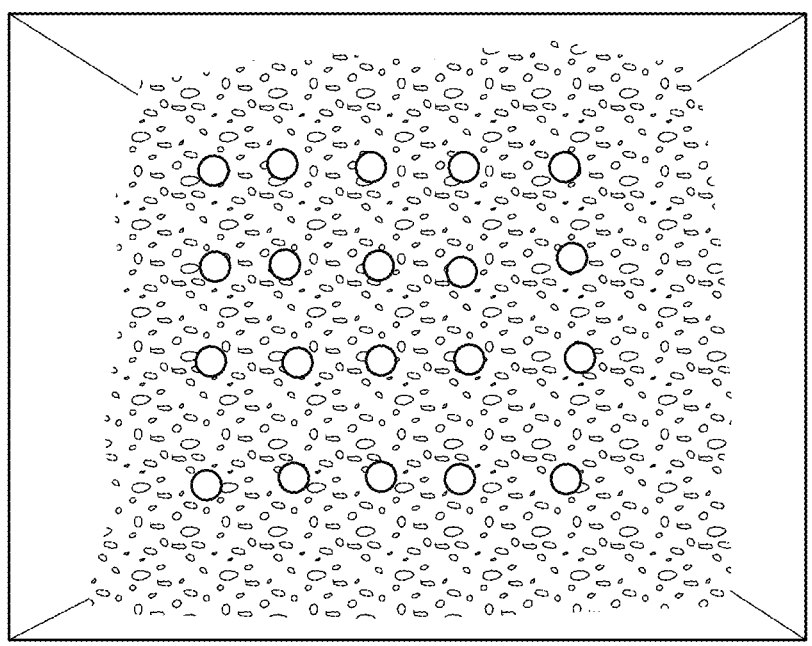
Figures 7, 19:
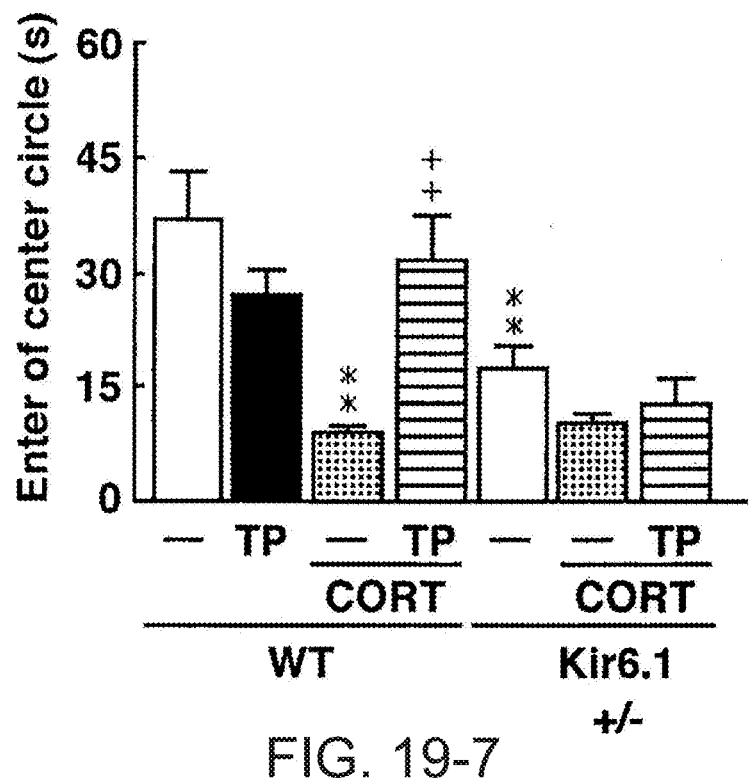
Figures 8, 19:
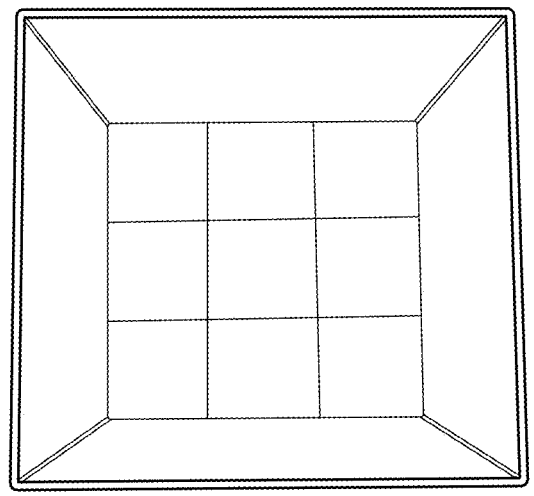
Figures 9, 19:
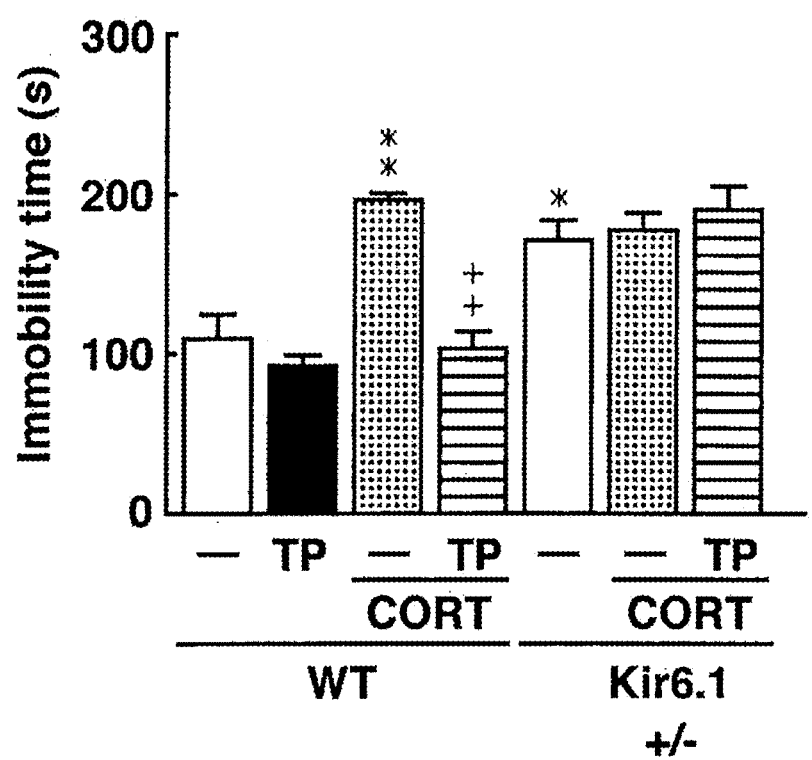
Figure 20:
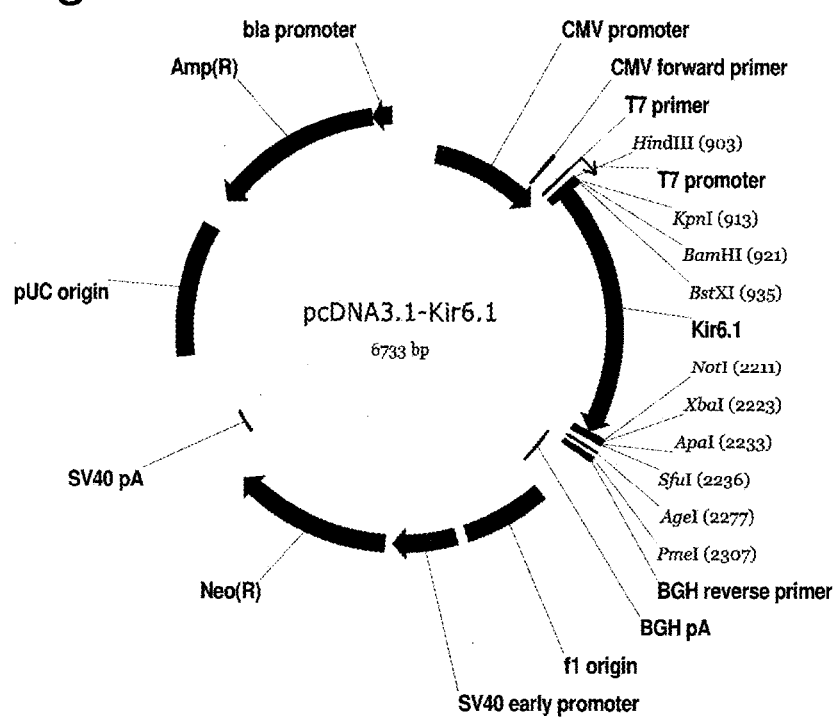
FIG. 20 is a diagram depicting the structure of the plasmid vector: pcDNA3.1-Kir6.1.

FIG. 19-1 shows the results of determining anxiety vulnerability of the different mice groups (n=5 per group) by elevated plus-maze test (as shown in FIG. 19-2). The apparatus used in this test consists of four arms arranged in a cross shape at an elevated position, which are either open or closed. Mice vulnerable to anxiety stay in the closed arms for a longer time, whereas those resistant to anxiety stay in the open arms. In FIG. 19-1, the time spent in the open arms is shown on the vertical axis.

FIG. 19-3 shows the results of a light/dark test (n=5 per group) (as shown in FIG. 19-4). Mice placed in a black box (dark place) feel anxious about light. The time spent until mice began to come out of the box (to a bright place) was measured. In FIG. 19-3, the time until mice begin to come out ("entry of open compartment(s)") is shown on the vertical axis.

FIG. 19-5 shows the results of a marble burying test (n=5 per group) (as shown in FIG. 19-6). In a cage with a mouse, wood chips are spread over the cage floor and 20 marbles are placed thereon in a manner that is visible to the mouse. The mouse is allowed to freely explore for 30 minutes, and the number of marbles buried and hidden by the mouse in wood chips is counted. Since mice do not like a glowing object, those resistant to anxiety handle more marbles. In FIG. 19-5, the number of marbles buried is shown on the vertical axis.

FIG. 19-7 shows the results of an open field test (n=5 per group) (as shown in FIG. 19-8). A mouse is placed in a square box and allowed to explore the box for 30 minutes. In general, mice are highly anxious and have a habit of walking along the edges of the box. However, those resistant to anxiety tend more frequently to walk through the center of the box. This tendency is used as a measure of anxiety-related behavior. The time of staying in the center of the box is indicated in FIG. 19-7.

FIG. 19-9 shows the results of a fear conditioning test (n=5 per group). The test apparatus used in this test was the same as used in the light/dark test method. A mouse is placed in a dark place, and sound (high-pitched) is emitted for 30 seconds and then electrical stimulation is applied for 3 seconds. This cycle of sound emission followed by electrical stimulation is repeated three times to make the mouse aware that sound emission is followed by electrical stimulation. On the following day, when sound is emitted for 5 minutes, the mouse is immobilized with a sense of fear and anxiety. Such an immobility time of mice is measured. In FIG. 19-9, the immobility time is shown on the vertical axis.

The results of all the tests described above confirmed that chronic treatment with TP-014 (for 2 weeks) ameliorates exacerbated anxiety-like symptoms. Further, Kir6.1-deficient mice developed anxiety-like symptoms following treatment with corticosterone, but no ameliorating effect was observed in those mice receiving treatment with TP-014. This fact demonstrated that the effect of the compound of the present invention to ameliorate exacerbated anxiety-like symptoms is mediated by Kir6.1.

With regard to significant differences shown in the figures presented herein, ** or ++ represents P<0.01, and + or * represents P<0.05.

The invention claimed is:

1. A compound represented by Formula (I):

[Chemical Formula 1]

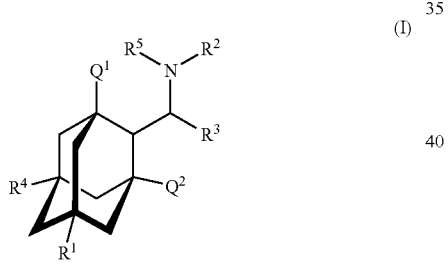

wherein $Q^1$, $Q^2$, $R^1$, and $R^4$ are each independently selected from a hydrogen atom, a halogen atom, $C_{1-6}$ alkyl optionally substituted with one or more halogen atoms, amino, $C_{6-10}$ aryl optionally substituted with one or more substituents selected from $X^1$, carboxy, —$OR^7$, and —$SR^8$;

$R^2$ represents a hydrogen atom, phenylsulfonyl optionally substituted with one or more substituents selected from $X^1$, ($C_{1-6}$ alkyl)sulfonyl optionally substituted with one or more halogen atoms, or —$COYR^6$;

Y represents a direct bond, O, or $NR^9$;

$R^3$ represents $C_{3-8}$ cycloalkyl optionally substituted with one or more substituents selected from $X^1$, $C_{6-10}$ aryl optionally substituted with one or more substituents selected from $X^1$, phenylaminocarboyl optionally substituted with one or more substituents selected from $X^1$, 5- to 10-membered monocyclic or bicyclic heteroaryl optionally substituted with one or more substituents selected from $X^1$, 5- to 10-membered monocyclic or bicyclic non-aromatic heterocyclyl optionally substituted with one or more substituents selected from $X^1$, or -$Q^3$-$R^{13}$;

$Q^3$ represents $C_{1-3}$ alkylene, or $C_{2-3}$ alkenylene;

$R^{13}$ represents $C_{6-10}$ aryl optionally substituted with one or more substituents selected from $X^1$;

$R^5$ represents a hydrogen atom, or $C_{1-6}$ alkyl optionally substituted with one or more halogen atoms;

$R^6$ represents $C_{1-6}$ alkyl, $C_{6-10}$ aryl optionally substituted with one or more substituents selected from $X^1$, or 5- or 6-membered heteroaryl optionally substituted with one or more substituents selected from $X^1$, wherein the alkyl is optionally substituted with one or more halogen atoms, and/or is optionally substituted with one substituent selected from $X^2$;

$R^7$ represents a hydrogen atom, $C_{1-6}$ alkyl optionally substituted with one or more halogen atoms, $C_{1-6}$ alkoxy$C_{1-6}$ alkyl, ($C_{1-6}$ alkyl)carbonyl optionally substituted with one or more halogen atoms, or $C_{6-10}$ aryl optionally substituted with one or more substituents selected from $X^1$;

$R^8$ represents a hydrogen atom, $C_{1-6}$ alkyl optionally substituted with one or more halogen atoms, or $C_{6-10}$ aryl optionally substituted with one or more substituents selected from $X^1$;

$R^9$ represents a hydrogen atom, or $C_{1-6}$ alkyl optionally substituted with one or more halogen atoms;

each $X^1$ is independently selected from $C_{1-6}$ alkyl, a halogen atom, $C_{1-6}$ alkoxy, hydroxy, nitro, and cyano;

$X^2$ is selected from $C_{1-6}$ alkoxy, $C_{2-6}$ alkenyloxy, $C_{2-6}$ alkynyloxy, and —$NR^{11}R^{12}$;

$R^{11}$ represents a hydrogen atom, $C_{1-6}$ alkyl, ($C_{1-6}$ alkoxy)carbonyl, or [($C_{6-10}$ aryl)$C_{1-3}$ alkoxy]carbonyl whose aryl moiety is optionally substituted with one or more substituents selected from $X^1$, wherein the alkyl or alkoxy moiety is optionally substituted with one or more halogen atoms;

R$^{12}$ represents a hydrogen atom, or C$_{1-6}$ alkyl optionally substituted with one or more halogen atoms;
wherein the methylene present in the adamantyl group is optionally substituted with one or more groups independently selected from C$_{1-6}$ alkyl, C$_{1-6}$ alkoxy, and hydroxy, wherein the alkyl or alkoxy is optionally substituted with one or more halogen atoms,
wherein the methylene moiety of the monocyclic or bicyclic non-aromatic heterocyclyl is optionally substituted with oxo,
an enantiomer thereof, a diastereomer thereof, or a pharmaceutically acceptable salt thereof.

2. The compound, enantiomer thereof, diastereomer thereof, or pharmaceutically acceptable salt thereof according to claim 1, wherein the compound is represented by Formula (I):

[Chemical Formula 2]

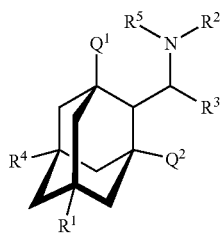

(I)

wherein Q$^1$ represents a hydrogen atom, a halogen atom, C$_{1-6}$ alkyl optionally substituted with one or more halogen atoms, amino, or —OR$^{10}$;
R$^{10}$ represents a hydrogen atom, C$_{1-6}$ alkyl optionally substituted with one or more halogen atoms, or (C$_{1-6}$ alkyl)carbonyl optionally substituted with one or more halogen atoms;
Q$^2$ represents a hydrogen atom, C$_{1-6}$ alkyl, or C$_{1-6}$ alkoxy, wherein the alkyl or alkoxy is optionally substituted with one or more halogen atoms;
R$^1$ represents a hydrogen atom, C$_{1-6}$ alkyl, or C$_{1-6}$ alkoxy, wherein the alkyl or alkoxy is optionally substituted with one or more halogen atoms;
R$^2$ represents a hydrogen atom, phenylsulfonyl optionally substituted with one or more substituents selected from X$^1$, (C$_{1-6}$ alkyl)sulfonyl optionally substituted with one or more halogen atoms, or —COYR$^6$;
Y represents a direct bond, O, or NR$^9$;
R$^3$ represents C$_{3-8}$ cycloalkyl, C$_{6-10}$ aryl optionally substituted with one or more substituents selected from X$^1$, phenylaminocarboyl optionally substituted with one or more substituents selected from X$^1$, 5- to 10-membered monocyclic or bicyclic heteroaryl optionally substituted with one or more substituents selected from X$^1$, or -Q$^3$-R$^{13}$;
Q$^3$ represents C$_{1-3}$ alkylene, or C$_{2-3}$ alkenylene;
R$^{13}$ represents C$_{6-10}$ aryl optionally substituted with one or more substituents selected from X$^1$;
R$^4$ represents a hydrogen atom, a halogen atom, C$_{1-6}$ alkyl optionally substituted with one or more halogen atoms, phenyl optionally substituted with one or more substituents selected from X$^3$, carboxy, —OR$^7$, or —SR$^8$;
R$^5$ represents a hydrogen atom or C$_{1-6}$ alkyl;
R$^6$ represents C$_{1-6}$ alkyl;

R$^7$ represents a hydrogen atom, C$_{1-6}$ alkyl optionally substituted with one or more halogen atoms, C$_{1-6}$ alkoxyC$_{1-6}$ alkyl, or (C$_{1-6}$ alkyl)carbonyl optionally substituted with one or more halogen atoms;
R$^8$ represents C$_{1-6}$ alkyl, or phenyl optionally substituted with one or more substituents selected from X$^1$;
R$^9$ represents a hydrogen atom or C$_{1-6}$ alkyl;
each X$^1$ is independently selected from C$_{1-6}$ alkyl, a halogen atom, C$_{1-6}$ alkoxy, nitro, and cyano;
X$^2$ is selected from C$_{1-6}$ alkoxy, C$_{2-6}$ alkenyloxy, C$_{2-6}$ alkynyloxy, and —NR$^{11}$R$^{12}$;
each X$^3$ is independently selected from C$_{1-6}$ alkyl, a halogen atom, C$_{1-6}$ alkoxy, hydroxy, nitro, and cyano;
R$^{11}$ represents a hydrogen atom, C$_{1-6}$ alkyl, (C$_{1-6}$ alkoxy)carbonyl, or benzyloxycarbonyl whose phenyl moiety is optionally substituted with one or more substituents selected from X$^1$;
R$^{12}$ represents a hydrogen atom or C$_{1-6}$ alkyl;
wherein the methylene present in the adamantyl group is optionally substituted with one or more groups independently selected from C$_{1-6}$ alkyl and C$_{1-6}$ alkoxy, wherein the alkyl or alkoxy is optionally substituted with one or more halogen atoms.

3. The compound, enantiomer thereof, diastereomer thereof, or pharmaceutically acceptable salt thereof according to claim 1, wherein the compound is represented by Formula (Ia):

[Chemical Formula 3]

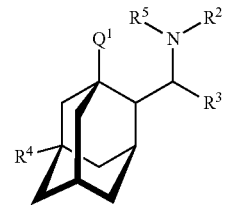

(Ia)

wherein Q$^1$ represents a hydrogen atom, a halogen atom, or —OR$^{10}$;
R$^{10}$ represents a hydrogen atom, or (C$_{1-6}$ alkyl)carbonyl optionally substituted with one or more halogen atoms;
R$^2$ represents a hydrogen atom, phenylsulfonyl optionally substituted with one or more substituents selected from X$^1$, (C$_{1-6}$ alkyl)sulfonyl optionally substituted with one or more halogen atoms, or —COYR$^6$;
Y represents a direct bond, O, or NR$^9$;
R$^3$ represents phenyl optionally substituted with one or more substituents selected from X$^1$, or 5- or 6-membered heteroaryl optionally substituted with one or more substituents selected from X$^1$;
R$^4$ represents a hydrogen atom, a halogen atom, —OR$^7$, or —SR$^8$;
R$^5$ represents a hydrogen atom or C$_{1-6}$ alkyl;
R$^6$ represents C$_{1-6}$ alkyl;
R$^7$ represents a hydrogen atom, C$_{1-6}$ alkyl, C$_{1-6}$ alkoxyC$_{1-6}$ alkyl, or (C$_{1-6}$ alkyl)carbonyl optionally substituted with one or more halogen atoms;
R$^8$ represents C$_{1-6}$ alkyl, or phenyl optionally substituted with one or more substituents selected from X$^1$;
R$^9$ represents a hydrogen atom or C$_{1-6}$ alkyl;

each $X^1$ is independently selected from $C_{1-6}$ alkyl, a halogen atom, $C_{1-6}$ alkoxy, nitro, and cyano;

$X^2$ is selected from $C_{1-6}$ alkoxy, $C_{2-6}$ alkenyloxy, $C_{2-6}$ alkynyloxy, and $-NR^{11}R^{12}$;

$R^{11}$ represents a hydrogen atom, $C_{1-6}$ alkyl, $(C_{1-6}$ alkoxy)carbonyl, or benzyloxycarbonyl whose phenyl moiety is optionally substituted with one or more substituents selected from $X^1$;

$R^{12}$ represents a hydrogen atom or $C_{1-6}$ alkyl.

4. The compound, enantiomer thereof, diastereomer thereof, or pharmaceutically acceptable salt thereof according to claim 1, wherein $Q^1$ and $R^4$ represent hydrogen atoms.

5. The compound, enantiomer thereof, diastereomer thereof, or pharmaceutically acceptable salt thereof according to claim 1, wherein $Q^1$ and $R^4$ are selected from halogen atoms.

6. The compound, enantiomer thereof, diastereomer thereof, or pharmaceutically acceptable salt thereof according to claim 1, wherein $Q^1$ and $R^4$ represent chlorine atoms.

7. The compound, enantiomer thereof, diastereomer thereof, or pharmaceutically acceptable salt thereof according to claim 1, wherein $R^2$ represents phenylsulfonyl optionally substituted with one or more substituents selected from $X^1$, $(C_{1-6}$ alkyl)sulfonyl optionally substituted with one or more halogen atoms, or $-COR^6$, $R^6$ represents $C_{1-6}$ alkyl.

8. The compound, enantiomer thereof, diastereomer thereof, or pharmaceutically acceptable salt thereof according to claim 7, wherein $R^2$ represents trifluoroacetyl.

9. The compound, enantiomer thereof, diastereomer thereof, or pharmaceutically acceptable salt thereof according to claim 1, wherein $R^3$ represents phenyl optionally substituted with one or more substituents selected from $X^1$.

10. The compound, enantiomer thereof, diastereomer thereof, or pharmaceutically acceptable salt thereof according to claim 1, wherein $R^5$ represents a hydrogen atom.

11. The compound, enantiomer thereof, diastereomer thereof, or pharmaceutically acceptable salt thereof according to claim 1, wherein the compound is selected from:

(1S,2R,3S,5S,7S)-5-chloro-2-((R)-phenyl(2,2,2-trifluoroacetamido)methyl)adamantan-1-yl 2,2,2-trifluoroacetate;

N—((R)-((1S,2R,3S,5S,7S)-5-chloro-1-hydroxyadamantan-2-yl)(phenyl)methyl)-2,2,2-trifluoroacetamide;

(1S,2R,3S,5R,7S)-2-((R)-phenyl(2,2,2-trifluoroacetamido)methyl)adamantan-1-yl 2,2,2-trifluoroacetate;

(1S,2R,3S,5S,7R)-5-(2-methoxyethoxy)-2-((R)-phenyl(2,2,2-trifluoroacetamido)methyl)adamantan-1-yl 2,2,2-trifluoroacetate;

N—((R)-((1S,2R,3S,5S,7S)-5-chloro-1-hydroxyadamantan-2-yl)(pyridin-3-yl)methyl)-2,2,2-trifluoroacetamide;

2,2,2-trifluoro-N—((R)-((1S,2R,3S,5R,7S)-1-hydroxyadamantan-2-yl)(phenyl)methyl)acetamide;

(1S,2R,3S,5S,7R)-5-methoxy-2-((R)-phenyl(2,2,2-trifluoroacetamido)methyl)adamantan-1-yl 2,2,2-trifluoroacetate;

N—((R)-((1S,2R,3S,5S,7R)-1,5-dichloroadamantan-2-yl)(phenyl)methyl)-2,2,2-trifluoroacetamide;

(R)-((1S,2R,3S,5S,7R)-1,5-dichloroadamantan-2-yl)(phenyl)methanamine;

N—((R)-((1S,2R,3S,5S,7R)-1,5-dichloroadamantan-2-yl)(phenyl)methyl)acetamide;

methyl ((R)-((1S,2R,3S,5S,7R)-1,5-dichloroadamantan-2-yl)(phenyl)methyl)carbamate;

1-((R)-((1S,2R,3S,5S,7R)-1,5-dichloroadamantan-2-yl)(phenyl)methyl)-3-phenylurea;

benzyl (2-(((R)-((1S,2R,3S,5S,7R)-1,5-dichloroadamantan-2-yl)(phenyl)methyl)amino)-2-oxoethyl)carbamate;

2-amino-N—((R)-((1S,2R,3S,5S,7R)-1,5-dichloroadamantan-2-yl)(phenyl)methyl)acetamide;

N—((R)-((1S,2R,3S,5S,7R)-1,5-dichloroadamantan-2-yl)(phenyl)methyl)methanesulfonamide;

2-bromo-N—((R)-((1S,2R,3S,5S,7R)-1,5-dichloroadamantan-2-yl)(phenyl)methyl)acetamide;

N—((R)-((1S,2R,3S,5S,7R)-1,5-dichloroadamantan-2-yl)(phenyl)methyl)-2-(prop-2-yn-1-yloxy)acetamide;

N—((R)-((1S,2R,3S,5S,7R)-1,5-dichloroadamantan-2-yl)(phenyl)methyl)-1,1,1-trifluoromethanesulfonamide;

N—((R)-((1S,2R,3S,5S,7R)-1,5-dichloroadamantan-2-yl)(phenyl)methyl)-2-nitrobenzenesulfonamide;

N—((R)-((1S,2R,3S,5S,7R)-1,5-dichloroadamantan-2-yl)(phenyl)methyl)-4-nitrobenzenesulfonamide;

N—((S)-((1S,3S,5S,7S)-adamantan-2-yl)(phenyl)methyl)-2,2,2-trifluoroacetamide;

N—((R)-((1R,3R,5R,7R)-adamantan-2-yl)(phenyl)methyl)-2,2,2-trifluoroacetamide;

(1S,2R,3S,5S,7S)-2-((R)-phenyl(2,2,2-trifluoroacetamido)methyl)-5-(phenylthio)adamantan-1-yl 2,2,2-trifluoroacetate;

N—((R)-((1S,2R,3S,5S,7R)-1,5-dichloroadamantan-2-yl)(phenyl)methyl)benzamide;

N—((R)-((1S,2R,3S,5S,7R)-1,5-dichloroadamantan-2-yl)(phenyl)methyl)picolinamide;

N—((R)-((1S,2R,3S,5S,7R)-1,5-dichloroadamantan-2-yl)(phenyl)methyl)benzenesulfonamide;

(1S,2R,3S,5S,7S)-5-chloro-2-((S)-phenyl(2,2,2-trifluoroacetamido)methyl)adamantan-1-yl 2,2,2-trifluoroacetate;

N-((1R)-((1R,2S,3R,5R,7R)-5-chloro-1-hydroxyadamantan-2-yl)(phenyl)methyl)-2,2,2-trifluoroacetamide;

(1R,2S,3R,5R,7R)-5-chloro-2-((R)-phenyl(2,2,2-trifluoroacetamido)methyl)adamantan-1-yl 2,2,2-trifluoroacetate;

(1S,2R,3S,5S,7S)-2-((R)-amino(phenyl)methyl)-5-chloroadamantan-1-ol;

N—((R)-((1S,2R,3S,5S,7S)-5-chloro-1-hydroxyadamantan-2-yl)(phenyl)methyl)acetamide;

N—((R)-((1S,2R,3S,5S,7S)-5-chloro-1-hydroxyadamantan-2-yl)(phenyl)methyl)propionamide;

N—((R)-((1S,2R,3S,5S,7S)-5-chloro-1-hydroxyadamantan-2-yl)(phenyl)methyl)butylamide;

N—((R)-((1S,2R,3S,5S,7S)-5-chloro-1-hydroxyadamantan-2-yl)(phenyl)methyl)hexanamide;

N—((R)-((1S,2R,3S,5S,7S)-5-chloro-1-hydroxyadamantan-2-yl)(phenyl)methyl)cyclopropanecarboxamide;

N—((R)-((1S,2R,3S,5S,7S)-5-chloro-1-hydroxyadamantan-2-yl)(phenyl)methyl)isobutylamide;

N—((R)-((1S,2R,3S,5S,7S)-5-chloro-1-hydroxyadamantan-2-yl)(phenyl)methyl)pivalamide;

N—((R)-((1S,2R,3S,5S,7S)-5-chloro-1-hydroxyadamantan-2-yl)phenyl)methyl)cyclobutanecarboxamide;

N—((R)-((1S,2R,3S,5S,7S)-5-chloro-1-hydroxyadamantan-2-yl)(phenyl)methyl)cyclopentanecarboxamide;

N—((R)-((1S,2R,3S,5S,7S)-5-chloro-1-hydroxyadamantan-2-yl)(phenyl)methyl)-2,2-difluoroacetamide;

N—((R)-((1S,2R,3S,5S,7S)-5-chloro-1-hydroxyadamantan-2-yl)(phenyl)methyl)-2,2-dimethylbutanamide; and N—((R)-((1S,2R,3S,5S,7S)-5-chloro-1-hydroxyadamantan-2-yl)(phenyl)methyl)-3-methylbutanamide.

12. The compound, enantiomer thereof, diastereomer thereof, or pharmaceutically acceptable salt thereof according to claim 1, wherein the compound is represented by Formula (Ic):

[Chemical Formula 4]

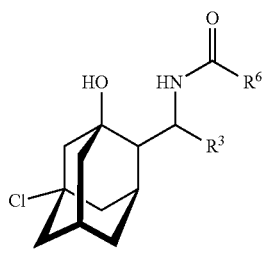

(Ic)

wherein $R^6$ is $C_{1-6}$ alkyl;

$R^3$ represents phenyl optionally substituted with one or two halogen atoms.

13. The compound, enantiomer thereof, diastereomer thereof, or pharmaceutically acceptable salt thereof according to claim 12, wherein $R^6$ is $C_{2-6}$ alkyl.

14. A pharmaceutical composition comprising the compound, enantiomer thereof, diastereomer thereof, or pharmaceutically acceptable salt thereof according to claim 1.

15. A method for treating a cognitive disease or disorder, wherein the method comprises administering, to a subject in need thereof, an effective amount of a compound according to claim 1, enantiomer thereof, or pharmaceutically acceptable salt thereof.

16. The method according to claim 15, wherein the cognitive disease or disorder is selected from Alzheimer's dementia, cerebrovascular dementia, Lewy body dementia, frontotemporal dementia, Parkinson's disease, a mental disease and a neurodegenerative disease.

17. A method for treating diabetes or a diabetic complication, wherein the method comprises administering, to a subject in need thereof, an effective amount of a compound according to claim 1, enantiomer thereof, diastereomer thereof, or pharmaceutically acceptable salt thereof.

18. A method for inhibiting a Kir6.2 channel inhibitor, wherein the method comprises administering, to a subject in need thereof, an effective amount of a compound according to claim 1.

19. A method for inhibiting a Kir6.1 channel inhibitor, wherein the method comprises administering, to a subject in need thereof, an effective amount of a compound according to claim 1.

* * * * *

SEQUENCE LISTING

```
<160> NUMBER OF SEQ ID NOS: 2

<210> SEQ ID NO 1
<211> LENGTH: 6631
<212> TYPE: DNA
<213> ORGANISM: Artificial Sequence
<220> FEATURE:
<223> OTHER INFORMATION: vector

<400> SEQUENCE: 1
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
```

```
gtaggcgtgt acggtgggag gtctatataa gcagagctct ctggctaact agagaaccca    840
ctgcttactg gcttatcgaa attaatacga ctcactatag ggagacccaa gctggctagt    900
taagcttggt accgagctcg gatccgccac catgctgtcc cgaaagggca ttatccctga    960
ggaatatgtg ctgacccggc tggcagagga ccctacagag cccaggtacc gtactcggga   1020
gaggagggcc cgcttcgtgt ccaagaaagg caactgcaac gtcgcccaca gaacatccg    1080 agagcagggc cgcttcctgc aagatgtgtt caccacgctg gtggacctca gtgccccca   1140 cacgctgctc attttcacca tgtccttcct gtgcagctgg ctgctcttcg ccatggtctg   1200
gtggctcatc gcctttgccc acggtgactt ggccccggga gagggcacca atgtgccctg   1260
cgtcacaagc atccactcct tttcgtctgc cttccttttc tccatcgagg tccaggtgac   1320
cattggtttc ggcgggcgca tggtgacaga ggaatgtccc ctggccatcc ttattctgat   1380
cgtgcagaat atcgtagggc taatgatcaa cgccatcatg ctgggctgca tcttcatgaa   1440
aacggcacag gcccatcggc gggcagaaac cctcatcttc agcaagcatg ccgtgatcac   1500
cctgcgacat ggccgcctgt gcttcatgct tcgcgtaggg gacctccgaa aaagcatgat   1560
cattagcgcc accattcata tgcaggtggt gcgcaagacc accagcccgg agggcgaggt   1620
tgtgcctctc caccaggtgg acatccccat ggagaacggt gtgggtggta acagcatctt   1680
tctggtggcc ccactcatca tctaccacgt catcgactcc aacagccgc tctacgacct   1740 ggctcctagt gacctgcacc accaccagga cctggagatc attgtcatct tggaaggtgt   1800
ggtagaaacc acaggcatta ccacccaggc ccgcacctcc tatctggctg acgagattct   1860 gtggggcag cgttttgtcc ccatcgtggc cgaggaggat ggccgctatt ctgtggacta   1920
ctccaaattc gggaacaccg ttaaagtgcc cacaccactc tgcacagccc gccagcttga   1980
tgaggaccgc agcctgctgg atgccctgac cctcgcctcg tcgcgagggc ccctgcgcaa   2040
gcgcagtgtg gctgtggcaa aggccaagcc caagtttagc atctctccgg attccttgtc   2100
ctgatagcgg ccgctcgagt ctagagggcc cttcgaacaa aaactcatct cagaagagga   2160
tctgaatatg cataccggtc atcatcacca tcaccattga gtttaaaccc gctgatcagc   2220
ctcgactgtg ccttctagtt gccagccatc tgttgtttgc ccctccccg tgccttcctt   2280 gaccctggaa ggtgccactc ccactgtcct ttcctaataa aatgaggaaa ttgcatcgca   2340
ttgtctgagt aggtgtcatt ctattctggg ggtggggtg gggcaggaca gcaaggggga   2400
ggattgggaa gacaatagca ggcatgctgg ggatgcggtg gctctatgg cttctgaggc   2460 ggaaagaacc agctggggct ctaggggta tccccacgcg ccctgtagcg cgcattaag   2520 cgcggcgggt gtggtggtta cgcgcagcgt gaccgctaca cttgccagcg ccctagcgcc   2580
cgctcctttc gctttcttcc cttcctttct cgccacgttc gccggctttc ccgtcaagc   2640 tctaaatcgg gggctccctt tagggttccg atttagtgct ttacggcacc tcgaccccaa   2700
aaaacttgat tagggtgatg gttcacgtag tgggccatcg ccctgataga cggtttttcg   2760 cccttgacg ttggagtcca cgttctttaa tagtggactc ttgttccaaa ctggaacaac   2820 actcaacccct atctcggtct attcttttga tttataaggg attttgccga tttcggccta   2880
ttggttaaaa aatgagctga tttaacaaaa atttaacgcg aattaattct gtggaatgtg   2940
tgtcagttag ggtgtggaaa gtccccaggc tccccagcag gcagaagtat gcaaagcatg   3000
catctcaatt agtcagcaac caggtgtgga aagtccccag gctccccagc aggcagaagt   3060
atgcaaagca tgcatctcaa ttagtcagca accatagtcc cgcccctaac tccgcccatc   3120
ccgcccctaa ctccgcccag ttccgcccat tctccgcccc atggctgact aattttttt   3180
```

-continued

```
atttatgcag aggccgaggc cgcctctgcc tctgagctat tccagaagta gtgaggaggc    3240
ttttttggag gcctaggctt ttgcaaaaag ctcccgggag cttgtatatc cattttcgga    3300
tctgatcaag agacaggatg aggatcgttt cgcatgattg aacaagatgg attgcacgca    3360
ggttctccgg ccgcttgggt ggagaggcta ttcggctatg actgggcaca acagacaatc    3420
ggctgctctg atgccgccgt gttccggctg tcagcgcagg ggcgcccggt tctttttgtc    3480
aagaccgacc tgtccggtgc cctgaatgaa ctgcaggacg aggcagcgcg gctatcgtgg    3540
ctggccacga cgggcgttcc ttgcgcagct gtgctcgacg ttgtcactga agcgggaagg    3600
gactggctgc tattgggcga agtgccgggg caggatctcc tgtcatctca ccttgctcct    3660
gccgagaaag tatccatcat ggctgatgca atgcggcggc tgcatacgct tgatccggct    3720
acctgcccat tcgaccacca agcgaaacat cgcatcgagc gagcacgtac tcggatggaa    3780
gccggtcttg tcgatcagga tgatctggac gaagagcatc aggggctcgc gccagccgaa    3840
ctgttcgcca ggctcaaggc gcgcatgccc gacggcgagg atctcgtcgt gacccatggc    3900
gatgcctgct tgccgaatat catggtggaa aatggccgct ttctggatt catcgactgt     3960
ggccggctgg gtgtggcgga ccgctatcag gacatagcgt tggctacccg tgatattgct    4020
gaagagcttg gcggcgaatg ggctgaccgc ttcctcgtgc tttacggtat cgccgctccc    4080
gattcgcagc gcatcgcctt ctatcgcctt cttgacgagt tcttctgagc gggactctgg    4140
ggttcgcgaa atgaccgacc aagcgacgcc caacctgcca tcacgagatt cgattccac     4200
cgccgccttc tatgaaaggt tgggcttcgg aatcgttttc cgggacgccg gctggatgat    4260
cctccagcgc ggggatctca tgctggagtt cttcgcccac ccaacttgt ttattgcagc     4320
ttataatggt tacaaataaa gcaatagcat cacaaatttc acaaataaag cattttttc     4380
actgcattct agttgtggtt tgtccaaact catcaatgta tcttatcatg tctgtatacc    4440
gtcgacctct agctagagct tggcgtaatc atggtcatag ctgtttcctg tgtgaaattg    4500
ttatccgctc acaattccac acaacatacg agccggaagc ataaagtgta aagcctgggg    4560
tgcctaatga gtgagctaac tcacattaat tgcgttgcgc tcactgcccg ctttccagtc    4620
gggaaacctg tcgtgccagc tgcattaatg aatcggccaa cgcgcgggga gaggcggttt    4680
gcgtattggg cgctcttccg cttcctcgct cactgactcg ctgcgctcgg tcgttcggct    4740
gcggcgagcg gtatcagctc actcaaaggc ggtaatacgg ttatccacag aatcagggga    4800
taacgcagga aagaacatgt gagcaaaagg ccagcaaaag gccaggaacc gtaaaaaggc    4860
cgcgttgctg gcgttttcc ataggctccg ccccctgac gagcatcaca aaaatcgacg      4920
ctcaagtcag aggtggcgaa acccgacagg actataaaga taccaggcgt ttccccctgg    4980
aagctccctc gtgcgctctc ctgttccgac cctgccgctt accggatacc tgtccgcctt    5040
tctcccttcg ggaagcgtgg cgctttctca tagctcacgc tgtaggtatc tcagttcggt    5100
gtaggtcgtt cgctccaagc tgggctgtgt gcacgaaccc cccgttcagc ccgaccgctg    5160
cgccttatcc ggtaactatc gtcttgagtc aacccggta agacacgact tatcgccact     5220
ggcagcagcc actggtaaca ggattagcag agcgaggtat gtaggcggtg ctacagagtt    5280
cttgaagtgg tggcctaact acggctacac tagaagaaca gtatttggta tctgcgctct    5340
gctgaagcca gttaccttcg gaaaaagagt tggtagctct tgatccggca acaaaccac     5400
cgctggtagc ggtggttttt tgtttgcaa gcagcagatt acgcgcagaa aaaaaggatc     5460
tcaagaagat cctttgatct tttctacggg gtctgacgct cagtggaacg aaaactcacg    5520
ttaagggatt ttggtcatga gattatcaaa aaggatcttc acctagatcc ttttaaatta    5580
```

-continued

```
aaaatgaagt tttaaatcaa tctaaagtat atatgagtaa acttggtctg acagttacca      5640
atgcttaatc agtgaggcac ctatctcagc gatctgtcta tttcgttcat ccatagttgc      5700
ctgactcccc gtcgtgtaga taactacgat acgggagggc ttaccatctg gccccagtgc      5760
tgcaatgata ccgcgagacc cacgctcacc ggctccagat ttatcagcaa taaaccagcc      5820
agccggaagg gccgagcgca gaagtggtcc tgcaacttta tccgcctcca tccagtctat      5880
taattgttgc cgggaagcta gagtaagtag ttcgccagtt aatagtttgc gcaacgttgt      5940
tgccattgct acaggcatcg tggtgtcacg ctcgtcgttt ggtatggctt cattcagctc      6000
cggttcccaa cgatcaaggc gagttacatg atcccccatg ttgtgcaaaa aagcggttag      6060
ctccttcggt cctccgatcg ttgtcagaag taagttggcc gcagtgttat cactcatggt      6120
tatggcagca ctgcataatt ctcttactgt catgccatcc gtaagatgct tttctgtgac      6180
tggtgagtac tcaaccaagt cattctgaga atagtgtatg cggcgaccga gttgctcttg      6240
cccggcgtca atacgggata ataccgcgcc acatagcaga actttaaaag tgctcatcat      6300
tggaaaacgt tcttcggggc gaaaactctc aaggatctta ccgctgttga tccagttc      6360 gatgtaaccc actcgtgcac ccaactgatc ttcagcatct tttactttca ccagcgtttc      6420
tgggtgagca aaaacaggaa ggcaaaatgc cgcaaaaaag gaataagggc gacacggaa      6480 atgttgaata ctcatactct tcctttttca atattattga agcatttatc agggttattg      6540
tctcatgagc ggatacatat ttgaatgtat ttagaaaaat aaacaaatag gggttccgcg      6600
cacatttccc cgaaaagtgc cacctgacgt c                                     6631
```

<210> SEQ ID NO 2
<211> LENGTH: 6733
<212> TYPE: DNA
<213> ORGANISM: Artificial Sequence
<220> FEATURE:
<223> OTHER INFORMATION: vector

<400> SEQUENCE: 2

```
gacggatcgg gagatctccc gatccccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttggt accgagctcg gatccgccac catgctggcc aggaagagca tcatcccgga     960
ggagtatgtg ctggcccgca tcgcggcgga gaacctgcgc aaaccgcgca tccgcgaccg    1020
```

```
cctccccaaa gcccgcttca tcgccaagag cggagcctgc aacctggctc acaagaacat   1080
ccgagagcaa ggtcgcttcc tgcaggacat cttcaccacc ttggtagacc tgaagtggcg   1140
tcacacgctg gtcatcttca ccatgtcctt cctctgcagc tggctgctct cgctatcat   1200
gtggtggctg gtggccttcg cccacgggga catctatgct tacatggaga aaggcatcac   1260
ggagaagagt ggcctggagt ctgccgtctg tgtgaccaat gtcaggtcat tcacttctgc   1320
gtttctcttc tccatcgagg ttcaagtgac cattgggttt ggaggagaa tgatgactga   1380
ggagtgccct ctggccatca cggttttgat tctgcagaac attgtgggtc tgatcatcaa   1440
cgcggtcatg ttgggctgca tcttcatgaa cacggcccag gcccacagaa gggcagagac   1500
gctgattttc agccgccatg ctgtaattgc ggtccgtaat ggcaagctgt gcttcatgtt   1560
ccgggtgggt gacctgagga aaagcatgat cattagcgcc tcggtgcgca tccaggtggt   1620
caagaaaacc acgacgccag aaggagaggt ggtgcctatt caccagcagg acatccctgt   1680
ggataatccc atcgagagca ataacatctt cctagtggcc cctttgatca tctgccatgt   1740
gattgataag cgtagccccc tgtacgatat ctcagccact gaccttgtca accaagacct   1800
ggaggtcata gtgattctcg agggcgtggt ggaaaccacg gcatcacca cgcaagcgcg   1860
gacctcctac attgcagagg agatccagtg gggacaccgc ttcgtgtcga ttgtgactga   1920
ggaggaggga gtgtactctg tggactattc taaatttggt aatactgtga gagtggcggc   1980
gccaagatgc agtgcccggg agctggacga gaaaccttcc atcttgattc agaccctcca   2040
aaagagtgaa ctgtcgcacc agaattctct gaggaagcgc aactctatga agaaaacaa   2100
ctccatgagg aggagcaact ccatccggag gaataactct tccctcatgg tgcccaaggt   2160
gcaattcatg actccagaag gaaaccagtg cccatcagaa tcatgatagc ggccgctcga   2220
gtctagaggg ccccttcgaac aaaaactcat ctcagaagag gatctgaata tgcataccgg   2280
tcatcatcac catcaccatt gagtttaaac ccgctgatca gcctcgactg tgccttctag   2340
ttgccagcca tctgttgttt gccccctccc cgtgccttcc ttgaccctgg aaggtgccac   2400
tcccactgtc ctttcctaat aaaatgagga aattgcatcg cattgtctga gtaggtgtca   2460
ttctattctg gggggtgggg tggggcagga cagcaagggg gaggattggg aagacaatag   2520
caggcatgct ggggatgcgg tgggctctat ggcttctgag gcggaaagaa ccagctgggg   2580
ctctaggggg tatccccacg cgccctgtag cggcgcatta gcgcggcgg gtgtggtggt   2640
tacgcgcagc gtgaccgcta cacttgccag cgccctagcg cccgctcctt cgctttctt   2700
cccttccttt ctcgccacgt tcgccggctt tccccgtcaa gctctaaatc ggggctccc   2760
tttagggttc cgatttagtg ctttacggca cctcgacccc aaaaaacttg attagggtga   2820
tggttcacgt agtgggccat cgccctgata gacggttttt cgccctttga cgttggagtc   2880
cacgttcttt aatagtggac tcttgttcca actggaaca cactcaacc ctatctcggt   2940
ctattctttt gatttataag ggattttgcc gatttcggcc tattggttaa aaaatgagct   3000
gatttaacaa aaatttaacg cgaattaatt ctgtggaatg tgtgtcagtt agggtgtgga   3060
aagtccccag gctccccagc aggcagaagt atgcaaagca tgcatctcaa ttagtcagca   3120
accaggtgtg gaaagtcccc aggctcccca gcaggcagaa gtatgcaaag catgcatctc   3180
aattagtcag caaccatagt cccgccccta actccgccca tcccgcccct aactccgccc   3240
agttccgccc attctccgcc ccatggctga ctaattttt ttatttatgc agaggccgag   3300
gccgcctctg cctctgagct attccagaag tagtgaggag gcttttttgg aggcctaggc   3360
ttttgcaaaa agctcccggg agcttgtata tccatttcg gatctgatca agagacagga   3420
```

```
tgaggatcgt tcgcatgat tgaacaagat ggattgcacg caggttctcc ggccgcttgg    3480
gtggagaggc tattcggcta tgactgggca acagacaa tcggctgctc tgatgccgcc    3540
gtgttccggc tgtcagcgca ggggcgcccg gttcttttg tcaagaccga cctgtccggt    3600
gccctgaatg aactgcagga cgaggcagcg cggctatcgt ggctggccac gacgggcgtt    3660
ccttgcgcag ctgtgctcga cgttgtcact gaagcgggaa gggactggct gctattgggc    3720
gaagtgccgg ggcaggatct cctgtcatct caccttgctc ctgccgagaa agtatccatc    3780
atggctgatg caatgcggcg gctgcatacg cttgatccgg ctacctgccc attcgaccac    3840
caagcgaaac atcgcatcga gcgagcacgt actcggatgg aagccggtct tgtcgatcag    3900
gatgatctgg acgaagagca tcaggggctc gcgccagccg aactgttcgc caggctcaag    3960
gcgcgcatgc ccgacggcga ggatctcgtc gtgacccatg gcgatgcctg cttgccgaat    4020
atcatggtgg aaaatggccg cttttctgga ttcatcgact gtggccggct gggtgtggcg    4080
gaccgctatc aggacatagc gttggctacc cgtgatattg ctgaagagct ggcggcgaa    4140
tgggctgacc gcttcctcgt gctttacggt atcgccgctc ccgattcgca gcgcatcgcc    4200
ttctatcgcc ttcttgacga gttcttctga gcgggactct ggggttcgcg aaatgaccga    4260
ccaagcgacg cccaacctgc catcacgaga tttcgattcc accgccgcct tctatgaaag    4320
gttgggcttc ggaatcgttt tccgggacgc cggctggatg atcctccagc gcgggatct    4380
catgctggag ttcttcgccc accccaactt gtttattgca gcttataatg ttacaaata    4440
aagcaatagc atcacaaatt tcacaaataa agcattttt tcactgcatt ctagttgtgg    4500
tttgtccaaa ctcatcaatg tatcttatca gtctgtata ccgtcgacct ctagctagag    4560
cttggcgtaa tcatggtcat agctgtttcc tgtgtgaaat tgttatccgc tcacaattcc    4620
acacaacata cgagccggaa gcataaagtg taaagcctgg ggtgcctaat gagtgagcta    4680
actcacatta attgcgttgc gctcactgcc cgctttccag tcgggaaacc tgtcgtgcca    4740
gctgcattaa tgaatcggcc aacgcgcggg gagaggcggt ttgcgtattg ggcgctcttc    4800
cgcttcctcg ctcactgact cgctgcgctc ggtcgttcgg ctgcggcgag cggtatcagc    4860
tcactcaaag gcggtaatac ggttatccac agaatcaggg gataacgcag gaaagaacat    4920
gtgagcaaaa ggccagcaaa aggccaggaa ccgtaaaaag gccgcgttgc tggcgttttt    4980
ccataggctc cgcccccctg acgagcatca aaaaatcga cgctcaagtc agaggtggcg    5040
aaacccgaca ggactataaa gataccaggc gtttccccct ggaagctccc tcgtgcgctc    5100
tcctgttccg accctgccgc ttaccggata cctgtccgcc tttctccctt cgggaagcgt    5160
ggcgctttct catagctcac gctgtaggta tctcagttcg gtgtaggtcg ttcgctccaa    5220
gctgggctgt gtgcacgaac ccccgttca gcccgaccgc tgcgccttat ccggtaacta    5280
tcgtcttgag tccaacccgg taagacacga cttatcgcca ctggcagcag ccactggtaa    5340
caggattagc agagcgaggt atgtaggcgg tgctacagag ttcttgaagt ggtggcctaa    5400
ctacggctac actagaagaa cagtatttgg tatctgcgct ctgctgaagc cagttacctt    5460
cggaaaaaga gttggtagct cttgatccgg caaacaaacc accgctggta gcggtggttt    5520
ttttgtttgc aagcagcaga ttacgcgcag aaaaaaagga tctcaagaag atcctttgat    5580
cttttctacg gggtctgacg ctcagtggaa cgaaaactca cgttaaggga ttttggtcat    5640
gagattatca aaaaggatct tcacctagat cctttaaat taaaatgaa gttttaaatc    5700
aatctaaagt atatatgagt aaacttggtc tgacagttac caatgcttaa tcagtgaggc    5760
acctatctca gcgatctgtc tatttcgttc atccatagtt gcctgactcc ccgtcgtgta    5820
```

```
gataactacg atacgggagg gcttaccatc tggccccagt gctgcaatga taccgcgaga    5880
cccacgctca ccggctccag atttatcagc aataaaccag ccagccggaa gggccgagcg    5940
cagaagtggt cctgcaactt tatccgcctc catccagtct attaattgtt gccgggaagc    6000
tagagtaagt agttcgccag ttaatagttt gcgcaacgtt gttgccattg ctacaggcat    6060
cgtggtgtca cgctcgtcgt ttggtatggc ttcattcagc tccggttccc aacgatcaag    6120
gcgagttaca tgatccccca tgttgtgcaa aaaagcggtt agctccttcg gtcctccgat    6180
cgttgtcaga agtaagttgg ccgcagtgtt atcactcatg gttatggcag cactgcataa    6240
ttctcttact gtcatgccat ccgtaagatg cttttctgtg actggtgagt actcaaccaa    6300
gtcattctga gaatagtgta tgcggcgacc gagttgctct tgcccggcgt caatacggga    6360
taataccgcg ccacatagca gaactttaaa agtgctcatc attggaaaac gttcttcggg    6420
gcgaaaactc tcaaggatct taccgctgtt gagatccagt tcgatgtaac ccactcgtgc    6480
acccaactga tcttcagcat cttttacttt caccagcgtt tctgggtgag caaaaacagg    6540
aaggcaaaat gccgcaaaaa agggaataag ggcgacacgg aaatgttgaa tactcatact    6600 cttcctttt caatattatt gaagcattta tcagggttat tgtctcatga gcggatacat    6660
atttgaatgt atttagaaaa ataaacaaat aggggttccg cgcacatttc cccgaaaagt    6720
gccacctgac gtc                                                      6733
```